(12) United States Patent
Johnson et al.

(10) Patent No.: US 7,063,967 B2
(45) Date of Patent: *Jun. 20, 2006

(54) AMINOALKYL GLUCOSAMINIDE PHOSPHATE COMPOUNDS AND THEIR USE AS ADJUVANTS AND IMMUNOEFFECTORS

(75) Inventors: David A. Johnson, Hamilton, MT (US); C. Gregory Sowell, Kirkland, WA (US)

(73) Assignee: Corixa Corporation, Seattle, WA (US)

( * ) Notice: Subject to any disclaimer, the term of this patent is extended or adjusted under 35 U.S.C. 154(b) by 311 days.

This patent is subject to a terminal disclaimer.

(21) Appl. No.: 10/043,086

(22) Filed: Jan. 8, 2002

(65) Prior Publication Data

US 2003/0092643 A1    May 15, 2003

Related U.S. Application Data

(63) Continuation-in-part of application No. 09/905,160, filed on Jul. 12, 2001, now Pat. No. 6,764,840, which is a continuation of application No. 09/439,839, filed on Nov. 12, 1999, now Pat. No. 6,303,347, which is a continuation-in-part of application No. 08/853,826, filed on May 8, 1997, now Pat. No. 6,113,918.

(51) Int. Cl.
*C12P 19/04* (2006.01)

(52) U.S. Cl. .................. 435/101; 424/270.1; 536/1.11; 536/18.4; 536/117; 536/119

(58) Field of Classification Search ................ 435/101; 424/278.1; 536/1.11, 18.4, 117, 119
See application file for complete search history.

(56) References Cited

U.S. PATENT DOCUMENTS

| 4,912,094 A | 3/1990 | Myers et al. .................. 514/54 |
| 6,113,918 A | 9/2000 | Johnson et al. ........... 424/278.1 |
| 6,303,347 B1 * | 10/2001 | Johnson et al. ............. 435/101 |

FOREIGN PATENT DOCUMENTS

WO   WO 98/50399   11/1998

OTHER PUBLICATIONS

Baldridge, "Synthetic Adjuvants: Recent Developments and Applicants," IBC Vaccine Conference, Washington DC, Feb. 1998.

Bulusu et al., "Cyclic Analogues of Lipid A: Synthesis and Biological Activities," *J. Med. Chem.* 35(19): 3463-3469, 1992.

Eustache et al., "New Acyclic Analogues of Lipid A: Synthesis of 4-Phosphonoxybutyl and 3-Phosphonoxypropyl Glycosides of 2-Amino-2-Deoxy-D-Glucose," *Carbohydrate Research* 251:251-267, Jan. 3, 1994.

Johnson et al., "Synthesis and Biological Evaluation of a New Class of Vaccine Adjuvants: Aminoalkyl Glucosaminide 4-Phosphates (AGPs)," *Bioorg. Med. Chem. Lett.* 9(15):2273-2278, Aug. 2, 1999.

Ikeda et al., "Synthesis of Biologically Active N-Acylated L-serine Containing Glucosamine-4-Phosphate Derivatives of Lipid A," *Chem. Pharm. Bull.* 41(10): 1879-1881, 1993.

Miyajima et al., "Lipid A and Related Compounds XXXI. Synthesis of Biologically Active N-Acylated L-Serine-Containing D-Glucosamine 4-Phosphate," *Chem. Pharm. Bull.* 44(12): 2268-2273, 1996.

Shimizu et al., "Antitumor Activity and Biological Effects of Chemically Synthesized Monosaccharide Analogues of Lipid A in Mice," *Chem. Pharm. Bull.* 33(10): 4621-4624, 1985.

Shimizu et al., "Biological Activities of Chemically Synthesized N-acylated Serine-linked Lipid A Analog in Mice," *Int. J. Immunopharmacol.* 16(8): 659-665, 1994.

Shimizu et al., "Biological Activities and Antitumor Effects of Synthetic Lipid A Analogs Linked N-Acylated Serine," *Int. J. Immunopharmacol.* 17(5): 425-431, 1995.

* cited by examiner

*Primary Examiner*—James Housel
*Assistant Examiner*—Emily M. Le
(74) *Attorney, Agent, or Firm*—Michael M. Conger

(57) ABSTRACT

Aminoalkyl glucosaminide phosphate (AGP) compounds that are adjuvants and immunoeffectors are described and claimed. The compounds have a 2-deoxy-2-amino glucose in glycosidic linkage with an aminoalkyl (aglycon) group. Compounds are phosphorylated at the 4 or 6 carbon on the glucosaminide ring and comprise three 3-alkanoyloxyalkanoyl residues. The compounds augment antibody production in immunized animals as well as stimulate cytokine production and activate macrophages. Compositions and methods for using the compounds as adjuvants and immunoeffectors are also disclosed.

13 Claims, 4 Drawing Sheets

US 7,063,967 B2

AMINOALKYL GLUCOSAMINIDE PHOSPHATE COMPOUNDS AND THEIR USE AS ADJUVANTS AND IMMUNOEFFECTORS

BACKGROUND OF THE INVENTION

1. Field of the Invention

This invention relates generally to aminoalkyl glucosaminide phosphate (AGP) compounds that have activity as adjuvants and immunoeffectors, and to methods employing and compositions comprising AGPs.

2. Description of the Related Art

Humoral immunity and cell-mediated immunity are the two major branches of the mammalian immune response. Humoral immunity involves the generation of antibodies to foreign antigens. Antibodies are produced by B-lymphocytes. Cell-mediated immunity involves the activation of T-lymphocytes that either act upon infected cells bearing foreign antigens or stimulate other cells to act upon infected cells. Both branches of the mammalian immune system are important in fighting disease. Humoral immunity is the major line of defense against bacterial pathogens. In the case of viral disease, the induction of cytotoxic T lymphocytes (CTLs) appears to be crucial for protective immunity. An effective vaccine stimulates both branches of the immune system to protect against disease.

Vaccines present foreign antigens from disease causing agents to a host so that the host can mount a protective immune response. Often vaccine antigens are killed or attenuated forms of the microbes that cause the disease. The presence of non-essential components and antigens in these killed or attenuated vaccines has encouraged considerable efforts to refine vaccine components including developing well-defined synthetic antigens using chemical and recombinant techniques. The refinement and simplification of microbial vaccines, however, has led to a concomitant loss in potency. Low-molecular weight synthetic antigens, though devoid of potentially harmful contaminants, are themselves not very immunogenic. These observations have led investigators to add adjuvants to vaccine compositions to potentiate the activity of the refined vaccine components.

Presently, the only adjuvant licensed for human use in the United States is alum, a group of aluminum salts (e.g., aluminum hydroxide, aluminum phosphate) in which vaccine antigens are formulated. Particulate carriers like alum serve to promote the uptake, processing and presentation of soluble antigens by macrophages. Alum, however, is not without side-effects and enhances humoral (antibody) immunity only.

An effective adjuvant potentiates both a humoral and cellular immune response in vaccinated animals. Further, an adjuvant must enhance a host's natural immune response and not aggravate the host system. A well-defined synthetic adjuvant free from extraneous matter, which is stable and easy to manufacture, would provide these qualities. Compounds that have been prepared and tested for adjuvanticity (Shimizu et al. 1985, Bulusu et al. 1992, Ikeda et al. 1993, Shimizu et al. 1994, Shimizu et al. 1995, Miyajima et al. 1996), however, often display toxic properties, are unstable and/or have unsubstantial immunostimulatory effects.

The discovery and development of effective adjuvants is essential for improving the efficacy and safety of existing vaccines. Adjuvants impart synthetic peptides and carbohydrate antigens with sufficient immunogenicity to insure the success of the synthetic vaccine approach. There remains a need for new compounds having potent immunomodulating effects.

BRIEF SUMMARY OF THE INVENTION

The compounds of the subject invention are aminoalkyl glucosaminide phosphate compounds (AGPs) that are adjuvants and immunoeffectors. An aminoalkyl (aglycon) group is glycosidically linked to a 2-deoxy-2-amino-α-D-glucopyranose (glucosaminide) to form the basic structure of the claimed molecules. The compounds are phosphorylated at the 4 or 6 carbon on the glucosaminide ring. Further, the compounds possess three 3-alkanoyloxyalkanoyl residues.

The compounds of the subject invention are immunoeffector molecules augmenting antibody production in immunized animals, stimulating cytokine production and activating macrophages. In accordance with the subject invention, methods for using these compounds as adjuvants and immunoeffectors are disclosed.

According to the present invention, methods for inducing an immune response employ the administration of one or more AGP either alone or in conjunction with one or more antigen such as a protein antigen or a polynucleotide that expresses a protein antigen. Inventive compositions for inducing an immune response employ one or more AGE either alone or in combination with one or more antigen such as a protein antigen or a polynucleotide that expresses a protein antigen. Exemplary antigens include, but are not limited to, tumor antigens and infectious disease antigens. Induction of an immune response may be determined by measuring antibody in immunized animals. Such measurements may include a determination of seroconversion and/or seroprotection. Alternatively, or additionally, an immune response may be determined by measureing the production of cytokines and/or the stimulation of a cell-mediated immune response including a cytotoxic T-lymphocyte response.

DETAILED DESCRIPTION OF THE INVENTION

Aminoalkyl Glucosaminide Phosphate (AGP) Compounds

Figure 1:
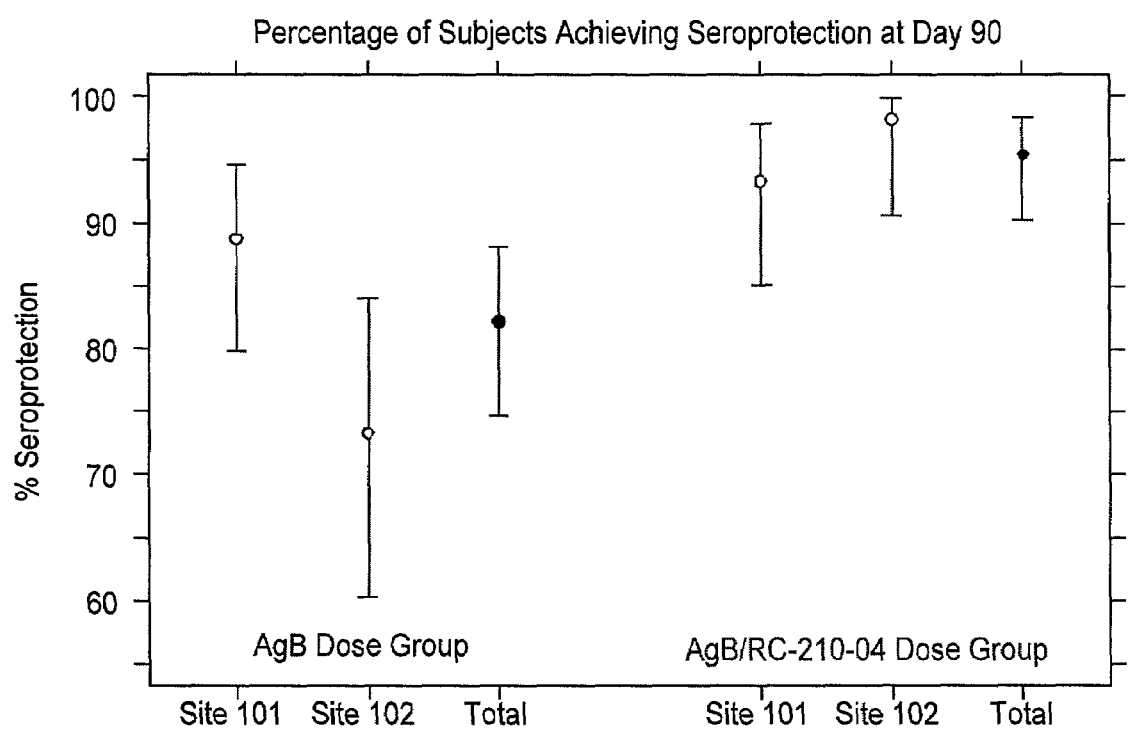
FIG. 1 is a graph depicting the percentage of human subjects achieving seroprotection following administration of Hepatitis B Surface Antigen (AgB) alone or in combination with the AGP designated RC-210-04 (B 19 in Table 1 and Example 20 herein below; chemical name 2-[(R)-3-Tetradecanoyloxytetradecanoylamino]ethyl 2-Deoxy-4-O-phosphono-3-O-[(R)-3-tetradecanoyloxytetradecanoyl]-2-[(R)-3-tetradecanoyloxytetradecanoylamino]-β-D-glucopyranoside Triethylammonium Salt). Plot symbols show the percentages of efficacy evaluable (EE) population subjects who achieved seroprotection (anti-HBsAg titer of ≦10 MIU/mL) at the Day 90 visit. The error bars show 95% confidence intervals for the percentages of subjects achieving seroprotection.

The compounds of the subject invention are adjuvant and immunoeffector molecules that are aminoalkyl glucosaminide phosphates (AGPs). The compounds comprise a 2-deoxy-2-amino-α-D-glucopyranose (glucosaminide) in glycosidic linkage with an aminoalkyl (aglycon) group. Compounds are phosphorylated at the 4 or 6 carbon on the glucosaminide ring and have three alkanoyloxyalkanoyl residues. The compounds of the subject invention are described generally by Formula I,

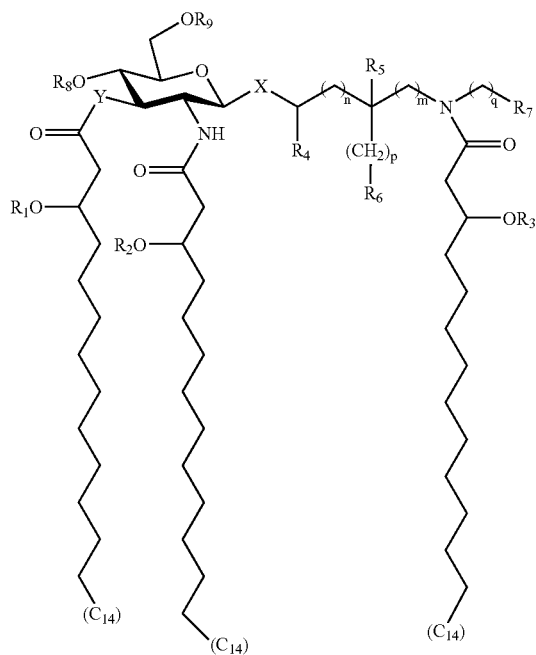

wherein X represents an oxygen or sulfur atom in either the axial or equitorial position, Y represents an oxygen atom or NH group, "n", "m", "p" and "q" are integers from 0 to 6, $R_1$, $R_2$, and $R_3$ represent normal fatty acyl residues having 1 to 20 carbon atoms and where one of $R_1$, $R_2$ or $R_3$ is optionally hydrogen, $R_4$ and $R_5$ are hydrogen or methyl, $R_6$ and $R_7$ are hydrogen, hydroxy, alkoxy, phosphono, phosphonooxy, sulfo, sulfooxy, amino, mercapto, cyano, nitro, formyl or carboxy and esters and amides thereof; $R_8$ and $R_9$ are phosphono or hydrogen. The configuration of the 3' stereogenic centers to which the normal fatty acyl residues are attached is R or S, but preferably R. The stereochemistry of the carbon atoms to which $R_4$ or $R_5$ are attached can be R or S. All stereoisomers, both enantiomers and diastereomers, and mixtures thereof, are considered to fall within the scope of the subject invention.

The heteroatom X of the compounds of the subject invention can be oxygen or sulfur. In a preferred embodiment, X is oxygen and typically in the equitorial position. Although the stability of the molecules could be effected by a substitution at X, the immunomodulating activity of molecules with these substitutions is not expected to change.

The number of carbon atoms between heteroatom X and the aglycon nitrogen atom is determined by variables "n" and "m". Variables "n" and "m" can be integers from 0 to 6. In a preferred embodiment, the total number of carbon atoms between heteroatom X and the aglycon nitrogen atom is from about 2 to about 6 and most preferably from about 2 to about 4.

The compounds of the subject invention are aminoalkyl glucosaminide compounds that are phosphorylated. Compounds can be phosphorylated at position 4 or 6 ($R_8$ or $R_9$) on the glucosaminide ring and are most effective if phosphorylated on at least one of these positions. In a preferred embodiment, $R_8$ is phosphono and $R_9$ is hydrogen.

In one embodiment, the compounds of the subject invention are hexaacylated; that is, they contain a total of six fatty acid residues. The aminoalkyl glucosaminide moiety is acylated at the 2-amino and 3-hydroxyl groups of the glucosaminide unit and at the amino group of the aglycon unit with 3-hydroxyalkanoyl residues. In Formula I, these three positions are acylated with 3-hydroxytetradecanoyl moieties. The 3-hydroxytetradecanoyl residues are, in turn, substituted with normal fatty acids ($R_1$–$R_3$), providing three 3-n-alkanoyloxytetradecanoyl residues or six fatty acid groups in total.

In another embodiment, the compounds of the subject invention are pentaacylated; that is, they contain a total of five fatty acid residues. More specifically, the 3-hydroxytetradecanoyl residues of Formula I are substituted with normal fatty acids at two of the three $R_1$, $R_2$ and $R_3$ positions, with the third $R_1$, $R_2$ or $R_3$ position being hydrogen. In other words, at least one of —$OR_1$, —$OR_2$ or —$OR_3$ is hydroxyl.

The chain length of normal fatty acids $R_1$–$R_3$ can be from 1 to about 20, and typically from about 7 to about 16 carbons. Preferably, $R_1$–$R_3$ are from about 9 to about 14 carbons. The chain lengths of these normal fatty acids can be the same or different. Although, only normal fatty acids are described, it is expected that unsaturated fatty acids (i.e. fatty acid moieties having double or triple bonds) substituted at $R_1$–$R_3$ on the compounds of the subject invention would produce biologically active molecules. Further, slight modifications in the chain length of the 3-hydroxyalkanoyl residues are not expected to dramatically effect biological activity.

The compounds of the subject invention are synthesized by coupling an N-acyloxyacylated or N-protected aminoalkanol or aminoalkanethiol (aglycon unit) with a suitably protected and/or 3-O-acyloxyacylated glucosaminide unit. In one preferred method for preparing the compounds of the subject invention (Scheme 1), an N-(2,2,2-trichloroethoxycarbonyl (Troc))-protected glycosyl halide 1 (Z=F, Cl, Br) is coupled with an N-[(R)-3-n-alkanoyloxytetradecanoyl]aminoalkanol or thiol 2 (possessing $R_5$ and $R_6$ in suitably protected form) via a Koenigs-Knorr type reaction in the presence of mercury or silver salts to give glycoside intermediate 3. Preferably, the glucosaminide unit 1 possesses an anomeric chloride atom (Z=Cl), and the coupling catalyst is silver trifluoromethanesulfonate. Intermediate 3 can also be prepared by coupling the aglycon unit 2 with an N-Troc-protected glycosyl acetate (Z=OAc) or related activated derivative in the presence of a Lewis acid such as boron trifluoride etherate. By "activated" is meant having an appropriate displaceable leaving group "Z" attached to the anomeric center of the glucosaminide unit. Glucosaminide unit 1 bears an (R)-3-n-alkanoyloxytetradecanoyl residue on the 3-position, and suitable protecting groups on the 6-hydroxyl and 4-phosphate moieties. Typical protecting groups for the phosphate group include, but are not limited to, phenyl, benzyl, and o-xylyl. The phosphate group is protected preferably with two phenyl groups. The 6-position can be temporarily protected by blocking groups commonly used in sugar chemistry such as silyl, benzyl, or benzyloxymethyl ethers or, alternatively, an alkyl carbonate. The 6-hydroxyl group is protected preferably as a 1,1-dimethyl-2,2,2-trichloroethyl carbonate (TCBOC).

The trichloroethyl-based protecting group(s) in the Koenigs-Knorr coupled product 3 are removed with zinc and the glucosaminide nitrogen is selectively acylated with a (R)-3-n-alkanoyloxytetradecanoic acid 4 in the presence of a suitable coupling reagent to give the hexaacylated derivative 5. The remaining protecting groups in 5 are then cleaved by catalytic hydrogenation in the presence of a palladium or platinum catalyst or by other appropriate means to give compounds of Formula (I).

A suitable starting material for the synthesis of glycosyl donor 1 is 2-(trimethylsilyl)ethyl 2-amino-2-deoxy-4,6-O-isopropylidene-β-D-glucopyranoside which can be prepared from commercially available D-glucosaminide hydrochloride using published procedures. The conversion of the 2-(trimethylsilyl)ethyl glycoside starting material to glycosyl donor 1 can be achieved by methods known in the art or modifications thereof which are described herein. The aglycon unit 2 can be prepared by N-acyloxyacylation of commercially available starting materials with an appropriate (R)-3-n-alkanoyloxytetradecanoic acid 4, or N-acyloxyacylation of starting materials that can be obtained by known methods in the chemical literature. Alternatively, the N-acyloxyacyl residue in 2 can be substituted with an appropriate amine protecting group which is removed subsequent to the coupling reaction such as is described in the second preferred embodiment below.

In a second preferred method for preparing the compounds of the subject invention (Scheme 2), introduction of the (R)-3-n-alkanoyloxytetradecanoyl and phosphate groups into the glucosaminide and aglycon units is performed subsequent to the glycosylation (coupling) reaction using N- and O-protecting groups suitable for the chemical differentiation of the amino and hydroxyl groups present. Preferably, the N-Troc-protected glycosyl donor 6 is coupled with an N-allyloxycarbonyl (AOC)-protected aminoalkanol or thiol 7 in the presence of an appropriate catalyst to give the aminoalkyl β-glycoside 8. Most preferably, the glycosyl donor 6 possesses an anomeric acetoxy group (Z=OAc), and the coupling catalyst is boron trifluoride etherate. Other N-protecting groups for the aglycon amino group include, but are not limited to, commonly employed carbamates obvious to one skilled in the art such as t-butyl (t-BOC), benzyl (Cbz), 2,2,2-trichloroethyl (Troc), and 9-fluorenylmethyl(Fmoc).

Base-induced cleavage of the acetate groups in coupling product 8 and 4,6-acetonide formation under standard conditions known in the art gives intermediate 9. 3-O-Acylation of 9 with (R)-3-n-alkanoyloxytetradecanoic acid 4, followed by palladium(0)-mediated removal of the aglycon N-AOC group and N-acylation with (R)-3-n-alkanoyloxytetradecanoic acid 4 provides intermediate 10. Acetonide hydrolysis and functionalization of the 4- and 6-positions as described herein for the preparation of glycosyl donor 1 gives intermediate 3 (Y=O), which is then processed as in Scheme 1 to afford compounds of general Formula (I).

AGP-Based Compositions

In compositions for eliciting an immune response, the AGPs of the subject invention are administered to a warm-blooded animal, including humans, with an antigen such as a protein or polypeptide antigen or a polynucleotide that expresses a protein or polypeptide antigen. The amount of antigen administered to elicit a desired response can be readily determined by one skilled in the art and will vary with the type of antigen administered, route of administration and immunization schedule. For example, 0.2 µg of tetanus toxoid administered with the claimed compounds subcutaneously to a mouse in two immunization 21 days apart elicited a humoral immune response to that antigen.

AGP-based Compositions Comprising One or More Polypeptide

As used herein, the term "polypeptide" is used in its conventional meaning, i.e., as a sequence of amino acids. The polypeptides are not limited to a specific length of the product; thus, peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising epitopes, i.e., antigenic determinants substantially responsible for the immunogenic properties of a polypeptide and being capable of evoking an immune response.

The polypeptides of the present invention are sometimes herein referred to as tumor proteins or tumor polypeptides, as an indication that their identification has been based at least in part upon their increased levels of expression in tumor samples. Thus, a "tumor polypeptide" or "tumor protein," refers generally to a polypeptide sequence of the present invention, or a polynucleotide sequence encoding such a polypeptide, that is expressed in a substantial proportion of tumor samples, for example preferably greater than about 20%, more preferably greater than about 30%, and most preferably greater than about 50% or more of tumor samples tested, at a level that is at least two fold, and preferably at least five fold, greater than the level of expression in normal tissues, as determined using a representative assay provided herein.

In certain preferred embodiments, the polypeptides of the invention are immunogenic, ie., they react detectably within an immunoassay (such as an ELISA or T-cell stimulation assay) with antisera and/or T-cells from a patient with cancer. Screening for immunogenic activity can be performed using techniques well known to the skilled artisan. For example, such screens can be performed using methods such as those described in Harlow and Lane, *Antibodies: A Laboratory Manual*, Cold Spring Harbor Laboratory, 1988. In one illustrative example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As would be recognized by the skilled artisan, immunogenic portions of the polypeptides disclosed herein are also encompassed by the present invention. An "immunogenic portion," as used herein, is a fragment of an immunogenic polypeptide of the invention that itself is immunologically reactive (i.e., specifically binds) with the B-cells and/or T-cell surface antigen receptors that recognize the polypeptide. Immunogenic portions may generally be identified using well known techniques, such as those summarized in Paul, *Fundamental Immunology*, 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well-known techniques.

In one preferred embodiment, an immunogenic portion of a polypeptide of the present invention is a portion that reacts with antisera and/or T-cells at a level that is not substantially less than the reactivity of the full-length polypeptide (e.g., in an ELISA and/or T-cell reactivity assay). Preferably, the level of immunogenic activity of the immunogenic portion is at least about 50%, preferably at least about 70% and most preferably greater than about 90% of the immunogenicity for the full-length polypeptide. In some instances, preferred immunogenic portions will be identified that have a level of immunogenic activity greater than that of the corresponding full-length polypeptide, e.g., having greater than about 100% or 150% or more immunogenic activity.

In certain other embodiments, illustrative immunogenic portions may include peptides in which an N-terminal leader sequence and/or transmembrane domain have been deleted. Other illustrative immunogenic portions will contain a small N- and/or C-terminal deletion (e.g., 1–30 amino acids, preferably 5–15 amino acids), relative to the mature protein.

In another embodiment, a polypeptide composition of the invention may also comprise one or more polypeptides that are immunologically reactive with T cells and/or antibodies generated against a polypeptide of the invention, particularly a polypeptide having an amino acid sequence disclosed herein, or to an immunogenic fragment or variant thereof.

In another embodiment of the invention, polypeptides are provided that comprise one or more polypeptides that are capable of eliciting T cells and/or antibodies that are immunologically reactive with one or more polypeptides described herein, or one or more polypeptides encoded by contiguous nucleic acid sequences contained in the polynucleotides disclosed herein, or immunogenic fragments or variants thereof.

Polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Within other illustrative embodiments, a polypeptide may be a fusion polypeptide that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the polypeptide or to enable the polypeptide to be targeted to desired intracellular compartments. Still further fusion partners include affinity tags, which facilitate purification of the polypeptide.

Fusion polypeptides may generally be prepared using standard techniques, including chemical conjugation. Preferably, a fusion polypeptide is expressed as a recombinant polypeptide, allowing the production of increased levels, relative to a non-fused polypeptide, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion polypeptide using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

The fusion polypeptide can comprise a polypeptide as described herein together with an unrelated immunogenic protein, such as an immunogenic protein capable of eliciting a recall response. Examples of such proteins include tetanus, tuberculosis and hepatitis proteins (see, for example, Stoute et al. *New Engl. J. Med.*, 336:86–91, 1997).

In one preferred embodiment, the immunological fusion partner is derived from a Mycobacterium sp., such as a Mycobacterium tuberculosis-derived Ra12 fragment. Ra12 compositions and methods for their use in enhancing the expression and/or immunogenicity of heterologous polynucleotide/polypeptide sequences is described in U.S. Patent Application No. 60/158,585, the disclosure of which is incorporated herein by reference in its entirety. Briefly, Ra12 refers to a polynucleotide region that is a subsequence of a *Mycobacterium tuberculosis* MTB32A nucleic acid. MTB32A is a serine protease of 32 KD molecular weight encoded by a gene in virulent and avirulent strains of *M. tuberculosis*. The nucleotide sequence and amino acid sequence of MTB32A have been described (for example, U.S. Patent Application No. 60/158,585; see also, Skeiky et al., *Infection and Immun*. (1999) 67:3998–4007, incorporated herein by reference). C-terminal fragments of the MTB32A coding sequence express at high levels and remain as a soluble polypeptides throughout the purification process. Moreover, Ra12 may enhance the immunogenicity of heterologous immunogenic polypeptides with which it is fused. One preferred Ra12 fusion polypeptide comprises a 14 KD C-terminal fragment corresponding to amino acid residues 192 to 323 of MTB32A. Other preferred Ra12 polynucleotides generally comprise at least about 15 consecutive nucleotides, at least about 30 nucleotides, at least about 60 nucleotides, at least about 100 nucleotides, at least about 200 nucleotides, or at least about 300 nucleotides that encode a portion of a Ra12 polypeptide. Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/or insertions such that the biological activity of the encoded fusion polypeptide is not substantially diminished, relative to a fusion polypeptide comprising a native Ra12 polypeptide. Variants preferably exhibit at least about 70% identity, more preferably at least about 80% identity and most preferably at least about 90% identity to a polynucleotide sequence that encodes a native Ra12 polypeptide or a portion thereof.

Within other preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion polypeptide. A repeat portion is found in the C-terminal region starting at residue 178. A particularly preferred repeat portion incorporates residues 188–305.

Yet another illustrative embodiment involves fusion polypeptides, and the polynucleotides encoding them, wherein the fusion partner comprises a targeting signal capable of directing a polypeptide to the endosomal/lysosomal compartment, as described in U.S. Pat. No. 5,633,234. An immunogenic polypeptide of the invention, when fused with this targeting signal, will associate more efficiently with MHC class II molecules and thereby provide enhanced in vivo stimulation of $CD4^+$ T-cells specific for the polypeptide.

Polypeptides of the invention are prepared using any of a variety of well known synthetic and/or recombinant techniques. Polypeptides, portions and other variants generally less than about 150 amino acids can be generated by synthetic means, using techniques well known to those of ordinary skill in the art. In one illustrative example, such polypeptides are synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems Division (Foster City, Calif.), and may be operated according to the manufacturer's instructions.

In general, polypeptide compositions (including fusion polypeptides) of the invention are isolated. An "isolated" polypeptide is one that is removed from its original environment. For example, a naturally-occurring protein or polypeptide is isolated if it is separated from some or all of the coexisting materials in the natural system. Preferably, such polypeptides are also purified, e.g., are at least about 90% pure, more preferably at least about 95% pure and most preferably at least about 99% pure.

AGP-Based Compositions Comprising One or More Polynucleotide

The present invention, in other aspects, provides AGP-based compositions comprising one or more polynucleotide that encodes a polypeptide antigen as set forth herein above. The terms "DNA" and "polynucleotide" are used essentially interchangeably herein to refer to a DNA molecule that has been isolated free of total genomic DNA of a particular species. "Isolated," as used herein, means that a polynucleotide is substantially away from other coding sequences, and that the DNA molecule does not contain large portions of unrelated coding DNA, such as large chromosomal fragments or other functional genes or polypeptide coding regions. Of course, this refers to the DNA molecule as originally isolated, and does not exclude genes or coding regions later added to the segment by the hand of man.

Polynucleotides may comprise a native sequence (i.e., an endogenous sequence that encodes a polypeptide/protein of the invention or a portion thereof) or may comprise a sequence that encodes a variant or derivative, preferably and immunogenic variant or derivative, of such a sequence. Typically, polynucleotide variants will contain one or more substitutions, additions, deletions and/or insertions, preferably such that the immunogenicity of the polypeptide encoded by the variant polynucleotide is not substantially diminished relative to a polypeptide encoded by a polynucleotide sequence specifically set forth herein). The term "variants" should also be understood to encompass homologous genes of xenogenic origin.

In certain preferred embodiments, the polynucleotides described above, e.g., polynucleotide variants, fragments and hybridizing sequences, encode polypeptides that are immunologically cross-reactive with an antigenic or immunogenic polypeptide as set forth herein above. In other preferred embodiments, such polynucleotides encode polypeptides that have a level of immunogenic activity of at least about 50%, preferably at least about 70%, and more preferably at least about 90% of that for a polypeptide sequence specifically set forth herein.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

Polynucleotides compositions of the present invention may be identified, prepared and/or manipulated using any of a variety of well established techniques (see generally, Sambrook et al., *Molecular Cloning: A Laboratory Manual*, Cold Spring Harbor Laboratories, Cold Spring Harbor, N.Y., 1989, and other like references). For example, a polynucleotide may be identified, as described in more detail below, by screening a microarray of cDNAs for tumor-associated expression (i.e., expression that is at least two fold greater in a tumor than in normal tissue, as determined using a representative assay provided herein). Such screens may be performed, for example, using the microarray technology of Affymetrix, Inc. (Santa Clara, Calif.) according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997). Alternatively, polynucleotides may be amplified from cDNA prepared from cells expressing the proteins described herein, such as tumor cells.

Many template dependent processes are available to amplify a target sequence of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR™ amplification procedure may be performed in order to quantify the amount of mRNA amplified. Polymerase chain reaction methodologies are well known in the art.

Any of a number of other template dependent processes, many of which are variations of the PCR™ amplification technique, are readily known and available in the art. Illustratively, some such methods include the ligase chain reaction (referred to as LCR), described, for example, in Eur. Pat. Appl. Publ. No. 320,308 and U.S. Pat. No. 4,883,750; Qbeta Replicase, described in PCT Intl. Pat. Appl. Publ. No. PCT/US87/00880; Strand Displacement Amplification (SDA) and Repair Chain Reaction (RCR). Still other amplification methods are described in Great Britain Pat. Appl. No. 2 202 328, and in PCT Intl. Pat. Appl. Publ. No. PCT/US89/01025. Other nucleic acid amplification procedures include transcription-based amplification systems (TAS) (PCT Intl. Pat. Appl. Publ. No. WO 88/10315), including nucleic acid sequence based amplification (NASBA) and 3SR. Eur. Pat. Appl. Publ. No. 329,822 describes a nucleic acid amplification process involving cyclically synthesizing single-stranded RNA ("ssRNA"), ssDNA, and double-stranded DNA (dsDNA). PCT Intl. Pat. Appl. Publ. No. WO 89/06700 describes a nucleic acid sequence amplification scheme based on the hybridization of a promoter/primer sequence to a target single-stranded DNA ("ssDNA") followed by transcription of many RNA copies of the sequence. Other amplification methods such as "RACE" (Frohman, 1990), and "one-sided PCR" (Ohara, 1989) are also well known to those of skill in the art.

An amplified portion of a polynucleotide of the present invention may be used to isolate a full length gene from a suitable library (e.g., a tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}$P) using well known techniques. A bacterial or bacteriophage library is then generally screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then assembled into a single contiguous sequence. A full-length cDNA molecule can be generated by ligating suitable fragments, using well known techniques.

Alternatively, amplification techniques, such as those described above, can be useful for obtaining a full length coding sequence from a partial cDNA sequence. One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111–19, 1991) and walking PCR (Parker et al., *Nucl. Acids. Res.* 19:3055–60, 1991). Other methods employing amplification may also be employed to obtain a full-length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well-known programs (e.g., NCBI BLAST searches), and such ESTs may be used to generate a contiguous full length sequence. Full-length DNA sequences may also be obtained by analysis of genomic fragments.

In other embodiments of the invention, polynucleotide sequences or fragments thereof which encode polypeptides set forth herein above, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

Sequences encoding a desired polypeptide may be synthesized, in whole or in part, using chemical methods well known in the art (see Caruthers, M. H. et al. (1980) *Nucl. Acids Res. Symp. Ser.* 215–223, Horn, T. et al. (1980) *Nucl. Acids Res. Symp. Ser.* 225–232).

In order to express a desired polypeptide, the nucleotide sequences encoding the polypeptide, or functional equivalents, may be inserted into appropriate expression vector, ie., a vector that contains the necessary elements for the transcription and translation of the inserted coding sequence. Methods well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used.

In mammalian cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus that is capable of expressing the polypeptide in infected host cells (Logan, J. and Shenk, T. (1984) *Proc. Natl. Acad. Sci.* 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125–162).

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; *J. Exp. Med.* 158:1211–1216).

AGP-Based Pharmaceutical Compositions

The AGP compounds of the subject invention are adjuvants and immunoeffectors which enhance the generation of antibody in immunized animals, stimulate the production of cytokines and stimulate a cell-mediated immune response including a cytotoxic T-lymphocyte response. In methods for effecting the immune response of an individual, the compounds and compositions of the subject invention can be formulated with a pharmaceutically acceptable carrier for injection or ingestion. As used herein, "pharmaceutically acceptable carrier" means a medium that does not interfere with the immunomodulatory activity of the active ingredient and is not toxic to the patient to whom it is administered. Pharmaceutically acceptable carriers include oil-in-water or water-in-oil emulsions, aqueous compositions, liposomes, microbeads and microsomes. For example, the carrier may be a microsphere or microparticle having a compound of this invention within the matrix of the sphere or particle or adsorbed on the surface of the sphere or particle. The carrier may also be an aqueous solution or micellar dispersion containing triethylamine, triethanolamine or other agent that renders the formulation alkaline in nature, or a suspension containing aluminum hydroxide, calcium hydroxide, calcium phosphate or tyrosine adsorbate.

Formulations of the compounds of the subject invention that can be administered parenterally, i.e. intraperitoneally, subcutaneously or intramuscularly include the following preferred carriers. Examples of preferred carriers for subcutaneous use include a phosphate buffered saline (PBS) solution and 0.01–0.1% triethanolamine in USP Water for Injection. Suitable carriers for intramuscular injection include 10% USP ethanol, 40% propylene glycol and the balance an acceptable isotonic solution such as 5% dextrose.

Examples of preferred carriers for intravenous use include 10% USP ethanol, 40% USP propylene glycol and the balance USP Water for Injection. Another acceptable carrier includes 10% USP ethanol and USP Water for Injection; yet another acceptable carrier is 0.01–0.1% triethanolamine in USP Water for Injection. Pharmaceutically acceptable parenteral solvents are such as to provide a solution or dispersion may be filtered through a 5 micron filter without removing the active ingredient.

Examples of carriers for administration via mucosal surfaces depend upon the particular route. When administered orally, pharmaceutical grades of mannitol, starch, lactose, magnesium stearate, sodium saccharide, cellulose, magnesium carbonate and the like, with mannitol being preferred. When administered intranasally, polyethylene glycol or glycols, sucrose, and/or methylcellulose, and preservatives such as benzalkonium chloride, EDTA, may be used, with polyethylene glycols being preferred, and when administered by inhalation, suitable carriers are polyethylene glycol or glycols, methylcellulose, dispensing agents, and preservatives, with polyethylene glycols being preferred.

While any suitable carrier known to those of ordinary skill in the art may be employed in the pharmaceutical compositions of this invention, the type of carrier will typically vary depending on the mode of administration. Compositions of the present invention may be formulated for any appropriate manner of administration, including for example, topical, oral, nasal, mucosal, intravenous, intracranial, intraperitoneal, subcutaneous and intramuscular administration.

Carriers for use within such pharmaceutical compositions are biocompatible, and may also be biodegradable. In certain embodiments, the formulation preferably provides a relatively constant level of active component release. In other embodiments, however, a more rapid rate of release immediately upon administration may be desired. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

The compounds of the subject invention are administered to an individual in "an effective amount" to effect or enhance the individual's immune response. As used herein, "an effective amount" is that amount which shows a response over and above the vehicle or negative controls. The precise dosage of the compounds of the subject invention to be administered to a patient will depend upon the particular AGP used, the route of administration, the pharmaceutical composition, and the patient. For example, when administered subcutaneously to enhance an antibody response, the amount of AGP used is from 1 to about 250 micrograms, preferably from about 25 to about 50 micrograms based upon administration to a typical 70 kg adult patient.

In another embodiment, illustrative immunogenic compositions, e.g., immunogenic and/or vaccine compositions, of the present invention comprise DNA encoding one or more of the polypeptides as described above, such that the polypeptide is generated in situ. As noted above, the polynucleotide may be administered within any of a variety of delivery systems known to those of ordinary skill in the art. Indeed, numerous gene delivery techniques are well known in the art, such as those described by Rolland, *Crit. Rev. Therap. Drug Carrier Systems* 15:143–198, 1998, and references cited therein. Appropriate polynucleotide expression systems will, of course, contain the necessary regulatory DNA regulatory sequences for expression in a patient (such as a suitable promoter and terminating signal).

Therefore, in certain embodiments, polynucleotides encoding immunogenic polypeptides described herein are introduced into suitable mammalian host cells for expression using any of a number of known viral-based systems. In one illustrative embodiment, retroviruses provide a convenient and effective platform for gene delivery systems. A selected nucleotide sequence encoding a polypeptide of the present invention can be inserted into a vector and packaged in retroviral particles using techniques known in the art. The recombinant virus can then be isolated and delivered to a subject. A number of illustrative retroviral systems have been described (e.g., U.S. Pat. No. 5,219,740; Miller and Rosman (1989) BioTechniques 7:980–990; Miller, A. D. (1990) Human Gene Therapy 1:5–14; Scarpa et al. (1991) Virology 180:849–852; Bums et al. (1993) Proc. Natl. Acad. Sci. USA 90:8033–8037; and Boris-Lawrie and Temin (1993) Cur. Opin. Genet. Develop. 3:102–109.

In addition, a number of illustrative adenovirus-based systems have also been described. Unlike retroviruses which integrate into the host genome, adenoviruses persist extrachromosomally thus minimizing the risks associated with insertional mutagenesis (Haj-Ahmad and Graham (1986) J. Virol. 57:267–274; Bett et al. (1993) J. Virol. 67:5911–5921; Mittereder et al. (1994) Human Gene Therapy 5:717–729; Seth et al. (1994) J. Virol. 68:933–940; Barr et al. (1994) Gene Therapy 1:51–58; Berkner, K. L. (1988) BioTechniques 6:616–629; and Rich et al. (1993) Human Gene Therapy 4:461–476).

Various adeno-associated virus (AAV) vector systems have also been developed for polynucleotide delivery. AAV vectors can be readily constructed using techniques well known in the art. See, e.g., U.S. Pat. Nos. 5,173,414 and 5,139,941; International Publication Nos. WO 92/01070 and WO 93/03769; Lebkowski et al. (1988) Molec. Cell. Biol. 8:3988–3996; Vincent et al. (1990) Vaccines 90 (Cold Spring Harbor Laboratory Press); Carter, B. J. (1992) Current Opinion in Biotechnology 3:533–539; Muzyczka, N. (1992) Current Topics in Microbiol. and Immunol. 158: 97–129; Kotin, R. M. (1994) Human Gene Therapy 5:793–801; Shelling and Smith (1994) Gene Therapy 1:165–169; and Zhou et al. (1994) J. Exp. Med. 179: 1867–1875.

Additional viral vectors useful for delivering the polynucleotides encoding polypeptides of the present invention by gene transfer include those derived from the pox family of viruses, such as vaccinia virus and avian poxyirus. By way of example, vaccinia virus recombinants expressing the novel molecules can be constructed as follows. The DNA encoding a polypeptide is first inserted into an appropriate vector so that it is adjacent to a vaccinia promoter and flanking vaccinia DNA sequences, such as the sequence encoding thymidine kinase (TK). This vector is then used to transfect cells that are simultaneously infected with vaccinia. Homologous recombination serves to insert the vaccinia promoter plus the gene encoding the polypeptide of interest into the viral genome. The resulting TK.sup.(-) recombinant can be selected by culturing the cells in the presence of 5-bromodeoxyuridine and picking viral plaques resistant thereto.

A vaccinia-based infection/transfection system can be conveniently used to provide for inducible, transient expression or coexpression of one or more polypeptides described herein in host cells of an organism. In this particular system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide or polynucleotides of interest, driven by a T7 promoter. The polymerase expressed in the cytoplasm from the vaccinia virus recombinant transcribes the transfected DNA into RNA that is then translated into polypeptide by the host translational machinery. The method provides for high level, transient, cytoplasmic production of large quantities of RNA and its translation products. See, e.g., Elroy-Stein and Moss, Proc. Natl. Acad. Sci. USA (1990) 87:6743–6747; Fuerst et al. Proc. Natl. Acad. Sci. USA (1986) 83:8122–8126.

Alternatively, avipoxyiruses, such as the fowlpox and canarypox viruses, can also be used to deliver the coding sequences of interest. Recombinant avipox viruses, expressing immunogens from mammalian pathogens, are known to confer protective immunity when administered to non-avian species. The use of an Avipox vector is particularly desirable in human and other mammalian species since members of the Avipox genus can only productively replicate in susceptible avian species and therefore are not infective in mammalian cells. Methods for producing recombinant Avipoxyiruses are known in the art and employ genetic recombination, as described above with respect to the production of vaccinia viruses. See, e.g., WO 91/12882; WO 89/03429; and WO 92/03545.

Any of a number of alphavirus vectors can also be used for delivery of polynucleotide compositions of the present invention, such as those vectors described in U.S. Pat. Nos. 5,843,723; 6,015,686; 6,008,035 and 6,015,694. Certain vectors based on Venezuelan Equine Encephalitis (VEE) can also be used, illustrative examples of which can be found in U.S. Pat. Nos. 5,505,947 and 5,643,576.

Moreover, molecular conjugate vectors, such as the adenovirus chimeric vectors described in Michael et al. J. Biol. Chem. (1993) 268:6866–6869 and Wagner et al. Proc. Natl. Acad. Sci. USA (1992) 89:6099–6103, can also be used for gene delivery under the invention.

Additional illustrative information on these and other known viral-based delivery systems can be found, for example, in Fisher-Hoch et al., Proc. Natl. Acad. Sci. USA 86:317–321, 1989; Flexner et al., Ann. N.Y Acad. Sci. 569:86–103, 1989; Flexner et al., Vaccine 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, Biotechniques 6:616–627, 1988; Rosenfeld et al., Science 252:431–434, 1991; Kolls et al., Proc. Natl. Acad. Sci. USA 91:215–219, 1994; Kass-Eisler et al., Proc. Natl. Acad. Sci. USA 90:11498–11502, 1993; Guzman et al., Circulation 88:2838–2848, 1993; and Guzman et al., Cir. Res. 73:1202–1207, 1993.

In certain embodiments, a polynucleotide may be integrated into the genome of a target cell. This integration may be in the specific location and orientation via homologous recombination (gene replacement) or it may be integrated in a random, non-specific location (gene augmentation). In yet further embodiments, the polynucleotide may be stably maintained in the cell as a separate, episomal segment of DNA. Such polynucleotide segments or "episomes" encode sequences sufficient to permit maintenance and replication independent of or in synchronization with the host cell cycle. The manner in which the expression construct is delivered to a cell and where in the cell the polynucleotide remains is dependent on the type of expression construct employed.

In another embodiment of the invention, a polynucleotide is administered/delivered as "naked" DNA, for example as described in Ulmer et al., Science 259:1745–1749, 1993 and reviewed by Cohen, Science 259:1691–1692, 1993. The uptake of naked DNA may be increased by coating the DNA onto biodegradable beads, which are efficiently transported into the cells.

In still another embodiment, a composition of the present invention can be delivered via a particle bombardment approach, many of which have been described. In one illustrative example, gas-driven particle acceleration can be achieved with devices such as those manufactured by Powderject Pharmaceuticals PLC (Oxford, UK) and Powderject Vaccines Inc. (Madison, Wis.), some examples of which are described in U.S. Pat. Nos. 5,846,796; 6,010,478; 5,865, 796; 5,584,807; and EP Patent No. 0500 799. This approach offers a needle-free delivery approach wherein a dry powder formulation of microscopic particles, such as polynucleotide or polypeptide particles, are accelerated to high speed within a helium gas jet generated by a hand held device, propelling the particles into a target tissue of interest.

In a related embodiment, other devices and methods that may be useful for gas-driven needle-less injection of compositions of the present invention include those provided by Bioject, Inc. (Portland, Oreg.), some examples of which are described in U.S. Pat. Nos. 4,790,824; 5,064,413; 5,312, 335; 5,383,851; 5,399,163; 5,520,639 and 5,993,412.

Within certain embodiments of the invention, the AGB-based pharmaceutical composition is preferably one that induces an immune response predominantly of the Th1 type. High levels of Th1-type cytokines (e.g., IFN-γ, TNFα, IL-2 and IL-12) tend to favor the induction of cell-mediated immune responses to an administered antigen. In contrast, high levels of Th2-type cytokines (e.g., IL-4, IL-5, IL-6 and IL-10) tend to favor the induction of humoral immune responses. Following application of an immunogenic composition as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, Ann. Rev. Immunol. 7:145–173, 1989.

The pharmaceutical compositions of the invention will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles. Alternatively, a pharmaceutical composition may be stored in a freeze-dried condition requiring only the addition of a sterile liquid carrier immediately prior to use.

The development of suitable dosing and treatment regimens for using the particular compositions described herein in a variety of treatment regimens, including e.g., oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (see, for example, Mathiowitz et al., Nature 1997 Mar. 27; 386(6623):410–4; Hwang et al., Crit Rev Ther Drug Carrier Syst 1998; 15(3):243–84; U.S. Pat. No. 5,641,515; U.S. Pat. No. 5,580,579 and U.S. Pat. No. 5,792,451). Tablets, troches, pills, capsules and the like may also contain any of a variety of additional components, for example, a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Of course, any material used in preparing any dosage unit form should be pharmaceutically pure and substantially non-toxic in the amounts employed. In addition, the active compounds may be incorporated into sustained-release preparation and formulations.

Typically, these formulations will contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

In certain circumstances it will be desirable to deliver the pharmaceutical compositions disclosed herein parenterally, intravenously, intramuscularly, or even intraperitoneally. Such approaches are well known to the skilled artisan, some of which are further described, for example, in U.S. Pat. No. 5,543,158; U.S. Pat. No. 5,641,515 and U.S. Pat. No. 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described, e.g., in U.S. Pat. No. 5,756,353 and U.S. Pat. No. 5,804,212. Likewise, the delivery of drugs using intranasal microparticle resins (Takenaga et al., J Controlled Release 1998 Mar. 2; 52(1–2):81–7) and lysophosphatidyl-glycerol compounds (U.S. Pat. No. 5,725,871) are also well-known in the pharmaceutical arts. Likewise, illustrative transmucosal drug delivery in the form of a polytetrafluoroetheylene support matrix is described in U.S. Pat. No. 5,780,045.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, Trends Biotechnol 1998 July; 16(7):307–21; Takakura, Nippon Rinsho 1998 March; 56(3):691–5; Chandran et al., Indian J Exp Biol. 1997 August; 35(8):801–9; Margalit, Crit Rev Ther Drug Carrier Syst. 1995; 12(2–3):233–61; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Liposomes have been used successfully with a number of cell types that are normally difficult to transfect by other procedures, including T cell suspensions, primary hepatocyte cultures and PC 12 cells (Renneisen et al., J Biol Chem. 1990 Sep. 25; 265(27):16337–42; Muller et al., DNA Cell Biol. 1990 April; 9(3):221–9). In addition, liposomes are free of the DNA length constraints that are typical of viral-based delivery systems. Liposomes have been used effectively to introduce genes, various drugs, radiotherapeutic agents, enzymes, viruses, transcription factors, allosteric effectors and the like, into a variety of cultured cell lines and animals. Furthermore, he use of liposomes does not appear to be associated with autoimmune responses or unacceptable toxicity after systemic delivery.

In certain embodiments, liposomes are formed from phospholipids that are dispersed in an aqueous medium and spontaneously form multilamellar concentric bilayer vesicles (also termed multilamellar vesicles (MLVs).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., Drug Dev Ind Pharm. 1998 December; 24(12):1113–28). To avoid side effects due to intracellular polymeric overloading, such ultrafine particles (sized around 0.1 μm) may be designed using polymers able to be degraded in vivo. Such particles can be made as described, for example, by Couvreur et al., Crit Rev Ther Drug Carrier Syst. 1988; 5(1):1–20; zur Muhlen et al., Eur J Pharm Biopharm. 1998 March; 45(2):149–55; Zambaux et al. J Controlled Release. 1998 Jan. 2; 50(1–3):31–40; and U.S. Pat. No. 5,145,684.

Cancer Therapies

Immunologic approaches to cancer therapy are based on the recognition that cancer cells can often evade the body's defenses against aberrant or foreign cells and molecules, and that these defenses might be therapeutically stimulated to regain the lost ground, e.g. pgs. 623–648 in Klein, Immunology (Wiley-Interscience, New York, 1982). Numerous recent observations that various immune effectors can directly or indirectly inhibit growth of tumors has led to renewed interest in this approach to cancer therapy, e.g. Jager, et al., Oncology 2001; 60(1):1–7; Renner, et al., Ann Hematol 2000 December; 79(12):651–9.

Four-basic cell types whose function has been associated with antitumor cell immunity and the elimination of tumor cells from the body are: i) B-lymphocytes which secrete immunoglobulins into the blood plasma for identifying and labeling the nonself invader cells; ii) monocytes which secrete the complement proteins that are responsible for lysing and processing the immunoglobulin-coated target invader cells; iii) natural killer lymphocytes having two mechanisms for the destruction of tumor cells, antibody-dependent cellular cytotoxicity and natural killing; and iv) T-lymphocytes possessing antigen-specific receptors and having the capacity to recognize a tumor cell carrying complementary marker molecules (Schreiber, H., 1989, in Fundamental Immunology (ed). W. E. Paul, pp. 923–955).

Cancer immunotherapy generally focuses on inducing humoral immune responses, cellular immune responses, or both. Moreover, it is well established that induction of $CD4^+$ T helper cells is necessary in order to secondarily induce either antibodies or cytotoxic $CD8^+$ T cells. Polypeptide antigens that are selective or ideally specific for cancer cells offer a powerful approach for inducing immune responses against cancer, and are an important aspect of the present invention.

Therefore, in further aspects of the present invention, the pharmaceutical compositions described herein may be used to stimulate an immune response against cancer. Within such methods, the pharmaceutical compositions described herein are administered to a patient, typically a warm-blooded animal, preferably a human. A patient may or may not be afflicted with cancer. Pharmaceutical compositions and vaccines may be administered either prior to or following surgical removal of primary tumors and/or treatment such as administration of radiotherapy or conventional chemotherapeutic drugs. As discussed above, administration of the pharmaceutical compositions may be by any suitable method, including administration by intravenous, intraperitoneal, intramuscular, subcutaneous, intranasal, intradermal, anal, vaginal, topical and oral routes.

Within certain embodiments, immunotherapy may be active immunotherapy, in which treatment relies on the in vivo stimulation of the endogenous host immune system to react against tumors with the administration of immune response-modifying agents (such as polypeptides and polynucleotides as provided herein).

Routes and frequency of administration of the therapeutic compositions described herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 25 µg to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a tumor protein generally correlate with an improved clinical outcome. Such immune responses may generally be evaluated using standard proliferation, cytotoxicity or cytokine assays, which may be performed using samples obtained from a patient before and after treatment.

The present invention is further described by way of the following non-limiting Examples and Test Examples that are given for illustrative purposes only. It is important to note that the introduction of the (R)-3-n-alkanoyloxytetradecanoyl groups and the phosphate group(s) into the glucosaminide and aglycon units do not necessarily have to be performed in the order shown in Schemes 1 and 2 or described in the Examples shown below.

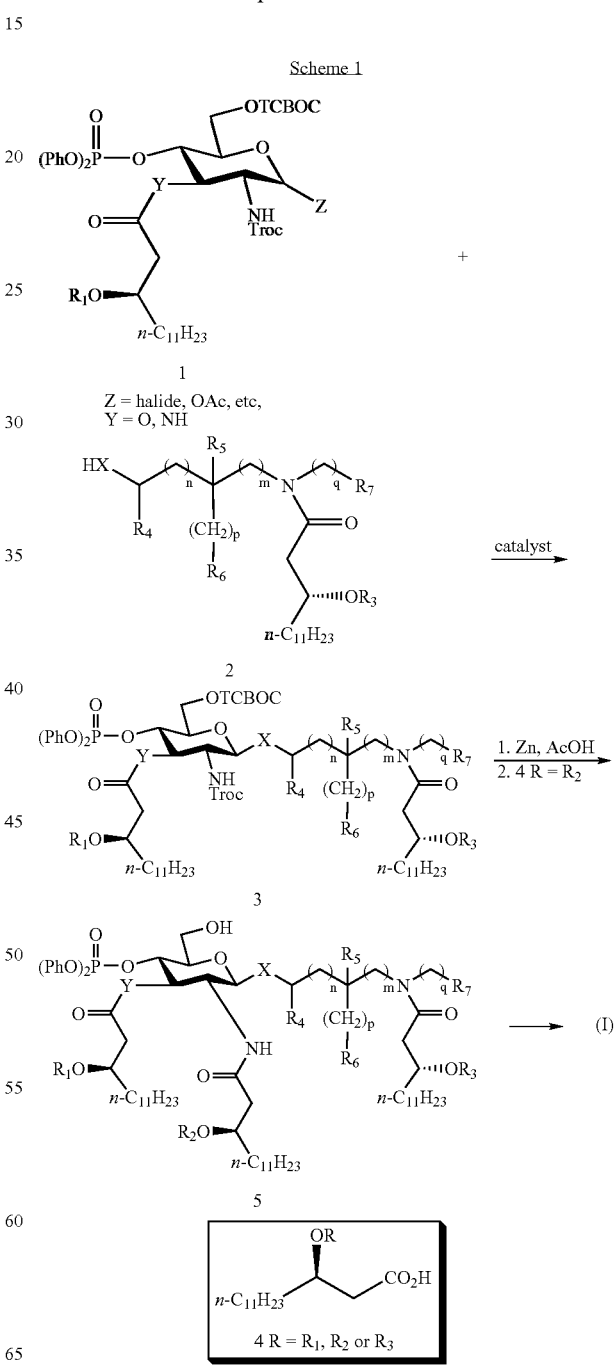

Scheme 2

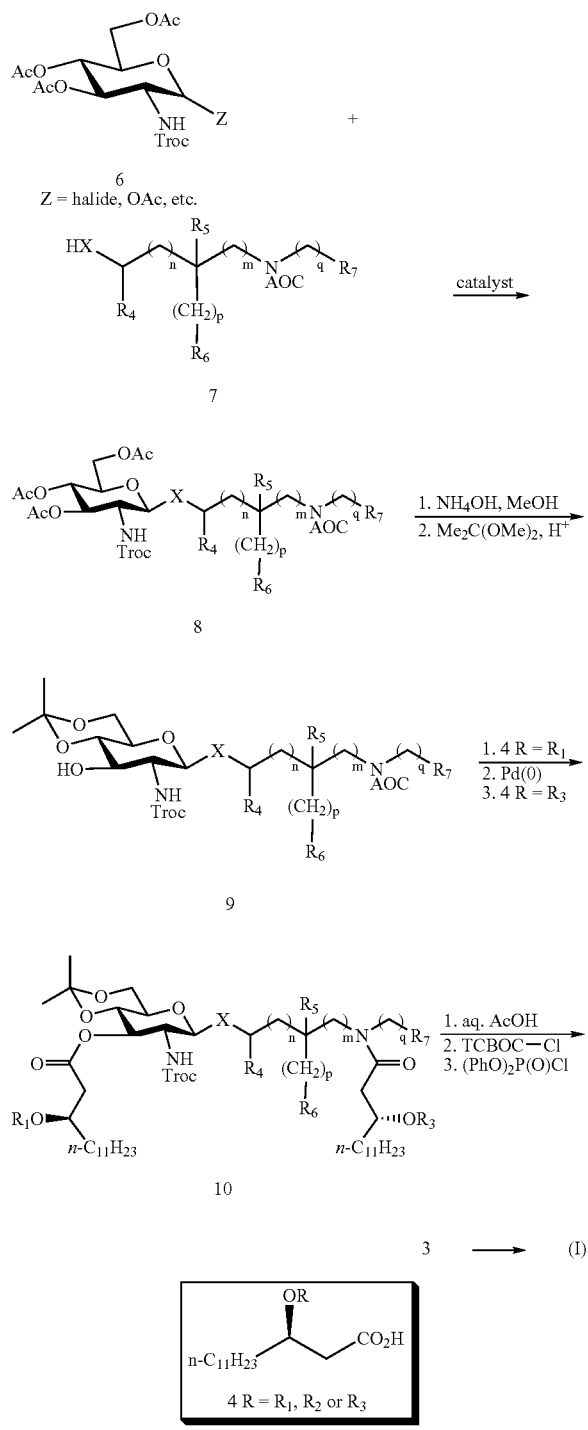

decanoyl]-2-[(R)-3-tetradecanoyloxytetradecanoylamino]-β-D-glucopyranoside Triethylammonium Salt) was co-administered with the Hepatits B Surface Antigen (AgB). Table 1 lists the chemical composition and experimental reference numbers for each compound in these examples.

TABLE 2

| Example | Ref. No. | R-R$_3$ | N | p | R$_6$ | q | R$_7$ |
|---|---|---|---|---|---|---|---|
| 1 | — | — | — | — | — | — | — |
| 2 | B1* | n-C$_{13}$H$_{27}$CO | 0 | 1 | OH | 0 | H |
| 3 | B2** | n-C$_{13}$H$_{27}$CO | 0 | 1 | OH | 0 | H |
| 4 | B3 | n-C$_{11}$H$_{23}$CO | 0 | 1 | OH | 0 | H |
| 5 | B4 | n-C$_{10}$H$_{21}$CO | 0 | 1 | OH | 0 | H |
| 6 | B5 | n-C$_9$H$_{19}$CO | 0 | 1 | OH | 0 | H |
| 7 | B6*** | n-C$_9$H$_{19}$CO | 0 | 1 | OH | 0 | H |
| 8 | B7 | n-C$_8$H$_{17}$CO | 0 | 1 | OH | 0 | H |
| 9 | B8 | n-C$_6$H$_{13}$CO | 0 | 1 | OH | 0 | H |
| 10 | B9 | n-C$_9$H$_{19}$CO | 1 | 1 | OH | 0 | H |
| 11 | B10 | n-C$_9$H$_{19}$CO | 0 | 2 | OH | 0 | H |
| 12 | B11 | n-C$_{13}$H$_{27}$CO | 0 | 0 | CO$_2$H | 0 | H |
| 13 | B12 | n-C$_{11}$H$_{23}$CO | 0 | 0 | CO$_2$H | 0 | H |
| 14 | B13 | n-C$_{10}$H$_{21}$CO | 0 | 0 | CO$_2$H | 0 | H |
| 15 | B14** | n-C$_9$H$_{19}$CO | 0 | 0 | CO$_2$H | 0 | H |
| 16 | B15* | n-C$_9$H$_{19}$CO | 0 | 0 | CO$_2$H | 0 | H |
| 17 | B16 | n-C$_8$H$_{17}$CO | 0 | 0 | CO$_2$H | 0 | H |
| 18 | B17 | n-C$_7$H$_{15}$CO | 0 | 0 | CO$_2$H | 0 | H |
| 19 | B18 | n-C$_6$H$_{13}$CO | 0 | 0 | CO$_2$H | 0 | H |
| 20 | B19 | n-C$_{13}$H$_{27}$CO | 0 | 0 | H | 0 | H |
| 21 | B20 | n-C$_9$H$_{19}$CO | 0 | 0 | H | 0 | H |
| 22 | B21 | n-C$_{13}$H$_{27}$CO | 1 | 0 | H | 0 | H |
| 23 | B22 | n-C$_{13}$H$_{27}$CO | 2 | 0 | H | 0 | H |
| 24 | B23 | n-C$_{13}$H$_{27}$CO | 4 | 0 | H | 0 | H |
| 25 | B24 | n-C$_{13}$H$_{27}$CO | 0 | 0 | CONH$_2$ | 0 | H |
| 26 | B25 | n-C$_9$H$_{19}$CO | 0 | 0 | CONH$_2$ | 0 | H |
| 27 | B26 | n-C$_{13}$H$_{27}$CO | 0 | 0 | CO$_2$Me | 0 | H |
| 28 | B27 | n-C$_{13}$H$_{27}$CO | 0 | 0 | H | 1 | CO$_2$H |
| 29 | B28 | n-C$_9$H$_{19}$CO | 1 | 0 | H | 1 | CO$_2$H |
| 30 | B29 | n-C$_5$H$_{11}$CO | 0 | 0 | CONH$_2$ | 0 | H |
| 31 | B30 | R$_1$ = R$_3$ = n-C$_9$H$_{19}$CO<br>R$_2$ = n-C$_5$H$_{11}$CO | 0 | 0 | CONH$_2$ | 0 | H |
| 32 | B31 | n-C$_5$H$_{11}$CO | 0 | 0 | H | 0 | H |
| 33 | B32 | R$_1$= n-C$_{13}$H$_{27}$CO<br>R$_2$= n-C$_{17}$H$_{35}$CO<br>R$_3$ = n-C$_{15}$H$_{31}$CO | 0 | 0 | H | 0 | H |
| 34 | B34 | n-C$_5$H$_{11}$CO | 0 | 0 | CO$_2$H | 0 | H |
| 35 | B35 | R$_1$ = n-C$_5$H$_{11}$CO<br>R$_2$ = R$_3$ = n-C$_9$H$_{19}$CO | 0 | 0 | CO$_2$H | 0 | H |
| 36 | B36 | R$_1$ = R$_3$ = n-C$_9$H$_{19}$CO<br>R$_2$ = n-C$_5$H$_{11}$CO | 0 | 0 | CO$_2$H | 0 | H |
| 37 | B37 | R$_1$ = R$_2$ = n-C$_9$H$_{19}$CO<br>R$_3$ = n-C$_5$H$_{11}$CO | 0 | 0 | CO$_2$H | 0 | H |
| 38 | B38 | R$_1$ = n-C$_9$H$_{11}$CO<br>R$_2$ = R$_3$ = n-C$_5$H$_{11}$CO | 0 | 0 | CO$_2$H | 0 | H |
| 39 | B39 | R$_1$ = R$_3$ = n-C$_5$H$_{11}$CO<br>R$_2$ = n-C$_9$H$_{19}$CO | 0 | 0 | CO$_2$H | 0 | H |
| 40 | B40 | R$_1$ = R$_2$ = n-C$_5$H$_{11}$CO<br>R$_3$ = n-C$_9$H$_{19}$CO | 0 | 0 | CO$_2$H | 0 | H |
| 41 | B41 | R$_1$ = R$_3$ = n-C$_9$H$_{19}$CO<br>R$_2$ = n-C$_5$H$_{11}$CO | 0 | 1 | OH | 0 | H |
| 42 | B42 | n-C$_9$H$_{19}$CO | 0 | 2 | CO$_2$H | 0 | H |
| 43 | B43 | R$_1$ = n-C$_{13}$H$_{27}$CO<br>R$_2$ = n-C$_{11}$H$_{23}$CO<br>R$_3$ = H | 0 | 0 | CO$_2$H | 0 | H |

For all Examples shown: X = Y = O; R$_4$ = R$_5$ = H; m = 0; R$_8$ = phosphono; R$_9$ = H.
*the stereochemistry of the carbon atom to which R$_5$ is attached is S.
**the stereochemistry of the carbon atom to which R$_5$ is attached is R.
***R$_8$ is H and R$_9$ is phosphono.

Examples 1–43 describe methods of making the AGP compounds of the subject invention. Test Examples 1–13 describe assays conducted to the determine the immunogenicity of these compounds. Test Example 14 describes results of a human clinical study in which the AGP RC-210-04 (designated B19 in Table 2; chemical name 2-[(R)-3-Tetradecanoyloxytetradecanoylamino]ethyl 2-Deoxy-4-O-phosphono-3-O-[(R)-3-tetradecanoyloxytetra-

EXAMPLE 1

PREPARATION OF (R)-3-N-ALKANOYLOXYTETRADECANOIC ACIDS (4)

(1) A solution of methyl 3-oxotetradecanoate (19 g, 0.074 mol) in MeOH (100 mL) was degassed by sparging with argon (15 min). [(R)-Ru(Binap)Cl]$_2$.NEt$_3$ catalyst (0.187 g, 0.111 mmol) and 2 N aqueous HCl (0.5 mL) were added and the resulting mixture was hydrogenated at 60 psig and 40–50° C. for 18 h. The reaction was diluted with hexanes (250 mL), filtered through a short column of silica gel, and concentrated. The crude product was dissolved in tetrahydrofuran (THF; 200 mL), treated 2.4 N aqueous LiOH (83 mL, 0.2 mol) and stirred vigorously at room temperature for 4 h. The resulting slurry was partitioned between ether (200 mL) and 1 N aqueous HCl (200 mL) and the layers separated. The aqueous layer was extracted with ether (100 mL) and the combined ethereal extracts were dried (Na$_2$SO$_4$) and concentrated. The crude hydroxy acid was dissolved in hot acetonitrile (250 mL), treated with dicyclohexylamine (DCHA; 17 mL, 0.085 mol) and stirred at 60° C. for 1 h. The product that crystallized upon cooling was collected and recrystallized from acetonitrile (650 mL) to yield 28.6 g (91%) of dicyclohexylammonium (R)-3-hydroxytetradecanoate as a colorless solid: mp 94–95° C.; $^1$H NMR (CDCl$_3$) δ 0.88 (~t, 3 H, J~6.5 Hz), 1.05–1.58 (m, 24 H), 1.65 (m, 2 H), 1.80 (m, 4 H), 2.01 (br d, 4 H) 2.18 (dd, 1 H, J=15.7, 9.4 Hz), 2.36 (dd, 1 H, J=15.7, 2.6 Hz), 2.94 (m, 2 H), 3.84 (m, 1 H)

(2) To a mixture of the compound prepared in (1) above (50 g, 0.117 mol) and 2,4'-dibromoacetophenone (39 g, 0.14 mol) in EtOAc (2.3 L) was added triethylamine (19.6 mL, 0.14 mol) and the resulting solution was stirred for 18 h at room temperature. The voluminous precipitate that formed was collected and triturated with warm EtOAc (3×400 mL). The combined triturates and filtrate were washed with 1 M aq. HCl, saturated aq. NaCl and dried (Na$_2$SO$_4$). Volatiles were removed under reduced pressure and the crude product obtained was crystallized from EtOAc-hexanes to give 47.2 g (91%) of (R)-3-hydroxytetradecanoic acid p-bromophenacyl ester as a colorless solid: mp 109–109.5° C.; $^1$H NMR (CDCl$_3$) δ 0.88 (~t, 3 H, J~6.5 Hz) 1.15–1.70 (m, 20 H), 2.56 (dd, 1 H, J=15.1, 9.1 Hz), 2.69 (dd, 1 H, J=15.1, 2.9 Hz), 3.27 (br s, 1 H), 4.12 (m, 1 H), 5.31 (d, 1 H, J=16.5 Hz), 5.42 (d, 1 H, J=16.5 Hz), 7.65 (d, 2 H, J=8.5 Hz), 7.78 (d, 2 H, J=8.5 Hz).

(3) A solution of the compound prepared in (2) above (4.6 g, 10.4 mmol) in CH$_2$Cl$_2$ (50 mL) containing 4-dimethylaminopyridine (0.12 g, 1.0 mmol) and pyridine (5 mL, 62 mmol) was treated at room temperature with myristoyl chloride (3.1 mL, 11.4 mmol). After stirring for 5 h at room temperature MeOH (0.5 mL) was added, and the reaction mixture was concentrated. The residue was partitioned between Et$_2$O (150 mL) and cold 10% aqueous HCl (50 mL) and the layers separated. The ethereal layer was dried (Na$_2$SO$_4$) and concentrated and the residue obtained was purified on a short pad of silica gel with 5% EtOAc-hexanes. The diester was dissolved in AcOH (42 mL) and treated with three equal portions of zinc dust (~6 g, 90 mmol) at 60° C. over a 1 h period. After an additional hour at 60° C., the cooled reaction mixture was sonicated (5 min), filtered through Celite® and concentrated. The residue was purified by flash chromatography on silica gel with 10% EtOAc-hexanes to give 4.17 g (82%) of (R)-3-tetradecanoyloxytetradecanoic acid as a colorless solid: mp 28–29° C.; $^1$H NMR (CDCl$_3$) δ 0.88 (~t, 6 H), 1.15–1.40 (m, 38 H), 1.50–1.70 (m, 4 H), 2.28 (t, 2 H, J=7.4 Hz), 2.56 (dd, 1 H, J=15.9, 5.8 Hz), 2.63 (dd, 1 H, J=15.9, 7.1 Hz), 5.21 (m, 1 H).

(4) In the same manner as described in Example 1-(3), the compound prepared in Example 1-(2) (2.5 g, 5.68 mmol) was acylated with lauroyl chloride (1.45 mL, 6.25 mmol) in the presence of pyridine (0.57 mL, 7.0 mmol) in CH$_2$Cl$_2$ (60 mL) and then deprotected with zinc (9.3 g, 142 mmol) in AcOH (40 mL) to afford (R)-3-dodecanoyloxytetradecanoic acid as a colorless oil: $^1$H NMR (CDCl$_3$) δ 0.90 (t, 6 H, J=6.5 Hz), 1.0–1.75 (m, 46 H), 2.30 (m, 2 H), 2.62 (m, 2 H), 5.22 (m, 1 H).

(5) A solution of the compound prepared in Example 1-(2) (2.5 g, 5.68 mmol) was treated with undecanoic acid (1.16 g, 6.25 mmol) and EDC MeI (2.08 g, 7.0 mmol) in CH$_2$Cl$_2$ (60 mL) and then deprotected as described in Example 1-(3) with zinc (9.3 g, 142 mmol) in AcOH (40 mL) to afford (R)-3-undecanoyloxytetradecanoic acid as a colorless oil: $^1$H NMR (CDCl$_3$) δ 0.89 (t, 6 H, J=6.7 Hz), 1.0–1.75 (m, 44 H), 2.29 (m, 2 H), 2.61 (m, 2 H), 5.22 (m, 1 H).

(6) In the same manner as described in Example 1-(3), the compound prepared in Example 1-(2) (4.4 g, 10 mmol) was acylated with decanoyl chloride (2.3 mL, 11 mmol) in the presence of pyridine (1.2 mL, 15.0 mmol) in CH$_2$Cl$_2$ (100 mL) and then deprotected with zinc (16.4 g, 250 mmol) in AcOH (60 mL) to afford (R)-3-decanoyloxytetradecanoic acid as a colorless oil: $^1$H NMR (CDCl$_3$) δ 0.89 (t, 6 H, J=6.8 Hz), 1.0–1.75 (m, 34 H), 2.29 (t, 2 H, J=7.4 Hz), 2.61 (t, 2 H, J=4.2 Hz), 5.22 (m, 1 H).

(7) In the same manner as described in Example 1-(3), the compound prepared in Example 1-(2) (2.5 g, 5.68 mmol) was acylated with nonanoyl chloride (1.13 mL, 6.25 mmol) in the presence of pyridine (0.57 mL, 7.0 mmol) in CH$_2$Cl$_2$ (60 mL) and then deprotected with zinc (9.3 g, 142 mmol) in AcOH (40 mL) to afford (R)-3-nonanoyloxytetradecanoic acid as a colorless oil: $^1$H NMR (CDCl$_3$) δ 0.89 (t, 6 H, J=6.9 Hz), 1.0–1.75 (m, 32 H), 2.29 (t, 2 H, J=7.5 Hz), 2.61 (m, 2 H), 5.22 (m, 1 H).

(8) In the same manner as described in Example 1-(3), the compound prepared in Example 1-(2) (2.5 g, 5.68 mmol) was acylated with octanoyl chloride (1.07 mL, 6.25 mmol) in the presence of pyridine (0.57 mL, 7.0 mmol) in CH$_2$Cl$_2$ (60 mL) and then deprotected with zinc (9.3 g, 142 mmol) in AcOH (40 mL) to afford (R)-3-octanoyloxytetradecanoic acid as a colorless oil: $^1$H NMR (CDCl$_3$) δ 0.92 (t, 6 H, J=6.9 Hz), 1.0–1.75 (m, 30 H), 2.32 (t, 2 H, J=7.4 Hz), 2.63 (t, 2 H, J=4.4 Hz), 5.23 (m, 1 H).

(9) In the same manner as described in Example 1-(3), the compound prepared in Example 1-(2) (2.5 g, 5.68 mmol) was acylated with heptanoyl chloride (0.97 mL, 6.25 mmol) in the presence of pyridine (0.57 mL, 7.0 mmol) in CH$_2$Cl$_2$ (60 mL) and then deprotected with zinc (9.3 g, 142 mmol) in AcOH (40 mL) to afford (R)-3-heptanoyloxytetradecanoic acid as a colorless oil: $^1$H NMR (CDCl$_3$) δ 0.89 (t, 6 H, J=6.8 Hz), 1.0–1.75 (m, 28 H), 2.29 (t, 2 H, J=7.4 Hz), 2.61 (d, 2 H, J=5.8 Hz), 5.22 (m, 1 H).

EXAMPLE 2 (B1)

PREPARATION OF 3-HYDROXY-(S)-2-[(R)-3-TETRADECANOYLOXYTETRADECANOYLAMINO]PROPYL 2-DEOXY-4-O-PHOSPHONO-2-[(R)-3-TETRADECANOYLOXYTETRADECANOYLAMINO]-3-O-[(R)-3-TETRADECANOYLOXYTETRADECANOYL]-β-D-GLUCOPYRANOSIDE TRIETHYLAMMONIUM SALT (COMPOUND (I), R$_1$=R$_2$=R$_3$=N—C$_{13}$H$_{27}$CO, X=Y=O, N=M=Q=0, R$_4$=R$_5$=R$_7$=R$_9$=H, R$_6$=OH, P=1, R$_8$=PO$_3$H$_2$)

(1) To a solution of 2-(trimethylsilyl)ethyl 2-amino-2-deoxy-4,6-O-isopropylidene-β-D-glucopyranoside (6.46 g, 20.2 mmol) in CHCl$_3$ (300 mL) was added 1 N aqueous NaHCO$_3$ (300 mL) and 2,2,2-trichloroethyl chloroformate (8.5 g, 40 mmol). The resulting mixture was stirred vigorously for 3 h at room temperature. The organic layer was separated, dried (Na$_2$SO$_4$) and concentrated to give a colorless syrup. Flash chromatography on silica gel (gradient elution, 30→40% EtOAc-hexanes) afforded 9.6 g (96%) of 2-(trimethylsilyl)ethyl 2-deoxy-4,6-O-isopropylidine-2-(2,2,2-trichloroethoxycarbonylamino)-β-D-glucopyranoside as a colorless solid: mp 69–70° C.; $^1$H NMR (CDCl$_3$) δ 0.0 (s, 9 H), 0.94 (m, 2 H), 1.44 and 1.52 (2s, 6 H), 2.94 (br s, 1 H), 3.23–3.37 (m, 2 H), 3.48–3.62 (m, 2 H), 3.79 (t, 1 H, J=~10.5 Hz), 3.88–4.08 (m, 3 H), 4.65 (d, 1 H, J=8.3 Hz), 4.74 (m, 2 H), 5.39 (d, 1 H, J=7.4 Hz).

(2) A solution of the compound prepared in (1) above (7.5 g, 15.2 mmol), (R)-3-tetradecanoyloxytetradecanoic acid (7.58 g, 16.7 mmol) and 4-pyrrolidinopyridine (0.25 g, 1.7 mmol) in CH$_2$Cl$_2$ (95 mL) was treated with 1-(3-dimethylaminopropyl)-3-ethylcarbodiimide methiodide (EDC.MeI; 4.94 g, 16.7 mmol) and stirred for 16 h at room temperature. The reaction mixture was filtered through a short pad of Celite®, concentrated, and the resulting residue was heated at 60° C. in 90% aqueous AcOH (100 mL) for 1 h. The mixture was concentrated and residual AcOH and water were removed by azeotroping with toluene (2×150 mL). The crude diol was purified by flash chromatography on silica gel (gradient elution, 30→40% EtOAc-hexanes) to give 11.8 g (83%) of 2-(trimethylsilyl)ethyl 2-deoxy-3-O-[(R)-3-tetradecanoyloxytetradecanoyl]-2-(2,2,2-trichloroethoxycarbonylamino)-β-D-glucopyranoside as an amorphous solid: $^1$H NMR (CDCl$_3$) δ 0.0 (s, 9 H), 0.9 (m, 8 H), 1.1–1.7 (m, 42 H), 2.30 (t, 2 H, J=7.4 Hz), 2.52 (m, 2 H), 3.36–3.72 (m, 4 H), 3.78–4.03 (m, 3 H), 4.57 (d, 1 H, J=8.3 Hz), 4.65 (d, 1 H, J=11 Hz), 4.77 (d, 1 H, J=11 Hz), 5.0–5.15 (m, 2 H), 5.20 (d, 1 H, J=7.4 Hz).

(3) A solution of the compound prepared in (2) above (10.9 g, 12 mmol) and pyridine (2 mL, 25 mmol) in CH$_2$Cl$_2$ (125 mL) at 0° C. was treated dropwise over 15 min with a solution of 2,2,2-trichloro-1,1-dimethylethyl chloroformate (3.17 g, 13.2 mmol) in CH$_2$Cl$_2$ (25 mL). The reaction mixture was allowed to warm slowly to ambient temperature over 3.5 h. 4-Pyrrolidinopyridine (0.89 g, 6.0 mmol), N,N-diisopropylethylamine (10.5 mL, 60 mmol) and diphenyl chlorophosphate (3.7 mL, 18 mmol) were added sequentially and the resulting mixture was stirred for 5 h at room temperature. The reaction mixture was diluted with CH$_2$Cl$_2$ (500 mL), washed with cold 7.5% aqueous HCl (2×250 mL), water (250 mL), saturated aqueous NaHCO$_3$ (250 mL), dried (Na$_2$SO$_4$), and then concentrated. The residue obtained was purified by flash chromatography on silica gel eluting with 12.5% EtOAc-hexanes to give 15.1 g (95%) of 2-(trimethylsilyl)ethyl 2-deoxy-4-O-diphenylphosphono-3-O-[(R)-3-tetradecanoyloxytetradecanoyl]-6-O-(2,2,2-trichloro-1,1-dimethylethoxycarbonyl)-2-(2,2,2-trichlorethoxycarbonylamino)-β-D-glucopyranoside as a viscous oil: $^1$H NMR (CDCl$_3$) δ 0.0 (s, 9 H), 0.8–1.0 (m, 8 H), 1.1–1.65 (m, 42 H), 1.83 and 1.90 (2s, 6 H), 2.15–2.45 (m, 4 H), 3.34 (q, 1 H, J=~8 Hz), 3.37 (m, 1 H), 3.81 (m, 1 H), 3.95 (m, 1 H), 4.27 (dd, 1 H, J=12, 5 Hz), 4.34 (d, 1 H, J=12 Hz), 4.58 (d, 1 H, J=12 Hz), 4.66 (q, 1 H, J=~9 Hz), 4.86 (d, 1 H, J=12 Hz), 5.03 (d, 1 H, J=7.9 Hz), 5.21 (m, 1 H), 5.54–5.70 (m, 2 H), 7.2–7.8 (m, 10 H).

(4) A solution of the compound prepared in (3) above (1.87 g, 1.41 mmol) in CH$_2$Cl$_2$ (3 mL) at 0° C. was treated dropwise over 10 min with trifluoroacetic acid (TFA; 6 mL) and then stirred for 4 h at 0° C. The reaction mixture was concentrated and residual TFA was removed by azeotroping with toluene (2×5 mL). A solution of the lactol and dimethylformamide (2.2 mL, 28.2 mmol) in CH$_2$Cl$_2$ (14 mL) at 0° C. was treated with oxalyl bromide (2.0 M in CH$_2$Cl$_2$; 2.1 mL, 4.2 mmol) dropwise over 15 min and the resulting suspension was stirred at 0° C. for 24 h. The reaction mixture was partitioned between cold saturated aqueous NaHCO$_3$ (25 mL) and ether (50 mL) and the layers were separated. The ethereal layer was washed with saturated aqueous NaCl, dried (Na$_2$SO$_4$) and concentrated to give 1.85 g (~100%) of 2-deoxy-4-O-diphenylphosphono-3-O-[(R)-3-tetradecanoyloxytetradecanoyl]-6-O-(2,2,2-trichloro-1,1-dimethylethoxycarbonyl-2-(2,2,2-trichloroethoxycarbonylamino)-α-D-glucopyranosyl bromide as a colorless glass.

(5) A solution of (R)-2-amino-3-benzyloxy-1-propanol (0.46 g, 2.33 mmol) and (R)-3-tetradecanoyloxytetradecanoic acid (1.29 g, 2.83 mmol) in CH$_2$Cl$_2$ (20 mL) was treated with EDC.MeI (0.78 g, 2.79 mmol) and stirred for 16 h at room temperature. The reaction mixture was filtered through a short pad of Celite® and concentrated. Flash chromatography on silica gel with 45% EtOAc-hexanes afforded 1.1 g (69%) of 3-benzyloxy-(R)-2-[(R)-3-tetradecanoyloxytetradecanoylamino]propanol as a colorless solid: mp 42–44.5° C.; $^1$H NMR δ 0.88 (t, 6 H, J=~6.5 Hz), 1.0–1.7 (m, 42 H), 2.50 (t, 2 H, J=7.5 Hz), 2.46 (m, 2 H), 3.56 (br s, 1 H), 3.5–3.75 (m, 3 H), 3.78 (dd, 1 H, J=11, 4 Hz), 4.08 (m, 1 H), 4.51 (s, 2 H), 5.17 (m, 1 H), 6.36 (d, 1 H, J=7.8 Hz), 7.2–7.4 (m, 5 H).

(6) To a solution of the compound prepared in (4) above (1.00 g, 0.776 mmol) and the compound prepared in (5) above (0.35 g, 0.57 mmol) in dichloroethane (4.5 mL) was added powdered 4 Å molecular sieves (1.25 g) and calcium sulfate (2.7 g, 20 mmol). After stirring for 10 min at room temperature, the mixture was treated with mercury cyamide (1.0 g, 4.0 mmol) and then heated to reflux for 12 h shielded from light. The reaction mixture was diluted with CH$_2$Cl$_2$ (25 mL) and filtered through a pad of Celite®. The filtrate was washed with 1 N aqueous KI (25 mL), dried (Na$_2$SO$_4$) and concentrated. The residue was chromatographed on silica gel with EtOAc-hexanes-MeOH (80:20:0→70:30:1, gradient elution) to give 0.66 g (63%) of 3-benzyloxy-(S)-2-[(R)-3-tetradecanoyloxytetradecanoylamino]propyl 2-deoxy-4-O-phosphono-3-O-[(R)-tetradecanoyloxytetradecanoyl]-6-O-(2,2,2-trichloro-1,1-dimethylethoxycarbonyl)-2-(2,2,2-trichloroethoxycarbonylamino)-β-D-glucopyranoside as an amorphous solid: $^1$H NMR δ 0.88 (t, 12 H, J=~6.5 Hz), 1.0–1.65 (m, 84 H), 1.79 and 1.86 (2s, 6 H), 2.1–2.5 (m, 8 H), 3.35–3.55 (m, 3 H), 3.65–3.8 (m, 3 H), 4.1–4.75 (m, 9 H), 5.05–5.3 (m, 2 H), 5.3–5.5 (m, 2 H), 6.04 (d, 1 H, J=8.4 Hz), 7.05–7.45 (m, 15 H).

(7) A stirred solution of the compound prepared in (6) above (0.60 g, 0.328 mmol) in AcOH (9 mL) at 55° C. was treated with zinc dust (1.1 g, 16 mmol) in three equal portions over 1 h. The cooled reaction mixture was sonicated, filtered through a bed of Celite® and concentrated. The resulting residue was partitioned between CH$_2$Cl$_2$ (60 mL) and cold 1 N aqueous HCl (35 mL) and the layers separated. The organic layer was washed with 5% aqueous NaHCO$_3$, dried (Na$_2$SO$_4$) and concentrated. A mixture of the residue obtained and (R)-3-tetradecanoyloxytetradecanoic acid (0.18 g, 0.39 mmol) in CH$_2$Cl$_2$ (3.5 mL) was stirred with powdered 4 Å molecular sieves (0.1 g) for 30 min at room temperature and then treated with 2-ethoxy-1-ethoxycarbonyl-1,2-dihydroquinoline (EEDQ; 0.12 g, 0.49 mmol). The resulting mixture was stirred for 6 h at room temperature, filtered through Celite® and then concentrated. Chromatography on silica gel (gradient elution, 0.5→1% MeOH—CHCl$_3$) afforded 0.31 g (50%) of 3-benzyloxy-(S)-2-[(R)-3-tetradecanoyloxytetradecanoylamino]propyl 2-deoxy-4-O-diphenylphosphono-2-[(R)-3-tetradecanoyloxytetradecanoylamino]-3-O-[(R)-3-tetradecanoyloxytetradecanoyl]-β-D-glucopyranoside as an amorphous solid: $^1$H NMR (CDCl$_3$) δ 0.88 (t, 18 H, J=~6.5 Hz), 1.0–1.8 (m, 126 H), 2.1–2.5 (m, 12 H), 3.35–3.75 (m, 6 H), 3.80 (m, 2 H), 4.23 (m, 1 H), 4.46 (d, 1 H, J=12 Hz), 4.51 (d, 1 H, J=12 Hz), 4.65 (q, 1 H, J=~9.5 Hz), 4.82 (d, 1 H, J=8.1 Hz), 5.05–5.25 (m, 3 H), 5.47 (t, 1 H, J=~9.5 Hz), 6.16 (d, 1 H, J=8.1 Hz), 6.31 (d, 1 H, J=8.4 Hz), 7.1–7.4 (m, 15 H).

(8) A solution of the compound prepared in (7) above (0.26 g, 0.138 mmol) in THF (25 mL) was hydrogenated in the presence of 5% palladium on carbon (50 mg) at room temperature and atmospheric pressure for 16 h. After removal of the catalyst by filtration, AcOH (3 mL) and platinum oxide (0.14 g) were added and the hydrogenation was continued at room temperature and 75 psig for 24 h. The resulting opalescent reaction mixture was diluted with 2:1 CHCl$_3$-MeOH (20 mL) and sonicated briefly to give a clear solution. The catalyst was collected, washed with 2:1 CHCl$_3$-MeOH (2×5 mL) and the combined filtrate and washings were concentrated. The residue was dissolved in 1% aqueous triethylamine (10 mL) by sonicating for 5 min at 35° C. and the resulting solution was lyophilized. Flash chromatography on silica gel with chloroform-methanol-water-triethylamine (94:6:0.5:0.5→88:12:1.0:1.0, gradient elution) afforded 0.20 g (84%) of product as a colorless powder. A portion of the chromatography product (0.166 g) was dissolved in cold 2:1 CHCl$_3$-MeOH (33 mL) and washed with cold 0.1 N aqueous HCl (14 mL). The lower organic layer was filtered and concentrated and the free acid obtained was lyophilized from 1% aqueous triethylamine (pyrogen free, 15 mL) to give 0.160 g of 3-hydroxy-(S)-2-[(R)-tetradecanoyloxytetradecanoylamino]propyl 2-deoxy-4-O-phosphono-2-[(R)-3-tetradecanoyloxytetradecanoylamino]-3-O-[(R)-3-tetradecanoyloxytetradecanoyl]-β-D-glucopyranoside triethylammonium salt as a colorless solid: mp 178–180° C. (dec); IR (film) 3293, 3103, 2959, 2924, 2855, 1732, 1654, 1640, 1553, 1467, 1377, 1259, 1175, 1106, 1086, 1050, 803, 720 cm$^{-1}$; HMR(CDCl$_3$-CD$_3$OD) δ 0.88 (t, 18 H, J=~7 Hz), 1.0–1.7 (m, 135 H), 2.15–2.75 (m, 12 H), 3.02 (q, 6 H, J=7 Hz), 3.35–4.1 (m, 7 H), 4.22 (q, 1 H, J=~9.5 Hz), 4.77 (d, 1 H, J=8 Hz), 5.05–5.35 (m, 4 H), 6.58 (d, 1 H, J=6 Hz), 6.73 (d, 1 H, J=7.5 Hz, NH); $^{13}$C NMR (CDCl$_3$) δ 173.5, 173.2, 170.7, 170.5, 170.0, 100.7, 75.9, 72.7, 71.2, 71.0, 70.8, 70.6, 67.9, 61.7, 60.5, 55.0, 50.4, 45.6, 41.4, 39.5, 34.5, 34.4, 32.0, 31.8, 30.3, 29.8, 29.4, 29.3, 25.3, 25.1, 22.7, 14.2, 8.6.

Anal. Calcd for C$_{19}$H$_{192}$N$_3$O$_{18}$P.5 H$_2$O: C, 64.84; H, 11.10; N, 2.29; P, 1.69. Found: C, 64.69; H, 11.24; N, 1.93; P, 1.44.

EXAMPLE 3 (B2)

PREPARATION OF 3-HYDROXY-(R)-2-[(R)-3-TETRADECANOYLOXYTETRADECANOYLAMINO]PROPYL 2-DEOXY-4-O-PHOSPHONO-2-[(R)-3-TETRADECANOYLOXYTETRADECANOYLAMINO]-3-O-[(R)-3-TETRADECANOYLOXYTETRADECANOYL]-β-D-GLUCOPYRANOSIDE TRIETHYLAMMONIUM SALT (COMPOUND (I), R$_1$=R$_2$=R$_3$=N—C$_{13}$H$_{27}$CO, X=Y=O, N=M=Q=0, R$_4$=R$_5$=R$_7$=R$_9$=H, R$_6$=OH, P=1, R$_8$=PO$_3$H$_2$)

(1) A solution of the compound prepared in Example 2-(5) (0.63 g, 1.02 mmol) in CH$_2$Cl$_2$ (7 mL) was treated sequentially with pyridine (0.4 mL, 5 mmol), 4-dimethylaminopyridine (cat.) and 2,2,2-trichloro-1,1-dimethylethyl chloroformate (0.307 g, 1.23 mmol) and stirred for 16 h at room temperature. The reaction mixture was diluted with CH$_2$Cl$_2$ (25 mL), washed with saturated aqueous NaHCO$_3$ (25 mL) and dried (Na$_2$SO$_4$). Removal of volatiles in vacuo gave a residue that was dissolved in THF-AcOH (10 mL, 9:1) and hydrogenated in the presence of 5% palladium on carbon (150 mg) at room temperature and atmospheric pressure for 24 h. After removal of the catalyst by filtration and concentration of the filtrate, the residue was purified by flash chromatography on silica gel with 35% EtOAc-hexanes to give 0.536 g (72%) of 3-(2,2,2-trichloro-1,1-dimethylethoxycarbonyloxy)-(S)-2-[(R)-3-tetradecanoyloxytetradecanoylamino]propanol as an amorphous solid: $^1$H NMR (CDCl$_3$) δ 0.88 (t, 6 H, J=~6.5 Hz), 1.1–1.7 (m, 42 H), 1.94 (s, 6 H), 2.30 (t, 2 H, J=7.5 Hz), 2.47 (d, 2 H, J=6 Hz), 3.50 (br s, 1 H), 3.72 (m, 2 H), 4.15–4.35 (m, 3 H), 5.15 (m, 1 H), 6.18 (d, 1 H, J=7.2 Hz).

(2) In the same manner as described in Example 2-(6), the compound prepared in (1) above (0.310 g, 0.426 mmol) and the compound prepared in Example 2-(4) (0.961 g, 0.745 mmol) were coupled in the presence of mercury cyamide (0.43 g, 1.7 mmol) to give 0.644 g (78%) of 3-(2,2,2-trichloro-1,1-dimethylethyloxycarbonyloxy)-(S)-2-[(R)-3-tetradecanoyloxytetradecanoylamino]propyl 2-deoxy-4-O-phosphono-3-O-[(R)-tetradecanoyloxytetradecanoyl]-6-O-(2,2,2-trichloro-1,1-dimethylethoxycarbonyl)-2-(2,2,2-trichloroethoxycarbonylamino)-β-D-glucopyranoside as an amorphous solid: $^1$H NMR (CDCl$_3$) δ 0.88 (t, 12 H, J=~6.5 Hz), 1.0–1.7 (m, 84 H), 1.81 and 1.89 (2s, 6 H), 1.93 (s, 6 H), 2.15–2.55 (m, 8 H), 3.45–3.7 (m, 2 H), 3.80 (br d, 1 H, J=9 Hz), 3.9–4.45 (m, 6 H), 4.6–4.8 (m, 3 H), 4.87 (d, 1 H, J=8.1 Hz), 5.0–5.25 (m, 2 H), 5.48 (t, 1 H, J=~9.5 Hz), 6.1–6.3 (m, 2 H).

(3) In the same manner as described in Example 2-(7), the compound prepared in (2) above (0.602 g, 0.310 mmol) was deprotected with zinc (1.5 g, 23 mmol) and acylated with (R)-3-tetradecanoyloxytetradecanoic acid, (0.17 g, 0.37 mmol) in the presence of EEDQ (0.115 g, 0.467 mmol) to give 0.365 g (66%) of 3-hydroxy-(R)-2-[(R)-3-tetradecanoyloxytetradecanoylamino]propyl 2-deoxy-4-O-diphenylphosphono-2-[(R)-3-tetradecanoyloxytetradecanoylamino]-3-O-[(R)-3-tetradecanoyloxytetradecanoyl]-β-D-glucopyranoside as an amorphous solid: $^1$H NMR (CDCl$_3$) δ 0.88 (t, 18 H, J=~6.5 Hz), 1.0–1.7 (m, 126 H), 2.15–2.55 (m, 12 H), 3.18 (br s, 1 H), 3.45–3.8 (m, 8 H), 3.85–4.05 (m, 2 H), 4.69 (q, 1 H, J=~9.5 Hz), 5.05–5.25 (m, 3 H), 5.42 (t, 1 H, J=~9.5 Hz), 6.42 (d, 1 H, J=7.8 Hz), 6.59 (d, 1 H, J=7.2 Hz), 7.1–7.4 (m, 10 H).

(4) In the same manner as described in Example 2-(8), the compound prepared in (3) above (0.355 g, 0.196 mmol) was hydrogenated in the presence of platinum oxide (175 mg) to give 0.265 g (77%) of 3-hydroxy-(R)-2-[(R)-3-tetradecanoyloxytetradecanoylamino]propyl 2-deoxy-4-O-phosphono-2-[(R)-3-tetradecanoyloxytetradecanoylamino]-3-O-[(R)-3-tetradecanoyloxytetradecanoyl]-β-D-glucopyranoside triethylammonium salt as a colorless solid: mp 159–160° C.; IR (film) 3291, 2956, 2922, 2853, 1738, 1732, 1716, 1650, 1643, 1556, 1468, 1171, 1109, 1083, 1051 cm$^{-1}$; $^1$H NMR (CDCl$_3$-CD$_3$OD) δ 0.88 (t, 18 H, J=~6.5 Hz), 1.0–1.7 (m, 135 H), 2.15–2.75 (m, 12 H), 3.06 (q, 6 H, J=7 Hz), 3.25–3.45 (m, 2 H), 3.5–4.05 (m, 12 H), 4.19 (q, 1 H, J=~9.5 Hz), 4.48 (d, 1 H, J=8.4 Hz), 5.04–5.26 (m, 4 H), 7.18 (d, 1 H, J=7.8 Hz), 7.27 (d, 1 H, J=8.7 Hz); $^{13}$C NMR (CDCl$_3$) δ 173.5, 173.4, 170.7, 170.6, 170.1, 101.0, 76.0, 72.6, 71.4, 71.0, 70.8, 70.6, 68.7, 61.8, 60.5, 55.3, 50.5, 45.6, 41.5, 41.4, 39.5, 34.6, 34.4, 34.3, 32.0, 29.8, 29.4, 25.4, 25.1, 22.7, 14.1, 8.6.

Anal. Calcd for $C_{99}H_{192}N_3O_{18}P \cdot H_2O$: C, 67.50; H, 11.10; N, 2.39; P, 1.76. Found: C, 67.40; H, 11.22; N, 2.34; P, 2.11.

EXAMPLE 4 (B3)

PREPARATION OF 3-HYDROXY-(S)-2-[(R)-3-DODECANOY-LOXYTETRADECANOYLAMINO]PROPYL 2-DEOXY-4-O-PHOSPHONO-2-[(R)-3-DODECANOYLOXYTETRADECANOY-LAMINO]-3-O-[(R)-3-DODECANOYLOXYTETRADECANOYL]-β-D-GLUCOPYRANOSIDE TRIETHYLAMMONIUM SALT (COMPOUND (I), $R_1=R_2=R_3=N-C_{11}H_{23}CO$, $X=Y=O$, n=m=q=0, $R_4=R_5=R_7=R_9=H$, $R_6=OH$, p=1, $R_8=PO_3H_2$)

(1) A solution of D-glucosaminide hydrochloride (20 g, 92.8 mmol) in $H_2O$ (250 mL) was treated with a saturated aqueous $NaHCO_3$ (250 mL) and 2,2,2-trichloroethyl chloroformate (14.05 mL, 102 mmol) and stirred vigorously for 18 h. The white solid that formed was collected on a fritted funnel and dried under vacuum for 24 h. A solution of the solid in pyridine (100 mL) was cooled to 0° C. and treated with acetic anhydride (100 mL) via addition funnel. The solution was stirred for 18 h at room temperature, poured into 1 L of $H_2O$ and extracted with $CHCl_3$ (3×500 mL). The solvent was removed in vacuo to afford 45 g (quant.) of N-(2,2,2-trichloroethoxycarbonylamino)-1,3,4,6-tetra-O-acetyl-2-deoxy-α-D-glucopyranoside which was used without further purification: $^1H$ NMR ($CDCl_3$) δ 2.06 (s, 6 H), 2.12 (s, 3 H), 2.22 (s, 3 H), 4.03 (m, 1 H), 4.07 (d, 1 H, J=12.4 Hz), 4.22 (dt, 1 H, J=9.9, 3.6 Hz), 4.30 (dd, 1 H, J=12.4, 4.0 Hz), 4.64 (d, 1 H, J=9.6 Hz), 5.28 (dt, 1 H, J=10.2, 9.9 Hz), 6.25 (d, 1 H, J=3.6 Hz).

(2) A solution of (R)-2-amino-3-benzyloxy-1-propanol (5 g, 27.6 mmol) in $CH_2Cl_2$ (250 mL) was treated with allyl chloroformate (3.2 mL, 30 mmol) and saturated aqueous $NaHCO_3$ (250 mL) for 18 h. The organic layer was separated and concentrated in vacuo. Purification by chromatography eluting with 30% EtOAc/hexanes afforded 6.9 g (94%) of (R)-2-(allyloxycarbonylamino)-3-benzyloxy-1-propanol as an amorphous solid: $^1H$ NMR ($CDCl_3$) δ 2.56 (br s, 1 H), 3.69 (m, 3 H), 3 88 (m, 2 H), 4.54 (s, 2 H), 4.58 (d, 2 H, J=5.6 Hz), 5.23 (dd, 1 H, J=10.4, 1.1 Hz), 5.33 (dd, 1 H, J=17.1, 1.1 Hz), 5.42 (m, 1 H), 5.93 (m, 1 H), 7.35 (m, 5 H).

(3) A solution of the compounds prepared in (1) and (2) above (8.9 g, 17 mmol and 3.6 g, 10 mmol, respectively) in $CH_2Cl_2$ was treated with boron trifluoride etherate (4.3 mL, 34 mmol) at room temperature for 16 h. The reaction mixture was quenched with saturated aq. $NaHCO_3$ (100 mL) and extracted with EtOAc (3×100 mL). The combined EtOAc extracts were dried ($Na_2SO_4$) and concentrated. The residue obtained was chromatographed with 20% EtOAc/hexanes to afford 6.03 g (83%) of 3-benzyloxy-(S)-2-(allyloxycarbonylamino)propyl 2-deoxy-3,4,6-tri-O-acetyl-2-(2,2,2-trichloroethoxycarbonylamino)-β-D-glucopyranoside as an amorphous solid: $^1H$ NMR ($CDCl_3$) δ 2.02 (s, 3 H), 2.03 (s, 3 H), 2.08 (s, 3 H), 3.45 (m, 1 H), 3.54 (m, 1 H), 3.64 (m, 1 H), 3.76 (d, 1 H, J=7.2 Hz), 3.91 (m, 2 H), 4.12 (d, 1 H, J=12.2 Hz), 4.26 (dd, 1 H, J=12.4, 4.7 Hz), 4.37 (d, 1 H, J=8.2 Hz), 4.43 (d, 1 H, J=12.1 Hz), 4.55 (m, 2 H), 4.68 (m, 2 H), 4.87 (d, 1 H, J=8.0 Hz), 5.07 (m, 2 H), 5.21 (d, 1 H, J=9.7 Hz), 5.29 (d, 1 H, J=17.3 Hz), 5.91 (m, 1 H), 7.36 (m, 5 H).

(4) A solution of the compound prepared in (3) above (6.0 g, 8.3 mmol) in methanol (83 mL) was treated with ammonium hydroxide (8.3 mL) at room temperature for 2 h. The solvent was removed in vacuo and replaced with 2,2-dimethoxypropane (50 mL) and camphorsulfonic acid (100 mg) was added. The reaction was stirred for 18 h, neutralized with solid $NaHCO_3$ (1 g), filtered and concentrated in vacuo. Purification by chromatography with 50% EtOAc/hexanes afforded 4.58 g (86%) of 3-benzyloxy-(S)-2-(allyloxycarbonylamino)propyl 2-deoxy-4,6-o-isopropylidine-2-(2,2,2-trichloroethoxycarbonylamino)-β-D-glucopyranoside: $^1H$ NMR ($CDCl_3$) δ 1.46 (s, 3 H), 1.53 (s, 3 H), 2.94 (m, 1 H), 3.25 (m, 1 H), 3.55 (m, 4 H), 3.83 (m, 3 H), 3.93 (m, 3 H), 4.52 (m, 5 H), 4.68 (d, 1 H, J=12.1 Hz), 4.77 (d, 1 H, J=12.1 Hz), 5.07 (m, 1 H), 5.26 (m, 2 H), 5.92 (m, 1 H), 7.37 (m, 5 H).

(5) A solution of the compound prepared in (4) above (1.0 g, 1.56 mmol) in $CH_2Cl_2$ (20 mL) was treated with (R)-3-dodecanoyloxytetradecanoic acid (730 mg, 1.71 mmol) in the presence of EDC.MeI (560 mg, 1.87 mmol) and 4-pyrrolidinopyridine (50 mg). The reaction was stirred at room temperature for 18 h and filtered through a 6×8 cm plug of silica gel using 20% EtOAc/hexanes as eluent to afford 1.33 g (82%) of 3-benzyloxy-(S)-2-(allyloxycarbonylamino)propyl 2-deoxy-4,6-O-isopropylidene-3-O-[(R)-3-dodecanoyloxytetradecanoyl]-2-(2,2,2-trichloroethoxycarbonylamino)-β-D-glucopyranoside as an amorphous solid: $^1H$ NMR ($CDCl_3$) δ 0.88 (t, 6 H, J=6.8 Hz), 1.1–1.6 (m, 38 H), 1.37 (s, 3 H), 1.46 (s, 3 H), 2.28 (t, 2 H, J=7.4 Hz), 2.49 (dd, 1 H, J=15.1, 6.0 Hz), 2.61 (dd, 1 H, J=15.1, 6.6 Hz), 3.25–4.0 (m, 9 H), 4.38 (m, 2 H), 4.54 (m, 2 H), 4.65 (m, 2 H), 4.97 (m, 2 H), 5.25 (m, 5 H), 5.88 (m, 1 H), 7.34 (m, 5 H).

(6) To a solution of the compound prepared in (5) above (1.31 g, 1.25 mmol) in THF (20 mL) was added dimethyl malonate (1.0 mL, 0.88 mmol) and the solution was degassed in a stream of argon for 30 min. Tetrakis(triphenylphosphine)palladium(0) (200 mg) was added and the reaction was stirred at room temperature for 2 h, and then concentrated in vacuo. The residue obtained was chromatographed on silica gel eluting with 5–10% EtOAc/$CHCl_3$. The free amine obtained was acylated with (R)-3-dodecanoyloxytetradecanoic acid (560 mg, 1.38 mmol) in the presence of EEDQ (370 mg, 1.5 mmol) in $CH_2Cl_2$ (15 mL). After stirring at room temperature for 18 h, the solvent was removed in vacuo and the resultant oil was chromatographed on silica gel eluting with 20%EtOAc/hexanes to afford 1.02 g (63%) of 3-benzyloxy-(S)-2-[(R)-3-dodecanoyloxytetradecanoylamino]propyl 2-deoxy-4,6-O-isopropylidene-3-O-[(R)-3-dodecanoyloxytetradecanoyl]-2-(2,2,2-trichloroethoxycarbonylamino)-β-D-glucopyranoside as a colorless amorphous solid: $^1H$ NMR ($CDCl_3$) δ 0.88 (t, 12 H, J=6.9 Hz), 1.1–1.7 (m, 78 H), 1.38 (s, 3 H), 1.46 (s, 3 H), 2.26 (m, 4 H), 2.49 (dd, 1 H, J=15.1, 6.0 Hz), 2.61 (dd, 1 H, J=15.1, 6.6 Hz), 3.25–4.0 (m, 9 H), 5.01 (m, 2 H), 6.02 (d, 1 H, J=8.4 Hz), 7.34 (m, 5 H).

(7) The compound prepared in (6) above (1.0 g, 0.78 mmol) was treated with 90% aqueous AcOH (20 mL) for 1 h at 60° C. The solution was concentrated in vacuo and residual AcOH and $H_2O$ were removed by azeotroping with toluene (10 mL). The residue was dissolved in $CH_2Cl_2$, cooled to 0° C., and treated with pyridine (0.076 mL, 0.94 mmol) and a solution of 2,2,2-trichloro-1,1-dimethylethyl chloroformate (205 mg, 0.86 mmol) in $CH_2Cl_2$ (5 mL). The reaction mixture was then allowed to warm and stir at room temperature for 18 h. The resulting light yellow solution was treated with diphenyl chlorophosphate (0.24 mL, 1.17 mmol), triethylamine (0.22 mL, 1.56 mmol) and catalytic 4-pyrrolidinopyridine (50 mg), and then stirred an additional 24 h at room temperature. The reaction mixture was diluted with $Et_2O$ (100 mL) and washed with 10% aq. HCl (50 mL). The organic phase was separated, dried over $Na_2SO_4$ and concentrated in vacuo. Chromatography over silica gel using 10% EtOAc/hexanes afforded 1.13 g (85%) of 3-benzyloxy-(S)-2-[(R)-3-dodecanoyloxytetradecanoylamino]propyl 2-deoxy-4-O-diphenylphosphono-3-O-[(R)-3-dodecanoyloxytetradecanoyl]-6-O-(2,2,2-trichloro-1,1-dimethylethoxycarbonyl)-2-(2,2,2-trichloroethoxycarbonylamino)-β-D-glucopyranoside as a colorless amorphous solid: $^1$H NMR (CDCl$_3$) δ 0.87 (t, 12 H, J=6.9 Hz), 1.1–1.6 (m, 78 H), 1.78 (s, 3 H), 1.86 (s, 3 H), 2.01 (m, H), 2.18 (m, 3 H), 2.40 (m, 2 H), 2.67 (m, 1 H), 2.88 (d, 1 H, J=6.6 Hz), 2.97 (d, 1 H, J=6.9 Hz), 3.41 (m, 2 H), 3.72 (m, 1 H), 3.82 (m, 1 H), 4.24 (m, 1 H), 4.42 (d, 1 H, J=11.8 Hz), 4.64 (m, 3 H), 5.16 (m, 1 H), 5.39 (m, 2 H), 5.75 (d, 1 H, J=4.3 Hz), 6.05 (d, 1 H, J=8.4 Hz), 7.23 (m, 15 H).

(8) In the same manner as described in Example 2-(7), the compound prepared in (7) above (1.1 g, 0.65 mmol) was deprotected with zinc (2.1 g, 32 mmol) and acylated with (R)-3-dodecanoyloxytetradecanoic acid (330 mg, 0.78 mmol) in the presence of EEDQ (230 mg, 0.94 mmol) to afford 399 mg (37%) of 3-benzyloxy-(S)-2-[(R)-3-dodecanoyloxytetradecanoylamino]propyl 2-deoxy-4-O-diphenylphosphono-2-[(R)-3-dodecanoyloxytetradecanoylamino]-3-O-[(R)-3-dodecanoyltetradecanoyl]-β-D-glucopyranoside as a colorless amorphous solid.

(9) In the same manner as described in Example 2-(8), the compound prepared in (8) above (399 mg, 0.24 mmol) was hydrogenated in the presence of palladium hydroxide (150 mg) on carbon in EtOH (10 mL) and platinum oxide (300 mg) in EtOH/AcOH (10:1) to afford 65 mg (16%) of 3-hydroxy-(S)-2-[(R)-3-dodecanoyloxytetradecanoylamino]propyl 2-deoxy-4-O-phosphono-2-[(R)-3-dodecanoyloxytetradecanoylamino]-3-O-[(R)-3-dodecanoyloxytetradecanoyl]-β-D-glucopyranoside triethylammonium salt as a white powder: mp 181–184° C. (dec): IR (film) 3306, 2956, 2922, 2852, 1732, 1644, 1549, 1467, 1377, 1164, 1106, 1051, 721 cm$^{-1}$; $^1$H NMR (CDCl$_3$-CD$_3$OD) δ 0.88 (t, 18 H, J=6.7 Hz), 1.1–1.7 (m, 123 H), 2.2–2.7 (m, 12 H), 3.06 (q, 6 H, J=7.1 Hz), 3.3–4.0 (m, 13 H), 4.23 (m, 1 H), 4.44 (d, 1 H, J=7.7 Hz), 5.0–5.3 (m, 4 H); $^{13}$C NMR (CDCl$_3$) δ 173.9, 173.5, 173.3, 170.8, 170.5, 170.1, 101.0, 75.5, 73.0, 71.1, 70.9, 70.6, 67.9, 61.6, 60.7, 54.4, 50.4, 45.8, 41.6, 41.4, 39.6, 34.6, 31.9, 29.7, 29.4, 29.3, 25.4, 25.1, 22.7, 14.2, 8.6.

Anal. Calcd. for C$_{93}$H$_{180}$N$_3$O$_{18}$P.H$_2$O: C, 66.59; H, 10.94; N, 2.50; P, 1.85. Found: C, 66.79; H, 10.65; N, 2.36; P, 1.70.

EXAMPLE 5 (B4)

PREPARATION OF 3-HYDROXY-(S)-2-[(R)-3-UNDECANOYLOXYTETRADECANOYLAMINO]PROPYL 2-DEOXY-4-O-PHOSPHONO-2-[(R)-3-UNDECANOYLOXYTETRADECANOYLAMINO]-3-O-[(R)-3-UNDECANOYLOXYTETRADECANOYL]-β-D-GLUCOPYRANOSIDE TRIETHYLAMMONIUM SALT (COMPOUND (I), R$_1$=R$_2$=R$_3$=N—C$_{10}$H$_{21}$CO, X=Y=O, N=M=Q=0, R$_4$=R$_5$=R$_7$=R$_9$=H, R$_6$=OH, P=1, R$_8$=PO$_3$H$_2$)

(1) In the same manner as described in Example 4-(5), the compound prepared in Example 4-(4) (1.0 g, 1.56 mmol) was acylated with (R)-3-undecanoyloxytetradecanoic acid (705 mg, 1.71 mmol) in the presence of EDC.MeI (560 mg, 1.87 mmol) and 4-pyrrolidinopyridine (50 mg) in CH$_2$Cl$_2$ (20 mL) to afford 1.23 g (77%) of 3-benzyloxy-(S)-2-(allyloxycarbonylamino)propyl 2-deoxy-4,6-O-isopropylidene-3-O-[(R)-3-undecanoyloxytetradecanoyl]-2-(2,2,2-trichloroethoxycarbonylamino)-β-D-glucopyranoside as an amorphous solid: $^1$H NMR (CDCl$_3$) δ 0.88 (t, 6 H, =6.9 Hz), 1.1–1.6 (m, 36 H), 1.37 (s, 3 H), 1.46 (s, 3 H), 2.28 (m, 2 H), 2.52 (dd, 1 H, J=15.1, 6.0 Hz), 2.61 (dd, 1 H, =15.5, 6.8 Hz), 3.25 (m, 1 H), 3.35–4.0 (m, 9 H), 4.31 (m, 2 H), 4.54 (m, 2 H), 4.64 (m, 2 H), 5.02 (m, 2 H), 5.18 (m, 2 H), 5.25 (m, 1 H), 5.86 (m, 1 H), 7.34 (m, 5 H).

(2) In the same manner as described in Example 4-(6) the compound prepared in (1) above (1.21 g, 1.17 mmol) was deprotected in THF (20 mL) in the presence of dimethyl malonate (1.0 mL, 0.88 mmol) and tetrakis(triphenylphosphine)palladium(0) (200 mg) and then acylated with (R)-3-undecanoyloxytetradecanoic acid (540 mg, 1.30 mmol) in the presence of EEDQ (370 mg, 1.5 mmol) to afford 921 mg (61%) of 3-benzyloxy-(S)-2-[(R)-3-undecanoyloxytetradecanoylamino]propyl 2-deoxy-4,6-O-isopropylidene-3-O-[(R)-3-undecanoyloxytetradecanoyl]-2-(2,2,2-trichloroethoxycarbonylamino)-β-D-glucopyranoside as a colorless amorphous solid: $^1$H NMR (CDCl$_3$) δ 0.88 (t, 12 H, J=6.6 Hz), 1.1–1.7 (m, 72 H), 1.38 (s, 3 H), 1.46 (s, 3 H), 2.26 (m, 3 H), 2.38 (m, 5 H), 2.49 (dd, 1 H, J=15.2, 6.0 Hz), 2.61 (dd, 1 H, J=15.0, 6.5 Hz), 3.25–4.0 (m, 9 H), 4.30 (m, 2 H), 4.59 (m, 3 H), 6.03 (d, 1 H, J=8.2 Hz), 7.34 (m, 5 H).

(3) In the same manner as described in Example 4-(7) the compound prepared in (2) above (910 g, 0.71 mmol) was deprotected in 90% aqueous AcOH (20 mL), and then treated with pyridine (0.071 mL, 0.88 mmol) and 2,2,2-trichloro-1,1-dimethylethyl chloroformate (195 mg, 0.80 mmol) in CH$_2$Cl$_2$ followed by diphenyl chlorophosphate (0.23 mL, 1.10 mmol), triethylamine (0.20 mL, 1.46 mmol) and catalytic 4-pyrrolidinopyridine (50 mg) to afford 1.10 g (89%) of 3-benzyloxy-(S)-2-[(R)-3-undecanoyloxytetradecanoylamino]propyl 2-deoxy-4-O-diphenylphosphono-3-O-[(R)-3-undecanoyloxytetradecanoyl]-6-O-(2,2,2-trichloro-1,1-dimethylethoxycarbonyl)-2-(2,2,2-trichloroethoxycarbonylamino)-β-D-glucopyranoside as a colorless amorphous solid: $^1$HNMR (CDCl$_3$) δ 0.87 (t, 12 H, J=6.7 Hz), 1.1–1.6 (m, 72 H), 1.78 (s, 3 H), 1.86 (s, 3 H), 2.01 (m, 1 H), 2.18 (m, 3 H), 2.40 (m, 2 H), 2.67 (m, 1 H), 2.88 (d, 1 H, J=6.7 Hz), 2.97 (d, 1 H, J=6.9 Hz), 3.41 (m, 2 H), 3.72 (m, 1 H), 3.82 (m, 1 H), 4.24 (m, 1 H), 4.42 (d, 1 H, J=11.8 Hz), 4.64 (m, 3 H), 5.16 (m, 1 H), 5.39 (m, 2 H), 5.75 (d, 1 H, J=4.6 Hz), 6.05 (d, 1 H, J=8.4 Hz), 7.22 (m, 15 H).

(4) In the same manner as described in Example 2-(7), the compound prepared in (3) above (1.0 g, 0.59 mmol) was deprotected with zinc (2.0 g, 30 mmol) and acylated with (R)-3-undecanoyloxytetradecanoic acid (292 mg, 0.71 mmol) in the presence of EEDQ (210 mg, 0.85 mmol) to afford 388 mg (40%) of 3-benzyloxy-(S)-2-[(R)-3-undecanoyloxytetradecanoylamino]propyl 2-deoxy-4-O-diphenylphosphono-2-[(R)-3-undecanoyloxytetradecanoylamino]-3-O-[(R)-3-undecanoyltetradecanoyl]-β-D-glucopyranoside as a colorless amorphous solid.

(5) In the same manner as described in Example 2-(8), the compound prepared in (4) above (388 mg, 0.24 mmol) was hydrogenated in the presence of palladium hydroxide (150 mg) on carbon in EtOH (10 mL) and platinum oxide (300 mg) in EtOH/AcOH (10:1) to afford 65 mg (17%) of 3-bydroxy-(S)-2-[(R)-3-undecanoyloxytetradecanoylamino]propyl 2-deoxy-4-O-phosphono-2-[(R)-3-undecanoyloxytetradecanoylamino]-3-O-[(R)-3-undecanoyloxytetradecanoyl]-β-D-glucopyranoside triethylammonium salt as a white powder: mp 183–184° C.; IR (film) 3306, 2956, 2922, 2852, 1732, 1644, 1550, 1467, 1377, 1164, 1106, 1052, 721 cm$^{-1}$; $^1$H NMR (CDCl$_3$-CD$_3$OD) δ 0.88 (t, 18 H, J=6.8 Hz), 1.1–1.7 (m, 117 H), 2.2–2.7 (m, 12 H), 3.07 (q, 6 H, J=7.1 Hz), 3.3–3.9 (m, 13 H), 4.23 (m, 1 H), 4.45

(d, 1 H, J=8.2 Hz), 5.0–5.3 (m, 4 H); $^{13}$C NMR (CDCl$_3$) δ 173.8, 173.5, 173.3, 170.8, 170.5, 170.1, 101.0, 75.5, 73.1, 71.5, 71.3, 70.9, 70.6, 67.8, 61.6, 60.7, 54.4, 50.5, 45.8, 41.5, 41.4, 39.5, 34.6, 34.4, 32.0, 31.2, 29.8, 29.7, 29.4, 28.6, 26.1, 25.4, 25.1, 22.7, 14.1, 8.6.

Anal. Calcd. for C$_{90}$H$_{174}$N$_3$O$_{18}$P.H$_2$O: C, 66.10; H, 10.85; N, 2.57; P, 1.89. Found: C, 66.34; H, 10.69; N, 2.32; P, 1.99.

EXAMPLE 6 (B5)

Preparation of 3-Hydroxy-(S)-2-[(R)-3-decanoyloxytetradecanoylamino]propyl 2-Deoxy-4-O-phosphono-2-[(R)-3-decanoyloxytetradecanoylamino]-3-O-[(R)-3-undecanoyloxytetradecanoyl]-β-D-glucopyranoside Triethylammonium Salt (Compound (I), R$_1$=R$_2$=R$_3$=N—C$_9$H$_{19}$CO, X=Y=O, n=m=q=0, R$_4$=R$_5$=R$_7$=R$_9$=H, R$_6$=OH, p=1 R$_8$=PO$_3$H$_2$)

(1) In the same manner as described in Example 4-(5), the compound prepared in Example 4-(4) (2.0 g, 3.12 mmol) was acylated with (R)-3-decanoyloxytetradecanoic acid (1.36 g, 3.42 mmol) in the presence of EDC.MeI (1.12 g, 3.74 mmol) and 4-pyrrolidinopyridine (100 mg) in CH$_2$Cl$_2$ (40 mL) to afford 2.49 g (79%) of 3-benzyloxy-(S)-2-(allyloxycarbonylamino)propyl 2-deoxy-4,6-O-isopropylidene-3-O-[(R)-3-decanoyloxytetradecanoyl]-2-(2,2,2-trichloroethoxycarbonylamino)-β-D-glucopyranoside as an amorphous solid: $^1$H NMR (CDCl$_3$) δ 0.88 (t, 6 H, J=6.7 Hz), 1.1–1.6 (m, 34 H), 1.36 (s, 3 H), 1.46 (s, 3 H), 2.27 (t, 2 H, J=6.9 Hz), 2.48 (dd, 1 H, J=15.1, 6.0 Hz), 2.60 (dd, 1 H, J=15.1, 6.7 Hz), 3.25 (m, 1 H), 3.35–4.0 (m, 9 H), 4.23 (m, 1 H), 4.42 (m, 1 H), 4.52 (m, 4 H), 4.95 (m, 2 H), 5.17 (m, 3 H), 5.88 (m, 1 H), 7.36 (m, 5 H).

(2) In the same manner as described in Example 4-(6) the compound prepared in (1) above (2.47 g, 2.42 mmol) was deprotected in THF (40 mL) in the presence of dimethyl malonate (2.0 mL, 1.75 mmol) and tetrakis(triphenylphosphine)palladium(0) (400 mg) and then acylated with (R)-3-decanoyloxytetradecanoic acid (1.06 g, 2.66 mmol) in the presence of EEDQ (740 mg, 3 mmol) to afford 1.86 g (60%) of 3-benzyloxy-(S)-2-[(R)-3-decanoyloxytetradecanoylamino]propyl 2-deoxy-4,6-O-isopropylidene-3-O-[(R)-3-decanoyloxytetradecanoyl]-2-(2,2,2-trichloroethoxycarbonylamino)-β-D-glucopyranoside as a colorless amorphous solid: $^1$H NMR (CDCl$_3$) δ 0.87 (t, 12 H, J=6.7 Hz), 1.1–1.7 (m, 68 H), 1.37 (s, 3 H), 1.46 (s, 3 H), 2.32 (m, 4 H), 2.50 (dd, 1 H, J=15.1, 6.0 Hz), 2.62 (dd, 1 H, J=15.1, 6.8 Hz), 3.29 (m, 2 H), 3.44 (m, 1 H), 3.55 (m, 1 H), 3.74 (m, 3 H), 3.93 (m, 1 H), 4.18 (m, 1 H), 4.34 (m, 1 H), 4.57 (d, 1 H, J=11.8 Hz), 4.65 (m, 2 H), 5.01 (m, 2 H), 6.04 (d, 1 H, J=8.3 Hz), 7.36 (m, 5 H).

(3) In the same manner as described in Example 4-(7) the compound prepared in (2) above (900 mg, 0.72 mmol) was deprotected in 90% aqueous AcOH (40 mL), and then treated with pyridine (0.071 mL, 0.88 mmol) and 2,2,2-trichloro-1,1-dimethylethyl chloroformate (195 mg, 0.80 mmol) in CH$_2$Cl$_2$ followed by diphenyl chlorophosphate (0.23 mL, 1.10 mmol), triethylamine (0.20 mL, 1.46 mmol) and catalytic 4-pyrrolidinopyridine (50 mg) to afford 1.05 g (86%) of 3-benzyloxy-(S)-2-[(R)-3-decanoyloxytetradecanoylamino]propyl 2-deoxy-4-O-diphenylphosphono-3-O-[(R)-3-decanoyloxytetradecanoyl]-6-O-(2,2,2-trichloro-1,1-dimethylethoxycarbonyl)-2-(2,2,2-trichloroethoxycarbonylamino)-β-D-glucopyranoside as a colorless amorphous solid: $^1$H NMR (CDCl$_3$) δ 0.87 (t, 12 H, J=6.3 Hz), 1.1–1.6 (m, 68 H), 1.78 (s, 3 H), 1.86 (s, 3 H), 2.01 (m, 1 H), 2.18 (m, 3 H), 2.40 (m, 2 H), 2.67 (m, 1 H), 2.88 (d, 1 H, J=6.5 Hz), 2.97 (d, 1 H, J=6.9 Hz), 3.41 (m, 2 H), 3.72 (m, 1 H), 3.82 (m, 1 H), 4.24 (m, 1 H), 4.42 (d, 1 H, J=11.8 Hz), 4.64 (m, 3 H), 5.16 (m, 1 H), 5.39 (m, 2 H), 5.75 (d, 1 H, J=4.3 Hz), 6.05 (d, 1 H, J=8.4 Hz), 7.22 (m, 15 H).

(4) In the same manner as described in Example 2-(7), the compound prepared in (3) above (1.0 g, 0.60 mmol) was deprotected with zinc (2.0 g, 30 mmol) and acylated with (R)-3-decanoyloxytetradecanoic acid (285 mg, 0.72 mmol) in the presence of EEDQ (210 mg, 0.86 mmol) to afford 332 mg (34%) of 3-benzyloxy-(S)-2-[(R)-3-decanoyloxytetradecanoylamino]propyl 2-deoxy-4-O-diphenylphosphono-2-[(R)-3-decanoyloxytetradecanoylamino]-3-O-[(R)-3-decanoyltetradecanoyl]-β-D-glucopyranoside as a colorless amorphous solid.

(5) In the same manner as described in Example 2-(8), the compound prepared in (4) above (332 mg, 0.20 mmol) was hydrogenated in the presence of palladium hydroxide (150 mg) on carbon in EtOH (10 mL) and platinum oxide (300 mg) in EtOH/AcOH (10:1) to afford 173 mg (55%) of 3-hydroxy-(S)-2-[(R)-3-decanoyloxytetradecanoylamino] propyl 2-deoxy-4-O-phosphono-2-[(R)-3-decanoyloxytetradecanoylamino]-3-O-[(R)-3-decanoyloxytetradecanoyl]-β-D-glucopyranoside triethylammonium salt as a white powder: mp 179–181° C.; IR (film) 3295, 2956, 2923, 2853, 1732, 1650, 1555, 1467, 1377, 1320, 1169, 1134, 1104, 1051, 979, 801, 721 cm$^{-1}$; $^1$H NMR (CDCl$_3$-CD$_3$OD) δ 0.88 (t, 18 H, J=6.9 Hz), 1.1–1.7 (m, 111 H), 2.2–2.7 (m, 12 H), 3.07 (q, 6 H, J=6.5 Hz), 3.3–4.3 (m, 14 H), 4.45 (d, 1 H, J=8.0 Hz), 5.0–5.3 (m, 4 H), 7.39 (m, 1 H), 7.53 (d, 1 H, J=9.1 Hz); $^{13}$C NMR (CDCl$_3$) δ 173.7, 173.4, 173.2, 170.7, 170.5, 170.1, 101.0, 75.4, 73.1, 71.6, 71.1, 70.8, 70.5, 67.8, 61.4, 60.8, 54.3, 50.4, 45.8, 41.3, 39.5, 34.5, 31.9, 29.8, 29.7, 29.4, 25.4, 25.1, 22.7, 14.1, 8.6.

Anal. Calcd. for C$_{87}$H$_{168}$N$_3$O$_{18}$P.H$_2$O: C, 65.58; H, 10.75; N, 2.64; P, 1.94. Found: C, 65.49; H, 10.75; N, 2.64; P, 1.97.

EXAMPLE 7 (B6)

Preparation of 3-Hydroxy-(S)-2-[(R)-3-decanoyloxytetradecanoylamino]propyl 2-Deoxy-6-O-phosphono-2-[(R)-3-decanoyloxytetradecanoylamino]-3-O-[(R)-3-decanoyloxytetradecanoyl]-β-D-glucopyranoside Triethylammonium Salt (Compound of R$_1$=R$_2$=R$_3$=N—C$_9$H$_{19}$CO, X=Y=O, n=m=q=0, R$_4$=R$_5$=R$_7$=R$_8$=H, R$_6$=OH, p=1, R$_9$=PO$_3$H$_2$)

(1) In the same manner as described in Example 4-(7) the compound prepared in Example 6-(2) (900 mg, 0.72 mmol) was deprotected in 90% aqueous AcOH (20 mL). The residue was dissolved in CH$_2$Cl$_2$ (20 mL), cooled to 0° C., and treated with triethylamine (0.14 mL, 1.0 mmol) and diphenyl chlorophosphate (0.17 mL, 0.8 mmol). The mixture was stirred for an additional 6 h, and then quenched with 50 mL of 10% HCl. The product was extracted with EtOAc (3×50 mL) and dried over Na$_2$SO$_4$. Chromatography on silica gel with 50% EtOAc/hexanes afforded 636 mg (63%) of 3-benzyloxy-(S)-2-[(R)-3-decanoyloxytetradecanoylamino]propyl 2-deoxy-6-O-diphenylphosphono-3-O-[(R)-3-decanoyloxytetradecanoyl]-2-(2,2,2-trichloroethoxycarbonylamino)-β-D-glucopyranoside as a colorless amorphous solid: $^1$H N(CDCl$_3$) δ 0.87 (t, 12 H, J=6.0 Hz), 1.1–1.6 (m, 68 H), 1.79 (s, 3 H), 1.86 (s, 3 H), 2.01 (m, 1 H), 2.18 (m, 3 H), 2.40 (m, 2 H), 2.67 (m, 1 H), 2.89 (d, 1 H, J=6.5 Hz), 2.97 (d, 1 H, J=6.9 Hz), 3.41 (m, 2 H), 3.75 (m, 1 H), 3.82 (m, 1 H), 4.24 (m, 1 H), 4.42 (d, 1 H, J=11.8 Hz), 4.65 (m, 3 H), 5.16 (m, 1 H), 5.39 (m, 2 H), 5.75 (d, 1 H, J=4.3 Hz), 6.05 (d, 1 H, J=8.4 Hz), 7.22 (m, 15 H).

(2) In the same manner as described in Example 2-(7), the compound prepared in (1) above (620 g, 0.44 mmol) was deprotected with zinc (722 mg, 11 mmol) and acylated with (R)-3-decanoyloxytetradecanoic acid (190 mg, 0.48 mmol) in the presence of EEDQ (170 mg, 0.58 mmol) to afford 254 mg (36%) of 3-benzyloxy-(S)-2-[(R)-3-decanoyloxytetradecanoylamino]propyl 2-deoxy-6-O-diphenylphosphono-2-[(R)-3-decanoyloxytetradecanoylamino]-3-O-[(R)-3-decanoyltetradecanoyl]-β-D-glucopyranoside as a colorless amorphous solid.

(3) In the same manner as described in Example 2-(8), the compound prepared in (2) above (254 mg, 0.16 mmol) was hydrogenated in the presence of palladium hydroxide (150 mg) on carbon in EtOH (10 mL) and platinum oxide (300 mg) in EtOH/AcOH (10:1) to afford 34 mg (13%) of 3-hydroxy-(S)-2-[(R)-3-decanoyloxytetradecanoylamino] propyl 2-deoxy-6-O-phosphono-2-[(R)-3-decanoyloxytetradecanoylamino]-3-O-[(R)-3-decanoyloxytetradecanoyl]-β-D-glucopyranoside triethylammonium salt as a white powder: mp 169–171° C.; IR (film) 3306, 2922, 2853, 1732, 1644, 1548, 1467, 1377, 1316, 1165, 1106, 1053, 856, 722 cm$^{-1}$; $^1$H NMR (CDCl$_3$-CD$_3$OD) δ 0.88 (t, 18 H, J=6.7 Hz), 1.1–1.7 (m, 111 H), 2.2–2.7 (m, 12 H), 3.05 (m, 6 H), 3.3–3.95 (m, 12 H), 4.11 (m, 1 H), 4.34 (m, 1 H), 4.89 (m, 1 H), 5.0–5.3 (m, 4 H). $^{13}$C NMR (CDCl$_3$) δ 173.8, 173.4, 171.1, 170.5, 101.3, 75.3, 74.9, 71.2, 71.0, 70.6, 68.8, 67.3, 65.1, 61.4, 53.4, 50.7, 45.9, 41.5, 41.3, 39.6, 34.6, 32.0, 29.8, 29.6, 29.4, 25.3, 25.1, 22.7, 14.1, 8.7.

Anal. Calcd. for C$_{87}$H$_{168}$N$_3$O$_{18}$P.H$_2$O: C, 65.58; H, 10.75; N, 2.64; P, 1.94. Found: C, 65.60; H, 10.34; N, 2.36; P, 2.01.

EXAMPLE 8 (B7)

PREPARATION OF 3-HYDROXY-(S)-2-[(R)-3-NONANOYLOXYTETRADECANOYLAMINO]PROPYL 2-DEOXY-4-O-PHOSPHONO-2-[(R)-3-NONANOYLOXYTETRADECANOYLAMINO]-3-O-[(R)-3-NONANOYLOXYTETRADECANOYL]-β-D-GLUCOPYRANOSIDE TRIETHYLAMMONIUM SALT (COMPOUND (I), R$_1$=R$_2$=R$_3$=N—C$_8$H$_{17}$CO, X=Y=O, N=M=Q=0, R$_4$=R$_5$=R$_7$=R$_9$=H, R$_6$=OH, P=1, R$_8$=PO$_3$H$_2$)

(1) In the same manner as described in Example 4-(5), the compound prepared in Example 4-(4) (1.0 g, 1.56 mmol) was acylated with (R)-3-nonanoyloxytetradecanoic acid (660 mg, 1.71 mmol) in the presence of EDC.MeI (560 mg, 1.87 mmol) and 4-pyrrolidinopyridine (50 mg) in CH$_2$Cl$_2$ (20 mL) to afford 1.31 g (83%) of 3-benzyloxy-(S)-2-(allyloxycarbonylamino)propyl 2-deoxy-4,6-O-isopropylidene-3-O-[(R)-3-nonanoyloxytetradecanoyl]-2-(2,2,2-trichloroethoxycarbonylamino)-β-D-glucopyranoside as an amorphous solid: $^1$H NMR (CDCl$_3$) δ 0.87 (t, 6 H, J=6.8 Hz), 1.1–1.6 (m, 32 H), 1.37 (s, 3 H), 1.46 (s, 3 H), 2.27 (t, 2 H, J=7.4 Hz), 2.50 (dd, 1 H, J=15.1, 6.0 Hz), 2.63 (dd, 1 H, J=15.1, 6.8 Hz), 3.26 (m, 1 H), 3.35–4.0 (m, 9 H), 4.32 (d, 1 H, J=7.8 Hz), 4.41 (d, 1 H, J=12.0 Hz), 4.51 (m, 4 H), 4.95 (m, 2 H), 5.18 (m, 2 H), 5.29 (d, 1 H, J=17.2 Hz), 5.88 (m, 1 H), 7.36 (m, 5 H).

(2) In the same manner as described in Example 4-(6) the compound prepared in (1) above (1.29 g, 1.28 mmol) was deprotected in THF (20 mL) in the presence of dimethyl malonate (1.0 mL, 0.88 mmol) and tetrakis(triphenylphosphine)palladium(0) (200 mg) and then acylated with (R)-3-nonanoyloxytetradecanoic acid (540 mg, 1.41 mmol) in the presence of EEDQ (370 mg, 1.5 mmol) to afford 1.02 g (65%) of 3-benzyloxy-(S)-2-[(R)-3-nonanoyloxytetradecanoylamino]propyl 2-deoxy-4,6-O-isopropylidene-3-O-[(R)-3-nonanoyloxytetradecanoyl]-2-(2,2,2-trichloroethoxycarbonylamino)-β-D-glucopyranoside as a colorless amorphous solid: $^1$H NMR (CDCl$_3$) δ 0.87 (t, 12 H, J=6.1 Hz), 1.1–1.7 (m, 64 H), 1.37 (s, 3 H), 1.46 (s, 3 H), 2.28 (m, 4 H), 2.50 (dd, 1 H, J=15.5, 6.0 Hz), 2.62 (dd, 1 H, J=14.8, 6.3 Hz), 3.27 (m, 2 H), 3.44 (m, 1 H), 3.55 (m, 1 H), 3.74 (m, 3 H), 3.93 (m, 1 H), 4.18 (m, 1 H), 4.34 (m, 2 H), 4.57 (d, 1 H, J=11.8 Hz), 4.65 (m, 2 H), 4.97 (t, 1 H, J=9.6 Hz), 5.06 (d, 1 H, J=8.6 Hz), 5.15 (m, 2 H), 6.05 (d, 1 H, J=8.2 Hz), 7.35 (m, 5 H).

(3) In the same manner as described in Example 4-(7) the compound prepared in (2) above (1.0 g, 0.81 mmol) was deprotected in 90% aqueous AcOH (20 mL), treated with pyridine (0.080 mL, 0.98 mmol) and 2,2,2-trichloro-1,1-dimethylethyl chloroformate (215 mg, 0.89 mmol) in CH$_2$Cl$_2$ followed by diphenyl chlorophosphate (0.25 mL, 1.22 mmol), triethylamine (0.21 mL, 1.52 mmol) and catalytic 4-pyrrolidinopyridine (50 mg) to afford 1.17 g (87%) of 3-benzyloxy-(S)-2-[(R)-3-nonanoyloxytetradecanoylamino] propyl 2-deoxy-4-O-diphenylphosphono-3-O-[(R)-3-nonanoyloxytetradecanoyl]-6-O-(2,2,2-trichloro-1,1-dimethylethoxycarbonyl)-2-(2,2,2-trichloroethoxycarbonylamino)-β-D-glucopyranoside as a colorless amorphous solid: $^1$H NMR (CDCl$_3$) δ 0.87 (t, 12 H, J=6.1 Hz), 1.1–1.6 (m, 64 H), 1.78 (s, 3 H), 1.86 (s, 3 H), 2.01 (m, 1 H), 2.18 (m, 3 H), 2.40 (m, 2 H), 2.67 (m, 1 H), 2.88 (d, 1 H, J=6.5 Hz), 2.97 (d, 1 H, J=6.9 Hz), 3.41 (m, 2 H), 3.72 (m, 1 H), 3.82 (m, 1 H), 4.24 (m, 1 H), 4.42 (d, 1 H, J=11.8 Hz), 4.64 (m, 3 H), 5.16 (m, 1 H), 5.39 (m, 2 H), 5.75 (d, 1 H, J=4.3 Hz), 6.05 (d, 1 H, J=8.4 Hz), 7.22 (m, 15 H).

(4) In the same manner as described in Example 2-(7), the compound prepared in (3) above (1.1 g, 0.66 mmol) was deprotected with zinc (2.2 g, 33 mmol) and acylated with (R)-3-nonanoyloxytetradecanoic acid (305 mg, 0.79 mmol) in the presence of EEDQ (235 mg, 0.95 mmol) to afford 373 mg (35%) of 3-benzyloxy-(S)-2-[(R)-3-nonanoyloxytetradecanoylamino]propyl 2-deoxy-4-O-diphenylphosphono-2-[(R)-3-nonanoyloxytetradecanoylamino]-3-O-[(R)-3-nonanoyltetradecanoyl]-β-D-glucopyranoside as a colorless amorphous solid.

(5) In the same manner as described in Example 2-(8), the compound prepared in (4) above (373 mg, 0.23 mmol) was hydrogenated in the presence of palladium hydroxide (150 mg) on carbon in EtOH (10 mL) and platinum oxide (300 mg) in EtOH/AcOH (10:1) to afford 43 mg (12%) of 3-hydroxy-(S)-2-[(R)-3-nonanoyloxytetradecanoylamino] propyl 2-deoxy-4-O-phosphono-2-[(R)-3-nonanoyloxytetradecanoylamino]-3-O-[(R)-3-nonanoyloxytetradecanoyl]-β-D-glucopyranoside triethylammonium salt as a white powder: mp 176–179° C.; IR (film) 3298, 2956, 2923, 2853, 1733, 1646, 1551, 1467, 1337, 1316, 1254, 1166, 1106, 1053, 722 cm$^{-1}$; $^1$H NMR (CDCl$_3$-CD$_3$OD) δ 0.87 (t, 18 H, J=6.7 Hz), 1.1–1.7 (m, 105 H), 2.2–2.7 (m, 12 H), 3.03 (q, 6 H, J=7.0 Hz), 3.3–4.3 (m, 14 H), 4.43 (d, 1 H, J=7.1 Hz), 5.0–5.3 (m, 4 H), 7.12 (d, 1 H, J=7.7 Hz), 7.17 (d, 1 H, J=8.2 Hz); $^{13}$C NMR (CDCl$_3$) δ 173.9, 173.5, 173.3, 170.8, 170.5, 170.1, 100.9, 75.5, 73.1, 71.4, 71.1, 70.9, 70.6, 67.8, 61.6, 60.7, 54.3, 50.5, 45.8, 41.6, 41.4, 39.5, 34.6, 34.4, 32.0, 31.9, 29.8, 29.4, 29.3, 25.4, 25.1, 22.7, 14.1, 8.6.

Anal. Calcd. for $C_{88}H_{164}N_3O_{18}P$: C, 65.81; H, 10.65; N, 2.74; P, 2.02. Found: C, 66.14; H, 10.46; N, 2.58; P, 1.84.

EXAMPLE 9 (B8)

PREPARATION OF 3-HYDROXY-(S)-2-[(R)-3-HEPTANOYLOXYTETRADECANOYLAMINO]PROPYL 2-DEOXY-4-O-PHOSPHONO-2-[(R)-3-HEPTANOYLOXYTETRADECANOYLAMINO]-3-O-[(R)-3-HEPTANOYLOXYTETRADECANOYL]-β-D-GLUCOPYRANOSIDE TRIETHYLAMMONIUM SALT (COMPOUND (I), $R_1=R_2=R_3=N-C_6H_{13}CO$, X=Y=O, N=M=Q=0, $R_4=R_5=R_7=R_9=H$, $R_6=OH$, P=1, $R_8=PO_3H_2$)

(1) In the same manner as described in Example 4-(5), the compound prepared in Example 4-(4) (1.0 g, 1.56 mmol) was acylated with (R)-3-heptanoyloxytetradecanoic acid (610 mg, 1.71 mmol) in the presence of EDC.MeI (560 mg, 1.87 mmol) and 4-pyrrolidinopyridine (50 mg) in $CH_2Cl_2$ (20 mL) to afford 1.24 g (82%) of 3-benzyloxy-(S)-2-(allyloxycarbonylamino)propyl 2-deoxy-4,6-O-isopropylidene-3-O-[(R)-3-heptanoyloxytetradecanoyl]-2-(2,2,2-trichloroethoxycarbonylamino)-β-D-glucopyranoside as an amorphous solid: $^1H$ NMR ($CDCl_3$) δ 0.88 (t, 6 H, J=6.0 Hz), 1.1–1.6 (m, 28 H), 1.38 (s, 3 H), 1.47 (s, 3 H), 2.29 (t, 2 H, J=7.4 Hz), 2.51 (dd, 1 H, J=15.1, 6.0 Hz), 2.63 (dd, 1 H, J=15.1, 6.8 Hz), 3.26 (m, 1 H), 3.35–4.0 (m, 9 H), 4.32 (d, 1 H, J=7.3 Hz), 4.41 (d, 1 H, J=12.0 Hz), 4.51 (m, 4 H), 4.95 (m, 2 H), 5.18 (m, 2 H), 5.29 (d, 1 H, J=17.3 Hz), 5.88 (m, 1 H), 7.36 (m, 5 H).

(2) In the same manner as described in Example 4-(6) the compound prepared in (1) above (1.22 g, 1.25 mmol) was deprotected in THF (20 mL) in the presence of dimethyl malonate (1.0 mL, 0.88 mmol) and tetrakis(triphenylphosphine)palladium(0) (200 mg) and then acylated with (R)-3-heptanoyloxytetradecanoic acid (490 mg, 1.38 mmol) in the presence of EEDQ (370 mg, 1.5 mmol) to afford 925 mg (62%) of 3-benzyloxy-(S)-2-[(R)-3-heptanoyloxytetradecanoylamino]propyl 2-deoxy-4,6-O-isopropylidene-3-O-[(R)-3-heptanoyloxytetradecanoyl]-2-(2,2,2-trichloroethoxycarbonylamino)-β-D-glucopyranoside as a colorless amorphous solid: $^1H$ NMR ($CDCl_3$) δ 0.87 (t, 12 H, J=6.7 Hz), 1.1–1.7 (m, 56 H), 1.37 (s, 3 H), 1.46 (s, 3 H), 2.32 (m, 4 H), 2.50 (dd, 1 H, J=15.1, 6.0 Hz), 2.62 (dd, 1 H, J=15.1, 6.8 Hz), 3.29 (m, 2 H), 3.44 (m, 1 H), 3.55 (m, 1 H), 3.74 (m, 3 H), 3.93 (m, 1 H), 4.18 (m, 1 H), 4.34 (m, 1 H), 4.57 (d, 1 H, J=11.8 Hz), 4.65 (m, 2 H), 5.01 (m, 2 H), 6.04 (d, 1 H, J=8.3 Hz), 7.36 (m, 5 H).

(3) In the same manner as described in Example 4-(7) the compound prepared in (2) above (920 mg, 0.76 mmol) was deprotected in 90% aqueous AcOH (20 mL), and then treated with pyridine (0.075 mL, 0.92 mmol) and 2,2,2-trichloro-1,1-dimethylethyl chloroformate (200 mg, 0.84 mmol) in $CH_2Cl_2$ followed by diphenyl chlorophosphate (0.24 mL, 1.14 mmol), triethylamine (0.21 mL, 1.52 mmol) and catalytic 4-pyrrolidinopyridine (50 mg) to afford 1.03 g (83%) of 3-benzyloxy-(S)-2-[(R)-3-heptanoyloxytetradecanoylamino]propyl 2-deoxy-4-O-diphenylphosphono-3-O-[(R)-3-heptanoyloxytetradecanoyl]-6-O-(2,2,2-trichloro-1,1-dimethylethoxycarbonyl)-2-(2,2,2-trichloroethoxycarbonylamino)-β-D-glucopyranoside as a colorless amorphous solid: $^1H$ NMR ($CDCl_3$) δ 0.87 (t, 12 H, J=6.3 Hz), 1.1–1.6 (m, 56 H), 1.78 (s, 3 H), 1.86 (s, 3 H), 2.01 (m, 1 H), 2.18 (m, 3 H), 2.40 (m, 2 H), 2.67 (m, 1 H), 2.88 (d, 1 H, J=6.5 Hz), 2.97 (d, 1 H, J=6.9 Hz), 3.41 (m, 2 H), 3.72 (m, 1 H), 3.82 (m, 1 H), 4.24 (m, 1 H), 4.42 (d, 1 H, J=11.8 Hz), 4.64 (m, 3 H), 5.16 (m, 1 H), 5.39 (m, 2 H), 5.75 (d, 1 H, J=4.3 Hz), 6.05 (d, 1 H, J=8.4 Hz), 7.22 (m, 15 H).

(4) In the same manner as described in Example 2-(7), the compound prepared in (3) above (1.0 g, 0.61 mmol) was deprotected with zinc (2.0 g, 31 mmol) and acylated with (R)-3-heptanoyloxytetradecanoic acid (260 mg, 0.73 mmol) in the presence of EEDQ (220 mg, 0.88 mmol) to afford 203 mg (21%) of 3-benzyloxy-(S)-2-[(R)-3-heptanoyloxytetradecanoylamino]propyl 2-deoxy-4-O-diphenylphosphono-2-[(R)-3-heptanoyloxytetradecanoylamino]-3-O-[(R)-3-heptanoyloxytetradecanoyl]-β-D-glucopyranoside as a colorless amorphous solid.

(5) In the same manner as described in Example 2-(8), the compound prepared in (4) above (203 mg, 0.13 mmol) was hydrogenated in the presence of palladium hydroxide (100 mg) on carbon in EtOH (10 mL) and platinum oxide (200 mg) in EtOH/AcOH (10:1) to afford 39 mg (21%) of 3-hydroxy-(S)-2-[(R)-3-heptanoyloxytetradecanoylamino]propyl 2-deoxy-4-O-phosphono-2-[(R)-3-heptanoyloxytetradecanoylamino]-3-O-[(R)-3-heptanoyloxytetradecanoyl]-β-D-glucopyranoside triethylammonium salt as a white powder: mp 171–172° C.; IR (film) 3305, 2955, 2924, 2853, 1734, 1644, 1553, 1466, 1377, 1170, 1102, 1052, 722 $cm^{-1}$; $^1H$ NMR ($CDCl_3$-$CD_3OD$) δ 0.88 (m, 18 H), 1.1–1.7 (m, 93 H), 2.2–2.7 (m, 12 H), 3.06 (q, 6 H, J=7.1 Hz), 3.3–4.0 (m, 13 H), 4.23 (q, 1 H, J=9.3 Hz), 4.43 (d, 1 H, J=8.2 Hz), 5.0–5.3 (m, 4 H), 7.30 (d, 1 H, J=8.5 Hz), 7.43 (d, 1 H, J=8.5 Hz); $^{13}C$ NMR ($CDCl_3$) δ 173.8, 173.5, 173.2, 170.8, 170.5, 170.2, 101.0, 77.2, 75.5, 73.1, 71.6, 71.1, 70.9, 70.6, 67.8, 61.6, 60.8, 54.4, 50.5, 45.8, 41.6, 41.4, 39.5, 34.6, 34.4, 32.0, 31.6, 29.8, 29.6, 29.4, 28.9, 25.4, 25.1, 22.7, 22.6, 14.1, 8.6.

Anal. Calcd. for $C_{78}H_{150}N_3O_{18}P.H_2O$: C, 63.86; H, 10.44; N, 2.86; P, 2.11. Found: C, 63.47; H, 10.20; N, 2.59; P, 2.02.

EXAMPLE 10 (B9)

PREPARATION OF 3-HYDROXY-(S)-3-[(R)-3-DECANOYLOXYTETRADECANOYLAMINO]BUTYL 2-DEOXY-4-O-PHOSPHONO-2-[(R)-3-DECANOYLOXYTETRADECANOYLAMINO]-3-O-[(R)-3-DECANOYLOXYTETRADECANOYL]-β-D-GLUCOPYRANOSIDE TRIETHYLAMMONIUM SALT (COMPOUND (I), $R_1=R_2=R_3=N-C_9H_{19}CO$, X=Y=O, N=P=1, M=Q=0, $R_4=R_5=R_7=R_9=H$, $R_6=OH$, $R_8=PO_3H_2$)

(1) In the same manner as described in Example 4-(3) the compound prepared in Example 4-(1) (3.1 g, 5.9 mmol) and (R)-3-(allyloxycarbonylamino)-4-benzyloxy-1-butanol (1.1 g, 3.94 mmol) were coupled in the presence of boron trifluoride etherate (3.0 mL, 23.6 mmol) to afford 1.96 g (67%) of 4-benzyloxy-(S)-3-(allyloxycarbonylamino)butyl 2-deoxy-3,4,6-tri-O-acetyl-2-(2,2,2-trichloroethoxycarbonylamino)-β-D-glucopyranoside as an amorphous solid. In the same manner as described in Example 4-(4) the compound prepared above (1.8 g, 2.43 mmol) was deacylated in methanol (25 mL) with ammonium hydroxide (5 mL) and then treated with 2,2-dimethoxypropane (25 mL) and camphorsulfonic acid (100 mg) to afford 1.34 g (84%) of 4-benzyloxy-(S)-3-(allyloxycarbonylamino)butyl 2-deoxy-4,6-O-isopropylidene-2-(2,2,2-trichloroethoxycarbonylamino-β-D-Glucopyranoside.

(2) In the same manner as described in Example 4-(5), the compound prepared in (1) above (1.0 g, 1.53 mmol) was acylated with (R)-3-decanoyloxytetradecanoic acid (670 mg, 1.68 mmol) in the presence of EDC.MeI (550 mg, 1.85 mmol) and 4-pyrrolidinopyridine (50 mg) in CH$_2$Cl$_2$ (15 mL) to afford 1.03 g (65%) of 4-benzyloxy-(S)-3-(allyloxycarbonylamino)butyl 2-deoxy-4,6-O-isopropylidene-3-O-[(R)-3-decanoyloxytetradecanoyl]-2-(2,2,2-trichloroethoxycarbonylamino)-β-D-glucopyranoside as an amorphous solid: $^1$H NMR (CDCl$_3$) δ 0.88 (t, 6 H, J=6.9 Hz), 1.1–1.6 (m, 34 H), 1.37 (s, 3 H), 1.47 (s, 3 H), 1.85 (m, 2 H), 2.28 (t, 2 H, J=7.6 Hz), 2.50 (dd, 1 H, J=15.1, 6.0 Hz), 2.63 (dd, 1 H, J=15.1, 6.7 Hz), 3.30 (m, 1 H), 3.49 (m, 4 H), 3.68 (t, 1 H, J=9.4 Hz), 3.77 (t, 1 H, J=10.4 Hz), 3.92 (m, 3 H), 4.54 (m, 5 H), 4.69 (m, 2 H), 5.1–5.4 (m, 4 H), 5.91 (m, 1 H), 7.33 (m, 5 H).

(3) In the same manner as described in Example 4-(6) the compound prepared in (2) above (1.0 g, 0.97 mmol) was deprotected in THF (20 mL) in the presence of dimethyl malonate (1.0 mL, 0.88 mmol) and tetrakis(triphenylphosphine)palladium(0) (200 mg) and then acylated with (R)-3-decanoyloxytetradecanoic acid (425 mg, 1.07 mmol) in the presence of EEDQ (317 mg, 1.28 mmol) to afford 660 mg (51%) of 4-benzyloxy-(S)-3-[(R)-3-decanoyloxytetradecanoylamino]propyl 2-deoxy-4,6-O-isopropylidene-3-O-[(R)-3-decanoyloxytetradecanoyl]-2-(2,2,2-trichloroethoxycarbonylamino)-β-D-glucopyranoside as a colorless amorphous solid: $^1$H NMR (CDCl$_3$) δ 0.88 (t, 12 H, J=6.6 Hz), 1.1–1.7 (m, 68 H), 1.37 (s, 3 H), 1.47 (s, 3 H), 2.26 (q, 2 H, J=7.1 Hz), 2.41 (m, 2 H), 2.62 (dd, 1 H, J=14.9, 6.4 Hz), 3.29 (m, 1 H), 3.48 (m, 3 H), 3.71 (m, 2 H), 3.92 (m, 2 H), 4.18 (m, 2 H), 4.49 (m, 2 H), 4.68 (q, 2 H, J=11.5 Hz), 5.15 (m, 2 H), 5.55 (d, 1 H, J=8.8 Hz), 6.17 (d, 1 H, J=7.2 Hz), 7.32 (m, 5 H).

(4) In the same manner as described in Example 4-(7) the compound prepared in (3) above (640 mg, 0.48 mmol) was deprotected in 90% aqueous AcOH (20 mL), and then treated with pyridine (0.047 mL, 0.58 mmol) and 2,2,2-trichloro-1,1-dimethylethyl chloroformate (127 mg, 0.53 mmol) in CH$_2$Cl$_2$ followed by diphenyl chlorophosphate (0.15 mL, 0.72 mmol), triethylamine (0.13 mL, 0.96 mmol) and catalytic 4-pyrrolidinopyridine (50 mg) to afford 389 mg (47%) of 4-benzyloxy-(S)-3-[(R)-3-decanoyloxytetradecanoyl]butyl 2-deoxy-4-O-diphenylphosphono-3-O-[(R)-3-decanoyloxytetradecanoyl]-6-O-(2,2,2-trichloro-1,1-dimethylethoxycarbonyl)-2-(2,2,2-trichloroethoxycarbonylamino)-β-D-glucopyranoside as a colorless amorphous solid: $^1$H NMR (CDCl$_3$) δ 0.88 (t, 12 H, J=6.6 Hz), 1.1–1.6 (m, 68 H), 1.79 (s, 3 H), 1.86 (s, 3 H), 2.22 (m, 4 H), 2.40 (m, 4 H), 3.49 (m, 4 H), 3.78 (m, 1 H), 3.93 (m, 1 H), 4.1–4.5 (m, 5 H), 4.9–4.6 (m, 4 H), 5.13 (m, 2 H), 5.51 (t, 1 H, J=8.9 Hz), 5.84 (d, 1 H, J=6.9 Hz), 6.09 (d, 1 H, J=8.0 Hz), 7.26 (m, 15 H).

(5) In the same manner as described in Example 2-(7), the compound prepared in (4) above (375 g, 0.23 mmol) was deprotected with zinc (752 mg, 11.5 mmol) and acylated with (R)-3-decanoyloxytetradecanoic acid (101 mg, 0.25 mmol) in the presence of EEDQ (70 mg, 0.28 mmol) to afford 270 mg (67%) of 4-benzyloxy-(S)-3-[(R)-3-decanoyloxytetradecanoyl]butyl 2-deoxy-4-O-diphenylphosphono-2-[(R)-3-decanoyloxytetradecanoylamino]-3-O-[(R)-3-decanoyltetradecanoyl]-β-D-glucopyranoside as a colorless amorphous solid.

(6) In the same manner as described in Example 2-(8), the compound prepared in (5) above (270 mg, 0.15 mmol) was hydrogenated in the presence of palladium hydroxide (150 mg) on carbon in EtOH (10 mL) and platinum oxide (300 mg) in EtOH/AcOH (10:1) to afford 93 mg (39%) of 4-hydroxy-(S)-3-[(R)-3-decanoyloxytetradecanoyl]butyl 2-deoxy-4-O-phosphono-2-[(R)-3-decanoyloxytetradecanoylamino]-3-O-[(R)-3-decanoyltetradecanoyl]-β-D-glucopyranoside triethylammonium salt as a white powder: mp 179–181° C. (dec): IR (film) 3287, 2956, 2923, 2853, 1734, 1654, 1552, 1466, 1378, 1246, 1164, 1106, 1085, 1052, 721 cm$^{-1}$; $^1$H NMR (CDCl$_3$-CD$_3$OD) δ 0.88 (t, 18 H, J=6.9 Hz), 1.1–1.7 (m, 111 H), 2.2–2.7 (m, 14 H), 3.06 (q, 6 H, J=6.9 Hz), 3.2–4.0 (m, 13 H), 4.21 (m, 1 H), 4.50 (d, 1 H, J=7.7 Hz), 5.0–5.3 (m, 4 H), 7.11 (m, 2 H); $^{13}$C NMR (CDCl$_3$) δ 173.8, 173.5, 173.3, 170.9, 170.5, 170.1, 101.1, 77.2, 75.5, 72.8, 71.3, 71.0, 70.6, 66.4, 64.0, 60.7, 54.8, 50.2, 45.8, 41.6, 39.5, 34.6, 34.5, 34.4, 32.0, 30.6, 29.8, 29.7, 29.6, 29.5, 29.4, 25.4, 25.1, 22.7, 14.2, 8.6.

Anal. Calcd. for C$_{88}$H$_{170}$N$_3$O$_{18}$P: C, 66.65; H, 10.78; N, 2.64; P, 1.95. Found: C, 66.65; H, 10.68; N, 2.50; P, 1.94.

EXAMPLE 11 (B10)

PREPARATION OF 4-HYDROXY-(S)-2-[(R)-3-DECANOYLOXYTETRADECANOYLAMINO]BUTYL 2-DEOXY-4-O-PHOSPHONO-2-[(R)-3-DECANOYLOXYTETRADECANOYLAMINO]-3-O-[(R)-3-DECANOYLOXYTETRADECANOYL]-β-D-GLUCOPYRANOSIDE TRIETHYLAMMONIUM SALT (COMPOUND (I), R$_1$=R$_2$=R$_3$=N—C$_9$H$_{19}$CO, X=Y=O, N=M=Q=0, R$_4$=R$_5$=R$_7$=R$_9$=H, R$_6$=OH, P=2, R$_8$=PO$_3$H$_2$)

(1) In the same manner as described in Example 4-(3) the compound prepared in Example 4-(1) (5.1 g, 9.7 mmol) and (R)-2-(allyloxycarbonylamino)-4-benzyloxy-1-butanol (1.8 g, 6.45 mmol) were coupled in the presence of boron trifluoride etherate (4.9 mL, 38.0 mmol) to afford 2.92 g (61%) of 4-benzyloxy-(S)-2-(allyloxycarbonylamino)propyl 2-deoxy-3,4,6-tri-O-acetyl-2-(2,2,2-trichloroethoxycarbonylamino)-β-D-glucopyranoside as an amorphous solid. In the same manner as described in Example 4-(4) the compound prepared above (2.6 g, 3.51 mmol) was deacylated in methanol (35 mL) with ammonium hydroxide (7 mL) and then treated with 2,2-dimethoxypropane (35 mL) and camphorsulfonic acid (100 mg) to afford 1.9 g (72%) of 4-benzyloxy-(S)-2-(allyloxycarbonylamino)butyl 2-deoxy-4,6-O-isopropylidine-2-(2,2,2-trichloroethoxycarbonylamino)-β-D-glucopyranoside.

(2) In the same manner as described in Example 4-(5), the compound prepared in (1) above (1.0 g, 1.53 mmol) was acylated with (R)-3-decanoyloxytetradecanoic acid (670 mg, 1.68 mmol) in the presence of EDC MeI (550 mg, 1.85 mmol) and 4-pyrrolidinopyridine (50 mg) in CH$_2$Cl$_2$ (15 mL) to afford 1.28 g (81%) of 4-benzyloxy-(S)-2-(allyloxycarbonylamino)butyl 2-deoxy-4,6-O-isopropylidene-3-O-[(R)-3-decanoyloxytetradecanoyl]-2-(2,2,2-trichloroethoxycarbonylamino)-β-D-glucopyranoside as an amorphous solid: $^1$H NMR (CDCl$_3$) δ 0.88 (t, 6 H, J=6.9 Hz), 1.1–1.7 (m, 34 H), 1.37 (s, 3 H), 1.47 (s, 3 H), 1.82 (m, 2 H), 2.28 (t, 2 H, J=7.7 Hz), 2.50 (dd, 1 H, J=15.3, 6.0 Hz), 2.63 (dd, 1 H, J=15.2, 6.7 Hz), 3.16 (m, 1 H), 3.56 (m, 3 H), 3.65 (t, 1 H, J=9.6 Hz), 3.75 (t, 1 H, J=10.4 Hz), 3.88 (m, 4 H), 4.32 (d, 1 H, J=8.5 Hz), 4.46 (s, 2 H), 4.54 (m, 2 H), 4.67 (m, 2 H), 4.90 (m, 1 H), 5.26 (m, 3 H), 5.89 (m, 1 H), 7.33 (m, 5 H).

(3) In the same manner as described in Example 4-(6) the compound prepared in (2) above (1.25 g, 1.21 mmol) was deprotected in THF (20 mL) in the presence of dimethyl malonate (1.0 mL, 0.88 mmol) and tetrakis(triphenylphosphine)palladium(0) (200 mg) and then acylated with (R)-3-decanoyloxytetradecanoic acid (530 mg, 1.33 mmol) in the presence of EEDQ (362 mg, 1.46 mmol) to afford 1.16 g (72%) of 4-benzyloxy-(S)-3-[(R)-3-decanoyloxytetradecanoylamino]propyl 2-deoxy-4,6-O-isopropylidene-3-O-[(R)-3-decanoyloxytetradecanoyl]-2-(2,2,2-trichloroethoxycarbonylamino)-β-D-glucopyranoside as a colorless amorphous solid: $^1$H NMR (CDCl$_3$) δ 0.88 (t, 12 H, J=6.4

Hz), 1.1–1.7 (m, 68 H), 1.37 (s, 3 H), 1.45 (s, 3 H), 2.26 (q, 2 H, J=7.4 Hz), 2.34 m, 1 H), 2.50 (dd, 1 H, J=15.1, 6.0 Hz), 2.62 (dd, 1 H, J=15.4, 6.3 Hz), 3.12 (m, 1 H), 3.5–3.95 (m, 7 H), 4.14 (m, 1 H), 4.29 (d, 1 H, J=8.0 Hz), 4.67 (m, 2 H), 4.86 (t, 1 H, J=9.6 Hz), 5.15 (m, 2 H), 6.16 (d, 1 H, J=8.3 Hz), 7.35 (m, 5 H).

(4) In the same manner as described in Example 4-(7) the compound prepared in (3) above (1.1 g, 0.83 mmol) was deprotected in 90% aqueous AcOH (20 mL), and then treated with pyridine (0.080 mL, 1.0 mmol) and 2,2,2-trichloro-1,1-dimethylethyl chloroformate (220 mg, 0.91 mmol) in $CH_2Cl_2$ followed by diphenyl chlorophosphate (0.26 mL, 1.25 mmol), triethylamine (0.23 mL, 1.66 mmol) and catalytic 4-pyrrolidinopyridine (50 mg) to afford 802 mg (56%) of 4-benzyloxy-(S)-2-[(R)-3-decanoyloxytetradecanoyl]butyl 2-deoxy-4-O-diphenylphosphono-3-O-[(R)-3-decanoyloxytetradecanoyl]-6-O-(2,2,2-trichloro-1,1-dimethylethoxycarbonyl)-2-(2,2,2-trichloroethoxycarbonylamino)-β-D-glucopyranoside as a colorless amorphous solid: $^1H$ NMR ($CDCl_3$) δ 0.87 (t, 12 H, J=6.8 Hz), 1.1–1.6 (m, 68 H), 1.79 (s, 3 H), 1.88 (s, 3 H), 2.23 (m, 4 H), 2.37 (m, 4 H), 3.57 (m, 4 H), 3.83 (m, 1 H), 4.29 (m, 3 H), 4.44 (m, 2 H), 4.69 (m, 4 H), 5.14 (m, 4 H), 5.62 (d, 1 H, J=7.6 Hz), 6.15 (d, 1 H, J=8.3 Hz), 7.25 (m, 15 H).

(5) In the same manner as described in Example 2-(7), the compound prepared in (4) above (750 mg, 0.43 mmol) was deprotected with zinc (1.42 g, 21.7 mmol) and acylated with (R)-3-decanoyloxytetradecanoic acid (190 mg, 0.48 mmol) in the presence of EEDQ (130 mg, 0.53 mmol) to afford 483 mg (64%) of 4-benzyloxy-(S)-2-[(R)-3-decanoyloxytetradecanoyl]butyl 2-deoxy-4-O-diphenylphosphono-2-[(R)-3-decanoyloxytetradecanoylamino]-3-O-[(R)-3-decanoyltetradecanoyl]-β-D-glucopyranoside as a colorless amorphous solid.

(6) In the same manner as described in Example 2-(8), the compound prepared in (5) above (483 mg, 0.27 mmol) was hydrogenated in the presence of palladium hydroxide (150 mg) on carbon in EtOH (10 mL) and platinum oxide (300 mg) in EtOH/AcOH (10:1) to afford 238 mg (55%) of 4-hydroxy-(S)-2-[(R)-3-decanoyloxytetradecanoyl]butyl 2-deoxy-4-O-phosphono-2-[(R)-3-decanoyloxytetradecanoylamino]-3-O-[(R)-3-decanoyltetradecanoyl]-β-D-glucopyranoside triethylammonium salt as a white powder: mp 181–183° C. (dec): IR (film) 3294, 2956, 2923, 2853, 1732, 1650, 1556, 1466, 1377, 1320, 1246, 1172, 1108, 1082, 1058, 859, 721 $cm^{-1}$; $^1H$ NMR ($CDCl_3$-$CD_3OD$) δ 0.88 (t, 18 H, J=6.9 Hz), 1.1–1.7 (m, 111 H), 2.2–2.7 (m, 14 H), 3.06 (q, 6 H, J=7.1 Hz), 3.2–4.0 (m, 13 H), 4.21 (m, 1 H), 4.46 (d, 1 H, J=8.3 Hz), 5.0–5.3 (m, 4 H); $^{13}C$ NMR ($CDCl_3$) δ 173.9, 173.4, 173.2, 171.2, 170.7, 101.0, 77.2, 75.4, 73.1, 71.4, 71.3, 71.1, 70.9, 70.6, 60.7, 58.4, 54.7, 46.3, 45.9, 41.6, 41.1, 39.7, 34.8, 34.6, 34.4, 31.9, 29.8, 29.6, 29.5, 29.3, 25.4, 25.3, 25.1, 22.7, 14.1, 8.6.

Anal. Calcd. for $C_{88}H_{170}N_3O_{18}P$: C, 66.51; H, 10.78; N, 2.64; P, 1.95. Found: C, 66.81; H, 10.68; N, 2.53; P, 1.79.

EXAMPLE 12 (B 11)

PREPARATION OF N-[(R)-3-TETRADECANOYLOXYTETRADECANOYL]-O-[2-DEOXY-4-O-PHOSPHONO-2-[(R)-3-TETRADECANOYLOXYTETRADECANOYLAMINO]-3-O-[(R)-3-TETRADECANOYLOXYTETRADECANOYL]-β-D-GLUCOPYRANOSYL]-L-SERINE TRIETHYLAMMONIUM SALT (COMPOUND (I), $R_1=R_2=R_3=N-C_{13}H_{27}CO$, X=Y=O, N=M=P=Q=0, $R_4=R_5=R_7=R_9$=H, $R_6=CO_2H$, $R_8=PO_3H_2$)

(1) In the same manner as described in Example 2-(5), L-serine benzyl ester (0.212 g, 1.08 mmol) was acylated with (R)-3-tetradecanoyloxytetradecanoic acid (0.541 g, 1.19 mmol) in the presence of EDC.MeI (0.353 g, 1.19 mmol) to give 0.642 g (94%) of N-[(R)-3-tetradecanoyloxytetradecanoyl]-L-serine benzyl ester as a waxy solid: mp 56–61° C.; $^1H$ NMR ($CDCl_3$) δ 0.88 (t, 6 H, J=~7 Hz), 1.1–1.7 (m, 42 H), 2.29 (t, 2 H, J=7.5 Hz), 2.50 (m, 2 H), 3.87 (br t, 1 H), 3.95 (m, 2 H), 4.65 (m, 1 H), 5.1–5.25 (m, 3 H), 6.69 (d, 1 H, J=7 Hz), 7.34 (br s, 5 H).

(2) In the same manner as described in Example 2-(6), the compound prepared in (1) above (0.19 g, 0.30 mmol) and the compound prepared in Example 2-(4) (0.635 g, 0.478 mmol) were coupled in the presence of mercury cyamide (0.3 g, 1.2 mmol) to give 0.425 g (77%) of N-[(R)-3-tetradecanoyloxytetradecanoyl]-O-[2-deoxy-4-O-diphenylphosphono-3-O-[(R)-3-tetradecanoyloxytetradecanoyl]-6-O-(2,2,2-trichloro-1,1-dimethylethoxycarbonyl)-2-(2,2,2-trichloroethoxycarbonylamino)-β-D-glucopyranosyl]-L-serine benzyl ester as an amorphous solid.

(3) In the same manner as described in Example 2-(7), the compound prepared in (2) above (0.405 g, 0.22 mmol) was deprotected with zinc (0.72 g, 11 mmol) and acylated with (R)-3-tetradecanoyloxytetradecanoic acid (0.12 g, 0.26 mmol) in the presence of EEDQ (0.082 g, 0.33 mmol) to give 0.277 g (66%) of N-[(R)-3-tetradecanoyloxytetradecanoyl]-O-[2-deoxy-4-O-diphenylphosphono-2-[(R)-3-tetradecanoyloxytetradecanoylamino]-3-O-[(R)-3-tetradecanoyloxytetradecanoyl]-β-D-glucopyranosyl]-L-serine benzyl ester as an amorphous solid: $^1H$ NMR ($CDCl_3$) δ 0.88 (t, 18 H, J=~6.5 Hz) 1.0–1.75 (m, 126 H), 2.15–2.45 (m, 10 H), 2.53 (dd, 1 H, J=14.7, 6.0 Hz), 2.67 (dd, 1 H, J=14, 6.0 Hz), 3.25 (br t, 1 H, J=7 Hz), 3.35–3.75 (m, 4 H), 3.88 (dd, 1 H, J=11.1 Hz), 4.23 dd, 1 H, J=11.1, 3 Hz), 4.6–4.75 (m, 2 H), 5.03 (d, 1 H, J=8.1 Hz), 5.05–5.25 (m, 4 H), 5.48 (t, 1 H, J=10 Hz), 6.40 (d, 1 H, J=7.5 Hz), 7.01 (d, 1 H, J=8.1 Hz), 7.1–7.4 (m, 15 H).

(4) In the same manner as described in Example 2-(8), the compound prepared in (3) above (0.253 g, 0.133 mmol) was hydrogenated in the presence of 5% palladium on carbon (50 mg) and platinum oxide (120 mg) to give 0.155 g (62%) of N-[(R)-3-tetradecanoyloxytetradecanoyl]-O-[2-deoxy-4-O-phosphono-2-[(R)-3-tetradecanoyloxytetradecanoylamino]-3-O-[(R)-3-tetradecanoyloxytetradecanoyl]-β-D-glucopyranosyl]-L-serine triethylammonium salt as a colorless solid: mp 180° C. (dec); IR (film) 3322, 2956, 2924, 2852, 1736, 1732, 1681, 1673, 1667, 1660, 1651, 1467, 1456, 1247, 1174, 1110, 1081 $cm^{-1}$; $^1H$ NMR ($CDCl_3$-$CD_3OD$) δ 0.88 (t, 18 H, J=~7 Hz), 1.0–1.7 (m, 135 H), 2.2–2.75 (m, 12 H), 3.05 (q, 6 H, J=7 Hz), 3.30 (br s, 13 H), 3.7–3.9 (m, 3 H), 3.96 (d, 1 H, J=12 Hz), 4.05–4.3 (m, 2 H), 4.34 (m, 1 H), 4.53 (d, 1 H, J=7.8 Hz), 5.05–5.3 (m, 4 H), 7.25–7.35 (m, 2 H); $^{13}C$ NMR ($CDCl_3$) δ 173.4, 173.2, 171.0, 170.3, 170.2, 169.9, 169.8, 100.8, 75.1, 73.4, 71.1, 70.7, 70.4, 70.3, 60.2, 54.3, 45.6, 41.2, 41.1, 39.2, 34.6, 34.4, 34.2, 32.0, 29.8, 29.5, 25.4, 25.2, 22.7, 14.2, 8.6.

Anal. Calcd for $C_{99}H_{190}N_3O_{19}P.5 H_2O$: C, 64.35; H, 10.91; N, 2.27; P, 1.68. Found: C, 64.16; H, 10.92; N, 2.37; P, 1.91.

EXAMPLE 13 (B12)

PREPARATION OF N-[(R)-3-DODECANOYLOXYTETRADECANOYL]-O-[2-DEOXY-4-O-PHOSPHONO-2-[(R)-3-DODECANOYLOXYTETRADECANOYLAMINO]-3-O-[(R)-3-DODECANOYLOXYTETRADECANOYL]-β-D-GLUCOPYRANOSYL]-L-SERINE TRIETHYLAMMONIUM SALT (COMPOUND (I), $R_1=R_2=R_3=N-C_{11}H_{23}CO$, X=Y=O, N=M=P=Q=0, $R_4=R_5=R_7=R_9$=H, $R_6=CO_2H$, $R_8=PO_3H_2$).

(1) In the same manner as described in Example 2-(5), L-serine benzyl ester (390 mg, 2.0 mmol) was acylated with (R)-3-dodecanoyloxytetradecanoic acid (935 mg, 2.2 mmol) in the presence of EDC.MeI (745 mg, 2.5 mmol) in CH$_2$Cl$_2$ to afford 1.08 g (90%) of N-[(R)-3-dodecanoyloxytetradecanoyl]-L-serine benzyl ester: mp 53–54° C. $^1$H NMR (CDCl$_3$) δ 0.88 (t, 6 H, J=6.5 Hz), 1.1–1.6 (m, 46 H), 2.30 (t, 2 H, J=7.7 Hz), 2.50 (d, 2 H, 5.6 Hz), 2.62 (t, 1 H, J=6.2 Hz), 3.97 (m, 2 H), 4.65 (m, 1 H), 5.19 (m, 3 H), 6.63 (d, 1 H, J=6.8 Hz), 7.35 (br s, 5 H).

(2) In the same manner as described in Example 2-(2), the compound prepared in Example 2-(1) (1.0 g, 2.02 mmol) was acylated with (R)-3-dodecanoyloxytetradecanoic acid (946 mg, 2.22 mmol) in the presence of EDC MeI (720 mg, 2.4 mmol) and 4-pyrrolidinopyridine (100 mg) in CH$_2$Cl$_2$, and then deprotected in aqueous AcOH (25 mL) to afford 1.30 g (81%) of 2-(trimethylsilyl)ethyl 2-deoxy-3-O-[(R)-3-dodecanoyloxytetradecanoyl]-2-(2,2,2-trichloroethoxycarbonylamino)-β-D-glucopyranoside as an amorphous solid: $^1$H NMR (CDCl$_3$) δ 0.00 (s, 9 H), 0.88 (m, 8 H), 1.25 (m, 28 H), 1.59 (m, 4 H), 2.30 (t, 2 H, J=7.5 Hz), 2.52 (m, 2 H), 3.42 (m, 1 H), 3.55 (m, 1 H), 3.66 (m, 1 H), 3.83 (dd, 1 H, J=11.8, 4.6 Hz), 3.94 (m, 2 H), 4.57 (d, 1 H, J=8.2 Hz), 4.71 (m, 2 H), 5.07 (m, 2 H), 5.27 (d, 1 H, J=8.8 Hz).

(3) In the same manner as described in Example 2-(3), the compound prepared in (2) above (1.30 g, 1.51 mmol) was treated with 2,2,2-trichloro-1,1-dimethylethyl chloroformate (398 mg, 1.66 mmol) and pyridine (0.15 mL, 1.83 mmol) in CH$_2$Cl$_2$ (25 mL) followed by triethylamine (0.42 mL, 3.02 mmol), diphenyl chlorophosphate (0.47 mL, 2.27 mmol) and 4-pyrrolidinopyridine (100 mg) to afford 1.39 g (71%) of 2-(trimethylsilyl)ethyl 2-deoxy-4-O-diphenylphosphono-3-O-[(R)-3-dodecanoyloxytetradecanoyl]-6-O-(2,2,2-trichloro-1,1-dimethylethoxycarbonyl)-2-(2,2,2-trichloroethoxycarbonylamino)-β-D-glucopyranoside as an amorphous solid: $^1$H NMR (CDCl$_3$) δ 0.0 (s, 9 H), 0.88 (m, 8 H), 1.1–1.7 (m, 46 H), 1.77 (s, 3 H), 1.85 (s, 3 H), 2.23 (m, 6 H), 3.34 (m, 1 H), 3.59 (m, 1 H), 3.80 (m, 1 H), 3.96 (m, 1 H), 4.32 (m, 2 H), 4.63 (m, 2 H), 4.83 (d, 1 H, J=11.9 Hz), 5.02 (d, 1 H, J=8.2 Hz), 5.20 (m, 1 H), 5.65 (m, 2 H), 7.29 (m, 10 H).

(4) The compound prepared in (3) above (1.30 g, 1.0 mmol) in CH$_2$Cl$_2$ (15 mL) was treated at 0° C. with TFA (5 mL) and then allowed to warm to room temperature for 18 h. The solvent was removed in vacuo and the remaining TFA was removed by azeotroping with toluene. The lactol was treated with the Vilsmeier reagent prepared from DMF (0.39 mL, 5.0 mmol) and oxalyl chloride (0.22 mL, 2.5 mmol) in CH$_2$Cl$_2$ (20 mL) at 0° C. The reaction was allowed to warm slowly to room temperature overnight and was partitioned between 50 mL of saturated aqueous NaHCO$_3$ and ether (50 mL). The layers were separated and the organic phase was dried over Na$_2$SO$_4$ and concentrated in vacuo. Purification by flash chromatography on silica gel with 10% EtOAc/hexanes afforded 1.09 g (90%) of 2-deoxy-4-O-diphenylphosphono-3-O-[(R)-3-dodecanoyloxytetradecanoyl]-6-O-(2,2,2-trichloro-1,1-dimethylethoxycarbonyl)-2-(2,2,2-trichloroethoxycarbonylamino)-α-D-glucopyranosyl chloride as a white foam: $^1$H NMR (CDCl$_3$) δ 0.88 (t, 6 H, J=6.8 Hz), 1.2–1.70 (m, 46 H), 1.78 (s, 3 H), 1.88 (s, 3 H), 2.18 (t, 2 H, J=7.7 Hz), 2.43 (m, 2 H), 4.30 (m, 4 H), 4.72 (m, 3 H), 5.09 (m, 1 H), 5.50 (t, 1 H, J=9.5 Hz), 5.79 (d, 1 H, J=8.0 Hz), 6.27 (d, 1 H, J=3.6 Hz), 7.19 (m, 10 H).

(5) To a solution of compounds prepared in (1) and (4) (540 mg, 0.90 mmol, and 1.0 g, 0.82 mmol, respectively) in 1,2-dichloroethane (20 mL), powdered 4A molecular sieves (300 mg) were added and the suspension was stirred for 30 min. AgOTf (1.16 g, 4.5 mmol) was added in one portion, after 30 min the slurry was filtered through silica gel and eluted with 30% EtOAc/hexanes to afford 1.10 g (75%) of N-[(R)-3-dodecanoyloxytetradecanoyl]-O-[2-deoxy-4-O-diphenylphosphono-3-O-[(R)-3-dodecanoyloxytetradecanoyl]-6-O-(2,2,2-trichloro-1,1-dimethylethoxycarbonyl)-2-(2,2,2-trichloroethoxycarbonylamino)-β-D-glucopyranosyl]-L-serine benzyl ester: $^1$H NMR (CDCl$_3$) δ 0.88 (t, 12 H, J=6.5 Hz), 1.1–1.65 (m, 92 H), 1.77 (s, 3 H), 1.85 (s, 3 H), 2.1–2.5 (m, 8 H), 3.67 (m, 2 H), 4.30 (m, 3 H), 4.72 (m, 5 H), 5.18 (m, 4 H), 5.46 (m, 1 H), 6.07 (m, 1 H), 6.62 (d, 1 H, J=7.9 Hz), 7.05–7.45 (m, 15 H).

(6) In the same manner as described in Example 2-(7), the compound prepared in (5) above (1.0 g, 0.56 mmol) was deprotected with zinc (1.83 g, 28 mmol) and acylated with (R)-3-dodecanoyloxytetradecanoic acid (285 mg, 0.67 mmol) in the presence of EEDQ (185 mg, 0.74 mmol) to afford 420 mg (44%) of N-[(R)-3-dodecanoyloxytetradecanoyl]-O-[2-deoxy-4-O-diphenylphosphono-2-[(R)-3-dodecanoyloxytetradecanoylamino]-3-O-[(R)-3-dodecanoyloxytetradecanoyl]-β-D-glucopyranosyl]-L-serine benzyl ester as an amorphous solid.

(7) In the same manner as described in Example 2-(8), the compound prepared in (6) above (420 mg, 0.24 mmol) was hydrogenated in the presence of palladium hydroxide on carbon in EtOH (10 mL) and platinum oxide (400 mg) in EtOH/AcOH (10:1) to afford 240 mg (60%) of N-[(R)-3-dodecanoyloxytetradecanoyl]-O-[2-deoxy-4-O-phosphono-2-[(R)-3-dodecanoyloxytetradecanoylamino]-3-O-[(R)-3-dodecanoyloxytetradecanoyl]-β-D-glucopyranosyl]-L-serine triethylammonium salt as a white powder: mp 181–182° C.; IR (film) 3289, 2956, 2920, 2851, 1731, 1656, 1557, 1467, 1378, 1182, 1108, 1080, 1052, 852, 721 cm$^{-1}$; $^1$H NMR (CDCl$_3$-CD$_3$OD) δ 0.88 (t, 18 H, J=6.7 Hz), 1.1–1.7 (m, 123 H), 2.2–2.7 (m, 12 H), 3.06 (q, 6 H, J=7.2 Hz), 3.35 (m, 1 H), 3.70 (m, 6 H), 3.88 (m, 2 H), 4.20 (m, 1 H), 4.56 (d, 1 H, J=8.1 Hz), 4.59 (br s, 1 H), 5.16 (m, 4 H); $^{13}$C NMR (CDCl$_3$) δ 176.9, 173.3, 173.2, 172.7, 169.6, 169.1, 101.5, 74.8, 71.2, 70.9, 69.2, 60.5, 53.1, 51.4, 46.1, 41.5, 41.0, 39.2, 34.3, 34.2, 34.0, 32.0, 29.8, 29.7, 29.4, 29.2, 25.6, 25.3, 25.2, 25.1, 22.7, 14.1, 8.7.

Anal. Calcd. for C$_{93}$H$_{178}$N$_3$O$_{19}$P.H$_2$O: C, 66.04; H, 10.73; N, 2.48; P, 1.83. Found: C, 66.04; H, 10.73; N, 2.48; P, 1.86.

EXAMPLE 14 (B13)

PREPARATION OF N-[(R)-3-UNDECANOYLOXYTETRADECANOYL]-O-[2-DEOXY-4-O-PHOSPHONO-2-[(R)-3-UNDECANOYLOXYTETRADECANOYLAMINO]-3-O-[(R)-3-UNDECANOYLOXYTETRADECANOYL]-β-D-GLUCOPYRANOSYL]-L-SERINE TRIETHYLAMMONIUM SALT (COMPOUND (I), $R_1$=$R_2$=$R_3$=N—C$_{10}$H$_{21}$CO, X=Y=O, N=M=P=Q=0, $R_4$=$R_5$=$R_7$=$R_9$=H, $R_6$=CO$_2$H, $R_8$=PO$_3$H$_2$)

(1) In the same manner as described in Example 2-(5), L-serine benzyl ester (390 mg, 2.0 mmol) was acylated with (R)-3-undecanoyloxytetradecanoic acid (905 mg, 2.2 mmol) in the presence of EDC MeI (745 mg, 2.5 mmol) in CH$_2$Cl$_2$ to afford 1.08 g (92%) of N-[(R)-3-undecanoyloxytetradecanoyl]-L-serine benzyl ester: mp 53–54° C.; $^1$H NMR (CDCl$_3$) δ 0.88 (t, 6 H, J=6.9 Hz), 1.1–1.7 (m, 44 H), 2.30 (t, 2 H, J=7.7 Hz), 2.49 (d, 2 H, J=5.8 Hz), 3.99 (m, 2 H), 4.65 (m, 1 H), 5.19 (m, 3 H), 6.58 (d, 1 H, J=6.9 Hz), 7.35 (br s, 5 H).

(2) In the same manner as described in Example 2-(2), the compound prepared in Example 2-(1) (1.0 g, 2.02 mmol) was acylated with (R)-3-undecanoyloxytetradecanoic acid (915 mg, 2.22 mmol) in the presence of EDC MeI (720 mg, 2.4 mmol) and 4-pyrrolidinopyridine (100 mg) in $CH_2Cl_2$, and then deprotected in aqueous AcOH (25 mL) to afford 1.41 g (82%) of 2-(trimethylsilyl)ethyl 2-deoxy-3-O-[(R)-3-undecanoyloxytetradecanoyl]-2-(2,2,2-trichloroethoxycarbonylamino)-β-D-glucopyranoside as an amorphous solid: $^1$H NMR ($CDCl_3$) δ 0.00 (s, 9 H), 0.88 (m, 8 H), 1.25 (m, 32 H), 1.60 (m, 4 H), 2.31 (t, 2 H, J=7.5 Hz), 2.52 (m, 2 H), 3.42 (m, 1 H), 3.55 (m, 1 H), 3.66 (m, 1 H), 3.83 (dd, 1 H, J=11.8, 4.6 Hz), 3.94 (m, 2 H), 4.57 (d, 1 H, J=8.2 Hz), 4.71 (m, 2 H), 5.07 (m, 2 H), 5.27 (d, 1 H, J=8.7 Hz).

(3) In the same manner as described in Example 2-(3), the compound prepared in (2) above (1.30, 1.53 mmol) was treated with 2,2,2-trichloro-1,1-dimethylethyl chloroformate (403 mg, 1.68 mmol) and pyridine (0.15 mL, 1.85 mmol) in $CH_2Cl_2$ (25 mL) followed by triethylamine (0.43 mL, 3.06 mmol), diphenyl chlorophosphate (0.48 mL, 2.30 mmol) and 4-pyrrolidinopyridine (100 mg) to afford 1.37 g (70%) of 2-(trimethylsilyl)ethyl 2-deoxy-4-O-diphenylphosphono-3-O-[(R)-3-undecanoyloxytetradecanoyl]-6-O-(2,2,2-trichloro-1,1-dimethylethoxycarbonyl)-2-(2,2,2-trichloroethoxycarbonylamino)-β-D-glucopyranoside as an amorphous solid: $^1$H NMR ($CDCl_3$) δ 0.0 (s, 9 H), 0.88 (m, 8 H), 1.1–1.7 (m, 44 H), 1.80 (s, 3 H), 1.89 (s, 3 H), 2.23 (m, 6 H), 3.58 (m, 3 H), 4.32 (m, 1 H), 4.71 (m, 2 H), 4.83 (d, 1 H, J=12.1 Hz), 5.01 (d, 1 H, J=8.1 Hz), 5.20 (m, 1 H), 5.62 (m, 2 H), 7.25 (m, 10 H).

(4) In the same manner as described in Example 13-(4), the compound prepared in (4) above (1.28 g, 1.0 mmol) was deprotected with TFA (5 mL) and then treated with the Vilsmeier reagent generated from DMF (0.39 mL, 5.0 mmol) and oxalyl chloride (0.22 mL, 2.5 mmol) to give 1.12 g (93%) of 2-deoxy-4-O-diphenylphosphono-3-O-[(R)-3-undecanoyloxytetradecanoyl]-6-O-(2,2,2-trichloro-1,1-dimethylethoxycarbonyl)-2-(2,2,2-trichloroethoxycarbonylamino)-α-D-glucopyranosyl chloride as a white foam: $^1$H NMR ($CDCl_3$) δ 0.88 (t, 6 H, J=6.7 Hz), 1.1–1.55 (m, 44 H), 1.78 (s, 3 H), 1.88 (s, 3 H), 2.18 (m, 2 H), 2.43 (m, 2 H), 4.34 (m, 4 H), 4.72 (m, 3 H), 5.09 (m, 1 H), 5.50 (t, 1 H, J=9.6 Hz), 5.80 (d, 1 H, J=8.0 Hz), 6.26 (d, 1 H, J=3.4 Hz), 7.26 (m, 10 H).

(5) In the same manner as described in Example 13-(5), compounds prepared in (1) and (4) above (530 mg, 0.90 mmol, and 1.0 g, 0.83 mmol, respectively) were coupled in the presence of AgOTf (1.16 g, 4.5 mmol) to afford 1.11 g (76%) of N-[(R)-3-undecanoyloxytetradecanoyl]-O-[2-deoxy-4-O-diphenylphosphono-3-O-[(R)-3-undecanoyloxytetradecanoyl]-6-O-(2,2,2-trichloro-1,1-dimethylethoxycarbonyl)-2-(2,2,2-trichloroethoxycarbonylamino)-β-D-glucopyranosyl]-L-serine benzyl ester: $^1$H NMR ($CDCl_3$) δ 0.88 (m, 12 H), 1.0–1.65 (m, 88 H), 1.77 (s, 3 H), 1.85 (s, 3 H), 2.1–2.5 (m, 8 H), 3.37 (m, 1 H), 3.64 (m, 1 H), 3.85 (m, 1 H), 4.30 (m, 3 H), 4.78 (m, 5 H), 5.18 (m, 4 H), 5.46 (m, 1 H), 6.07 (m, 1 H), 6.62 (d, 1 H, J=7.7 Hz), 7.05–7.45 (m, 15 H).

(6) In the same manner as described in Example 2-(7), the compound prepared in (5) above (1.0 g, 0.57 mmol) was deprotected with zinc (2.0 g, 30.5 mmol) and acylated with (R)-3-undecanoyloxytetradecanoic acid (280 mg, 0.68 mmol) in the presence of EEDQ (185 mg, 0.75 mmol) to afford 470 mg (50%) of N-[(R)-3-undecanoyloxytetradecanoyl]-O-[2-deoxy-4-O-diphenylphosphono-2-[(R)-3-undecanoyloxytetradecanoylamino]-3-O-[(R)-3-undecanoyloxytetradecanoyl]-β-D-glucopyranosyl]-L-serine benzyl ester as an amorphous solid.

(7) In the same manner as described in Example 2-(8), the compound prepared in (6) above (470 mg, 0.27 mmol) was hydrogenated in the presence of palladium hydroxide on carbon in EtOH (10 mL) and platinum oxide (400 mg) in EtOH 25/AcOH (10:1) to afford 130 mg (30%) of N-[(R)-3-undecanoyloxytetradecanoyl]-O-[2-deoxy-4-O-phosphono-2-[(R)-3-undecanoyloxytetradecanoylamino]-3-O-[(R)-3-undecanoyloxytetradecanoyl]-β-D-glucopyranosyl]-L-serine triethylammonium salt as a white powder: mp 181–183° C.; IR (film) 3294, 2923, 2853, 1734, 1655, 1466, 1377, 1163, 1080, 721 $cm^{-1}$; $^1$H NMR ($CDCl_3$-$CD_3OD$) δ 0.88 (t, 18 H, J=6.8 Hz), 1.1–1.7 (m, 117 H), 2.2–2.7 (m, 12 H), 3.06 (q, 6 H, J=7.1 Hz), 3.4–3.2 (m, 5 H), 3.6–3.9 (m, 4 H), 4.20 (d, 1 H, 9.8 Hz), 4.54 (d, 1 H, J=8.0 Hz), 4.62 (br. s, 1 H), 5.17 (m, 4H); $^{13}$C NMR ($CDCl_3$) δ 173.5, 173.3, 172.8, 172.2, 169.6, 169.1, 101.5, 77.2, 74.8, 70.9, 69.2, 60.5, 58.5, 53.1, 51.5, 46.1, 41.5, 41.1, 39.2, 34.6, 34.4, 34.1, 32.0, 29.8, 29.7, 29.4, 29.2, 25.6, 25.2, 25.1, 22.7, 18.5, 14.2, 8.7.

Anal. Calcd. for $C_{90}H_{172}N_3O_{19}P$: C, 66.26; H, 10.63; N, 2.58; P, 1.90. Found: C, 66.56; H, 10.57; N, 2.47; P, 1.91.

EXAMPLE 15 (B14)

Preparation of N-[(R)-3-Decanoyloxytetradecanoyl]-O-[2-deoxy-4-O-phosphono-2-[(R)-3-decanoyloxytetradecanoylamino]-3-O-[(R)-3-decanoyloxytetradecanoyl]-β-D-glucopyranosyl]-D-serine Triethylammonium Salt (Compound (I), $R_1=R_2=R_3=N-C_9H_{19}CO$, $X=Y=O$, $N=M=P=Q=0$, $R_4=R_5=R_7=R_9=H$, $R_6=CO_2H$, $R_8=PO_3H_2$)

(1) In the same manner as described in Example 2-(5), D-serine benzyl ester (390 mg, 2.0 mmol) was acylated with (R)-3-decanoyloxytetradecanoic acid (875 mg, 2.2 mmol) in the presence of EDC.MeI (745 mg, 2.5 mmol) in $CH_2Cl_2$ to afford 1.05 g (91%) of N-[(R)-3-decanoyloxytetradecanoyl]-D-serine benzyl ester: mp 51–52° C.; $^1$H NMR ($CDCl_3$) δ 0.88 (m, 6 H), 1.1–1.7 (m, 34 H), 2.30 (t, 2 H, J=7.7 Hz), 2.50 (m, 2 H), 3.68 (s, 1 H), 3.93 (d, 2 H, J=3.1 Hz), 4.62 (m, 1 H), 5.22 (m, 3 H), 6.63 (d, 1 H, J=6.9 Hz), 7.35 (br s, 5 H).

(2) In the same manner as described in Example 2-(2), the compound prepared in Example 2-(1) (1.0 g, 2.02 mmol) was acylated with (R)-3-decanoyloxytetradecanoic acid (884 mg, 2.22 mmol) in the presence of EDC.MeI (720 mg, 2.4 mmol) and 4-pyrrolidinopyridine (100 mg) in $CH_2Cl_2$, and then deprotected in aqueous AcOH (25 mL) to afford 1.30 g (77%) of 2-(trimethylsilyl)ethyl 2-deoxy-3-O-[(R)-3-decanoyloxytetradecanoyl]-2-(2,2,2-trichloroethoxycarbonylamino)-β-D-glucopyranoside as an amorphous solid: $^1$H NMR ($CDCl_3$) δ 0.00 (s, 9 H), 0.88 (m, 8 H), 1.25 (m, 30 H), 1.59 (m, 4 H), 2.30 (t, 2 H, J=7.5 Hz), 2.52 (m, 2 H), 3.42 (m, 1 H), 3.55 (m, 1 H), 3.66 (m, 1 H), 3.83 (dd, 1 H, J=11.8, 4.6 Hz), 3.94 (m, 2 H), 4.57 (d, 1 H, J=8.2 Hz), 4.71 (m, 2 H), 5.07 (m, 2 H), 5.27 (d, 1 H, J=8.8 Hz).

(3) In the same manner as described in Example 2-(3), the compound prepared in (2) above (1.25 g, 1.50 mmol) was treated with 2,2,2-trichloro-1,1-dimethylethyl chloroformate (396 mg, 1.65 mmol) and pyridine (0.15 mL, 1.81 mmol) in $CH_2Cl_2$ (25 mL) followed by triethylamine (0.42 mL, 3.00 mmol), diphenyl chlorophosphate (0.47 mL, 2.25 mmol) and 4-pyrrolidinopyridine (100 mg) to afford 1.31 g (69%) of 2-(trimethylsilyl)ethyl 2-deoxy-4-O-diphenylphosphono-3-O-[(R)-3-decanoyloxytetradecanoyl]-6-O-(2,2,2-trichloro-1,1-dimethylethoxycarbonyl)-2-(2,2,2- trichloroethoxycarbonylamino)-β-D-glucopyranoside as an amorphous solid: $^1$H NMR (CDCl$_3$) δ 0.0 (s, 9 H), 0.89 (m, 8 H), 1.1–1.7 (m, 34 H), 1.82 (s, 3 H), 1.90 (s, 3 H), 2.30 (m, 4 H), 3.40 (q, 1 H, J=9.6 Hz), 3.65 (m, 1 H), 3.89 (m, 1 H), 4.32 (m, 2 H), 4.63 (m, 2 H), 4.82 (d, 1 H, J=12.1 Hz), 5.01 (d, 1 H, J=8.2 Hz), 5.63 (m, 2 H), 7.29 (m, 10 H).

(4) In the same manner as described in Example 13-(4), the compound prepared in (3) above (1.27 g, 1.0 mmol) was deprotected with TFA (5 mL) and then treated with the Vilsmeier reagent generated from DMF (0.39 mL, 5.0 mmol) and oxalyl chloride (0.22 mL, 2.5 mmol) to give 1.06 g (89%) of 2-deoxy-4-O-diphenylphosphono-3-O-[(R)-3-decanoyloxytetradecanoyl]-6-O-(2,2,2-trichloro-1,1-dimethylethoxycarbonyl)-2-(2,2,2-trichloroethoxycarbonylamino)-α-D-glucopyranosyl chloride as a white foam: $^1$H NMR (CDCl$_3$) δ 0.88 (t, 6 H, J=6.6 Hz), 1.1–1.55 (m, 34 H), 1.78 (s, 3 H), 1.88 (s, 3 H), 2.18 (t, 2 H, J=7.7 Hz), 2.43 (m, 2 H), 4.32 (m, 4 H), 4.71 (m, 3 H), 4.83 (m, 3 H), 5.09 (m, 1 H), 5.50 (t, 1 H, J=9.5 Hz), 5.77 (d, 1 H, J=8.0 Hz), 6.26 (d, 1 H, J=3.4 Hz), 7.20 (m, 10 H).

(5) In the same manner as described in Example 13-(5), compounds prepared in (1) and (4) above above (520 mg, 0.90 mmol, and 1.0 g, 0.84 mmol, respectively) were coupled in the presence of AgOTf (1.16 g, 4.5 mmol) to afford 1.13 g (78%) of N-[(R)-3-decanoyloxytetradecanoyl]-O-[2-deoxy-4-O-diphenylphosphono-3-O-[(R)-3-decanoyloxytetradecanoyl]-6-O-(2,2,2-trichloro-1,1-dimethylethoxycarbonyl)-2-(2,2,2-trichloroethoxycarbonylamino)-β-D-glucopyranosyl]-D-serine benzyl ester: $^1$H NMR (CDCl$_3$) δ 0.88 (t, 12 H, J=6.6 Hz), 1.1–1.65 (m, 68 H), 1.82 (s, 3 H), 1.89 (s, 3 H), 2.2–2.6 (m, 8 H), 3.40 (m, 1 H), 3.64 (m, 1 H), 4.01 (m, 2 H), 4.27 (m, 2 H), 4.44 (m, 1 H, J=7.1 Hz), 4.60 (m, 2 H), 4.77 (m, 2 H), 5.19 (m, 6 H), 6.61 (d, 1 H, J=8.3 Hz), 7.05–7.45 (m, 15 H).

(6) In the same manner as described in Example 2-(7), the compound prepared in (5) above (1.0 g, 0.58 mmol) was deprotected with zinc (1.9 g, 29 mmol) and acylated with (R)-3-decanoyloxytetradecanoic acid (280 mg, 0.70 mmol) in the presence of EEDQ (190 mg, 0.77 mmol) to afford 420 mg (44%) of N-[(R)-3-decanoyloxytetradecanoyl]-O-deoxy-4-O-diphenylphosphono-2-[(R)-3-decanoyloxytetradecanoylamino]-3-O-[(R)-3-decanoyloxytetradecanoyl]-β-D-glucopyranosyl]-D-serine benzyl ester as an amorphous solid.

(7) In the same manner as described in Example 2-(8), the compound prepared in (6) above (420 mg, 0.25 mmol) was hydrogenated in the presence of palladium hydroxide on carbon in EtOH (10 mL) and platinum oxide (400 mg) in EtOH/AcOH (10:1) to afford 118 mg (30%) of N-[(R)-3-decanoyloxytetradecanoyl]-O-[2-deoxy-4-O-phosphono-2-[(R)-3-decanoyloxytetradecanoylamino]-3-O-[(R)-3-decanoyloxytetradecanoyl]-β-D-glucopyranosyl]-D-serine triethylammonium salt as a white powder: mp 179–181° C.; IR (film) 3283, 3100, 2921, 2852, 1732, 1660, 1651, 1564, 1556, 1464, 1417, 1378, 1322, 1181, 1061, 856, 722 cm$^{-1}$; $^1$H NMR (CDCl$_3$-CD$_3$OD) δ 0.88 (t, 18 H, J=6.8 Hz), 1.1–1.7 (m, 111 H), 2.2–2.7 (m, 12 H), 3.06 (m, 6 H), 3.33 (m, 5 H), 3.78 (m, 2 H), 3.95 (m, 2 H), 4.22 (m, 1 H), 4.45 (d, 1 H, J=7.5 Hz), 4.68 (br. s, 1 H), 5.13 (m, 3 H), 5.26 (m, 1 H); $^{13}$C NMR (CDCl$_3$) δδ 173.7, 173.5, 173.1, 171.1, 169.9, 100.3, 75.1, 73.9, 71.9, 71.1, 70.9, 70.2, 60.9, 53.9, 52.7, 46.0, 41.3, 40.8, 39.4, 34.6, 34.4, 31.9, 29.8, 29.7, 29.5, 29.4, 25.6, 25.4, 25.2, 25.1, 22.7, 14.1, 8.6.

Anal. Calcd. for C$_{87}$H$_{166}$N$_3$O$_{19}$P: C, 65.75; H, 10.53; N, 2.64; P, 1.95. Found: C, 65.32; H, 10.28; N, 2.53; P, 1.89.

EXAMPLE 16 (B 15)

PREPARATION OF OF N-[(R)-3-DECANOYLOXYTETRADECANOYL]-O-[2-DEOXY-4-O-PHOSPHONO-2-[(R)-3-DECANOYLOXYTETRADECANOYLAMINO]-3-O-[(R)-3-DECANOYLOXYTETRADECANOYL]-β-D-GLUCOPYRANOSYL]-L-SERINE TRIETHYLAMMONIUM SALT. (COMPOUND (I), R$_1$=R$_2$=R$_3$=N—C$_9$H$_{19}$CO, X=Y=O, N=M=P=Q=0, R$_4$=R$_5$=R$_7$=R$_9$=H, R$_6$=CO$_2$H, R$_8$=PO$_3$H$_2$)

(1) In the same manner as described in Example 2-(5), L-serine benzyl ester (250 mg, 1.08 mmol) was acylated with (R)-3-decanoyloxytetradecanoic acid (478 mg, 1.2 mmol) in the presence of EDC.MeI (357 mg, 1.2 mmol) in CH$_2$Cl$_2$ to afford 0.52 g (84%) of N-[(R)-3-heptanoyloxytetradecanoyl]-L-serine benzyl ester: mp 52–53° C.; $^1$H NMR (CDCl$_3$) δ 0.87 (t, 6 H, J=6.9 Hz), 1.1–1.7 (m, 34 H), 2.29 (t, 2 H, J=7.5 Hz), 2.49 (d, 2 H, J=5.8 Hz), 3.67 (s, 1 H), 3.97 (m, 2 H), 4.63 (m, 1 H), 5.19 (m, 3 H), 6.61 (d, 1 H, J=7.1 Hz), 7.35 (br s, 5 H).

(2) In the same manner as described in Example 13-(5), the compound prepared in (1) above (500 mg, 0.87 mmol), and the compound prepared in Example 15-(4) (1.08 g, 0.90 mmol) were coupled in the presence of AgOTf (1.16 g, 4.5 mmol) to afford 1.35 g (89%) of N-[(R)-3-decanoyloxytetradecanoyl]-O-[2-deoxy-4-O-diphenylphosphono-3-O-[(R)-3-decanoyloxytetradecanoyl]-6-O-(2,2,2-trichloro-1,1-dimethylethoxycarbonyl)-2-(2,2,2-trichloroethoxycarbonylamino)-β-D-glucopyranosyl]-L-serine benzyl ester: $^1$H NMR (CDCl$_3$) δ 0.88 (t, 12 H, J=6.6 Hz), 1.0–1.65 (m, 68 H), 1.77 (s, 3 H), 1.85 (s, 3 H), 2.1–2.5 (m, 8 H), 3.38 (q, 1 H, J=9.1 Hz), 3.65 (m, 1 H), 3.84 (m, 1 H), 4.27 (m, 3 H), 4.70 (m, 5 H), 4.84 (m, 4 H), 5.14 (m, 3 H), 5.46 (t, 1 H, J=9.7 Hz), 6.07 (m, 1 H), 6.62 (d, 1 H, J=8.0 Hz), 7.05–7.45 (m, 15 H).

(3) In the same manner as described in Example 2-(7), the compound prepared in (2) above (600 mg, 0.34 mmol) was deprotected with zinc (1.13 g, 17.2 mmol) and acylated with (R)-3-decanoyloxytetradecanoic acid (150 mg, 0.38 mmol) in the presence of EEDQ (124 mg, 0.50 mmol) to afford 362 mg (60%) of N-[(R)-3-decanoyloxytetradecanoyl]-O-[2-deoxy-4-O-diphenylphosphono-2-[(R)-3-decanoyloxytetradecanoylamino]-3-O-[(R)-3-decanoyloxytetradecanoyl]-β-D-glucopyranosyl]-L-serine benzyl ester as an amorphous solid.

(4) In the same manner as described in Example 2-(8), the compound prepared in (3) above (300 mg, 0.17 mmol) was hydrogenated in the presence of palladium on carbon (100 mg) and platinum oxide (200 mg) in THF/AcOH (10:1) to afford 120 mg (44%) of N-[(R)-3-decanoyloxytetradecanoyl]-O-[2-deoxy-4-O-phosphono-2-[(R)-3-decanoyloxytetradecanoylamino]-3-O-[(R)-3-decanoyloxytetradecanoyl]-β-D-glucopyranosyl]-L-serine triethylammonium salt as a white powder: mp 175–176° C.; IR (film) 3304, 2956, 2923, 2853, 1733, 1654, 1541, 1466, 1377, 1164, 1107, 1080, 845, 721 cm$^{-1}$; $^1$H NMR (CDCl$_3$-CD$_3$OD) δ 0.88 (t, 18H, J=6.9 Hz), 1.1–1.7 (m, 111 H), 2.2–2.75 (m, 12 H), 3.07 (q, 6 H, J=7.2 Hz), 3.37 (m, 1 H), 3.5–3.95 (m, 8 H), 4.21 (q, 1 H, 11.0 Hz), 4.54 (d, 1 H, J=8.9 Hz), 4.61 (br. s, 1 H), 5.17 (m, 4 H), 7.10 (d, 1 H, J=9.0 Hz), 7.43 (d, 1 H, J=7.9 Hz); $^{13}$C NMR (CDCl$_3$) δ 176.3, 173.4, 173.2, 172.8, 172.0, 169.6, 169.2, 101.4, 74.7, 70.9, 69.3, 60.4, 53.2, 51.6, 46.1, 41.4, 41.0, 39.1, 34.5, 34.3, 34.2, 34.1, 31.9, 29.8, 29.7, 29.6, 29.4, 29.3, 29.2, 25.5, 25.1, 25.0, 22.7, 14.1, 8.6.

Anal. Calcd. for $C_{87}H_{166}N_3O_{19}P \cdot H_2O$: C, 65.01; H, 10.54; N, 2.61; P, 1.93. Found: C, 64.92; H, 10.38; N, 2.58; P, 2.06.

EXAMPLE 17 (B16)

PREPARATION OF N-[(R)-3-NONANOYLOXYTETRADECANOYL]-O-[2-DEOXY-4-O-PHOSPHONO-2-[(R)-3-NONANOYLOXYTETRADECANOYLAMINO]-3-O-[(R)-3-NONANOYLOXYTETRADECANOYL]-β-D-GLUCOPYRANOSYL]-L-SERINE TRIETHYLAMMONIUM SALT. (COMPOUND (I), $R_1=R_2=R_3=$N—$C_8H_{17}$CO, X=Y=O, N=M=P=Q=0, $R_4=R_5=R_7=R_9=$H, $R_6=CO_2H$, $R_8=PO_3H_2$)

(1) In the same manner as described in Example 2-(5), L-serine benzyl ester (390 mg, 2.0 mmol) was acylated with (R)-3-nonanoyloxytetradecanoic acid (780 mg, 2.2 mmol) in the presence of EDC.MeI (845 mg, 2.5 mmol) in $CH_2Cl_2$ to afford 1.0 g (89%) of N-[(R)-3-nonanoyloxytetradecanoyl]-L-serine benzyl ester: mp 52–53° C.; $^1$H NMR (CDCl$_3$) δ 0.88 (t, 6 H, J=6.6 Hz), 1.1–1.7 (m, 32 H), 2.30 (t, 2H, J=7.7 Hz), 2.51 (d, 2 H, J=5.8 Hz), 2.62 (t, 1 H, J=6.0 Hz), 3.98 (m, 2 H), 4.65 (m, 1 H), 5.19 (m, 3 H), 6.58 (d, 1 H, J=6.8 Hz), 7.35 (br s, 5 H).

(2) In the same manner as described in Example 2-(2), the compound prepared in Example 2-(1) (1.0 g, 2.02 mmol) was acylated with (R)-3-nonanoyloxytetradecanoic acid (852 mg, 2.22 mmol) in the presence of EDC.MeI (720 mg, 2.4 mmol) and 4-pyrrolidinopyridine (100 mg) in $CH_2Cl_2$, and then deprotected in aqueous AcOH (25 mL) to afford 1.31 g (79%/) of 2-(trimethylsilyl)ethyl 2-deoxy-3-O-[(R)-3-nonanoyloxytetradecanoyl]-2-(2,2,2-trichloroethoxycarbonylamino)-β-D-glucopyranoside as an amorphous solid: $^1$H NMR (CDCl$_3$) δ 0.00 (s, 9 H), 0.88 (m, 8 H), 1.25 (m, 28 H), 1.59 (m, 4 H), 2.30 (t, 2 H, J=7.5 Hz), 2.52 (m, 2 H), 3.42 (m, 1 H), 3.55 (m, 1 H), 3.66 (m, 1 H), 3.83 (dd, 1 H, J=11.8, 4.6 Hz), 3.94 (m, 2 H), 4.57 (d, 1 H, J=8.2 Hz), 4.71 (m, 2 H), 5.07 (m, 2 H), 5.27 (d, 1 H, J=8.8 Hz).

(3) In the same manner as described in Example 2-(3), the compound prepared in (2) above (1.25 g, 1.52 mmol) was treated with 2,2,2-trichloro-1,1-dimethylethyl chloroformate (400 mg, 1.67 mmol) and pyridine (0.15 mL, 1.84 mmol) in $CH_2Cl_2$ (25 mL) followed by triethylamine (0.42 mL, 3.04 mmol), diphenyl chlorophosphate (0.47 mL, 2.28 mmol) and 4-pyrrolidinopyridine (100 mg) to afford 1.30 g (67%) of 2-(trimethylsilyl)ethyl 2-deoxy-4-O-diphenylphosphono-3-O-[(R)-3-nonanoyloxytetradecanoyl]-6-O-(2,2,2-trichloro-1,1-dimethylethoxycarbonyl)-2-(2,2,2-trichloroethoxycarbonylamino)-β-D-glucopyranoside as an amorphous solid: $^1$H NMR (CDCl$_3$) δ 0.0 (s, 9 H), 0.88 (m, 8 H), 1.1–1.7 (m, 32 H), 1.82 (s, 3 H), 1.89 (s, 3 H), 2.22 (m, 6 H), 3.33 (m, 1 H), 3.53 (m, 1 H), 3.80 (m, 1 H), 3.96 (m, 1 H), 4.31 (m, 2 H), 4.55 (m, 2 H), 4.83 (d, 1 H, J=12.0 Hz), 5.01 (d, 1 H, J=7.9 Hz), 5.62 (m, 1 H), 7.28 (m, 10 H).

(4) In the same manner as described in Example 13-(4), the compound prepared in (3) above (1.26 g, 1.0 mmol) was deprotected with TFA (5 mL) and then treated with the Vilsmeier reagent generated from DMF (0.39 mL, 5.0 mmol) and oxalyl chloride (0.22 mL, 2.5 mmol) to give 1.07 g (91%) of 2-deoxy-4-O-diphenylphosphono-3-O-[(R)-3-nonanoyloxytetradecanoyl]-6-O-(2,2,2-trichloro-1,1-dimethylethoxycarbonyl)-2-(2,2,2-trichloroethoxycarbonylamino)-α-D-glucopyranosyl chloride as a white foam: $^1$H NMR (CDCl$_3$) δ 0.88 (t, 6 H, J=6.9 Hz), 1.25–1.55 (m, 32 H), 1.78 (s, 3 H), 1.88 (s, 3 H), 2.18 (t, 2 H, J=7.7 Hz), 2.43 (m, 2 H), 4.34 (m, 4 H), 4.70 (m, 3 H), 4.83 (m, 3 H), 5.09 (m, 1 H), 5.51 (t, 1 H, J=10.2 Hz), 5.78 (d, 1 H, J=8.0 Hz), 6.25 (d, 1 H, J=3.6 Hz), 7.19 (m, 10 H).

(5) In the same manner as described in Example 13-(5), compounds prepared in (1) and (4) above (505 mg, 0.90 mmol, and 1.0 g, 0.85 mmol, respectively) were coupled in the presence of AgOTf (1.16 g, 4.5 mmol) to afford 1.03 g (71%) of N-[(R)-3-nonanoyloxytetradecanoyl]-O-[2-deoxy-4-O-diphenylphosphono-3-O-[(R)-3-nonanoyloxytetradecanoyl]-6-O-(2,2,2-trichloro-1,1-dimethylethoxycarbonyl)-2-(2,2,2-trichloroethoxycarbonylamino)-β-D-glucopyranosyl]-L-serine benzyl ester: $^1$H NMR (CDCl$_3$) δ 0.88 (t, 12 H, J=6.9 Hz), 1.0–1.65 (m, 64 H), 1.78 (s, 3 H), 1.82 (s, 3 H), 2.1–2.5 (m, 8 H), 3.38 (m, 1 H), 3.64 (m, 1 H), 3.83 (m, 1 H), 4.25 (m, 3 H), 4.73 (m, 5 H), 5.18 (m, 5 H), 6.07 (m, 1 H), 6.60 (d, 1 H, J=7.8 Hz), 7.05–7.45 (m, 15 H).

(6) In the same manner as described in Example 2-(7), the compound prepared in (5) above (1.0 g, 0.59 mmol) was deprotected with zinc (1.93 g, 29.5 mmol) and acylated with (R)-3-nonanoyloxytetradecanoic acid (273 mg, 0.71 mmol) in the presence of EEDQ (195 mg, 0.78 mmol) to afford 405 mg (42%) of N-[(R)-3-nonanoyloxytetradecanoyl]-O-[deoxy-4-O-diphenylphosphono-2-[(R)-3-nonanoyloxytetradecanoylamino]-3-O-[(R)-3-nonanoyloxytetradecanoyl]-β-D-glucopyranosyl]-L-serine benzyl ester as an amorphous solid.

(7) In the same manner as described in Example 2-(8), the compound prepared in (6) above (405 mg, 0.25 mmol) was hydrogenated in the presence of palladium hydroxide on carbon in EtOH (10 mL) and platinum oxide (400 mg) in EtOH/AcOH (10:1) to afford 185 mg (48%) of N-[(R)-3-nonanoyloxytetradecanoyl]-O-[2-deoxy-4-O-phosphono-2-[(R)-3-nonanoyloxytetradecanoylamino]-3-O-[(R)-3-nonanoyloxytetradecanoyl]-β-D-glucopyranosyl]-L-serine triethylammonium salt as a white powder: mp 177–179° C.; IR (film) 3306, 2955, 2923, 2853, 1732, 1660, 1538, 1467, 1378, 1252, 1165, 1106, 1080, 960, 844, 722 cm$^{-1}$; $^1$H NMR (CDCl$_3$-CD$_3$OD) δ 0.88 (t, 18 H, J=6.8 Hz), 1.1–1.7 (m, 105 H), 2.2–2.75 (m, 12 H), 3.07 (q, 6 H, J=7.1 Hz), 3.2–3.5 (m, 5 H), 3.85 (m, 4 H), 4.23 (d, 1 H, 10.2 Hz), 4.51 (d, 1 H, J=8.0 Hz), 4.64 (br. s, 1 H), 5.18 (m, 4 H); $^{13}$C NMR (CDCl$_3$) δ 173.3, 172.8, 172.2, 169.6, 169.1, 101.5, 74.8, 70.9, 70.8, 69.3, 60.5, 53.2, 51.5, 46.1, 41.5, 41.0, 39.2, 34.5, 34.3, 34.1, 32.0, 31.9, 29.8, 29.6, 29.4, 29.3, 25.6, 25.2, 25.1, 22.7, 14.1, 8.7.

Anal. Calcd. for $C_{84}H_{160}N_3O_{19}P$: C, 65.21; H, 10.42; N, 2.72; P, 2.00. Found: C, 65.48; H, 10.32; N, 2.62; P, 2.12.

EXAMPLE 18 (B17)

PREPARATION OF N-[(R)-3-OCTANOYLOXYTETRADECANOYL]-O-[2-DEOXY-4-O-PHOSPHONO-2-[(R)-3-OCTANOYLOXYTETRADECANOYLAMINO]-3-O-[(R)-3-OCTANOYLOXYTETRADEcANOYL]-β-D-GLUCOPYRANOSYL]-L-SERINE TRIETHYLAMMONIUM SALT (COMPOUND (I), $R_1=R_2=R_3=$N—$C_7H_{15}$CO, X=Y=O, N=M=P=Q=0, $R_4=R_5=R_7=R_9=$H, $R_6=CO_2H$, $R_8=PO_3H_2$)

(1) In the same manner as described in Example 2-(5), L-serine benzyl ester (390 mg, 2.0 mmol) was acylated with (R)-3-octanoyloxytetradecanoic acid (815 mg, 2.2 mmol) in the presence of EDC.MeI (745 mg, 2.5 mmol) in $CH_2Cl_2$ to afford 1.02 g (93%) of N-[(R)-3-octanoyloxytetradecanoyl]-L-serine benzyl ester: mp 50–51° C.; $^1$H NMR (CDCl$_3$) δ 0.88 (t, 6 H, J=6.8 Hz), 1.1–1.7 (m, 30 H), 2.30 (t, 2 H, J=7.7 Hz), 2.51 (d, 2 H, J=5.8 Hz), 2.60 (t, 1 H, J=6.0 Hz), 3.97 (m, 2 H), 4.65 (m, 1 H), 5.22 (m, 3 H), 6.61 (d, 1 H, J=6.9 Hz), 7.35 (br s, 5 H).

(2) In the same manner as described in Example 2-(2), the compound prepared in Example 2-(1) (1.0 g, 2.02 mmol) was acylated with (R)-3-octanoyloxytetradecanoic acid (821 mg, 2.22 mmol) in the presence of EDC MeI (720 mg, 2.4 mmol) and 4-pyrrolidinopyridine (100 mg) in $CH_2Cl_2$, and then deprotected in 90% aqueous AcOH (25 mL) to afford 1.35 g (83%) of 2-(trimethylsilyl)ethyl 2-deoxy-3-O-[(R)-3-octanoyloxytetradecanoyl]-2-(2,2,2-trichloroethoxycarbonylamino)-β-D-glucopyranoside as an amorphous solid: $^1$H NMR ($CDCl_3$) δ 0.00 (s, 9 H), 0.88 (m, 8 H), 1.25 (m, 26 H), 1.60 (m, 4 H), 2.30 (t, 2 H, J=7.5 Hz), 2.53 (m, 2 H), 3.42 (m, 1 H), 3.53 (m, 1 H), 3.66 (m, 1 H), 3.83 (dd, 1 H, J=11.8, 4.4 Hz), 3.94 (m, 2 H), 4.56 (d, 1 H, J=8.3 Hz), 4.64 (d, 1 H, J=11.8 Hz), 4.77 (d, 1 H, J=11.8 Hz), 5.08 (m, 2 H), 5.30 (br. s, 1 H).

(3) In the same manner as described in Example 2-(3), the compound prepared in (2) above (1.30 g, 1.61 mmol) was treated with 2,2,2-trichloro-1,1-dimethylethyl chloroformate (425 mg, 1.77 mmol) and pyridine (0.16 mL, 1.95 mmol) in $CH_2Cl_2$ (25 mL) followed by triethylamine (0.45 mL, 3.22 mmol), diphenyl chlorophosphate (0.50 mL, 2.42 mmol) and 4-pyrrolidinopyridine (100 mg) to afford 1.42 g (71%) of 2-(trimethylsilyl)ethyl 2-deoxy-4-O-diphenylphosphono-3-O-[(R)-3-octanoyloxytetradecanoyl]-6-O-(2,2,2-trichloro-1,1-dimethylethoxycarbonyl)-2-(2,2,2-trichloroethoxycarbonylamino)-β-D-glucopyranoside as an amorphous solid: $^1$H NMR ($CDCl_3$) δ 0.0 (s, 9 H), 0.88 (m, 8 H), 1.1–1.7 (m, 30 H), 1.82 (s, 3 H), 1.89 (s, 3 H), 2.23 (m, 6 H), 3.37 (m, 1 H), 3.65 (m, 1 H), 3.83 (m, 1 H), 3.96 (m, 1 H), 4.55 (m, 2 H), 4.83 (d, 1 H, J=11.8 Hz), 5.01 (d, 1 H, J=8.2 Hz), 5.20 (m, 1 H), 7.29 (m, 10 H).

(4) In the same manner as described in Example 13-(4), the compound prepared in (3) above (1.24 g, 1.0 mmol) was deprotected with TFA (5 mL) and then treated with the Vilsmeier reagent generated from DMF (0.39 mL, 5.0 mmol) and oxalyl chloride (0.22 mL, 2.5 mmol) to give 1.0 g (87%) of 2-deoxy-4-O-diphenylphosphono-3-O-[(R)-3-octanoyloxytetradecanoyl]-6-O-(2,2,2-trichloro-1,1-dimethylethoxycarbonyl)-2-(2,2,2-trichloroethoxycarbonylamino)-α-D-glucopyranosyl chloride as a white foam: $^1$H NMR ($CDCl_3$) δ 0.88 (t, 6 H, J=6.7 Hz), 1.25–1.55 (m, 30 H), 1.78 (s, 3 H), 1.88 (s, 3 H), 2.18 (t, 2 H, J=7.7 Hz), 2.43 (m, 2 H), 4.29 (m, 4 H), 4.72 (m, 3 H), 5.09 (m, 1 H), 5.51 (t, 1 H, J=9.9 Hz), 5.79 (d, 1 H, J=7.9 Hz), 6.25 (d, 1 H, J=3.5 Hz), 7.29 (m, 10 H).

(5) In the same manner as described in Example 13-(5), compounds prepared in (1) and (4) above (490 mg, 0.90 mmol, and 1.0 g, 0.86 mmol, respectively) were coupled in the presence of AgOTf (1.16 g, 4.5 mmol) to afford 0.99 g (69%) of N-[(R)-3-octanoyloxytetradecanoyl]-O-[2-deoxy-4-O-diphenylphosphono-3-O-[(R)-3-octanoyloxytetradecanoyl]-6-O-(2,2,2-trichloro-1,1-dimethylethoxycarbonyl)-2-(2,2,2-trichloroethoxycarbonylamino)-β-D-glucopyranosyl]-L-serine benzyl ester: $^1$H NMR ($CDCl_3$) δ 0.88 (t, 12 H, J=6.9 Hz), 1.0–1.65 (m, 60 H), 1.77 (s, 3 H), 1.85 (s, 3 H), 2.1–2.5 (m, 8 H), 3.37 (m, 1 H), 3.65 (m, 1 H), 3.83 (m, 1 H), 4.27 (m, 3 H), 4.72 (m, 5 H), 5.18 (m, 4 H), 5.46 (t, 1 H, J=9.8 Hz), 6.06 (m, 1 H), 6.60 (d, 1 H, J=8.0 Hz), 7.05–7.45 (m, 15 H).

(6) In the same manner as described in Example 2-(7), the compound prepared in (5) above (0.95 g, 0.57 mmol) was deprotected with zinc (1.86 g, 28.5 mmol) and acylated with (R)-3-octanoyloxytetradecanoic acid (252 mg, 0.68 mmol) in the presence of EEDQ (185 mg, 0.75 mmol) to afford 433 mg (47%) of N-[(R)-3-octanoyloxytetradecanoyl]-O-[2-deoxy-4-O-diphenylphosphono-2-[(R)-3-octanoyloxytetradecanoylamino]-3-O-[(R)-3-octanoyloxytetradecanoyl]-β-D-glucopyranosyl]-L-serine benzyl ester as an amorphous solid.

(7) In the same manner as described in Example 2-(8), the compound prepared in (6) above (433 mg, 0.27 mmol) was hydrogenated in the presence of palladium hydroxide on carbon (250 mg) in EtOH (10 mL) and platinum oxide (400 mg) in EtOH/AcOH (10:1) to afford 196 mg (48%) of N-[(R)-3-octanoyloxytetradecanoyl]-O-[2-deoxy-4-O-phosphono-2-[(R)-3-octanoyloxytetradecanoylamino]-3-O-[(R)-3-octanoyloxytetradecanoyl]-β-D-glucopyranosyl]-L-serine triethylammonium salt as a white powder: mp 177–178° C.; IR (film) 3296, 2956, 2923, 2853, 1732, 1645, 1546, 1466, 1378, 1315, 1170, 1082, 1056, 961, 846, 722 $cm^{-1}$; $^1$H NMR ($CDCl_3$-$CD_3OD$) δ 0.88 (t, 18 H, J=6.6 Hz), 1.1–1.7 (m, 99 H), 2.2–2.75 (m, 12 H), 3.08 (q, 6 H, J=7.1 Hz), 3.39 (d, 1 H, J=8.8 Hz), 3.6–4.0 (m, 8 H), 4.22 (q, 1 H, 10.3 Hz), 4.53 (d, 1 H, J=8.2 Hz), 4.63 (m, 1 H), 5.18 (m, 4 H), 7.04 (d, 1 H, J=8.8 Hz), 7.42 (d, 1 H, J=8.0 Hz); $^{13}$C NMR ($CDCl_3$) δ 176.8, 173.3, 173.2, 172.7, 172.2, 169.6, 169.1, 101.5, 74.8, 70.9, 70.8, 69.3, 60.5, 53.2, 51.5, 46.2, 41.5, 41.1, 39.2, 34.5, 34.3, 34.1, 34.0, 32.0, 31.8, 29.8, 29.6, 29.4, 29.3, 29.2, 29.1, 25.6, 25.3, 25.2, 25.0, 22.7, 14.1, 8.7.

Anal. Calcd. for $C_{81}H_{154}N_3O_{19}P$ $H_2O$: C, 63.87; H, 10.32; N, 2.76; P, 2.03. Found: C, 63.96; H, 10.29; N, 2.69; P, 1.67.

EXAMPLE 19 (B18)

PREPARATION OF N-[(R)-3-HEPTANOYLOXYTETRADE-CANOYL]-O-[2-DEOXY-4-O-PHOSPHONO-2-[(R)-3-HEP-TANOYLOXYTETRADECANOYLAMINO]-3-O-[(R)-3-HEPTANOY-LOXYTETRADECANOYL]-β-D-GLUCOPYRANOSYL]-L-SERINE TRIETHYLAMMONIUM SALT (COMPOUND (I), $R_1$=$R_2$=$R_3$=N—$C_6H_{13}$CO, X=Y=O, N=M=P=Q=0, $R_4$=$R_5$=$R_7$=$R_9$=H, $R_6$=$CO_2$H, $R_8$=$PO_3H_2$).

(1) In the same manner as described in Example 2-(5), L-serine benzyl ester (390 mg, 2.0 mmol) was acylated with (R)-3-heptanoyloxytetradecanoic acid (780 mg, 2.2 mmol) in the presence of EDC.MeI (745 mg, 2.5 mmol) in $CH_2Cl_2$ to afford 0.97 g (91%) of N-[(R)-3-heptanoyloxytetradecanoyl]-L-serine benzyl ester: mp 46–48° C.; $^1$H NMR ($CDCl_3$) δ 0.88 (t, 6 H, J=6.9 Hz), 1.1–1.7 (m, 28 H), 2.30 (t, 2 H, J=7.7 Hz), 2.50 (d, 2 H, J=5.8 Hz), 2.62 (t, 1 H, J=6.0 Hz), 3.97 (m, 2 H), 4.65 (m, 1 H), 5.19 (m, 3 H), 6.61 (d, 1 H, J=6.9 Hz), 7.35 (br s, 5 H).

(2) In the same manner as described in Example 2-(2), the compound prepared in Example 2-(1) (1.0 g, 2.02 mmol) was acylated with (R)-3-heptanoyloxytetradecanoic acid (790 mg, 2.22 mmol) in the presence of EDC.MeI (720 mg, 2.4 mmol) and 4-pyrrolidinopyridine (100 mg) in $CH_2Cl_2$, and then deprotected in 90% aqueous AcOH (25 mL) to afford 1.30 g (81%) of 2-(trimethylsilyl)ethyl 2-deoxy-3-O-[(R)-3-heptanoyloxytetradecanoyl]-2-(2,2,2-trichloroethoxycarbonylamino)-β-D-glucopyranoside as an amorphous solid: $^1$H NMR ($CDCl_3$) δ 0.00 (s, 9 H), 0.88 (m, 8 H), 1.25 (m, 24 H), 1.59 (m, 4 H), 2.30 (t, 2 H, J=7.5 Hz), 2.52 (m, 2 H), 3.42 (m, 1 H), 3.55 (m, 1 H), 3.66 (m, 1 H), 3.83 (dd, 1 H, J=11.5, 4.2 Hz), 3.94 (m, 2 H), 4.57 (d, 1 H, J=8.3 Hz), 4.64 (d, 1 H, J=12.1 Hz), 4.76 (d, 1 H, J=11.9 Hz), 5.09 (m, 2 H), 5.31 (d, 1 H, J=8.7 Hz).

(3) In the same manner as described in Example 2-(3), the compound prepared in (2) above (1.25 g, 1.58 mmol) was treated with 2,2,2-trichloro-1,1-dimethylethyl chloroformate (417 mg, 1.74 mmol) and pyridine (0.15 mL, 1.91 mmol) in CH$_2$Cl$_2$ (25 mL) followed by triethylamine (0.44 mL, 3.16 mmol), diphenyl chlorophosphate (0.49 mL, 2.37 mmol) and 4-pyrrolidinopyridine (100 mg) to afford 1.34 g (69%) of 2-(trimethylsilyl)ethyl 2-deoxy-4-O-diphenylphosphono-3-O-[(R)-3-heptanoyloxytetradecanoyl]-6-O-(2,2,2-trichloro-1,1-dimethylethoxycarbonyl)-2-(2,2,2-trichloroethoxycarbonylamino)-β-D-glucopyranoside as an amorphous solid: $^1$H NMR (CDCl$_3$) δ 0.0 (s, 9 H), 0.88 (m, 8 H), 1.1–1.7 (m, 28 H), 1.82 (s, 3 H), 1.89 (s, 3H), 2.35 (m, 4 H), 3.37 (m, 1 H), 3.61 (m, 1 H), 3.80 (m, 1 H), 4.32 (m, 2 H), 4.63 (m, 1 H), 4.83 (d, 1 H, J=12.0 Hz), 5.01 (d, 1 H, J=8.2 Hz), 5.62 (m, 2 H), 7.29 (m, 10 H).

(4) In the same manner as described in Example 13-(4), the compound prepared in (3) above (1.23 g, 1.0 mmol) was deprotected with TFA (5 mL) and then treated with the Vilsmeier reagent generated from DMF (0.39 mL, 5.0 mmol) and oxalyl chloride (0.22 mL, 2.5 mmol) to give 1.0 g (87%) of 2-deoxy-4-O-diphenylphosphono-3-O-[(R)-3-heptanoyloxytetradecanoyl]-6-O-(2,2,2-trichloro-1,1dimethylethoxycarbonyl)-2-(2,2,2-trichloroethoxycarbonylamino)-α-D-glucopyranosyl chloride as a white foam: $^1$H NMR (CDCl$_3$) δ 0.88 (t, 6 H, J=6.9 Hz), 1.25–1.55 (m, 28 H), 1.78 (s, 3 H), 1.88 (s, 3 H), 2.18 (t, 2 H, J=7.6 Hz), 2.43 (m, 2 H), 4.26 (m, 4H), 4.73 (m, 3 H), 5.09 (m, 1 H), 5.51 (t, 1 H, J=10.2 Hz), 5.77 (d, 1 H, J=8.0 Hz), 6.25 (d, 1 H, J=3.3 Hz), 7.19 (m, 10 H).

(5) In the same manner as described in Example 13-(5), compounds prepared in (1) and (4) above (480 mg, 0.90 mmol, and 0.98 g, 0.86 mmol, respectively) were coupled in the presence of AgOTf (1.16 g, 4.5 mmol) to afford 1.06 g (75%) of N-[(R)-3-heptanoyloxytetradecanoyl]-O-[2-deoxy-4-O-diphenyl phosphono-3-O-[(R)-3-heptanoyloxytetradecanoyl]-6-O-(2,2,2-trichloro-1,1-dimethylethoxycarbonyl)-2-(2,2,2-trichloroethoxycarbonylamino)-β-D-glucopyranosyl]-L-serine benzyl ester: $^1$H NMR (CDCl$_3$) δ 0.88 (m, 12 H), 1.0–1.65 (m, 56 H), 1.77 (s, 3 H), 1.85 (s, 3 H), 2.1–2.5 (m, 8 H), 3.38 (m, 1 H), 3.64 (m, 1 H), 3.83 (m, 1 H), 4.25 (m, 3 H), 4.78 (m, 5 H), 5.16 (m, 4 H), 5.46 (t, 1 H, J=9.9 Hz), 6.06 (m, 1 H), 6.60 (d, 1 H, J=7.7 Hz), 7.05–7.45 (m, 15 H).

(6) In the same manner as described in Example 2-(7), the compound prepared in (5) above (1.0 g, 0.61 mmol) was deprotected with zinc (2.0 g, 30.5 mmol) and acylated with (R)-3-heptanoyloxytetradecanoic acid (260 mg, 0.73 mmol) in the presence of EEDQ (200 mg, 0.80 mmol) to afford 440 mg (45%) of N-[(R)-3-heptanoyloxytetradecanoyl]-O-[2-deoxy-4-O-diphenylphosphono-2-[(R)-3-heptanoyloxytetradecanoylamino]-3-O-[(R)-3-heptanoyloxytetradecanoyl]-β-D-glucopyranosyl]-L-serine benzyl ester as an amorphous solid.

(7) In the same manner as described in Example 2-(8), the compound prepared in (6) above (440 mg, 0.28 mmol) was hydrogenated in the presence of palladium hydroxide on carbon (250 mg) in EtOH (10 mL) and platinum oxide (400 mg) in EtOH/AcOH (10:1) to afford 208 mg (51%) of N-[(R)-3-heptanoyloxytetradecanoyl]-O-[2-deoxy-4-O-phosphono-2-[(R)-3-heptanoyloxytetradecanoylamino]-3-O-[(R)-3-heptanoyloxytetradecanoyl]-β-D-glucopyranosyl]-L-serine triethylammonium salt as a white powder: mp 176–177° C.; IR (film) 3307, 2956, 2924, 2854, 1732, 1650, 1545, 1466, 1378, 1316, 1170, 1080, 956, 841, 722 cm$^{-1}$; $^1$H NMR (CDCl$_3$-CD$_3$OD) δ 0.88 (m, 18 H), 1.1–1.7 (m, 93 H), 2.2–2.75 (m, 12 H), 3.08 (q, 6 H, J=7.2 Hz), 3.40 (d, 1 H, J=10.2 Hz), 3.6–4.0 (m, 7H), 4.24 (m, 2 H), 4.52 (d, 1 H, J=8.0 Hz), 4.63 (m, 1 H), 5.19 (m, 4 H), 7.04 (d, 1 H, J=8.6 Hz), 7.40 (d, 1 H, J=8.4 Hz); $^{13}$C NMR (CDCl$_3$) δ 177.1, 173.2, 173.1, 172.7, 172.3, 169.5, 168.9, 101.5, 75.0 74.8, 71.2, 70.9, 69.1, 60.5, 53.1, 51.4, 46.1, 41.5, 41.0, 39.2, 34.5, 34.3, 34.1, 34.0, 31.9, 31.6, 31.5, 29.8, 29.6, 29.4, 29.0, 28.9, 28.8, 25.6, 25.3, 25.1, 25.0, 22.7, 22.6, 14.1, 8.7.

Anal. Calcd. for C$_{78}$H$_{148}$N$_3$O$_{19}$P: C, 64.04; H, 10.20; N, 2.87; P, 2.12. Found: C, 63.77; H, 10.11; N, 2.85; P, 2.02.

EXAMPLE 20 (B 19)

PREPARATION OF 2-[(R)-3-TETRADECANOYLOXYTETRADECANOYLAMINO]ETHYL 2-DEOXY-4-O-PHOSPHONO-3-O-[(R)-3-TETRADECANOYOXYTETRADECANOYL]-2-[(R)-3-TETRADECANOYOXYTETRADECANOYLAMINO]-β-D-GLUCOPYRANOSIDE TRIETHYLAMMONIUM SALT (COMPOUND (I), R$_1$=R$_2$=R$_3$=N—C$_{13}$H$_{27}$CO, X=Y=O, n=m=p=q=0, R$_4$=R$_5$=R$_6$=R$_7$=R$_9$=H, R$_8$=PO$_3$H$_2$)

(1) 2-Amino-1-(t-butyldiphenylsilyloxy)ethane (330 mg, 1.1 mmol) and (R)-3-tetradecanoyloxytetradecanoic acid (500 mg, 1.1 mmol) were dissolved in CH$_2$Cl$_2$ (10 mL) and treated with powdered 4 A molecular sieves (500 mg). After 1 h EEDQ (297 mg, 1.2 mmol) was added and the reaction was stirred for 18 h, filtered through Celite® and concentrated in vacuo. The residue was chromatographed over silica gel using 15% EtOAc/hexanes to give 675 mg (92%) of a colorless solid. A portion of this material (500 mg, 0.68 mmol) was deprotected with TBAF (1 M in THF, 1 mL, 1 mmol) in THF (5 mL) by stirring at room temperature for 2 h. The reaction mixture was diluted with Et$_2$O (50 mL) and washed with brine (2×50 mL). The brine was back extracted with Et$_2$O (2×50 mL) and the combined organic extracts were dried over Na$_2$SO$_4$ and concentrated in vacuo to afford 338 mg (62%) of 2-[(R)-3-tetradecanoyloxytetradecanoylamino]ethanol as an off-white solid.

(2) In the same manner as described in Example 2-(6), the compound prepared in (1) above (338 mg, 0.68 mmol) and the compound prepared in Example 2-(4) (786 mg, 0.61 mmol) were coupled in the presence of mercury cyamide (770 mg, 3.05 mmol) to give 245 mg (24%) of 2-[(R)-3-tetradecanoyloxytetradecanoylamino]ethyl 2-deoxy-4-O-diphenylphosphono-3-O-[(R)-3-tetradecanoyoxytetradecanoyl]-6-O-(2,2,2-trichloro-1,1-dimethylethoxycarbonyl)-2-(2,2,2-trichloroethoxycarbonylamino)-β-D-glucopyranoside as an amorphous solid: $^1$H NMR (CDCl$_3$) δ 0.88 (t, 12 H, J=6.9 Hz), 1.1–1.8 (m, 84 H), 1.81 (s, 3 H), 1.89 (s, 3 H), 2.15–2.55 (m, 8 H), 3.25 (m, 1 H), 3.47 (m, 2 H), 3.67 (m, 1 H), 3.83 (m, 2 H), 4.28 (dd, 1 H, J=12.2, 4.9 Hz), 4.36 (d, 1 H, J=11.0 Hz), 4.68 (m, 2 H), 4.78 (d, 1 H, J=11.6 Hz), 4.94 (d, 1 H, J=11.6 Hz), 5.16 (m, 2 H), 5.53 (t, 1 H, J=10.0 Hz), 6.06 (d, 1 H, J=4.9 Hz), 6.19 (m, 1 H), 7.25 (m, 10 H).

(3) In the same manner as described in Example 2-(7), the compound prepared in (2) above (500 mg, 0.29 mmol) was deprotected with zinc (980 mg, 15 mmol) and then acylated with (R)-3-tetradecanoyloxytetradecanoic acid (155 mg, 0.34 mmol) in the presence of EEDQ (110 mg, 0.44 mmol) to give 315 mg (62%) of 2-[(R)-3-tetradecanoyloxytetradecanoylamino]ethyl 2-deoxy-4-O-diphenylphosphono-3-O-[(R)-3-tetradecanoyoxytetradecanoyl]-2-[(R)-3-tetradecanoyoxytetradecanoylamino]-β-D-glucopyranoside as an amorphous solid.

(4) In the same manner as described in Example 2-(8), the compound prepared in (3) above (200 mg, 0.113 mmol) was hydrogenated in the presence of platinum oxide (100 mg) to give 142 mg (76%) of 2-[(R)-3-tetradecanoyloxytetradecanoylamino]ethyl 2-deoxy-4-O-phosphono-3-O-[(R)-3-tetradecanoyoxytetradecanoyl]-2-[(R)-3-tetradecanoyoxytetradecanoylamino]-β-D-glucopyranoside triethylammonium salt as a white solid: mp 175–176° C.; IR (film) 3285, 3098, 2955, 2919, 2851, 1731, 1659, 1642, 1556, 1468, 1379, 1250, 1228, 1174, 1110, 1083, 1046, 962, 857 cm$^{-1}$; $^1$H NMR (CDCl$_3$-CD$_3$OD) δ 0.88 (t, 18 H, J=6.0 Hz), 1.1–1.7 (m, 135 H), 2.2–2.7 (m, 15 H), 3.06 (q, 6 H, J=7.1 Hz), 3.2–4.1 (m, 8 H), 4.21 (q, 1 H, J=9.9 Hz), 4.51 (d, 1 H, J=8.2 Hz), 5.05–5.25 (m, 4 H), 7.33 (d, 1 H, J=8.5 Hz), 7.50 (br t, 1 H, J=4.8 Hz); $^{13}$C NMR (CDCl$_3$) δ 173.7, 173.3, 170.6, 170.3, 169.9, 100.9, 75.8, 73.0, 71.3, 71.1, 70.9, 70.6, 68.3, 60.6, 55.1, 45.7, 41.6, 41.2, 39.5, 34.6, 34.5, 34.2, 32.0, 29.8, 29.4, 29.3, 25.4, 25.1, 22.7, 14.2, 8.6.

Anal. Calcd. for C$_{98}$H$_{190}$N$_3$O$_{17}$P.2 H$_2$O: C, 67.28; H, 11.18; N, 2.40; P, 1.77. Found: C, 67.01; H, 11.18; N, 2.15; P, 2.01.

EXAMPLE 21 (B20)

PREPARATION OF 2-[(R)-3-DECANOYLOXYTETRADECANOYLAMINO]ETHYL 2-DEOXY-4-O-PHOSPHONO-3-O-[(R)-3-DECANOYOXYTETRADECANOYL]-2-[(R)-3-DECANOYLOXYTETRADECANOYLAMINO]-β-D-GLUCOPYRANOSIDE TRIETHYLAMMONIUM SALT (COMPOUND (I), R$_1$=R$_2$=R$_3$=N—C$_9$H$_{19}$CO, X=Y=O, N=M=P=Q=0, R$_4$=R$_5$=R$_6$=R$_7$=R$_9$=H, R$_8$=PO$_3$H$_2$).

(1) In the same manner as described in Example 20-(1), 2-amino-1-(t-butyldiphenylsilyloxy)ethane (450 mg, 1.5 mmol) was acylated with (R)-3-decanoyloxytetradecanoic acid (600 mg, 1.5 mmol) in the presence of EDC.MeI (594 mg, 2.0 mmol) and then deprotected with TBAF (1.0 M in THF, 2.5 mL, 2.5 mmol) in THF (10 mL) to afford 488 mg (81%) of 2-[(R)-3-decanoyloxytetradecanoylamino]ethanol as an off-white solid.

(2) In the same manner as described in Example 13-(5), the compound prepared in (1) above (385 g, 0.87 mmol) and the compound prepared in Example 15-(4) (1.05 g, 0.87 mmol) were coupled in the presence of AgOTf (560 mg, 2.2 mmol) to give 1.04 g (74%) of 2-[(R)-3-decanoyloxytetradecanoylamino]ethyl 2-deoxy-4-O-diphenylphosphono-3-O-[(R)-3-decanoyoxytetradecanoyl]-6-O-(2,2,2-trichloro-1,1-dimethylethoxycarbonyl)-2-(2,2,2-trichloroethoxycarbonylamino)-β-D-glucopyranoside as an amorphous solid: $^1$H NMR (CDCl$_3$) δ 0.88 (t, 12 H, J=6.9 Hz), 1.1–1.6 (m, 68 H), 1.78 (s, 3 H), 1.88 (s, 3 H), 2.18 (t, 2 H, J=7.7 Hz), 2.44 (m, 2 H), 4.34 (m, 5 H), 4.72 (m, 2 H), 4.83 (q, 1 H, J=9.3 Hz), 5.09 (m, 1 H), 5.51 (t, 1 H, J=10.2 Hz), 5.79 (d, 1 H, J=8.0 Hz), 6.26 (d, 1 H, J=3.4 Hz), 7.31 (m, 10 H).

(3) In the same manner as described in Example 2-(7), the compound prepared in (2) above (700 mg, 0.44 mmol) was deprotected with zinc (1.42 g, 21.7 mmol) and then acylated with (R)-3-decanoyloxytetradecanoic acid (190 mg, 0.48 mmol) in the presence of EEDQ (148 mg, 0.6 mmol) to give 432 mg (62%) of 2-[(R)-3-decanoyloxytetradecanoylamino]ethyl 2-deoxy-4-O-diphenylphosphono-3-O-[(R)-3-decanoyoxytetradecanoyl]-2-[(R)-3-decanoyloxytetradecanoylamino]-β-D-glucopyranoside as an amorphous solid.

(4) In the same manner as described in Example 2-(8), the compound prepared in (3) above (400 mg, 0.25 mmol) was hydrogenated in the presence of platinum oxide (200 mg) to give 200 mg (52%) of 2-[(R)-3-decanoyloxytetradecanoylamino]ethyl 2-deoxy-4-O-phosphono-3-O-[(R)-3-decanoyoxytetradecanoyl]-2-[(R)-3-decanoyloxytetradecanoylamino]-β-D-glucopyranoside triethylammonium salt as a white solid: mp 165–166° C.; IR (film) 3289, 3094, 2956, 2922, 2853, 1732, 1658, 1644, 1556, 1467, 1379, 1247, 1164, 1107, 1081, 1048 cm$^{-1}$; $^1$H NMR (CDCl$_3$-CD$_3$OD) δ 0.88 (t, 18 H, J=6.9 Hz), 1.1–1.7 (m, 111 H), 2.2–2.7 (m, 15 H), 3.05 (q, 6 H, J=7.1 Hz), 3.2–3.85 (m, 9 H), 4.52 (d, 1 H, J=8.2 Hz), 5.05–5.25 (m, 4 H), 7.21 (d, 1 H, J=8.5 Hz), 7.42 (br t, 1 H); $^{13}$C NMR (CDCl$_3$) δ 173.8, 173.3, 170.7, 170.3, 170.0, 100.9, 75.6, 73.0, 71.3, 70.9, 70.6, 68.3, 60.7, 55.0, 45.8, 41.6, 41.2, 39.5, 34.5, 34.4, 34.1, 31.9, 29.8, 29.6, 29.5, 29.4, 25.4, 25.1, 22.7, 14.2, 8.6.

Anal. Calcd. for C$_{86}$H$_{166}$N$_3$O$_{17}$P H$_2$O: C, 66.08; H, 10.83; N, 2.69; P, 1.98. Found: C, 65.80; H, 10.63; N, 2.63; P, 2.04.

EXAMPLE 22 (B21)

PREPARATION OF 3-[(R)-3-TETRADECANOYLOXYTETRADECANOYLAMINO]PROPYL 2-DEOXY-4-O-PHOSPHONO-3-O-[(R)-3-TETRADECANOYOXYTETRADECANOYL]-2-[(R)-3-TETRADECANOYLOXYTETRADECANOYLAMINO]-β-D-GLUCOPYRANOSIDE TRIETHYLAMMONIUM SALT (COMPOUND (I), R$_1$=R$_2$=R$_3$=N—C$_{13}$H$_{27}$CO, X=Y=O, N=1, M=P=Q=0, R$_4$=R$_5$=R$_6$=R$_7$=R$_9$=H, R$_8$=PO$_3$H$_2$)

(1) In the same manner as described in Example 20-(1), 3-amino-1-(t-butyldiphenylsilyloxy)propane (470 mg, 1.5 mmol) was acylated with (R)-3-tetradecanoyloxytetradecanoic acid (680 mg, 1.5 mmol) in the presence of EDC MeI (595 mg, 2.0 mmol) and then deprotected with TBAF (1.0 M in THF, 2.0 mL, 2.0 mmol) in THF (10 mL) to afford 698 mg (91%) of 3-[(R)-3-tetradecanoyloxytetradecanoylamino]-1-propanol as an off-white solid.

(2) In the same manner as described in Example 13-(4), the compound prepared in Example 2-(3) (7.9 g, 5.88 mmol) was deprotected with TFA (10 mL) and then treated with the Vilsmeier reagent generated from DMF (1.8 mL, 23.5 mmol) and oxalyl chloride (1.03 mL, 11.76 mmol) in CH$_2$Cl$_2$ (60 mL) to give 6.32 g (85%) of 2-deoxy-4-O-diphenylphosphono-3-O-[(R)-3-tetradecanoyloxytetradecanoyl]-6-O-(2,2,2-trichloro-1,1-dimethylethoxycarbonyl)-2-(2,2,2-trichloroethoxycarbonylamino)-α-D-glucopyranosyl chloride as a white foam: $^1$H NMR (CDCl$_3$) δ 0.88 (t, 6 H, J=6.8 Hz), 1.2–1.55 (m, 42 H), 1.78 (s, 3 H), 1.88 (s, 3 H), 2.18 (t, 2 H, J=7.5 Hz), 2.43 (m, 2 H), 4.31 (m, 4 H), 4.68 (d, 1 H, J=11.9 Hz), 4.74 (d, 1 H, J=11.9 Hz), 4.83 (q, 1 H, J=9.3 Hz), 5.09 (m, 1 H), 5.51 (t, 1 H, J=9.7 Hz), 5.78 (d, 1 H, J=8.0 Hz), 6.26 (d, 1 H, J=3.4 Hz), 7.31 (m, 10 H).

(3) In the same manner as described in Example 13-(5), the compound prepared in (1) above (613 mg, 1.2 mmol) and the compound prepared in (2) above (1.5 g, 1.2 mmol) were coupled in the presence of AgOTf (642 mg, 2.5 mmol) to give 1.43 g (68%) of 3-[(R)-3-tetradecanoyloxytetradecanoylamino]propyl 2-deoxy-4-O-diphenylphosphono-3-O-[(R)-3-tetradecanoyoxytetradecanoyl]-6-O-(2,2,2-trichloro-1,1-dimethylethoxycarbonyl)-2-(2,2,2-trichloroethoxycarbonylamino)-β-D-glucopyranoside as an amorphous solid: $^1$H NMR (CDCl$_3$) δ 0.88 (t, 12 H, J=6.9 Hz), 1.1–1.8 (m, 86 H), 1.82 (s, 3 H), 1.89 (s, 3 H), 2.20 (t, 2 H, J=7.6 Hz), 2.29 (t, 2 H, J=7.7 Hz), 2.44 (m, 4 H), 3.21 (m, 1 H), 3.42 (m, 1 H), 3.54 (m, 2 H), 3.80 (m, 1 H), 3.94 (m, 1 H), 4.28 (dd, 1 H, J=12.3, 5.2 Hz), 4.38 (d, 1 H, J=10.8 Hz), 4.70 (m, 3 H), 4.81 (d, 1 H, J=8.2 Hz), 5.14 (m, 2 H), 5.47 (t, 1 H, J=9.6 Hz), 6.13 (d, 1 H, J=7.6 Hz), 6.22 (br. s, 1 H), 7.25 (m, 10 H).

(4) In the same manner as described in Example 2-(7), the compound prepared in (3) above (700 mg, 0.40 mmol) was deprotected with zinc (1.32 g, 20.1 mmol) and then acylated with (R)-3-tetradecanoyloxytetradecanoic acid (200 mg, 0.44 mmol) in the presence of EEDQ (125 mg, 0.5 mmol) to give 435 mg (60%) of 3-[(R)-3-tetradecanoyloxytetradecanoylamino]propyl 2-deoxy-4-O-diphenylphosphono-3-O-[(R)-3-tetradecanoyoxytetradecanoyl]-2-[(R)-3-tetradecanoyloxytetradecanoylamino])-β-D-glucopyranoside as an amorphous solid.

(5) In the same manner as described in Example 2-(8), the compound prepared in (4) above (400 mg, 0.22 mmol) was hydrogenated in the presence of platinum oxide (200 mg) to give 170 mg (45%) of 3-[(R)-3-tetradecanoyloxytetradecanoylamino]propyl 2-deoxy-4-O-phosphono-3-O-[(R)-3-tetradecanoyoxytetradecanoyl]-2-[(R)-3-tetradecanoyloxytetradecanoylaminol)-β-D-glucopyranoside triethylammonium salt as a white solid: mp 171–172° C.; IR (film) 3288, 3094, 2955, 2919, 2850,1731, 1658,1344, 1556, 1468, 1378, 1320, 1251, 1226, 1172, 1106, 1083, 1044 cm$^{-1}$; $^1$H NMR (CDCl$_3$-CD$_3$OD) δ 0.88 (t, 18 H, J=6.0 Hz), 1.1–1.7 (m, 135 H), 2.2–2.7 (m, 15 H), 3.06 (q, 6 H, J=7.1 Hz), 3.2–4.1 (m, 8 H), 4.21 (q, 1 H, J=9.9 Hz), 4.51 (d, 1 H, J=8.3 Hz), 5.05–5.25 (m, 4 H), 7.23 (t, 1 H, J=5.3 Hz), 7.33 (d, 1 H, J=8.6 Hz); $^{13}$C NMR (CDCl$_3$) δ 173.5, 173.4, 170.6, 170.2, 169.9, 100.6, 75.8, 71.5, 70.9, 70.5, 66.8, 60.4, 55.3, 45.6, 41.4, 39.4, 36.3, 34.6, 34.5, 34.2, 31.9, 29.7, 29.4, 29.3, 29.1, 25.4, 25.1, 22.7, 14.1, 8.5.

Anal. Calcd. for C$_{99}$H$_{192}$N$_3$O$_{17}$P 2 H$_2$O: C, 67.42; H, 11.20; N, 2.38; P, 1.76. Found: C, 66.97; H, 11.01; N, 2.38; P, 1.95.

EXAMPLE 23 (B22)

Preparation of 4-[(R)-3-Tetradecanoyloxytetradecanoylamino]butyl 2-Deoxy-4-O-phosphono-3-O-[(R)-3-tetradecanoyoxytetradecanoyl]-2-[(R)-3-tetradecanoyloxytetradecanoylamino])-β-D-glucopyranoside Triethylammonium Salt(Compound (I), R$_1$=R$_2$=R$_3$=N—C$_{13}$H$_{27}$CO, X=Y=O, n=2, m=p=q=0, R$_4$=R$_5$=R$_6$=R$_7$=R$_9$=H, R$_8$=PO$_3$H$_2$)

(1) In the same manner as described in Example 20-(1), 4-amino-1-(t-butyldiphenylsilyloxy)butane (500 mg, 1.53 mmol) was acylated with (R)-3-tetradecanoyloxytetradecanoic acid (695 mg, 1.53 mmol) in the presence of EDC-MeI (595 mg, 2.0 mmol) and then deprotected with TBAF (1.0 M in THF, 2.5 mL, 2.5 mmol) in THF (15 mL) to afford 651 mg (81%) of 4-[(R)-3-tetradecanoyloxytetradecanoylamino]-1-butanol as an off-white solid.

(2) In the same manner as described in Example 13-(5), the compound prepared in (1) above (650 mg, 1.25 mmol) and the compound prepared in Example 22-(2) (1.6 g, 1.25 mmol) were coupled in the presence of AgOTf (1.16 g, 4.5 mmol) to give 1.65 g (75%) of 4-[(R)-3-tetradecanoyloxytetradecanoylamino]butyl 2-deoxy-4-O-diphenylphosphono-3-O-[(R)-3-tetradecanoyoxytetradecanoyl]-6-O-(2,2,2-trichloro-1,1-dimethylethoxycarbonyl)-2-(2,2,2-trichloroethoxycarbonylamino)-β-D-glucopyranoside as an amorphous solid: $^1$H NMR (CDCl$_3$) δ 0.88 (t, 12 H, J=6.9 Hz), 1.1–1.8 (m, 88 H), 1.82 (s, 3 H), 1.89 (s, 3 H), 2.15–2.55 (m, 8 H), 3.24 (m, 2H), 3.50 (m, 2 H), 3.83 (m, 2 H), 4.27 (dd, 1 H, J=12.1, 3.8 Hz), 4.32 (d, 1 H, J=11.5 Hz), 4.66 (m, 2 H), 4.78 (d, 1 H, J=12.1 Hz), 4.89 (d, 1 H, J=8.0 Hz), 5.15 (m, 2 H), 5.54 (t, 1 H, J=9.7 Hz), 5.95 (m, 2 H), 7.25 (m, 10H).

(3) In the same manner as described in Example 2-(7), the compound prepared in (2) above (700 mg, 0.39 mmol) was deprotected with zinc (1.30 g, 19.8 mmol) and then acylated with (R)-3-tetradecanoyloxytetradecanoic acid (195 mg, 0.43 mmol) in the presence of EEDQ (125 mg, 0.5 mmol) to give 421 mg (60%) of 4-[(R)-3-tetradecanoyloxytetradecanoylamino]butyl 2-deoxy-4-O-diphenylphosphono-3-O-[(R)-3-tetradecanoyoxytetradecanoyl]-2-[(R)-3-tetradecanoyloxytetradecanoylamino])-β-D-glucopyranoside as an amorphous solid.

(4) In the same manner as described in Example 2-(8), the compound prepared in (3) above (400 mg, 0.22 mmol) was hydrogenated in the presence of platinum oxide (200 mg) to give 212 mg (55%) of 4-[(R)-3-tetradecanoyloxytetradecanoylamino]butyl 2-deoxy-4-O-phosphono-3-O-[(R)-3-tetradecanoyoxytetradecanoyl]-2-[(R)-3-tetradecanoyloxytetradecanoylamino])-β-D-glucopyranoside triethylammonium salt as a white solid: mp 171–172° C.; IR (film) 3298, 2955, 2920, 2851, 1732, 1645, 1550, 1467, 1378, 1181, 1107, 1083, 1044, 721 cm$^{-1}$; $^1$H NMR (CDCl$_3$-CD$_3$OD) δ 0.88 (t, 18 H, J=6.9 Hz), 1.1–1.7 (m, 135 H), 2.2–2.7 (m, 19 H), 3.05 (q, 6 H, J=7.1 Hz), 3.18 (m, 2 H), 3.3–3.5 (m, 6 H), 3.78 (m, 3 H), 3.97 (d, 1 H, J=12.5 Hz), 4.23 (q, 1 H, J=10.0 Hz), 4.50 (d, 1 H, J=8.5 Hz), 5.13 (m, 4 H), 7.12 (d, 1 H, J=9.1 Hz); $^{13}$C NMR (CDCl$_3$) δ 173.9, 173.4, 173.3, 170.8, 169.9, 169.8, 101.0, 75.6, 73.2, 71.4, 71.1, 70.6, 68.9, 60.7, 54.8, 45.9, 41.5, 39.6, 38.9, 34.6, 34.3, 32.0, 29.8, 29.5, 29.0, 28.9, 26.3, 25.4, 25.1, 22.7, 14.2, 8.7.

Anal. Calcd. for C$_{100}$H$_{194}$N$_3$O$_{17}$P.H$_2$O: C, 68.26; H, 11.23; N, 2.39; P, 1.76. Found: C, 68.21; H, 11.03; N, 2.26; P, 1.73.

EXAMPLE 24 (B23)

Preparation of 4-[(R)-3-Tetradecanoyloxytetradecanoylamino]hexyl 2-Deoxy-4-O-phosphono-3-O-[(R)-3-tetradecanoyoxytetradecanoyl]-2-[(R)-3-Tetradecanoyloxytetradecanoylamino]-β-D-glucopyranoside Triethylammonium Salt (Compound (I), R$_1$=R$_2$=R$_3$=N—C$_{13}$H$_{27}$CO, X=Y=O, n=4, m=p=q=0, R$_4$=R$_5$=R$_6$=R$_7$=R$_9$=H, R$_8$=PO$_3$H$_2$)

(1) In the same manner as described in Example 20-(1), 6-amino-1-(t-butyldiphenylsilyloxy)hexane (1.48 g, 4.15 mmol) was acylated with (R)-3-tetradecanoyloxytetradecanoic acid (2.07 g, 4.56 mmol) in the presence of EDC-MeI (1.35 g, 4.56 mmol) and then deprotected with TBAF (1.0 M in THF, 1.53 mL, 1.53 mmol) in THF (46 mL) to afford 700 mg (30%) of 6-[(R)-3-tetradecanoyloxytetradecanoylamino]-1-hexanol as an off-white solid.

(2) In the same manner as described in Example 13-(5), the compound prepared in (1) above (689 mg, 1.20 mmol) and the compound prepared in Example 22-(2) (1.25 g, 1.00 mmol) were coupled in the presence of AgOTf (1.28 g, 5.0 mmol) to give 1.59 g (94%) of 4-[(R)-3-tetradecanoyloxytetradecanoylamino]hexyl 2-deoxy-4-O-diphenylphosphono-3-O-[(R)-3-tetradecanoyoxytetradecanoyl]-6-O-(2,2,2-trichloro-1,1-dimethylethoxycarbonyl)-2-(2,2,2-trichloroethoxycarbonylamino)-β-D-glucopyranoside as an amorphous solid: $^1$H NMR (CDCl$_3$) δ 0.88 (t, 12 H, J=6.6 Hz), 1.1–1.8 (m, 92 H), 1.82 (s, 3 H), 1.89 (s, 3 H), 2.22 (t, 2 H, J=7.6 Hz), 2.29 (t, 2 H, J=7.4 Hz), 2.45 (m, ~4 H), 3.22 (m, 1 H), 3.46 (m, 2 H), 3.83 (m, 2 H), 3.94 (m, 1 H), 4.31 (m, 2 H), 4.64 (m, 2 H), 4.83 (d, 1 H, J=12.1 Hz), 4.97 (d, 1 H, J=7.8 Hz), 5.17 (m, 2 H), 5.59 (t, 1 H, J=8.8 Hz), 5.75 (m, 1 H), 5.84 (d, 1 H, J=7.6 Hz), 7.25 (m, 10 H).

(3) In the same manner as described in Example 2-(7), the compound prepared in (2) above (1.57 g, 0.88 mmol) was deprotected with zinc (2.88 g, 44.1 mmol) and then acylated with (R)-3-tetradecanoyloxytetradecanoic acid (481 mg, 1.06 mmol) in the presence of EEDQ (327 mg, 1.32 mmol)

to give 1.57 g (97%) of 4-[(R)-3-tetradecanoyloxytetradecanoylamino]hexyl 2-deoxy-4-O-diphenylphosphono-3-O-[(R)-3-tetradecanoyoxytetradecanoyl]-2-[(R)-3-tetradecanoyloxytetradecanoylamino])-β-D-glucopyranoside as an amorphous solid.

(4) In the same manner as described in Example 2-(8), the compound prepared in (3) above (1.57 g, 0.85 mmol) was hydrogenated in the presence of platinum oxide (157 mg) to give 130 mg (10%) of 4-[(R)-3-tetradecanoyloxytetradecanoylamino]hexyl 2-deoxy-4-O-phosphono-3-O-[(R)-3-tetradecanoyoxytetradecanoyl]-2-[(R)-3-tetradecanoyloxytetradecanoylamino]-β-D-glucopyranoside triethylammonium salt as a white solid: mp 150–152° C.; IR (film) 3284, 3099, 2954, 2920, 2851, 1731, 1657, 1637, 1557, 1467, 1418, 1378, 1320, 1249, 1179, 1108, 1083, 1044, 856, 721 cm$^{-1}$; $^1$H NMR (CDCl$_3$-CD$_3$OD) δ 0.89 (t, 18 H, J=6.6 Hz), 1.1–1.7 (m, 135 H), 2.2–2.7 (m, 23 H), 3.05 (q, 6 H, J=7.1 Hz), 3.18 (m, 2 H), 3.39 (d, 1 H, J=8.2 Hz), 3.49 (q, 1 H, J=7.5 Hz), 3.82 (m, 2 H), 3.99 (d, 1 H, J=11.9 Hz), 4.25 (q, 1 H, J=8.9 Hz), 4.59 (m, 2 H), 5.18 (m, 4 H); $^{13}$C NMR (CDCl$_3$) δ 173.7, 173.3, 170.6, 169.7, 169.4, 100.6, 75.5, 73.1, 71.3, 70.9, 70.6, 69.2, 60.6, 55.2, 45.8, 41.7, 41.4, 39.5, 39.4, 34.6, 34.3, 34.2, 34.1, 31.9, 29.7, 29.4, 29.2, 26.5, 25.5, 25.3, 25.1, 22.7, 14.1, 8.6.

Anal. Calcd. for $C_{102}H_{198}N_3O_{17}P \cdot H_2O$: C, 68.53; H, 11.28; N, 2.33; P, 1.73. Found: C, 68.63; H, 11.12; N, 2.26; P, 1.66.

EXAMPLE 25 (B24)

PREPARATION OF N-[(R)-3-TETRADECANOYLOXYTETRADECANOYL]-O-PHOSPHONO-2-[(R)-3-TETPADECANOYLOXYTETRADECANOYLAMINO]-3-O-[(R)-3-TETRADECANOYLOXYTETRADECANOYL]-β-D-GLUCOPYRANOSYL]-L-SEPINAMIDE TRIETHYLAMMONIUM SALT (COMPOUND (I), $R_1$=$R_2$=$R_3$=N—$C_{13}H_{27}$CO, X=Y=O, N=M=P=Q=0, $R_4$=$R_5$=$R_7$=$R_9$=H, $R_6$=CONH$_2$, $R_8$=PO$_3$H$_2$)

(1) A suspension of L-serinamide hydrochloride (0.157 g, 1.18 mmol) and (R)-3-tetradecanoyloxytetradecanoic acid (0.61 g, 1.34 mmol) in CH$_2$Cl$_2$ (6 mL) was treated with triethylamine (0.18 mL, 1.3 mmol) and the resulting solution was stirred with 4 Å molecular sieves for 30 min. EEDQ (0.437 g, 1.77 mmol) was then added and the mixture was stirred for 16 h at room temperature. The product that precipitated was collected and washed with CH$_2$Cl$_2$ (2×25 mL) to give 0.455 g (71%) of N-[(R)-3-tetradecanoyloxytetradecanoyl]-L-serinamide as a colorless powder: mp 126–130° C.; $^1$H NMR (CDCl$_3$) δ 0.88 (t, 6H, J=~7 Hz), 1.15–1.7 (m, 42 H), 2.31 (t, 2 H, J=7.5 Hz), 2.51 (d, 2 H, J=6.3 Hz), 3.56 (br s, 1 H), 3.65 (dd, 1 H, J=11.2, 5.5 Hz), 3.86 (dd, 1 H, J=11.2, 4.5 Hz), 4.21 (s, 2 H), 4.40 (m, 1 H), 5.22 (m, 1 H).

(2) In the same manner as described in Example 2-(6), the compound prepared in (1) above (0.23 g, 0.246 mmol) and the compound prepared in Example 2-(4) (0.961 g, 0.745 mmol) were coupled in the presence of mercury cyamide (0.43 g, 1.7 mmol) to give 0.527 g (71%) of N-[(R)-3-tetradecanoyloxytetradecanoyl]-O-[2-deoxy-4-O-diphenylphosphono-3-O-[(R)-3-tetradecanoyloxytetradecanoyl]-6-O-(2,2,2-trichloro-1,1-dimethylethoxycarbonyl)-2-(2,2,2,-trichloroethoxycarbonylamino)-β-D-glucopyranosyl]-L-serinamide as an amorphous solid: $^1$H NMR (CDCl$_3$) δ 0.88 (t, 12 H, J=~7 H), 1.0–1.7 (m, 84 H), 1.80 and 1.89 (2s, 6 H), 2.21 (t, 2 H, J=7.5 Hz), 2.30 (t, 2 H, J=7.5 Hz), 2.37 (m, 2 H), 2.47 (m, 2 H), 3.54 (m, 1 H), 3.68 (dd, 1 H, J=8, J=11 Hz), 3.86 (br d, 1 H, J=11 Hz), 4.16 (dd, 1 H, J=11, 4 Hz), 4.24 (dd, 1 H, J=12, 4.3 Hz), 4.40 (d, 1 H, J=12 Hz), 4.6–4.8 (m, 4 H), 5.00 (d, 1 H, J=8 Hz), 5.1–5.25 (m, 2 H), 5.4–5.55 (m, 2 H), 5.84 (br s, 1 H), 6.61 (br s, 2 H), 7.1–7.35 (m, 10 H).

(3) In the same manner as described in Example 2-(7), the compound prepared in (2) above (0.44 g, 0.254 mmol) was deprotected with zinc (0.83 g, 13 mmol) and then acylated with (R)-3-tetradecanoyloxytetradecanoic acid (0.14 g, 0.31 mmol) in the presence of EEDQ (0.095 g, 0.38 mmol) to give 0.271 g (59%) of N-[(R)-3-tetradecanoyloxytetradecanoyl]-O-[2-deoxy-4-O-diphenylphosphono-2-[(R)-3-tetradecanoyloxytetradecanoylamino]-3-O-[(R)-3-tetradecanoyloxytetradecanoyl]-β-D-glucopyranosyl]-L-serinamide as an amorphous solid: $^1$H NMR (CDCl$_3$) δ 0.88 (t, 18 H, J=~6.5 Hz), 1.0–1.7 (m, 126 H), 2.03 (br s, 1 H), 2.15–2.55 (m, 12 H), 3.5–4.05 (m, 5 H), 4.14 (dd, 1 H, J=10, 3.5 Hz), 4.5–4.65 (m, 2 H), 4.68 (d, 1 H, J=8.1 Hz), 5.05–5.25 (m, 3 H), 5.31 (t, 1 H, J=10 Hz), 5.58 (br s, 1 H), 6.31 (d, 1 H, J=8 Hz), 6.85–6.95 (m, 2 H), 7.1–7.4 (m, 10 H).

(4) In the same manner as described in Example 2-(8), the compound prepared in (3) above (0.25 g, 0.14 mmol) was hydrogenated in the presence of platinum oxide (0.125 g) to give 0.195 (80%) of N-[(R)-3-tetradecanoyloxytetradecanoyl]-O-[2-deoxy-4-O-phosphono-2-[(R)-3-tetradecanoyloxytetradecanoylamino]-3-O-[(R)-3-tetradecanoyloxytetradecanoyl]-β-D-glucopyranosyl]-L-serinamide triethylammonium salt as a colorless solid: mp 190–191° C. (dec); IR (film) 3418, 3293, 2921, 2850, 1732, 1717, 1651, 1636, 1557, 1540, 1458, 1165, 1033 cm$^{-1}$; $^1$H NMR (CDCl$_3$-CD$_3$OD) δ 0.88 (t, 18 H, J=~7 Hz), 1.0–1.7 (m, 135 H), 2.2–2.7 (m, 12 H), 3.05 (q, 6 H, J=7.2 Hz), 3.2–3.45 (m,), 3.5–4.15 (m, 5 H), 4.21 (q, 1 H, J=~10 Hz), 4.53 (d, 1 H, J=8.1 Hz), 4.58 (m, 1 H), 5.0–5.3 (m, 4 H), 7.25 (d, 1 H, J=8.4 Hz), 7.40 (d, 1 H, J=7.2 Hz); $^{13}$C NMR (CDCl$_3$-CD$_3$OD) δ 173.7, 173.5, 172.5, 170.7, 170.5, 170.4, 101.4, 75.5, 73.4, 71.1, 70.9, 70.2, 68.6, 60.0, 53.9, 52.2, 45.6, 41.2, 41.0, 38.9, 34.4, 34.2, 31.8, 29.6, 29.5, 29.3, 29.1, 25.2, 24.9, 22.6, 14.0, 8.3.

Anal. Calcd for $C_{99}H_{191}N_4O_{18}P \cdot 2.5\ H_2O$: C, 66.00; H, 10.97; N, 3.11; P, 1.72. Found: C, 66.04; H, 10.99; N, 3.03; P, 1.95.

EXAMPLE 26 (B25)

PREPARATION OF N-[(R)-3-DECANOYLOXYTETRADECANOYL]-O-[2-DEOXY-4-O-PHOSPHONO-2-[(R)-3-DECANOYLOXYTETRADECANOYLAMINO]-3-O-[(R)-3-DECANOYLOXYTETRADECANOYL]-β-D-GLUCOPYRANOSYL]-L-SERINAMIDE TRIETHYLAMMONIUM SALT (COMPOUND (I), $R_1$=$R_2$=$R_3$=N—$C_9H_{19}$CO, X=Y=O, N=M=P=Q=0, $R_4$=$R_5$=$R_7$=$R_9$=H, $R_6$=CONH$_2$, $R_8$=PO$_3$H$_2$).

(1) In the same manner as described in Example 25-(1), L-serinamide hydrochloride (169 mg, 1.2 mmol) was acylated with (R)-3-decanoyloxytetradecanoic acid (478 mg, 1.2 mmol) in the presence of EEDQ (371 mg, 1.5 mmol) in CH$_2$Cl$_2$ to afford 428 mg (74%) of N-[(R)-3-decanoyloxytetradecanoyl]-L-serinamide as a white solid: $^1$H NMR (CDCl$_3$) δ 0.88 (t, 6 H), 1.1–1.7 (m, 34 H), 2.33 (t, 2 H, J=7.5 Hz), 2.54 (d, 2 H, J=6.6 Hz), 3.35 (s, 2 H), 3.72 (dd, 1 H, J=11.0, 5.2 Hz), 3.84 (dd, 1 H, J=11.3, 5.0 Hz), 4.20 (t, 1 H, J=5.1 Hz), 5.26 (t, 1 H, J=6.4 Hz).

(2) In the same manner as described in Example 13-(5), the compound prepared in (1) above (410 mg, 0.85 mmol) and the compound prepared in Example 15-(4) (1.05 g, 0.87 mmol) were coupled in the presence of AgOTf (560 mg, 2.2 mmol) to afford 780 g (56%) of N-[(R)-3-decanoyloxytetradecanoyl]-O-[2-deoxy-4-O-diphenyl phosphono-3-O-[(R)-3-decanoyloxytetradecanoyl]-6-O-(2,2,2-trichloro-1,1-dimethylethoxycarbonyl)-2-(2,2,2-trichloroethoxycarbonylamino)-β-D-glucopyranosyl]-L-serinamide as an amorphous solid: $^1$H NMR (CDCl$_3$) δ 0.88 (t, 12 H), 1.1–1.6 (m, 68 H), 1.80 (s, 3 H), 1.89 (s, 3 H), 2.30 (m, 8 H), 3.53 (m, 1 H), 3.68 (m, 1 H), 3.85 (br. d, 1 H, J=9.4 Hz), 4.15 (dd, 1 H, J=10.8, 3.7 Hz), 4.24 (dd, 1 H, J=12.3, 4.6 Hz), 4.40 (d, 1 H, J=10.8), 4.65 (m, 4 H), 5.00 (d, 1 H, J=8.2 Hz), 5.18 (m, 2 H), 5.46 (m, 2 H), 5.83 (m, 1 H), 6.60 (m, 2 H), 7.30 (m, 10 H).

(3) In the same manner as described in Example 2-(7), the compound prepared in (2) above (600 mg, 0.36 mmol) was deprotected with zinc (1.19 g, 18.2 mmol) and acylated with (R)-3-decanoyloxytetradecanoic acid (160 mg, 0.4 mmol) in the presence of EEDQ (124 mg, 0.50 mmol) to afford 371 mg (62%) of N-[(R)-3-decanoyloxytetradecanoyl]-O-[2-deoxy-4-O-diphenylphosphono-2-[(R)-3-decanoyloxytetradecanoylamino]-3-O-[(R)-3-decanoyloxytetradecanoyl]-β-D-glucopyranosyl]-L-serinamide as an amorphous solid.

(4) In the same manner as described in Example 2-(8), the compound prepared in (3) above (330 mg, 0.20 mmol) was hydrogenated in the presence of platinum oxide (200 mg) to afford 120 mg (44%) of N-[(R)-3-decanoyloxytetradecanoyl]-O-[2-deoxy-4-O-phosphono-2-[(R)-3-decanoyloxytetradecanoylamino]-3-O-[(R)-3-decanoyloxytetradecanoyl]-β-D-glucopyranosyl]-L-serinamide triethylammonium salt as a white powder: mp 187–189° C.; IR (film) 3419, 3286, 3220, 3098, 2955, 2922, 2852, 1732, 1680, 1662, 1644, 1559, 1467, 1247, 1167, 1107, 1080, 1051, 965, 913 cm$^{-1}$; $^1$H NMR (CDCl$_3$-CD$_3$OD) δ 0.89 (t, 18 H, J=7.0 Hz), 1.1–1.7 (m, 111 H), 2.2–2.7 (m, 12 H), 3.07 (q, 6 H, J=7.1 Hz), 3.68 (m, 1 H), 3.87 (m, 1 H), 4.09 (dd, 1 H, J=10.8, 3.6 Hz), 4.22 (m, 1 H), 4.53 (d, 1 H, J=8.2 Hz), 4.58 (m, 1 H), 5.13 (m, 3 H), 5.28 (m, 1 H), 7.53 (d, 1 H, J=9.0 Hz), 7.56 (d, 1 H, J=7.7 Hz); $^{13}$C NMR (CDCl$_3$) δ 173.5, 173.2, 170.2, 169.8, 102.3, 75.7, 73.5, 71.3, 70.7, 70.1, 68.8, 60.8, 53.9, 51.7, 45.8, 41.5, 41.1, 39.1, 34.6, 34.5, 34.2, 32.0, 29.7, 29.6, 29.5, 29.4, 25.7, 25.4, 25.1, 22.7, 14.1, 8.6.

Anal. Calcd. for C$_{87}$H$_{167}$N$_4$O$_{18}$P H$_2$O: C, 65.05; H, 10.60; N, 3.49; P, 1.93. Found: C, 65.06; H, 10.40; N, 3.31; P, 2.00.

EXAMPLE 27 (B26)

PREPARATION OF N-[(R)-3-TETRADECANOYLOXYTETRADECANOYL]-O-[2-DEOXY-4-O-PHOSPHONO-2-[(R)-3-TETRADECANOYLOXYTETRADECANOYLAMINO]-3-O-[(R)-3-TETRADECANOYLOXYTETRADECANOYL]-β-D-GLUCOPYRANOSYL]-l-SERINE METHYL ESTER TIETHYLAMMONIUN SALT (COMPOUND (I), R$_1$=R$_2$=R$_3$=N—C$_{13}$H$_{27}$CO, X=Y=O, N=M=P=Q=0, R$_4$=R$_5$=R$_7$=R$_9$=H, R$_6$=CO$_2$Me, R$_8$=PO$_3$H$_2$)

(1) A solution of the compound prepared in Example 12-(2) (0.290 g, 0.157 mmol) in THF (20 mL) was hydrogenated in the presence of 5% palladium on carbon (50 mg) at room temperature and atmospheric pressure for 3 h. The catalyst was removed by filtration and the filtrate concentrated. A solution of the residue in CHCl$_3$ (5 mL) at 0° C. was treated with a solution of diazomethane (0.5 mmol) in ether (5 mL) and then stirred for 30 min at 0° C. AcOH (0.5 mL) was added and the resulting colorless solution was diluted with ether (50 mL), washed with saturated aqueous NaHCO$_3$ (25 mL), dried (Na$_2$SO$_4$) and concentrated. Flash chromatography on silica gel (gradient elution, 20→25% EtOAcs-hexanes) afforded 0.199 g (72%) of N-[(R)-3-tetradecanoy-loxytetradecanoyl]-O-[2-deoxy-4-O-diphenylphosphono-3-O-[(R)-3-tetradecanoyloxytetradecanoyl]-6-O-(2,2,2-trichloro-1,1-dimethylethoxycarbonyl)-2-(2,2,2-trichloroethoxycarbonylamino)-β-D-glucopyranosyl]-L-serine methyl ester as an amorphous solid: $^1$H NMR (CDCl$_3$) δ 0.88 (t, 12 H, J=6.5 Hz), 1.1–1.75 (m, 84 H), 1.81 and 1.89 (2s, 6 H), 2.36 (t, 2 H, J=7.5 Hz), 2.25–2.6 (m, 6 H), 3.48 (q, 1 H, J=~8 Hz), 3.7–3.9 (m, 5 H), 4.2–4.4 (m, 3 H), 4.6–4.85 (m, 4 H), 4.88 (d, 1 H, J=7.8 Hz), 5.03–5.22 (m, 2 H), 5.49 (t, 1 H, J=9.5 Hz), 6.21 (br s, 1 H), 6.59 (d, 1 H, J=7.8 Hz), 7.1–7.4 (m, 10 H).

(2) In the same manner as described in Example 2-(7), the compound prepared in (1) above (0.195 g, 0.111 mmol) was deprotected with zinc (0.36 g, 5.5 mmol) and acylated with (R)-3-tetradecanoyloxytetradecanoic acid (0.060 g, 0.13 mmol) in the presence of EEDQ (0.041 g, 0.17 mmol) to give 0.138 g (69%) of N-[(R)-3-tetradecanoyloxytetradecanoyl]-O-[(R)-4-O-diphenylphosphono-2-[(R)-3-tetradecanoyloxytetradecanoylamino]-3-O-[(R)-3-tetradecanoyloxytetradecanoyl-β-D-glucopyranosyl]-L-serine methyl ester as an amorphous solid: $^1$H NMR (CDCl$_3$) δ 0.88 (t, 18 H, J=~6.5 Hz), 1.0–1.75 (m, 126 H), 2.15–2.45 (m, 10H), 2.52 (dd, 1 H, J=14.7, 6 Hz), 2.66 (dd, 1 H, J=14.7, 6 Hz), 3.35 (br s, 1 H), 3.4–3.8 (m, 7 H), 3.88 (dd, 1 H, J=11 Hz), 4.18 (dd, 1 H, J=11 Hz), 4.6–4.75 (m, 2 H), 5.03 (d, 1 H, J=7.8 Hz), 5.1–5.25 (m, 3 H), 5.50 (t, 1 H, J=~9.5 Hz), 6.50 (d, 1 H, J=7.2 Hz), 6.97 (d, 1 H, J=7.8 Hz), 7.1–7.4 (m, 10 H).

(3) In the same manner as described in Example 2-(8), the compound prepared in (2) above (0.100 g, 0.055 mmol) was hydrogenated in the presence of platinum oxide (50 mg) to give 0.055 g (57%) of N-[(R)-3-tetradecanoyloxytetradecanoyl]-O-[2-deoxy-4-O-phosphono-2-[(R)-3-tetradecanoyloxytetradecanoylamino]-3-O-[(R)-3-tetradecanoyloxytetradecanoyl]-β-D-glucopyranosyl]-L-serine methyl ester triethylammonium salt as a colorless solid: mp 142–143° C. (dec); IR (film) 3289, 2955, 2921, 2852, 1733, 1718, 1699, 1652, 1558, 1540, 1521, 1506, 1469, 1457, 1375, 1360, 1259 cm$^{-1}$; $^1$H NMR (CDCl$_3$-CD$_3$OD) δ 0.88 (t, 18 H, J=~6.5 Hz), 1.0–1.7 (m, 135 H), 2.2–2.7 (m, 12 H), 3.05 (q, 6 H, J=7.5 Hz), 3.31 (d, 1 H, J=9.3 Hz), 3.37 (s, 1 H), 3.55–3.9 (m, 10 H), 3.97 (d, 1 H, J=12 Hz), 4.1–4.25 (m, 2 H), 4.55–4.65 (m, 2 H), 5.05–5.25 (m, 3 H), 7.23 (d, 1 H, J=8.1 Hz), 7.47 (d, 1 H, J=7.2 Hz); $^{13}$C NMR (CDCl$_3$) δ 173.6, 173.4, 170.5, 170.4, 170.1, 100.7, 75.9, 72.8, 71.2, 70.8, 70.6, 68.5, 60.3, 55.3, 52.7, 52.4, 47.7, 41.5, 40.9, 39.7, 34.6, 34.5, 34.3. 32.0, 29.8, 29.4, 25.4, 25.1, 22.7, 14.2, 8.5.

Anal. Calcd for C$_{100}$H$_{192}$N$_3$O$_{19}$P.H$_2$O: C, 67.11; H, 10.93; N, 2.35; P, 1.73. Found: C, 66.91; H, 10.93; N, 2.31; P, 2.11.

EXAMPLE 28 (B27)

PREPARATION OF N-(CARBOXYMETHYL)-N-[(R)-3-TETRADECANOYLOXYTETRADECANOYL]-2-AMINOETHYL 2-DEOXY-4-O-PHOPHONO-2-[(R)-3-TETRADECANOYLOXYTETRADECANOYLAMINO]-3-O-[(R)-3-TETRADECANOYLOXYTETRADECANOYL]-β-d-GLUCOPYRANOSIDE TRIETHYLAMMONIUM SALT (COMPOUND (I), R$_1$=R$_2$=R$_3$=N—C$_{13}$H$_{27}$CO, X=Y=O, N=M=P=0, R$_4$=R$_5$=R$_6$=R$_9$=H, R$_7$=CO$_2$H, Q=1, R$_8$=PO$_3$H$_2$)

(1) In the same manner as described in Example 2-(5), N-(2-hydroxyethyl)glycine t-butyl ester (0.25 g, 1.43 mmol) was acylated with (R)-3-tetradecanoyloxytetradecanoic acid (0.714 g, 1.57 mmol) in the presence of EDC-MeI (0.466 g, 1.57 mmol) to give 0.46 g (51%) of N-(2-hydroxyethyl)-N-[(R)-3-tetradecanoyloxytetradecanoyl]glycine t-butyl ester as an amorphous solid: $^1$H NMR (CDCl$_3$) δ 0.88 (t, 6 H, J=~6.5 Hz), 1.15–1.7 (m, 51 H), 2.26 (t, 2 H, J=7.5 Hz), 2.60 (dd, 1 H, J=6.5, 15 Hz), 2.86 (dd, 1 H, J=6.7, 15 Hz), 3.40–4.15 (m, 7 H), 5.25 (m, 1H).

(2) In the same manner as described in 13-(5), the compound prepared in (1) above (0.21 g, 0.334 mmol) and the compound prepared in Example 22-(2) (0.458 g, 0.368 mmol) were coupled in the presence of AgOTf (0.688 g, 2.68 mmol) to give 0.39 g (64%) of N-(t-butyloxycarbonylmethyl)-N-[(R)-3-tetradecanoyloxytetradecanoyl]-2-aminoethyl 2-deoxy-4-O-diphenylphosphono-3-O-[(R)-3-tetradecanoyloxytetradecanoyl]-6-O-(2,2,2-trichloro-1,1-dimethylethoxycarbonyl)-2-(2,2,2-trichloroethoxycarbonylamino)-β-D-glucopyranoside as an amorphous solid: $^1$H NMR (CDCl$_3$) δ 0.88 (t, 12 H, J=~6.5 Hz), 1.0–1.95 (m, 99 H), 2.1–2.6 (m, 7 H), 2.84 (dd, 1 H, J=5, 15 Hz), 3.2–4.15 (m, 8 H), 4.15–4.45 (m, 2 H), 4.55–4.9 (m, 3 H), 5.00 (d, 1 H, J=8 Hz), 5.13 (m, 2 H), 5.4–5.65 (m, 1 H), 6.16 (d, 1 H, J=7 Hz), 7.05–7.4 (m, 10 H).

(3) In the same manner as described in Example 2-(7), the compound prepared in (2) above (0.339 g, 0.185 mmol) was deprotected with zinc (0.36 g, 5.54 mmol) and then acylated with (R)-3-tetradecanoyloxytetradecanoic acid (0.100 g, 0.221 mmol) in the presence of EEDQ (0.068 g, 0.276 mmol) to give 0.25 g (71%) of N-(t-butyloxycarbonylmethyl)-N-[(R)-3-tetradecanoyloxytetradecanoyl]-2-aminoethyl 2-deoxy-4-O-phosphono-2-[(R)-3-tetradecanoyloxytetradecanoylamino]-3-O-[(R)-3-tetradecanoyloxytetradecanoyl]-β-D-glucopyranoside as a colorless solid.

(4) In the same manner as described in Example 2-(8), the compound prepared in (3) above (0.25 g, 0.131 mmol) was hydrogenated in the presence of platinum oxide (125 mg) in 9:1 THF-AcOH (15 mL). The crude hydrogenolysis product was dissolved in CH$_2$Cl$_2$ (1 mL), cooled to 0C, and treated dropwise with TFA (0.5 mL). After stirring for 2 h at 0° C., the reaction mixture was concentrated and residual TFA was removed by azeotroping with toluene. The resulting residue (0.23 g) was dissolved in 1% aqueous triethylamine (12 mL) and lyophilized. Flash chromatography on silica gel with chloroform-methanol-water-triethylamine (91:8:0.5:0.5→85:15:0.5:0.5, gradient elution) and further purification by means of acidic extraction as described in Example 2-(8) and lyophilization from 1% aqueous triethylamine (6 mL) afforded 99 mg (43%) of N-(carboxymethyl)-N-[(R)-3-tetradecanoyloxytetradecanoyl]-2-aminoethyl 2-deoxy-4-O-phosphono-2-[(R)-3-tetradecanoyloxytetradecanoylamino]-3-O-[(R)-3-tetradecanoyloxytetradecanoyl]-β-D-glucopyranoside triethylammonium salt as colorless solid: mp 162–163° C. (dec); IR (film) 3286, 2922, 2852, 1732, 1651, 1556, 1455, 1434, 1378, 1260, 1088, 801 cm$^{-1}$; $^1$H NMR (CDCl$_3$) δ 0.88 (t, 18 H, J=6.5 Hz), 1.0–1.75 (m, 135 H), 2.2–3.0 (m, 14 H), 3.04 (q, 6 H, J=7.2 Hz), 3.25–3.8 (m, 5 H), 3.85–4.3 (m, 5 H), 4.55 (d, 1 H, J=7.5 Hz), 4.68 (d, 1 H, J=8.1 Hz), 5.05–5.35 (m, 4 H).

Anal. Calcd for C$_{100}$H$_{192}$N$_3$O$_{19}$P.3 H$_2$O: C, 65.79; H, 10.60; N, 2.30; P, 1.70. Found: C, 65.82; H, 10.44; N, 2.40; P, 1.79.

EXAMPLE 29 (B28)

PREPARATION OF N-CARBOXYMETHYL-N-[(R)-3-DECANOYLOXYTETRADECANOYL]-3-AMINOPROPYL 2-DEOXY-4-O-PHOSPHONO-2-[(R)-3-DECANOYLOXYTETRADECANOYLAMINO])-3-O-[(R)-3-DECANOYOXYTETRADECANOYL]-β-D-GLUCOPYRANOSIDE TRIETHYLAMMONIUM SALT (COMPOUND (I), R$_1$=R$_2$=R$_3$=N—C$_9$H$_{19}$CO, X=Y=O, N=1, M=P=0, R$_4$=R$_5$=R$_6$=R$_9$=H, R$_7$=CO$_2$H, Q=1, R$_8$=PO$_3$H$_2$)

(1) In the same manner as described in Example 2-(5), N-(3-hydroxypropyl)glycine benzyl ester (450 mg, 2.0 mmol) was acylated with (R)-3-decanoyloxytetradecanoic acid (1.0 g, 2.5 mmol) in the presence of EDC-MeI (900 mg, 3.0 mmol) in CH$_2$Cl$_2$ to afford 0.76 g (63%) of N-(3-hydroxypropyl)-N-[(R)-3-decanoyloxytetradecanoyl]glycine benzyl ester as a colorless oil: $^1$H NMR (CDCl$_3$) (1:1 mixture of rotomers) δ 0.88 (t, 6 H, J=6.6 Hz), 1.1–1.7 (m, 35 H), 1.78 (m, 1 H), 2.26 (q, 2 H, J=7.6 Hz), 2.37 and 2.54 (2 dd, 1 H, J=14.9, 6.9 Hz), 2.60 and 2.89 (2 dd, 1 H, J=14.8, 6.0 Hz), 3.51 (m, 4 H), 3.70 (m, 1 H), 3.95–4.25 (m, 2 H), 5.1–5.25 (m, 3 H), 7.35 (m, 5 H).

(2) In the same manner as described in Example 13-(5), the compound prepared in (1) above (500 mg, 0.83 mmol), and the compound prepared in Example 15-(4) (1.0 g, 0.83 mmol) were coupled in the presence of AgOTf (1.07 g, 4.15 mmol) to afford 1.27 g (72%) of N-(benzyloxycarbonylmethyl)-N-[(R)-3-decanoyloxytetradecanoyl]-3-aminopropyl 2-deoxy-4-O-diphenylphosphono-3-O-[(R)-3-decanoyoxytetradecanoyl]-6-O-(2,2,2-trichloro-1,1-dimethylethoxycarbonyl)-2-(2,2,2-trichloroethoxycarbonylamino)-β-D-glucopyranoside benzyl ester: $^1$H NMR (CDCl$_3$) (2:1 mixture of rotomers) δ 0.88 (t, 12 H, J=6.9 Hz), 1.1–1.7 (m, 69 H), 1.80 (s, 3 H), 1.88 (s, 3 H), 2.1–2.6 (m, 11 H), 2.81 (dd, 1 H, J=14.8, 6.2 Hz), 3.37 (m, 1 H), 3.52 (m, 2 H), 3.76 (m, 1 H), 3.87 (m, 1 H), 4.05 (m, 2 H), 4.28 (m, 3 H), 4.62 (m, 3 H), 4.77 (m, 1 H), 4.93 (d, 1 H, J=8.2 Hz), 5.15 (m, 4 H), 5.46 and 5.61 (2 t, 1 H, J=9.5 Hz), 5.95 and 6.05 (2 d, 1 H, J=7.5 Hz), 7.1–7.4 (m, 15 H).

(3) In the same manner as described in Example 2-(7), the compound prepared in (2) above (1.25 g, 0.71 mmol) was deprotected with zinc (2.31 g, 3.53 mmol) and acylated with (R)-3-decanoyloxytetradecanoic acid (353 mg, 0.89 mmol) in the presence of EEDQ (264 mg, 1.07 mmol) to afford 670 mg (54%) of N-benzyloxycarbonylmethyl-N-[(R)-3-decanoyloxytetradecanoyl]-3-aminopropyl 2-deoxy-4-O-diphenylphosphono-3-O-[(R)-3-decanoyoxytetradecanoyl]-2-[(R)-3-decanoyloxytetradecanoylamino])-β-D-glucopyranoside as an amorphous solid.

(4) In the same manner as described in Example 2-(8), the compound prepared in (3) above (670 mg, 0.38 mmol) was hydrogenated in the presence of palladium hydroxide on carbon (270 mg) and platinum oxide (200 mg) in EtOH/AcOH (10:1) to afford 240 mg (39%) of N-carboxymethyl-N-[(R)-3-decanoyloxytetradecanoyl]-3-aminopropyl 2-deoxy-4-O-phosphono-2-[(R)-3-decanoyloxytetradecanoylamino])-3-O-[(R)-3-decanoyoxytetradecanoyl]-β-D-glucopyranoside triethylammonium salt as a white powder: mp 156–157° C.; IR (film) 3284, 2929, 2853, 2729, 1732, 1655, 1628, 1551, 1466, 1378, 1314, 1164, 1108, 1047, 955, 844, 722 cm$^{-1}$; $^1$H NMR (CDCl$_3$-CD$_3$OD) δ 0.88 (t, 18 H, J=6.9 Hz), 1.1–1.7 (m, 111 H), 2.27 (q, 6 H, J=6.2 Hz), 2.35–2.80 (m, 9 H), 3.05 (q, 6 H, J=7.2 Hz), 3.25–3.60 (m, 4 H), 3.75–4.10 (m, 4 H), 4.23 (m, 2 H), 4.47 (d, 1 H, J=8.2 Hz), 4.61 (d, 1 H, J=8.3 Hz), 5.05–5.25 (m, 4 H); $^3$C NMR (CDCl$_3$) δ 173.4, 173.0, 171.1, 170.6, 170.3, 169.6, 100.5, 74.5, 73.9, 71.4, 71.2, 70.7, 70.2, 67.0, 65.8, 60.7, 54.6, 54.3, 51.4, 49.2, 46.0, 45.4, 42.1, 41.2, 39.4, 38.0, 37.7, 34.5, 34.3, 34.2, 31.9, 29.8, 29.7, 29.6, 29.5, 29.2, 28.1, 25.4, 25.3, 25.1, 22.7, 14.1, 11.1, 8.6.

Anal. Calcd. for C$_{89}$H$_{170}$N$_3$O$_{19}$P H$_2$O: C, 65.37; H, 10.60; N, 2.57; P, 1.89. Found: C, 65.35; H, 10.42; N, 2.43; P, 2.05.

EXAMPLE 30 (B29)

PREPARATION OF N-[(R)-3-HEXANOYLOXYTETRADE-CANOYL]-O-[2-DEOXY-4-O-PHOSPHONO-2-[(R)-3-HEX-ANOYLOXYTETRADECANOYLAMINO]-3-O-[(R)-3-HEXANOY-LOXYTETRADECANOYL]-α-D-GLUCOPYRANOSYL]-L-SERINAMIDE TRIETHYLAMMONIUM SALT (COMPOUND (I), $R_1=R_2=R_3=N-C_5H_{11}CO$, X=Y=O, N=M=P=Q=0, $R_4=R_5=R_7=R_9$=H, $R_6$=CONH$_2$, $R_8$=PO$_3$H$_2$)

In the same manner as described in Example 26 and cognate steps, N-[(R)-3-hexanoyloxytetradecanoyl]-O-[2-deoxy-4-O-phosphono-2-[(R)-3-hexanoyloxytetradecanoylamino]-3-O-[(R)-3-hexanoyloxytetradecanoyl]-α-D-glucopyranosyl]-L-serinamide triethylammonium salt was prepared from 2-(trimethylsilyl)ethyl 2-deoxy-4,6-O-isopropylidine-2-(2,2,2-trichloroethoxycarbonylamino)-α-D-glucopyranoside, L-serinamide hydrochloride, and (R)-3-hexanoyloxytetradecanoic acid: mp 184–185° C.; IR (film) 3416, 3284, 3210, 3096, 2954, 2923, 2853, 1735, 1721, 1680, 1664, 1646, 1560, 1466, 1246, 1169, 1080, 1038 cm$^{-1}$; $^1$H NMR (CDCl$_3$-CD$_3$OD) δ 0.90 (m, 18 H), 1.1–1.7 (mH), 2.23–2.47 (m, 6 H), 2.48–2.7 (m, 6 H), 3.06 (q, 6 H, J=6 Hz), 3.26–3.34 (mH), 3.66 (m, 1 H), 3.77 (d, 1 H, J=9.5 Hz), 3.82–3.96 (m, 2 H), 4.12 (dd, 1 H, J=2, 8 Hz), 4.21 (q, 1 H, J=8 Hz), 4.56 (d, 1 H, J=7 Hz), 4.61 (m, 1 H), 5.05–5.18 (m, 3 H), 5.24 (m, 1 H), 7.26 (d, 1 H, J=6.5 Hz), 7.40 (d, 1 H, J=5.7 Hz).

Anal. Calcd. for $C_{75}H_{143}N_4O_{18}P\cdot H_2O$: C, 62.65; H, 10.16; N, 3.90; P, 2.15. Found: C, 62.60; H, 9.97; N, 3.72; P, 2.25.

EXAMPLE 31 (B30)

PREPARATION OF N-[(R)-3-DECANOYLOXYTETRADE-CANOYL]-O-[2-DEOXY-4-O-PHOSPHONO-2-[(R)-3-HEX-ANOYLOXYTETRADECANOYLAMINO]-3-O-[(R)-3-DECANOY-LOXYTETRADECANOYL]-α-D-GLUCOPYRANOSYL]-L-SERINAMIDE TRIETHYLAMMONIUM SALT (COMPOUND (I), $R_1=R_3=N-C_9H_{19}CO$ $R_2=N-C_5H_{11}CO$, X=Y=O, N=M=P=Q=0, $R_4=R_5=R_7=R_9$=H, $R_6$=CONH$_2$, $R_8$=PO$_3$H$_2$)

In the same manner as described in Example 26 and cognate steps, N-[(R)-3-decanoyloxytetradecanoyl]-O-[2-deoxy-4-O-phosphono-2-[(R)-3-hexanoyloxytetradecanoylamino]-3-O-[(R)-3-decanoyloxytetradecanoyl]-α-D-glucopyranosyl]-L-serinamide triethylammonium salt was prepared from 2-(trimethylsilyl)ethyl 2-deoxy-4,6-O-isopropylidine-2-(2,2,2-trichloroethoxycarbonylamino)-α-D-glucopyranoside, L-serinamide hydrochloride, and (R)-3-hexa- and decanoyloxytetradecanoic acids: mp 200–201° C. dec; IR (film) 3420, 3286, 2956, 2923, 2853, 1733, 1680, 1663, 1645, 1556, 1466, 1418, 1378, 1248, 1168, 1106, 1081, 1051 859, 722 cm$^{-1}$; $^1$H NMR (CDCl$_3$-CD$_3$OD) δ 0.88 (t, 18 H, J=6.9 Hz), 1.0–1.7 (m, 103 H), 2.15–2.71 (m, 12 H), 3.06 (q, 6 H, J=7 Hz), 3.68 (m, 1 H), 3.87 (m, 1 H), 4.09 (dd, 1 H, J=10.8, 3.6 Hz), 3.35–4.0 (mH), 4.15–4.3 (m, 2 H), 4.57–4.7 (m, 2 H), 5.05–5.3 (m, 4 H), 7.42 (m, 1 H); $^{13}$C NMR (CDCl$_3$) δ 173.5, 173.1, 170.2, 169.8, 102.2, 75.8, 73.7, 71.3, 70.7, 70.2, 69.0, 60.7, 53.9, 51.7, 45.8, 41.3, 41.1, 39.1, 34.6, 34.5, 34.2, 32.0, 29.7, 32.0, 31.4, 29.8, 29.6, 29.5, 29.4, 25.6, 25.4, 25.1, 24.7, 22.7, 22.4, 13.9, 8.6.

Anal. Calcd. for $C_{83}H_{159}N_4O_{18}P\cdot H_2O$: C, 64.31; H, 10.47; N, 3.61. Found: C, 64.31; H, 10.27; N, 3.41.

EXAMPLE 32 (B31)

PREPARATION OF 2-[(R)-3-HEXANOYLOXYTETRADECANOY-LAMINO]ETHYL 2-DEOXY-4-O-PHOSPHONO-3-O-[(R)-3-HEXANOYLOXYTETRADECANOYL]-2-[(R)-3-HEXANOYLOX-YTETRADECANOYLAMINO]-α-D-GLUCOPYRANOSIDE TRIETHYLAMMONIUM SALT (COMPOUND (I), $R_1=R_2=R_3=N-C_5H_{11}CO$, X=Y=O, N=M=P=Q=0, $R_4=R_5=R_6=R_7=R_9$=H, $R_8$=PO$_3$H$_2$)

In the same manner as described in Example 21 and cognate steps, 2-[(R)-3-hexanoyloxytetradecanoylamino] ethyl 2-deoxy-4-O-phosphono-3-O-[(R)-3-hexanoyloxytetradecanoyl]-2-[(R)-3-hexanoyloxytetradecanoylamino]-α-D-glucopyranoside triethylammonium salt was prepared from 2-(trimethylsilyl)ethyl 2-deoxy-4,6-O-isopropylidine-2-(2,2,2-trichloroethoxycarbonylamino)-α-D-glucopyranoside, 2-amino-1-(t-butyldiphenylsilyloxy)ethane, and (R)-3-hexanoyloxytetradecanoic acid: mp 161–162° C.; IR (film) 3288, 3096, 2956, 2924, 2854, 1732, 1657, 1645, 1557, 1466, 1378, 1316, 1245, 1173, 1080, 1041 cm$^{-1}$; $^1$H NMR (CDCl$_3$-CD$_3$OD) δ 0.89 (m, 18 H), 1.15–1.67 (m, 87 H), 2.23–2.70 (m, 15 H), 3.06 (q, 6 H, J=7.4 Hz), 3.2–3.85 (m, 9 H), 4.52 (d, 1 H, J=8.0 Hz), 5.05–5.27 (m, 4 H), 7.24 (d, 1 H, J=8.5 Hz), 7.43 (br t, 1 H); $^{13}$C NMR (CDCl$_3$) δ 173.7, 173.3, 173.3, 170.6, 170.2, 169.9, 100.9, 75.6, 73.0, 71.3, 70.9, 70.6, 68.3, 60.7, 55.0, 45.8, 41.6, 41.2, 39.5, 34.5, 34.4, 34.4, 31.9, 31.3, 29.7, 29.4, 25.4, 24.7, 22.7, 22.4, 14.1, 8.6.

Anal. Calcd. for $C_{74}H_{142}N_3O_{17}P\cdot H_2O$: C, 63.72; H, 10.40; N, 3.01; P, 2.22. Found: C, 63.72; H, 10.21; N, 2.96; P, 2.46.

EXAMPLE 33 (B32)

PREPARATION OF 2-[(R)-3-HEXADECANOYLOXYTETRADE-CANOYLAMINO]ETHYL 2-DEOXY-4-O-PHOSPHONO-2-[(R)-3-OCTADECANOYLOXYTETRADECANOYLAMINO]-3-O-[(R)-3-TETRADECANOYLOXYTETRADECANOYL]-α-D-GLUCOPYRANOSIDE TRIETHYLAMMONIUM SALT (COMPOUND (I), $R_1=C_{13}H_{27}CO$, $R_2=C_{17}H_{35}CO$, $R_3=N-C_{15}H_{31}CO$, X=Y=O, N=M=P=Q=0, $R_4=R_5=R_6=R_7=R_9$=H, $R_8$=PO$_3$H$_2$).

In the same manner as described in Example 21 and cognate steps, 2-[(R)-3-hexadecanoyloxytetradecanoylamino]ethyl 2-deoxy-4-O-phosphono-2-[(R)-3-octadecanoyloxytetradecanoylamino]-3-O-[(R)-3-tetradecanoyloxytetradecanoyl]-α-D-glucopyranoside triethylammonium salt was prepared from 2-(trimethylsilyl)ethyl 2-deoxy-4,6-O-isopropylidine-2-(2,2,2-trichloroethoxycarbonylamino)-α-D-glucopyranoside, 2-amino-1-(t-butyldiphenylsilyloxy)ethane, and (R)-3-tetra-, octa- and hexadecanoyloxytetradecanoic acids: mp 180–181° C.; IR (film) 3284, 3097, 2920, 2851, 1731, 1657, 1699, 1683, 1653, 1558, 1541, 1521, 1506, 1467, 1435, 1418, 1376, 1258, 1173, 1033 cm$^{-1}$; $^1$H NMR (CDCl$_3$-CD$_3$OD) δ 0.8–1.75 (mH), 2.2–2.7 (mH), 3.08 (q, 6 H, J=7.2 Hz), 3.2–3.5 (m, 5 H), 3.55–4.05 (mH), 4.24 (q, 1 H, J=7 Hz), 4.53 (d, 1 H, J=8 Hz), 5.05–5.3 (m, 4 H), 7.32 (d, 1 H, J=9 Hz), 7.49 (br t, 1 H); $^{13}$C NMR (CDCl$_3$) δ 173.8, 173.4, 173.3, 170.6, 170.3, 169.9, 100.9, 75.7, 73.0, 71.3, 70.9, 70.6, 68.3, 60.7, 55.0, 45.8, 41.3, 39.5, 34.6, 34.4, 32.0, 29.8, 29.4, 25.4, 25.1, 22.7, 14.2, 8.6.

Anal. Calcd. for $C_{104}H_{202}N_3O_{17}P\cdot 4H_2O$: C, 66.81; H, 11.32; N, 2.25. Found: C, 66.52; H, 10.80; N, 2.19.

EXAMPLE 34 (B34)

Preparation of N-[(R)-3-Hexanoyloxytetradecanoyl]-O-[2-deoxy-4-O-phosphono-2-[(R)-3-hexanoyloxytetradecanoylamino]-3-O-[(R)-3-hexanoyloxytetradecanoyl]-α-D-glucopyranosyl]-L-serine Triethylammonium Salt. (Compound (I), $R_1=R_2=R_3=N-C_5H_{11}CO$, $X=Y=O$, $N=M=P=Q=0$, $R_4=R_5=R_7=R_9=H$, $R_6=CO_2H$, $R_8=PO_3H_2$).

In the same manner as described in Example 16 and cognate steps, N-[(R)-3-hexanoyloxytetradecanoyl]-O-[2-deoxy-4-O-phosphono-2-[(R)-3-hexanoyloxytetradecanoylamino]-3-O-[(R)-3-hexanoyloxytetradecanoyl]-α-D-glucopyranosyl]-L-serine triethylammonium salt was prepared from 2-(trimethylsilyl)ethyl 2-deoxy-4,6-O-isopropylidine-2-(2,2,2-trichloroethoxycarbonylamino)-α-D-glucopyranoside, L-serine benzyl ester, and (R)-3-hexanoyloxytetradecanoic acid: mp 159–160° C.; IR (film) 3317, 2954, 2924, 2854, 1734, 1654, 1540, 1466, 1377, 1316, 1245, 1173, 1082, 846, 722 cm$^{-1}$; $^1$H NMR (CDCl$_3$-CD$_3$OD) δ 0.88 (m, 18 H), 1.15–1.7 (mH), 2.2–2.75 (m, 12 H), 3.08 (q, 6 H, J=7.2 Hz), 3.40 (d, 1 H, J=9.9 Hz), 3.55–3.95 (mH), 4.15–4.3 (m, 1 H), 4.51 (d, 1 H, J=8.0 Hz), 4.63 (br. s, 1 H), 5.1–5.3 (m, 4 H), 7.01 (d, 1 H, J=9.1 Hz), 7.37 (d, 1 H, J=8.8 Hz); $^{13}$C NMR (CDCl$_3$) δ 177.0, 173.2, 173.2, 172.7, 172.3, 169.6, 169.0, 101.5, 75.0, 71.2, 70.9, 70.8, 69.1, 60.5, 53.1, 51.4, 46.1, 41.4, 41.0, 39.1, 34.5, 34.2, 34.1, 34.0, 31.9, 31.4, 31.3, 29.8, 29.6, 29.4, 25.6, 25.3, 25.1, 24.7, 24.7, 22.7, 22.5, 22.4, 14.1, 14.0, 8.7.

Anal. Calcd. for $C_{75}H_{142}N_3O_{19}P \cdot 2H_2O$: C, 61.83; H, 10.10; N, 2.88; P, 2.13. Found: C, 62.07; H, 10.01; N, 2.94; P, 2.40.

EXAMPLE 35 (B35)

Preparation of N-[(R)-3-Decanoyloxytetradecanoyl]-O-[2-deoxy-4-O-phosphono-2-[(R)-3-decanoyloxytetradecanoylamino]-3-O-[(R)-3-hexanoyloxytetradecanoyl]-α-D-glucopyranosyl]-L-serine Triethylammonium Salt. (Compound (I), $R_1=N-C_5H_{11}CO$, $R_2=R_3=N-C_9H_{19}CO$, $X=Y=O$, $N=M=P=Q=0$, $R_4=R_5=R_7=R_9=H$, $R_6=CO_2H$, $R_8=PO_3H_2$)

In the same manner as described in Example 16 and cognate steps, N-[(R)-3-decanoyloxytetradecanoyl]-O-[2-deoxy-4-O-phosphono-2-[(R)-3-decanoyloxytetradecanoylamino]-3-O-[(R)-3-hexanoyloxytetradecanoyl]-α-D-glucopyranosyl]-L-serine triethylammonium salt was prepared from 2-(trimethylsilyl)ethyl 2-deoxy-4,6-O-isopropylidine-2-(2,2,2-trichloroethoxycarbonylamino)-α-D-glucopyranoside, L-serine benzyl ester, and (R)-3-hexa- and decanoyloxytetradecanoic acids: mp 158–159° C.; IR (film) 3304, 2956, 2923, 2853, 1732, 1658, 1547, 1466, 1378, 1317, 1246, 1174, 1082, 960, 846, 722 cm$^{-1}$; $^1$H NMR (CDCl$_3$-CD$_3$OD) δ 0.88 (m, 18 H), 1.15–1.7 (mH), 2.2–2.75 (m, 12 H), 3.06 (q, 6 H, J=7.2 Hz), 3.3–3.63 (mH), 3.66–3.98 (m, 4 H), 4.1–4.3 (m, 1 H), 4.54 (d, 1 H, J=8.0 Hz), 4.6 (m, 1 H), 5.05–5.27 (m, 4 H), 7.15 (d, 1 H, J=8.7 Hz), 7.46 (d, 1 H, J=8.2 Hz); $^{13}$C NMR (CDCl$_3$) δ 173.6, 173.3, 172.8, 172.1, 169.6, 169.2, 101.5, 74.8, 70.9, 70.8, 69.3, 60.5, 53.2, 51.5, 46.1, 41.9, 41.5, 41.0, 39.2, 34.5, 34.3, 34.1, 31.9, 31.4, 29.8, 29.6, 29.4, 25.6, 25.3, 25.1, 25.1, 25.0, 24.8, 22.7, 22.5, 14.1, 11.1, 8.7.

Anal. Calcd. for $C_{83}H_{158}N_3O_{19}P \cdot H_2O$: C, 64.27; H, 10.40; N, 2.71; P, 2.00. Found: C, 64.14; H, 10.33; N, 2.70; P, 2.05.

EXAMPLE 36 (B36)

Preparation of N-[(R)-3-Decanoyloxytetradecanoyl]-O-[2-deoxy-4-O-phosphono-2-[(R)-3-hexanoyloxytetradecanoylamino]-3-O-[(R)-3-decanoyloxytetradecanoyl]-α-D-glucopyranosyl]-L-serine Trethylammonium Salt. (Compound (I), $R_1=R_3=N-C_9H_{19}CO$, $R_2=N-C_5H_{11}CO$, $X=Y=O$, $N=M=P=Q=0$, $R_4=R_5=R_7=R_9=H$, $R_6=CO_2H$, $R_8=PO_3H_2$)

In the same manner as described in Example 16 and cognate steps, N-[(R)-3-decanoyloxytetradecanoyl]-O-[2-deoxy-4-O-phosphono-2-[(R)-3-hexanoyloxytetradecanoylamino]-3-O-[(R)-3-decanoyloxytetradecanoyl]-α-D-glucopyranosyl]-L-serine triethylammonium salt was prepared from 2-(trimethylsilyl)ethyl 2-deoxy-4,6-O-isopropylidine-2-(2,2,2-trichloroethoxycarbonylamino)-α-D-glucopyranoside, L-serine benzyl ester, and (R)-3-hexa- and decanoyloxytetradecanoic acids: mp 157–158° C.; IR (film) 3306, 2955, 2924, 2853, 1734, 1657, 1545, 1466, 1378, 1245, 1170, 1081, 954, 842, 722 cm$^{-1}$; $^1$H NMR (CDCl$_3$-CD$_3$OD) δ 0.88 (m, 18 H), 1.15–1.7 (mH), 2.2–2.75 (m, 12 H), 3.06 (q, 6 H, J=7.2 Hz), 3.36 (d, 1 H, J=9.8 Hz), 3.43–3.63 (mH), 3.68–3.95 (m, 4H), 4.13–4.27 (m, 2 H), 4.54 (d, 1 H, J=8.3 Hz), 4.6 (m, 1 H), 5.08–5.27 (m, 4 H); $^{13}$C NMR (CDCl$_3$) δ 176.9, 173.4, 173.2, 172.8, 172.2, 169.5, 169.1, 101.4, 74.8, 71.1, 70.9, 70.8, 69.3, 53.2, 51.6, 46.1, 41.8, 41.4, 41.0, 39.2, 34.5, 34.4, 34.3, 34.1, 34.0, 32.0, 31.4, 29.8, 29.6, 29.4, 29.3, 25.6, 25.3, 25.2, 25.1, 24.8, 22.7, 22.4, 14.1, 14.0, 8.7.

Anal. Calcd. for $C_{83}H_{158}N_3O_{19}P \cdot H_2O$: C, 64.27; H, 10.40; N, 2.71; P, 2.00. Found: C, 64.09; H, 10.31; N, 2.70; P, 2.06.

EXAMPLE 37 (B37)

Preparation of N-[(R)-3-Hexanoyloxytetradecanoyl]-O-[2-deoxy-4-O-phosphono-2-[(R)-3-decanoyloxytbtradecanoylamino]-3-O-[(R)-3-decanoyloxytetradecanoyl]-α-D-glucopyranosyl]-L-serine Triethylammonium Salt. (Compound (I), $R_1=R_2=N-C_9H_{19}CO$, $R_3=N-C_5H_{11}CO$, $X=Y=O$, $N=M=P=Q=0$, $R_4=R_5=R_7=R_9=H$, $R_6=CO_2H$, $R_8=PO_3H_2$)

In the same manner as described in Example 16 and cognate steps, N-[(R)-3-hexanoyloxytetradecanoyl]-O-[2-deoxy-4-O-phosphono-2-[(R)-3-decanoyloxytetradecanoylamino]-3-O-[(R)-3-decanoyloxytetradecanoyl]-α-D-glucopyranosyl]-L-serine triethylammonium salt was prepared from 2-(trimethylsilyl)ethyl 2-deoxy-4,6-O-isopropylidine-2-(2,2,2-trichloroethoxycarbonylamino)-α-D-glucopyranoside, L-serine benzyl ester, and (R)-3-hexa- and decanoyloxytetradecanoic acids: mp 156–157° C. dec; IR (film) 3306, 2956, 2923, 2852, 1732, 1659, 1545, 1466, 1378, 1246, 1173, 1081, 958, 847, 722 cm$^{-1}$; $^1$H NMR (CDCl$_3$-CD$_3$OD) δ 0.88 (m, 18 H), 1.0–1.7 (mH), 2.2–2.75 (m, 12 H), 2.9–3.3 (mH), 3.06 (q, overlaps preceding multiplet, J=7.2 Hz), 3.36 (d, 1 H, J=9.6 Hz), 3.43–3.63 (mH), 3.63–3.95 (m, 4H), 4.21 (m, 2 H), 4.53 (d, 1 H, J=8.0 Hz), 4.6 (br s, 1 H), 5.06–5.28 (m, 4 H); $^{13}$C NMR (CDCl$_3$) δ 176.6, 173.6, 173.3, 172.8, 172.1, 169.6, 169.2, 101.5, 74.8, 70.9, 70.9, 69.4, 60.5, 53.2, 51.5, 46.1, 41.9, 41.5, 41.1, 39.2, 34.6, 34.5, 34.4, 34.1, 31.9, 31.3, 29.8, 29.7, 29.6, 29.5, 29.4, 29.3, 25.6, 25.3, 25.2, 24.7, 22.7, 22.4, 14.1, 14.0, 11.1, 8.7.

Anal. Calcd. for $C_{83}H_{158}N_3O_{19}P\cdot H_2O$: C, 64.27; H, 10.40; N, 2.71. Found: C, 64.29; H, 10.30; N, 2.61.

EXAMPLE 38 (B38))

PREPARATION OF N-[(R)-3-HEXANOYLOXYTETRADE-CANOYL]-O-[2-DEOXY-4-O-PHOSPHONO-2-[(R)-3-HEX-ANOYLOXYTETRADECANOYLAMINO]-3-O-[(R)-3-DECANOY-LOXYTETRADECANOYL]-α-D-GLUCOPYRANOSYL]-L-SERINE TRIETHYLAMMONIUM SALT. (COMPOUND (I), $R_1$=N—$C_9H_{19}CO$, $R_2$=$R_3$=N—$C_5H_{11}CO$, X=Y=O, N=M=P=Q=0, $R_4$=$R_5$=$R_7$=$R_9$=H, $R_6$=$CO_2H$, $R_8$=$PO_3H_2$)

In the same manner as described in Example 16 and cognate steps, N-[(R)-3-hexanoyloxytetradecanoyl]-O-[2-deoxy-4-O-phosphono-2-[(R)-3-hexanoyloxytetradecanoylamino]-3-O-[(R)-3-decanoyloxytetradecanoyl]-α-D-glucopyranosyl]-L-serine triethylammonium salt was prepared from 2-(trimethylsilyl)ethyl 2-deoxy-4,6-O-isopropylidine-2-(2,2,2-trichloroethoxycarbonylamino)-α-D-glucopyranoside, L-serine benzyl ester, and (R)-3-hexa- and decanoyloxytetradecanoic acids: mp 152–153° C. dec; IR (film) 3307, 2956, 2924, 2853, 1734, 1658, 1544, 1466, 1378, 1316, 1245, 1173, 1081, 955, 843, 722 cm$^{-1}$; $^1$H NMR (CDCl$_3$-CD$_3$OD) δ 0.88 (m, 18 H), 1.15–1.7 (mH), 2.2–2.75 (m, 12 H), 3.06 (q, 6 H, J=7.2 Hz), 3.28–3.55 (mH), 3.67–3.97 (m, 4H), 4.13–4.27 (m, 2 H), 4.55 (d, 2 H, J=7.2 Hz), 4.60 (m, 1 H), 5.08–5.28 (m, 4 H), 7.11 (d, 1 H, J=8.7 Hz), 7.42 (d, 1 H, J=8.0 Hz); $^{13}$C NMR (CDCl$_3$) δ 176.9, 173.5, 173.2, 172.8, 172.2, 169.5, 169.1, 101.4, 74.8, 71.1, 70.9, 70.8, 69.3, 60.5, 53.2, 51.5, 46.1, 41.8, 41.4, 41.1, 39.2, 34.5, 34.3, 34.2, 34.1, 34.0, 31.9, 31.7, 31.4, 31.3, 29.8, 29.6, 29.4, 29.3, 25.6, 25.3, 25.2, 24.7, 22.7, 22.4, 14.1, 14.0, 11.1, 8.7.

Anal. Calcd. for $C_{79}H_{150}N_3O_{19}P$: C, 64.24; H, 10.24; N, 2.85. Found: C, 64.06; H, 10.35; N, 2.88.

EXAMPLE 39 (B39)

PREPARATION OF N-[(R)-3-HEXANOYLOXYTETRADE-CANOYL]-O-[2-DEOXY-4-O-PHOSPHONO-2-[(R)-3-DE-CANOYLOXYTETRADECANOYLAMINO]-3-O-[(R)-3-HEXANOY-LOXYTETRADECANOYL]-α-D-GLUCOPYRANOSYL]-L-SERINE TRIETHYLAMMONIUM SALT. (COMPOUND (I), $R_1$=$R_3$=N—$C_5H_{11}CO$, $R_2$=N—$C_9H_{19}CO$, X=Y=O, N=M=P=Q=0, $R_4$=$R_5$=$R_7$=$R_9$=H, $R_6$=$CO_2H$, $R_8$=$PO_3H_2$)

In the same manner as described in Example 16 and cognate steps, N-[(R)-3-hexanoyloxytetradecanoyl]-O-[2-deoxy-4-O-phosphono-2-[(R)-3-decanoyloxytetradecanoylamino]-3-O-[(R)-3-hexanoyloxytetradecanoyl]-α-D-glucopyranosyl]-L-serine triethylammonium salt was prepared from 2-(trimethylsilyl)ethyl 2-deoxy-4,6-O-isopropylidine-2-(2,2,2-trichloroethoxycarbonylamino)-α-D-glucopyranoside, L-serine benzyl ester, and (R)-3-hexa- and decanoyloxytetradecanoic acids: mp 151–152° C. dec; IR (film) 3308, 2956, 2924, 2854, 1732, 1660, 1544, 1466, 1378, 1317, 1246, 1173, 1081, 957, 843, 722 cm$^{-1}$; $^1$H NMR (CDCl$_3$-CD$_3$OD) δ 0.88 (m, 18 H), 1.0–1.7 (mH), 2.18–2.72 (m, 12 H), 3.06 (q, 6 H, J=7.4 Hz), 3.23–3.51 (mH), 3.66–3.98 (m, 4H), 4.12–4.28 (m, 2 H), 4.55 (d, 1 H, J=7.4 Hz), 4.60 (m, 1 H), 5.05–5.28 (m, 4 H), 7.10 (d, 1 H, J=8.2 Hz), 7.43 (d, 1 H, J=8.5 Hz); $^{13}$C NMR (CDCl$_3$) δ 176.9, 173.6, 173.2, 172.7, 172.2, 169.5, 169.0, 101.5, 75.0, 74.8, 71.2, 70.9, 70.8, 69.2, 60.5, 53.1, 51.5, 46.1, 41.8, 41.5, 41.1, 39.1, 34.6, 34.5, 34.2, 34.0, 32.0, 31.4, 31.3, 29.8, 29.7, 29.6, 29.4, 29.3, 25.6, 25.3, 25.1, 24.8, 24.7, 22.7, 22.5, 22.4, 14.1, 14.0, 11.1, 8.7.

Anal. Calcd. for $C_{79}H_{150}N_3O_{19}P\cdot H_2O$: C, 63.47; H, 10.25; N, 2.81. Found: C, 63.63; H, 10.35; N, 2.84.

EXAMPLE 40 (B40)

PREPARATION OF N-[(R)-3-DECANOYLOXYTETRADE-CANOYL]-O-[2-DEOXY-4-O-PHOSPHONO-2-[(R)-3-HEX-ANOYLOXYTETRADECANOYLAMINO]-3-O-[(R)-3-HEXANOY-LOXYTETRADECANOYL]-α-D-GLUCOPYRANOSYL]-L-SERINE TRIETHYLAMMONIUM SALT. (COMPOUND (I), $R_1$=$R_3$=N—$C_5H_{11}CO$, $R_2$=N—$C_9H_{19}CO$, X=Y=O, N=M=P=Q=0, $R_4$=$R_5$=$R_7$=$R_9$=H, $R_6$=$CO_2H$, $R_8$=$PO_3H_2$)

In the same manner as described in Example 16 and cognate steps, N-[(R)-3-decanoyloxytetradecanoyl]-O-[2-deoxy-4-O-phosphono-2-[(R)-3-hexanoyloxytetradecanoylamino]-3-O-[(R)-3-hexanoyloxytetradecanoyl]-α-D-glucopyranosyl]-L-serine triethylammonium salt was prepared from 2-(trimethylsilyl)ethyl 2-deoxy-4,6-O-isopropylidine-2-(2,2,2-trichloroethoxycarbonylamino)-α-D-glucopyranoside, L-serine benzyl ester, and (R)-3-hexa- and decanoyloxytetradecanoic acids: mp 158–159° C.; IR (film) 3308, 2956, 2924, 2854, 1734, 1659, 1545, 1466, 1378, 1316, 1245, 1173, 1081, 956, 844, 722 cm$^{-1}$; $^1$H NMR (CDCl$_3$-CD$_3$OD) δ 0.8–1.0 (m, 18 H), 1.15–1.73 (mH), 2.18–2.72 (m, 12 H), 3.06 (q, 6 H, J=7.4 Hz), 3.35 (d, 1 H, J=10 Hz), 3.47–3.67 (mH), 3.68–3.97 (m, 4 H), 4.1–4.3 (m, 2 H), 4.54 (d, 1 H, J=8.0 Hz), 4.61 (m, 1 H), 5.07–5.28 (m, 4 H); $^{13}$C NMR (CDCl$_3$) δ 176.9, 173.5, 173.2, 172.8, 172.2, 169.6, 169.1, 101.5, 75.0, 74.8, 71.2, 70.9, 70.8, 69.2, 60.5, 53.2, 51.4, 46.1, 41.9, 41.5, 41.0, 39.2, 34.5, 34.2, 34.0, 31.9, 31.4, 29.8, 29.6, 29.4, 29.2, 25.6, 25.3, 25.1, 25.0, 24.8, 24.7, 22.7, 22.5, 22.4, 14.1, 14.0, 11.1, 8.7.

Anal. Calcd. for $C_{79}H_{150}N_3O_{19}P\cdot H_2O$: C, 63.47; H, 10.25; N, 2.81; P, 2.07. Found: C, 63.43; H, 10.22; N, 2.83; P, 2.13.

EXAMPLE 41 (B41)

PREPARATION OF 3-HYDROXY-(R)-2-[(R)-3-DECANOYLOX-YTETRADECANOYLAMINO]PROPYL 2-DEOXY-4-O-PHOSPHONO-2-[(R)-3-HEXANOYLOXYTETRADECANOY-LAMINO]-3-O-[(R)-3-DECANOYLOXYTETRADECANOYL]-α-D-GLUCOPYRANOSIDE TRIETHYLAMMONIUM SALT (COMPOUND (I), $R_1$=$R_3$=N—$C_9H_{19}CO$, $R_2$=N—$C_5H_{11}CO$, X=Y=O, N=M=Q=0, $R_4$=$R_5$=$R_7$=$R_9$=H, $R_6$=OH, P=1 $R_8$=$PO_3H_2$)

In the same manner as described in Example 6 and cognate steps, 3-hydroxy-(R)-2-[(R)-3-decanoyloxytetradecanoylamino]propyl 2-deoxy-4-O-phosphono-2-[(R)-3-hexanoyloxytetradecanoylamino]-3-O-[(R)-3-decanoyloxytetradecanoyl]-α-D-glucopyranoside triethylammonium salt was prepared from N-(2,2,2-trichloroethoxycarbonylamino)-1,3,4,6-tetra-O-acetyl-2-deoxy-α-D-glucopyranoside, (S)-2-amino-3-benzyloxy-1-propanol, and (R)-3-hexa- and decanoyloxytetradecanoic acids: mp 151–153° C.; IR (film) 3287, 2956, 2923, 2853, 1732, 1643, 1552, 1466, 1378, 1318, 1147, 1176, 1108, 1082, 1052, 856, 722 cm$^{-1}$; $^1$H NMR (CDCl$_3$-CD$_3$OD) δ 0.88 (t, 18 H, J=6.9 Hz), 1.0–1.72 (mH), 2.17–2.71 (m, 12 H), 2.9–3.3 (mH), 3.08 (q, overlaps preceding multiplet, J=7.2 Hz), 3.31 (d, 1 H, J=9.6

Hz), 3.5–4.02 (m, 8 H), 4.20 (d, 1 H, J=9.5 Hz), 4.60 (d, 1 H, J=8.0 Hz), 5.05–5.25 (m, 4 H); $^{13}$C NMR (CDCl$_3$) δ 173.7, 173.5, 173.4, 170.6, 170.1, 101.1, 75.5, 73.0, 71.6, 71.3, 70.8, 70.5, 68.2, 61.4, 60.7, 54.8, 50.5, 45.8, 41.4, 39.4, 34.6, 34.5, 34.2, 31.9, 31.4, 29.8, 29.7, 29.5, 29.4, 29.3, 25.4, 25.1, 22.7, 22.4, 14.1, 14.0, 8.6.

Anal. Calcd. for $C_{83}H_{160}N_3O_{18}P \cdot H_2O$: C, 64.84; H, 10.62; N, 2.55. Found: C, 65.01; H, 10.50; N, 2.55.

EXAMPLE 42 (B42)

PREPARATION OF 5-[2-DEOXY-4-O-PHOSPHONO-2-[(R)-3-DECANOYLOXYTETRADECANOYLAMINO]-3-O-[(R)-3-DECANOYLOXYTETRADECANOYL]-α-D-GLUCOPYRANOSYLOXY]-(S)-4-[(R)-3-DECANOYLOXYTETRADECANOYLAMINO] PENTANOIC ACID TRIETHYLAMMONIUM SALT (COMPOUND (I), $R_1=R_2=R_3=$N—$C_9H_{19}$CO, X=Y=O, N=M=Q=0, $R_4=R_5=R_7=R_9=$H, $R_6=CO_2H$, P=2, $R_8=PO_3H_2$)

(1) In the same manner described in Example 13-(5), benzyl (S)-4-(t-butyloxycarbonylamino)-5-hydroxypentanoate (0.338 g, 0.954 mmol) and the compound prepared in Example 15-(4) (1.15 g, 0.954 mmol) were coupled in the presence of AgOTf (1.22 g, 4.77 mmol) to give 0.70 g (50%) of benzyl (S)-4-(t-butyloxycarbonylamino)-5-[2-deoxy-4-O-diphenylphosphono-3-O-[(R)-3-decanoyloxytetradecanoyl]-6-O-(2,2,2-trichloro-1,1-dimethylethoxycarbonyl)-2-(2,2,2-trichloroethoxycarbonylamino)-α-D-glucopyranosyloxy]pentanoate: $^1$H NMR (CDCl$_3$) δ 0.88 (m, 6 H), 1.0–2.05 (m, 55 H), 2.12–2.5 (m, 6 H), 3.28–3.90 (m, 5 H), 4.26 (dd, 1 H, J=4.5, 11.5 Hz), 4.38 (d, 1 H, J=11.5 Hz), 4.57–4.98 (m, 5 H), 5.11 (s, 2 H), 5.18 (m, 1 H), 5.49 (t, 1 H, J=9 Hz), 5.78 (d, 1 H, J=7.7 Hz), 7.04–7.45 (m, 15 H).

(2) A solution of the compound prepared in (1) above (0.67 g, 0.45 mmol) in CH$_2$Cl$_2$ (5 mL) was cooled to 0° C., treated dropwise with TFA (70 μL), and stirred for 3 h at room temperature. The reaction mixture was diluted with CH$_2$Cl$_2$ (15 mL), washed with saturated aqueous NaHCO$_3$ and dried (Na$_2$SO$_4$). (R)-3-Decanoyloxytetradecanoic acid (0.20 g, 0.50 mmol) and EDC.MeI (0.15 g, 0.5 mmol) were added and the resulting mixture was stirred for 16 h at room temperature. The reaction mixture was filtered through a pad of Celite® and concentrated. The crude product obtained was purified by flash chromatography on silica gel (gradient elution, 15→30% EtOAc-hexanes) to give 0.36 g (45%) of benzyl (S)-4-[(R)-3-decanoyloxytetradecanoylamino]-5-[2-deoxy-4-O-diphenylphosphono-3-O-[(R)-3-decanoyloxytetradecanoyl]-6-O-(2,2,2-trichloro-1,1-dimethylethoxycarbonyl)-2-(2,2,2-trichloroethoxycarbonylamino)-α-D-glucopyranosyloxy]pentanoate: $^1$H NMR (CDCl$_3$) δ 0.89 (m, 12 H), 1.0–1.978 (mH), 2.12–2.5 (m, 10 H), 3.45–3.65 (m, 2 H), 3.79 (dd, 2 H, J=3.8, 10 Hz), 4.06 (m, 1 H), 4.27 (dd, 1 H, J=4.9, 12 Hz), 4.35 (d, 1 H, J=12 Hz), 4.6–4.8 (m, 3 H), 4.83 (d, 1 H, J=8.3 Hz), 5.10 (s, 2 H), 5.17 (m, 2 H), 5.48 (t, 1 H, J=10 Hz), 5.79 (d, 1 H, J=7.7 Hz), 6.05, (d, 1 H, J=8.8 Hz), 7.07–7.42 (m, 15 H).

(3) In the same manner as described for the preparation of compound B14 from the compound prepared in Example 15-(5), 5-[2-deoxy-4-O-phosphono-2-[(R)-3-decanoyloxytetradecanoylamino]-3-O-[(R)-3-decanoyloxytetradecanoyl]-α-D-glucopyranosyloxy]-(S)-4-[(R)-3-decanoyloxytetradecanoylamino]pentanoic acid triethylammonium salt was prepared from the compound prepared in (2) above: mp 184–188° C.; IR (film) 3284, 2955, 2919, 2848, 1730, 1654, 1548, 1459, 1374, 1259, 1165, 1081, 1032, 800 cm$^{-1}$; $^1$H NMR (CDCl$_3$-CD$_3$OD) δ 0.88 (t, 18 H, J=7 Hz), 1.0–2.0 (mH), 2.18–2.75 (m, 12 H), 3.08 (q, 6 H, J=7.4 Hz), 3.33–4.42 (mH), 4.44 (d, 1 H, J=8.5 Hz), 5.02–5.31 (m, 4 H), 7.54 (d, 1 H, J=8 Hz), ), 7.61 (d, 1 H, J=7 Hz); $^{13}$C NMR (CDCl$_3$) δ 176.8, 173.6, 173.3, 170.8, 170.2, 101.1, 75.1, 73.7, 71.7, 71.1, 70.8, 70.1, 60.8, 54.1, 48.8, 45.9, 41.4, 41.2, 39.4, 34.5, 34.4, 34.1, 31.9, 31.3, 29.8, 29.7, 29.6, 29.5, 29.4, 26.9, 25.5, 25.3, 25.1, 22.7, 14.1, 8.6.

Negative FAB-MS calcd for [M–H]$^-$ 1514.0889. found 1514.0816.

EXAMPLE 43 (B43)

PREPARATION OF N-[(R)-3-HYDROXYTETRADECANOYL]-O-[2-DEOXY-4-O-PHOSPHONO-2-[(R)-3-DODECANOYLOXYTETRADECANOYLAMINO]-3-O-[(R)-3-TETRADECANOYLOXYTETRADECANOYL]-α-D-GLUCOPYRANOSYL]-L-SERINE TRIETHYLAMMONIUM SALT. (COMPOUND (I), $R_1=$N—$C_{13}H_{27}$CO, $R_2=$N—$C_{11}H_{23}$CO, $R_3=$H, X=Y=O, N=M=P=Q=0, $R_4=R_5=R_7=R_9=$H, $R_6=CO_2H$, $R_8=PO_3H_2$)

(1) In the same manner described in Example 13-(5), N-allyloxycarbonyl-L-serine benzyl ester (0.225 g, 0.806 mmol) and the compound prepared in Example 22-(2) (1.104 g, 0.886 mmol) were coupled in the presence of AgOTf (0.828 g, 3.22 mmol) to give 1.01 g (83%) of N-allyloxycarbonyl-O-[2-deoxy-4-O-diphenylphosphono-3-O-[(R)-3-tetradecanoyloxytetradecanoyl]-6-O-(2,2,2-trichloro-1,1-dimethylethoxycarbonyl)-2-(2,2,2-trichloroethoxycarbonylamino)-α-D-glucopyranosyl]-L-serine benzyl ester: $^1$H NMR (CDCl$_3$) δ 0.88 (m, 6 H), 1.0–1.7 (m, 42 H), 1.78 (s, 3 H), 1.86 (s, 3 H), 2.12–2.48 (m, 4 H), 3.26 (m, 1 H), 3.66 (m, 1 H), 3.80 (dd, 1 H, J=3, 10 Hz), 4.19–4.38 (m, 4 H), 4.48–4.85 (m, 6 H), 4.98 (d, 1 H, J=7.7 Hz), 5.08–5.38 (m, 5 H), 5.49 (m, 1 H), 5.60–5.75 (m, 2 H), 5.82–6.0 (m, 1 H), 7.06–7.42 (m, 15 H).

(2) A solution of the compound prepared in (1) above (1.01 g, 0.68 mmol) and diethyl malonate (1.50 g, 9.48 mmol) in THF was degassed with argon (1 h), treated with tetrakis(triphenylphosphine)palladium(0) (0.10 g, 0.09 mmol), and stirred overnight at room temperature. The reaction mixture was filtered through a pad of silica with 2% MeOH—CHCl$_3$ and the filtrate concentrated. A solution of the crude amine obtained in CH$_2$Cl$_2$ (20 mL) was treated with (R)-3-hydroxytetradecanoic acid (0.18 g, 0.75 mmol) and EDC.MeI (0.66 g, 1.02 mmol), stirred overnight at room temperature, and then concentrated. The crude product obtained was purified by flash chromatography on silica gel (gradient elution, 30→40% EtOAc-hexanes) to give 0.506 g (46%) of N-[(R)-3-hydroxytetradecanoyl]-O-[2-deoxy-4-O-diphenylphosphono-3-O-[(R)-3-tetradecanoyloxytetradecanoyl]-6-O-(2,2,2-trichloro-1,1-dimethylethoxycarbonyl)-2-(2,2,2-trichloroethoxycarbonylamino)-α-D-glucopyranosyl]-L-serine benzyl ester: $^1$H NMR (CDCl$_3$) δ 0.88 (m, 9 H), 1.0–1.7 (m, 62 H), 1.79 (s, 3 H), 1.87 (s, 3 H), 2.19 (t, 2 H, J=7 Hz), 2.3–2.5 (m, 4 H), 3.1 (br s, 1 H), 3.55 (q, 1 H, J=9 Hz), 4.0–4.43 (m, 5 H), 4.56–4.85 (m, 4 H), 5.13–5.32 (m, 4 H), 6.59 (d, 1 H, J=7.4 Hz), 6.83 (br s, 1 H), 7.17–7.41 (m, 15 H).

(3) In the same manner as described for the preparation of compound B12 from the compound prepared in Example 13-(5), N-[(R)-3-hydroxytetradecanoyl]-O-[2-deoxy-4-O-phosphono-2-[(R)-3-dodecanoyloxytetradecanoylamino]-3-O-[(R)-3-tetradecanoyloxytetradecanoyl]-α-D-glucopyranosyl]-L-serine triethylammonium salt was prepared from the compound prepared in (2) above: mp 170–173° C. dec; IR (film) 3313, 2955, 2923, 2853, 1734, 1662, 1655, 1558, 1541, 1467, 1458, 1376, 1248, 1166, 1108, 1078, 1049, 953, 942, 842 cm$^{-1}$; $^1$H NMR (CDCl$_3$-CD$_3$OD) δ 0.88 (m, 18 H), 1.15–1.7 (mH), 2.2–2.75 (m, 12 H), 3.06 (q, 6 H, J=7.2 Hz), 3.3–3.63 (mH), 3.66–3.98 (m, 4 H), 4.1–4.3 (m, 2 H), 4.54 (d, 1 H, J=8.0 Hz), 4.6 (m, 1 H), 5.05–5.27 (m, 4 H), 7.15

(d, 1 H, J=8.7 Hz), 7.46 (d, 1 H, J=8.2 Hz); $^{13}$C NMR (CDCl$_3$) δ 177.0, 173.3, 172.8, 172.3, 171.9, 169.2, 101.2, 74.9, 74.8, 74.3, 70.8, 70.6, 69.3, 68.4, 59.9, 53.1, 51.5, 42.5, 41.5, 39.2, 37.1, 34.6, 34.4, 34.3, 34.1, 32.0, 29.8, 29.4, 25.6, 25.2, 22.7, 22.5, 14.5, 8.7.

Anal. Calcd. for $C_{83}H_{160}N_3O_{18}P\cdot2H_2O$: C, 64.10; H, 10.63; N, 2.70; P, 1.99. Found: C, 64.28; H, 10.42; N, 2.70; P, 1.84.

TEST EXAMPLE 1

STIMULATION OF ANTI-TETANUS TOXOID ANTIBODY PRODUCTION

The AGPs of the subject invention enhanced antibody production to purified tetanus toxoid in a murine model. Ten mg of each AGP sample was added to 1 ml of an oil-lecithin mixture containing squalene oil plus 12% lecithin. The mixtures were heated in a 56° C. water bath and sonicated to achieve clear solutions. Fifty (50) µl of each solution was emulsified by vortexing in 2 ml of sterile, pre-warmed 0.1% Tween 80 saline containing 1.0 µg tetanus toxoid antigen/ml. Preparations were vortexed again just prior to administration to mice. Female C57BL/6×DBA/2 F$_1$ mice (8 per group) were treated with 0.2 ml of the appropriate preparation distributed as a 0.1 ml subcutaneous injection into each flank. The final mouse dosage of the tetanus toxoid and AGP compounds was 0.2 µg and 50 µg, respectively. Control mice received tetanus toxoid in vehicle (oil-Tween saline). All mice were treated on day 0 followed by a second immunization on day 21. Fourteen days following the second immunization mice were bled and sera were isolated by centrifugation.

Serum samples from each mouse were evaluated for anti-tetanus toxoid antibodies by enzyme immunoassay (EIA) analysis using tetanus toxoid coated microtiter plates. Anti-tetanus antibody titers were evaluated for IgM, total Ig, as well as, IgG$_1$, IgG$_{2a}$ and IgG$_{2b}$ isotypes. Each serum sample was diluted 2-fold for eleven dilutions starting with an initial serum dilution of 1:200. Results are shown in Tables 2–4.

TABLE 2

Anti-tetanus toxoid antibody titers of treated mice.

| | Total IgG | | IgG$_1$ | | IgG$_{2a}$ | | IgG$_{2b}$ | | IgM | |
|---|---|---|---|---|---|---|---|---|---|---|
| Material | T/C* | Titer | T/C | Titer | T/C | Titer | T/C | Titer | T/C | Titer |
| B11 | 3.6 | 23,200 | 1.86 | 400,000 | 2.06 | 10,450 | 0.93 | 26,800 | 4.75 | 7,600 |
| B2 | 3.84 | 24,800 | 2.16 | 464,000 | 4.28 | 21,700 | 1.57 | 45,200 | 4.50 | 7,200 |
| B1 | 3.97 | 25,600 | 3.42 | 736,000 | 3.78 | 19,200 | 2.45 | 70,400 | 2.38 | 3,800 |
| B25 | 8.93 | 57,600 | 2.68 | 576,000 | 1.67 | 8,500 | 3.28 | 94,400 | 2.0 | 3,200 |
| B21 | 4.71 | 30,400 | 2.23 | 480,000 | 5.83 | 29,600 | 6.07 | 174,400 | 5.50 | 8,800 |
| B15 | 18.85 | 121,600 | 4.17 | 896,000 | 6.80 | 34,500 | 2.79 | 80,256 | 4.0 | 6,400 |
| Vehicle | | 6,450 | | 215,000 | | 5,075 | | 28,750 | | 1,600 |

*T/C Ratio = Experimental Test Titer ÷ Vehicle Control Titer.

TABLE 3

Anti-tetanus toxoid antibody titers of treated mice.

| Material | T/C* | IgM | T/C | IgG$_{2a}$ | T/C | IgG$_{2b}$ |
|---|---|---|---|---|---|---|
| B12 | 3.1 | 4800 | 139.4 | 2370 | 149 | 9840 |
| B16 | 1.6 | 2560 | 66.8 | 1135 | 104 | 6880 |
| B13 | 3.9 | 6080 | 220 | 3740 | >208 | >13,760 |
| B11 | 3.3 | 5120 | 347 | 5900 | 127.3 | 8400 |
| Vehicle | — | 1760 | — | 25 | — | 98 |

*T/C Ratio = Experimental Test Titers ÷ Vehicle Control Titers

TABLE 4

Anti-tetanus toxoid antibody titers of treated mice.

| | Total Ig | | IgM | | IgG$_1$ | | IgG$_{2a}$ | | IgG$_{2b}$ | |
|---|---|---|---|---|---|---|---|---|---|---|
| Material | T/C | Titer | T/C | Titer | T/C | Titer | T/C | Titer | T/C | Titer |
| B26 | 10.5 | 2,490 | 1.1 | 600 | 16.9 | 25,200 | 29.3 | 440 | 42.6 | 2,260 |
| B15 | 144.5 | 34,400 | 2.7 | 1,520 | 118.3 | 176,000 | 259.3 | 3,890 | 603.8 | 32,000 |
| B22 | 60.0 | 19,050 | 0.8 | 440 | 18.4 | 27,400 | 345.8 | 5,187 | 59.6 | 3,160 |
| B28 | 228.6 | 54,500 | 3.7 | 2,080 | 92.5 | 137,600 | 664.7 | 9,970 | 519.2 | 27,520 |
| Vehicle | | 238 | | 560 | | 1,488 | | 15 | | 53 |

*T/C Ratio = Experimental Test Titer − Vehicle Control Titer.

Compounds of the subject invention showed a dose response when administered with tetanus toxoid. BFD1 (C57B1/6×DBA/2) female mice (8 per group) were immunized with 0.2 ml of emulsions containing AGP+0.2 µg of tetanus toxoid. A second immunization was administered 21 days post primary immunization. Each mouse was bled 21 days after the second injection. The results are shown in Tables 5 and 6.

TABLE 5

Dose response of AGPs in mice immunized with tetanus toxoid.

| | Total Ig | | IgM | | IgG$_1$ | | IgG$_{2a}$ | | IgG$_{2b}$ | |
|---|---|---|---|---|---|---|---|---|---|---|
| Material | T/C Ratio* | Titer | T/C Ratio | Titer | T/C Ratio | Titer | T/C Ratio | Titer | T/C Ratio | Titer |
| B15 50 μg | 3.3 | 7,000 | 13.4 | 37,600 | 4.1 | 26,300 | 150.0 | 11,225 | 3.2 | 2500 |
| B15 25 μg | 5.8 | 12,400 | 2.1 | 6,000 | 4.5 | 28,800 | 52.0 | 3900 | 7.0 | 5400 |
| B15 10 μg | 5.3 | 11,450 | 1.4 | 4,000 | 5.5 | 35,100 | 33.8 | 2538 | 9.9 | 7650 |
| B27 50 μg | 3.2 | 6,800 | 4.0 | 11,200 | 1.6 | 10,400 | 12.0 | 900 | 11.6 | 9,000 |
| Vehicle | | 2150 | | 2800 | | 6350 | | 75 | | 775 |

*T/C Ratio = Experimental Test Titer ÷ Vehicle Control Titer.

TABLE 6

Dose response of AGPs in mice immunized with tetanus toxoid.

| | IgM | | Total Ig | | IgG$_1$ | | IgG$_{2a}$ | | IgG$_{2b}$ | |
|---|---|---|---|---|---|---|---|---|---|---|
| Material | T/C* | Titer | T/C | Titer | T/C | Titer | T/C | Titer | T/C | Titer |
| B12 50 μg | 5.43 | 869 | 368.55 | 47,543 | 141.22 | 259,429 | nd | | 499.35 | 12,983 |
| B12 25 μg | 3.14 | 503 | 403.98 | 52,114 | 145.21 | 266,743 | 16.86 | 354 | 196.92 | 5,120 |
| B12 10 μg | 3.71 | 594 | 248.06 | 32,000 | 81.12 | 149,029 | 6.81 | 143 | 181.12 | 4,709 |
| B12 5 μg | 3.43 | 549 | 489.92 | 63,200 | 84.11 | 154,514 | 34.14 | 717 | 352.54 | 9,166 |
| B12 1 μg | 1.71 | 274 | 326.02 | 42,057 | 90.08 | 165,486 | 73.71 | 1,548 | 175.81 | 4,571 |
| B15 50 μg | 3.14 | 503 | 233.88 | 30,171 | 90.08 | 165,486 | 50.05 | 1,051 | 235.62 | 6,126 |
| B15 25 μg | 2.29 | 366 | 181.91 | 23,467 | 106.14 | 194,971 | 10.43 | 219 | 158.23 | 4,114 |
| B15 10 μg | 2.86 | 457 | 170.10 | 21,943 | 39.07 | 71,771 | 2.57 | 54 | 84.38 | 2,194 |
| B15 5 μg | 1.71 | 274 | 248.06 | 32,000 | 103.15 | 189,486 | 3.00 | 63 | 210.88 | 5,483 |
| B15 1 μg | 1.57 | 251 | 166.56 | 21,486 | 72.04 | 132,343 | 7.62 | 160 | 114.27 | 2,971 |
| Vehicle | | 160 | | 129 | | 1837 | | 21 | | 26 |

*T/C = Experimental Test Titer ÷ Vehicle Control Titer.
nd-not done

TEST EXAMPLE 2

STIMULATION OF ANTIOVALBUMIN ANTIBODY PRODUCTION

BDF1 female mice (8 per group) were immunized with 0.2 ml of emulsions containing 50 μg of the AGPs+50 μg of ovalbumin. A second immunization was administered 21 days post primary. Each mouse was bled 14 days after the second injection. Antibody titers of immunized mice showing total IgG and IgM as well as titers for the subgroups of IgG including IgG$_1$, IgG$_{2a}$ and IgG$_{2b}$ are given in Table 7.

TABLE 7

Adjuvant activity in BDF1 mice immunized with ovalbumin.

| | Total Ig | | IgM | | IgG1 | | IgG2a | | IgG2b | |
|---|---|---|---|---|---|---|---|---|---|---|
| Material | T/C* | Titer | T/C | Titer | T/C* | Titer | T/C | Titer | T/C | Titer |
| B11 | 0.7 | 150 | 1.3 | 250 | 1.6 | 2650 | 1.7 | 550 | 1.6 | 375 |
| B2 | 2.5 | 563 | 0.9 | 175 | 5.0 | 8300 | 2.5 | 825 | 2.3 | 550 |
| B1 | 0.5 | 119 | 0.8 | 150 | 0.5 | 763 | 0.2 | 56 | 0.8 | 188 |
| B25 | 1.9 | 438 | 0.8 | 150 | 5.2 | 8500 | 0.5 | 163 | 5.0 | 1188 |
| B21 | 0.5 | 113 | 1.3 | 250 | 0.6 | 1000 | 0.1 | 25 | 0.8 | 200 |
| B15 | 4.1 | 925 | 2.3 | 438 | 0.6 | 950 | 0.3 | 113 | 16.7 | 3963 |
| B27 | 0.6 | 138 | 1.6 | 300 | 0.8 | 1275 | 0.1 | 38 | 0.5 | 113 |
| Vehicle | — | 225 | — | 188 | — | 1650 | — | 325 | — | 238 |

*T/C Ratio = Experimental Test Titer ÷ Vehicle Control Titer

The AGP compounds of the subject invention when administered to a warm-blooded animal with the antigen ovalbumin stimulates the production of antibody to that antigen.

TEST EXAMPLE 3

GENERATION OF A PROTECTIVE IMMUNE RESPONSE TO INFECTIOUS INFLUENZA

Mice vaccinated with formalin-inactivated influenza and the AGP compounds of the subject invention mounted a protective immune response to an influenza challenge as well as produced antibody to that antigen. Animals were vaccinated with the antigen and AGP compounds in various carriers. The degree of protection was determined by challenging the mice with intranasal (IN) administration of approximately 10 $LD_{50}$ infectious influenza A/HK/68. Mortality was assessed for 21 days following the challenge. The number of mice surviving the challenge dose is a direct assessment of the efficacy of the vaccine. For the experiments provided this data does not necessarily correlate with the amount of antibody produced.

1) Vaccines were formulated in 0.2% triethanolamine (TEoA)/water solution containing: 1 hemagglutinating unit (HAU) of formalin-inactivated influenza A/HK/68 (FI-Flu), and 50 μg of AGP except the vehicle control vaccines which contained no AGP. ICR mice (10/group) were vaccinated 1 time only. The vaccines were administered by subcutaneous (SQ) injection of 0.1 ml/site at 2 distinct sites near the inguinal lymph nodes for a total of 0.2 ml of vaccine/mouse. Mice (only 5 mice/group) were bled from the orbital plexus 14 days following the vaccination. Sera was harvested and frozen at −20° C. until used for enzyme-linked immunosorbent assay (ELISA). All mice were challenged 30 days post vaccination by intranasal (IN) administration of approximately 10 $LD_{50}$ infectious influenza A/HK/68. Mortality was assessed for 21 days following the challenge. Anti-influenza antibody titers obtained from vaccinations with TEoA formulations and corresponding survival rates of mice vaccinated with this formulation are shown in Table 8.

TABLE 8

Anti-influenza antibody titers and survival rates of treated mice.

| Material | Titer[-1] Total IgG | Percent Survival |
| --- | --- | --- |
| Nonimmune | <100 | 0 |
| Vehicle | <100 | 0 |
| B9 | 6400 | 44 |
| B10 | 1600 | 40 |
| B7 | 200 | 33 |
| B3 | 1600 | 33 |
| B14 | 6400 | 44 |
| B15 | 6400 | 50 |

2) Vaccines were formulated in 2% Squalene solution containing: 1 hemagglutinating unit (HAU) of formalin-inactivated influenza A/HK/68 (FI-Flu), and 25 μg of AGP except the saline and vehicle control vaccines which contained no AGP. BALB/c mice (10/group) were vaccinated 1 time only. The vaccines were administered by subcutaneous (SQ) injection of 0.1 ml/site at 2 distinct sites near the inguinal lymph nodes for a total of 0.2 ml of vaccine/mouse. Mice (only 5 mice/group) were bled from the orbital plexus 14 days following the vaccination. Sera was harvested and frozen at −20° C. until used for enzyme-linked immunosorbent assay (ELISA). All mice were challenged 35 days post vaccination by intranasal (IN) administration of approximately 10 $LD_{50}$ infectious influenza A/HK/68. Mortality was assessed for 21 days following the challenge. Anti-influenza antibody titers obtained from vaccinations with the squalene formulations as well as corresponding survival rates of vaccinated animals are shown in Table 9.

TABLE 9

Anti-influenza antibody titers and survival rates of treated mice.

| Material | Titer[-1] | | | | Percent Survival |
| --- | --- | --- | --- | --- | --- |
| | Total IgG | IgG1 | IgG2a | IgG2b | |
| Nonimmune | <100 | <100 | <100 | <100 | 0 |
| Saline | 800 | 100 | 800 | 100 | 62.5 |
| Vehicle | 1600 | 1600 | 1600 | 1600 | 100 |
| B25 | 3200 | 1600 | 6400 | 1600 | 100 |
| B15 | 1600 | 3200 | 3200 | 400 | 100 |
| B9 | 1600 | 1600 | 3200 | 800 | 87.5 |
| B10 | 400 | 400 | 400 | 400 | 62.5 |
| B3 | 3200 | 3200 | 6400 | 800 | 87.5 |
| B6 | 800 | 800 | 400 | 1600 | 75 |
| B14 | 3200 | 6400 | 3200 | 6400 | 87.5 |
| B28 | 800 | 400 | 400 | 100 | 50 |

3) The antibody titers and survival rate of vaccinated mice were compared after a primary then a secondary vaccination. Vaccines were formulated in 0.2% TEoA/water solution containing: 1 hemagglutinating unit of formalin-inactivated influenza A/HK/68, 25 μg AGP, except the vehicle control vaccine that contained no AGP. ICR mice (20/group) were administered vaccines by subcutaneous injection of 0.1 ml/site at 2 distinct sites near the inguinal lymph nodes for a total of 0.2 ml of vaccine/mouse. Each group was split into 2 subgroups 35 days after the primary vaccination. One of each subgroup was challenged at this time, the remaining subgroups received a secondary vaccination. Mice (only 5/subgroup) were bled from the orbital plexus 14 days following vaccination (primary or secondary). Sera was harvested and frozen at −20° C. until used for ELISA. Mice were challenged 35 post primary, or secondary, vaccination by intranasal administration of approximately 10 LD50, or 40 LD50, infectious influenza A/HK/68, respectively. Mortality was assessed for 21 days following the challenge. Anti-influenza antibody titers and survival rates of mice post primary and post secondary vaccination are shown in Table 10. Antibody titers as well as survival rates of mice vaccinated a second time were higher.

TABLE 10

Antibody titers and survival rates of treated mice.

| Material | IgG Titer-1 | | Percent Survival | |
| --- | --- | --- | --- | --- |
| | post 1° | post 2° | post 1° | post 2° |
| Nonimmune | 200 | 100 | 0 | 0 |
| Vehicle | 800 | 102,400 | 20 | 40 |
| B9 | 6400 | 12,800 | 80 | 50 |
| B10 | 1600 | 25,600 | 60 | 90 |
| B7 | 3200 | >102,400 | 60 | 60 |
| B4 | 800 | 25,600 | 50 | 70 |
| B3 | 3200 | 102,400 | 70 | 60 |
| B5 | 1600 | >102,400 | 60 | 90 |
| B6 | 1600 | 102,400 | 80 | 70 |
| B14 | 800 | 51,200 | 33 | 70 |

TEST EXAMPLE 4

THE EFFECT OF FATTY ACID CHAIN LENGTH ON ADJUVANTICITY

The effect of the length of fatty acid chains $R_1$–$R_3$ on activity was tested. Vaccines were formulated in 0.2% TEoA/water solution containing: 1 hemagglutinating unit of formalin-inactivated influenza A/HK/68, and 25 µg of AGP, except the vehicle control vaccines, which contained no AGP. ICR mice (10/group) were vaccinated 1 time only. The vaccines were administered by subcutaneous injection of 0.1 ml/site at 2 distinct sites near the inguinal lymph nodes for a total of 0.2 ml of vaccine/mouse. Mice (only 5 mice/group) were bled from the orbital plexus 14 days following the vaccination. Sera was harvested and frozen at −20° C. until used for ELISA. All mice were challenged 35 post vaccination by intranasal administration of approximately 10 $LD_{50}$ infectious influenza A/HK/68. Mortality was assessed for 21 days following the challenge. The length of the fatty acid chain appears to mildly affect biological activity. Results are shown in Tables 11 and 12.

TABLE 11

Antibody titers and survival rates of treated mice.

| Material | Length | Total IgG | IgG1 | IgG2a | IgG2b | Percent Survival |
|---|---|---|---|---|---|---|
| Nonimmune | — | 200 | 100 | 100 | 800 | 0 |
| Vehicle | — | 200 | 100 | 100 | 200 | 11 |
| B18 | 7 | 800 | 800 | 800 | 400 | 20 |
| B17 | 8 | 6400 | 3200 | 3200 | 1600 | 40 |
| B16 | 9 | 800 | 1600 | 100 | 800 | 40 |
| B15 | 10 | 3200 | 200 | 3200 | 6400 | 70 |
| B14 | 10 | 800 | 1600 | 100 | 400 | 30 |
| B13 | 11 | 1600 | 800 | 400 | 800 | 50 |
| B12 | 12 | 200 | 200 | 100 | 200 | 0 |
| B11 | 14 | 1600 | 200 | 1600 | 400 | 30 |

Titer$^{-1}$

TABLE 12

Antibody titers and survival rates of treated mice.

| Material | Length | Total IgG | IgG1 | IgG2a | IgG2b | Percent Survival |
|---|---|---|---|---|---|---|
| Nonimmune | — | 100 | 100 | 50 | 800 | 0 |
| Vehicle | — | 100 | 200 | 50 | 100 | 30 |
| B8 | 7 | 6400 | 3200 | 400 | 1600 | 80 |
| B7 | 9 | 3200 | 3200 | 100 | 1600 | 70 |
| B5 | 10 | 800 | 200 | 50 | 400 | 44 |
| B4 | 11 | 3200 | 400 | 100 | 1600 | 60 |
| B3 | 12 | 1600 | 1600 | 50 | 800 | 0 |
| B1 | 14 | 12,800 | 6400 | 1600 | 15600 | 40 |

Titer$^{-1}$

TEST EXAMPLE 5

THE EFFECT OF VARIATIONS IN THE CARBON CHAIN LENGTH BETWEEN THE

HETEROATOM X AND THE AGLYCON NITROGEN ATOM ON ADJUVANTICITY

The length of the carbon chain between X and the aglycon nitrogen atom was extended progressively by a single atom. The effect of lengthening the chain between these two components on adjuvanticity was explored. Vaccines were formulated in 0.2% TEoA/water solution containing: 1 hemagglutinating unit of formalin-inactivated influenza A/HK/68, and 25 µg of AGP, except the vehicle control vaccines, which contained no AGP. ICR mice (10/group) were vaccinated 1 time only. The vaccines were administered by subcutaneous injection of 0.1 ml/site at 2 distinct sites near the inguinal lymph nodes for a total of 0.2 ml of vaccine/mouse. Mice (only 5 mice/group) were bled from the orbital plexus 14 days following the vaccination. Sera was harvested and frozen at −20° C. until used for ELISA. All mice were challenged 35 days post vaccination by intranasal administration of approximately 10 $LD_{50}$ infectious influenza A/HK/68. Mortality was assessed for 21 days following the challenge. Adjuvant activity appears to lessen as the length of the carbon chain between the heteroatom X and aglycon nitrogen atom increases. However, depending upon the residues attached to this carbon chain the biologic and metabolic stability of the molecules may be affected. Results are shown in Tables 13.

TABLE 13

Antibody titers and survival rates of treated mice.

| Material | Carbon Chain | Total IgG | IgG1 | IgG2a | IgG2b | Percent Survival |
|---|---|---|---|---|---|---|
| Nonimmune | — | <50 | <50 | <50 | <50 | 0 |
| Vehicle | — | 200 | 200 | 50 | 200 | 25 |
| B19 | 2 | 12,800 | 100 | 800 | 6400 | 50 |
| B21 | 3 | 6400 | 800 | 100 | 1600 | 40 |
| B22 | 4 | 3200 | 100 | 3200 | 200 | 40 |

Titer-1

TEST EXAMPLE 6

CYTOKINE INDUCTION BY THE AGP COMPOUNDS

The AGP compounds of the subject invention induced cytokines in human whole blood ex vivo culture assays. AGP compounds were solubilized in 10% EtOH-water and diluted to various concentrations. Fifty µl of each dilution were added to 450 µl of whole human blood. Controls were treated with culture media (RPMI). The reaction mixture was incubated at 37° C. for 4 hr with constant mixing on a rotator. Sterile PBS (1.5 ml) was added to the reaction mixture, the cells were centrifuged and the supernatents removed for cytokine testing. The concentration of TNF-α and IL-1β in each supernatent was determined using immunoassay ELISA kits from R&D Systems. Results from these studies are shown in Tables 14–19.

TABLE 14

Stimulation of cytokine secretion in an ex vivo assay.

| Material | Dosage (µg) | TNF-α (pg/ml) | IL-1β (pg/ml) |
|---|---|---|---|
| B26 | 20 | 498.90 | 33.25 |
|  | 10 | 254.94 | 25.34 |
|  | 5 | 75.62 | 9.89 |
|  | 1 | 38.85 | 3.90 |
| B2 | 20 | 1338.42 | 155.07 |
|  | 10 | 817.67 | 114.41 |
|  | 5 | 235.32 | 34.72 |
|  | 1 | 105.52 | 14.53 |
| RPMI | — | 2 | 0 |

TABLE 15

Stimulation of cytokines in an ex vivo assay.

| Material | Dosage (ng/ml) | TNF-α (pg/ml) | IL-1β (pg/ml) |
|---|---|---|---|
| B16 | 10,000 | 291 | 55 |
|  | 5000 | 277 | 53 |
|  | 1000 | 155 | 39 |

TABLE 15-continued

Stimulation of cytokines in an ex vivo assay.

| Material | Dosage (ng/ml) | TNF-α (pg/ml) | IL-1β (pg/ml) |
|---|---|---|---|
| B13 | 10,000 | 775 | THTC* |
|  | 5000 | 716 | 187 |
|  | 1000 | 740 | 177 |
| B9 | 10,000 | 449 | 96 |
|  | 5000 | 247 | 84 |
|  | 1000 | 145 | 53 |
| B10 | 10,000 | 207 | 43 |
|  | 5000 | 127 | 61 |
|  | 1000 | 73 | 17 |
| B7 | 10,000 | 83 | 16 |
|  | 5000 | 57 | 14 |
|  | 1000 | 26 | 6 |
| RPMI | — | 2 | 0 |

*THTC-To high to Count

TABLE 16

Stimulation of cytokines in an ex vivo assay.

| Material | Dosage (ng/ml) | TNF-α (pg/ml) | IL-1β (pg/ml) |
|---|---|---|---|
| B4 | 10,000 | 432 | 213 |
|  | 5000 | 205 | 164 |
|  | 1000 | 94 | 70 |
| B3 | 10,000 | 567 | 269 |
|  | 5000 | 390 | 342 |
|  | 1000 | 189 | 204 |
| B5 | 10,000 | 169 | 79 |
|  | 5000 | 143 | 162 |
|  | 1000 | 43 | 36 |
| B6 | 10,000 | 94 | 52 |
|  | 5000 | 59 | 29 |
|  | 1000 | 30 | 13 |
| B14 | 10,000 | 249 | 91 |
|  | 5000 | 120 | 71 |
|  | 1000 | 56 | 46 |
| RPMI | — | 2 | 0 |

TABLE 17

Stimulation of cytokine secretion in an ex vivo assay.

| Material | Dosage (ng/ml) | TNF-α (pg/ml) | IL-1β (pg/ml) |
|---|---|---|---|
| B11 | 10,000 | 181 | 62.3 |
|  | 5000 | 139 | 61.7 |
|  | 1000 | 115 | 54.5 |
|  | 500 | 125 | 55.8 |
|  | 100 | 127 | 59.8 |
| B13 | 10,000 | 583 | 282 |
|  | 5000 | 592 | 390 |
|  | 1000 | 478 | 327 |
|  | 500 | 411 | 352 |
|  | 100 | 302 | 261 |
| B15 | 10,000 | 320 | 153 |
|  | 5000 | 280 | 126 |
|  | 1000 | 209 | 94.4 |
|  | 500 | 183 | 104 |
|  | 100 | 133 | 51.6 |
| B16 | 10,000 | 121 | 41.0 |
|  | 5000 | 114 | 34.0 |
|  | 1000 | 72 | 19.5 |
|  | 500 | 55 | 17.1 |
| B14 | 10,000 | 114 | 24.6 |
|  | 5000 | 87 | 19.0 |
|  | 1000 | 51 | 10.0 |
|  | 500 | 49 | 19.9 |
| RPMI | — | 2 | 0 |

TABLE 18

Stimulation of cytokine secretion in an ex vivo assay.

| Material | Dosage (ng/ml) | TNF-α (pg/ml) | IL-1β (pg/ml) |
|---|---|---|---|
| B2 | 10,000 | 100 | 22.2 |
|  | 5000 | 75 | 14.0 |
|  | 1000 | 38 | 9.0 |
|  | 500 | 28 | 8.3 |
|  | 100 | 6.1 | 3.5 |
| B1 | 10,000 | 20 | 10.0 |
|  | 5000 | 11 | 5.5 |
|  | 1000 | 2.8 | 4.0 |
|  | 500 | 1.1 | 0 |
|  | 100 | 0 | 0 |
| B7 | 10,000 | 61 | 14.7 |
|  | 5000 | 44 | 8.3 |
|  | 1000 | 30 | 4.3 |
|  | 500 | 27 | 3.8 |
|  | 100 | 10 | 5.1 |
| B4 | 10,000 | 232 | 66.9 |
|  | 5000 | 173 | 66.5 |
|  | 1000 | 130 | 32.0 |
|  | 500 | 116 | 19.3 |
|  | 100 | 89 | 65.2 |
| B3 | 10,000 | 433 | 151.9 |
|  | 5000 | 316 | 200.4 |
|  | 1000 | 229 | 75.1 |
|  | 500 | 212 | 67.9 |
|  | 100 | 130 | 35.9 |
| B5 | 10,000 | 142 | 24.1 |
|  | 5000 | 99 | 23.0 |
|  | 1000 | 96 | 10.5 |
|  | 500 | 59 | 16.9 |
|  | 100 | 33 | 5.4 |
| RPMI | — | 2 | 0 |

TABLE 19

Stimulation of cytokine secretion in an ex vivo assay.

| Material | Dosage (ng/ml) | TNF-α (pg/ml) | IL-1β (pg/ml) |
|---|---|---|---|
| B17 | 10,000 | 2.8 | 0 |
|  | 5000 | 2.2 | 0 |
|  | 1000 | 2.6 | 0.2 |
| B8 | 10,000 | 2.8 | 0 |
|  | 5000 | 0.7 | 0.5 |
|  | 1000 | 1.5 | 0.1 |
| B22 | 10,000 | 287 | 17 |
|  | 5000 | 11 | 1.9 |
|  | 1000 | 2.2 | 0.1 |
| B28 | 10,000 | 198 | 13 |
|  | 5000 | 197 | 13 |
|  | 1000 | 139 | 8 |
| B12 | 10,000 | 1017 | 135 |
|  | 5000 | 957 | 153 |
|  | 1000 | 863 | 175 |
| RPMI | — | 3.9 | 0 |

TEST EXAMPLE 7

STIMULATION OF A CYTOTOXIC T-LYMPHOCYTE RESPONSE

The induction of a cytotoxic T-lymphocyte response after administration of the AGP compounds of the subject invention and a protein antigen was detected by a cytotoxicity assay. Groups of C57BL/6 mice were given a primary immunization subcutaneously (inguinal region) with 25 μg ovalbumin (OVA) formulated in AGP preparations. The injected volume was 200 μl. Twenty-one days later three mice per experimental group were killed and spleens removed and pooled as single cell suspensions and counted.

Spleen cells (75×10$^6$ cells in 3–4 ml media) from the experimental groups were placed in a 25 cm$^2$ T-flask. Next, 1.0 ml of irradiated (20,000 rads) E.G7 (OVA) cells at 5×10$^6$/ml were added to the flask. The volume was brought to 10 ml. The cultures were maintained by placing the T-flasks upright in a 37° C., 5% CO$_2$ incubator for four days. On day 4 the surviving cells were recovered from the flasks, washed 1× in fresh media resuspended in 5.0 ml, and counted.

Recovered effector cells were adjusted to 5×10$^6$ viable cells/ml and 100 µl volumes were diluted serially in triplicate in wells of 96 well round-bottom plates (Coming 25850) using 100 µl/well of media as a diluent. Next, 100 µl volumes of $^{51}$Cr-labelled (see below) targets [E.G7 (OVA)-an ovalbumin gene transfected EL-4 cell line] at 1×10$^5$ cells/ml were added to the wells. Spontaneous release (SR) wells contained 100 µl of targets and 100 µl of media. Maximal release (MR) wells contained 100 µl of targets and 100 µl detergent (2% Tween 20). Effector/target (E/T) ratios were 50:1, 25:1, 12.5:1. The plates were centrifuged at 400×g and incubated at 37° C., 5% CO$_2$ for 4 hr. After the incubation the well supernatants were collected using a Skatron Supernatant Collection System.

Percent Specific Lysis=

$$100 \times \left[ \frac{(\text{Exp. Release} - SR)}{(MR - SR)} \right]$$

Target cells, E.G7 (OVA), were labelled with $^{51}$Cr (sodium chromate) as follows. In a total volume of 1.0 ml were mixed 5×10$^6$ target cells and 250 µCi $^{51}$Cr in 15 ml conical tube. The cell suspension was incubated in a 37° C. water bath for 90 min., with gentle mixing every 15 min. After incubation the labelled cells were washed 3× by centrifugation and decanting with 15 ml volumes of media. After the third centrifugation the cells were resuspended in 10 ml of fresh media and allowed to stand at room temperature for 30 min. and then centrifuged. The cells were finally resuspended in media at 1×10$^5$ cells/ml.

Mice immunized according to the procedure above with the AGPs of the subject invention displayed a cytotoxic T-lymphocyte response to the OVA antigen as shown in Table 20.

TABLE 20

Cytotoxic T-lymphocyte response of treated cells.

| | % Cytotoxicity E:T | | |
|---|---|---|---|
| Material | 50:1 | 25:1 | 12.5:1 |
| B11 | 14 | 8 | 5 |
| B12 | 13 | 7 | 4 |
| B13 | 28 | 15 | 10 |
| B15 | 58 | 49 | 30 |
| B16 | 42 | 29 | 20 |
| B17 | 39 | 26 | 15 |
| B18 | 36 | 20 | 15 |
| B14 | 45 | 36 | 25 |
| B28 | 28 | 15 | 9 |
| B27 | 17 | 9 | 5 |
| B1 | 34 | 24 | 15 |
| B3 | 65 | 54 | 42 |
| B4 | 72 | 66 | 60 |
| B5 | 28 | 18 | 11 |
| B7 | 57 | 44 | 29 |

TABLE 20-continued

Cytotoxic T-lymphocyte response of treated cells.

| | % Cytotoxicity E:T | | |
|---|---|---|---|
| Material | 50:1 | 25:1 | 12.5:1 |
| B8 | 36 | 20 | 15 |
| B10 | 65 | 56 | 38 |
| B9 | 65 | 55 | 36 |
| B6 | 54 | 41 | 37 |
| B2 | 21 | 12 | 6 |
| B25 | 65 | 55 | 43 |
| B26 | 14 | 8 | 4 |
| B22 | 58 | 42 | 31 |
| B21 | 38 | 26 | 15 |
| B19 | 59 | 42 | 33 |
| B20 | 36 | 25 | 13 |
| B29 | 16 | 9 | 5 |
| B31 | 19 | 11 | 7 |
| B35 | 9 | 5 | 2 |
| B36 | 13 | 7 | 4 |
| B37 | 12 | 8 | 6 |
| B38 | 38 | 25 | 16 |
| B39 | 33 | 21 | 13 |
| B40 | 20 | 12 | 8 |
| B43 | 19 | 12 | 6 |
| Vehicle Control | <10 | | |

TEST EXAMPLE 8

GENERATION OF SERUM AND MUCOSAL ANTIBODY TITERS TO TETANUS-TOXOID

The AGPs of the subject invention elicited both a serum and mucosal immune response to purified tetanus toxoid when administered intranasally. Groups of BALB/c mice were given a primary immunization (1°) intranasally with 10 µg tetanus toxoid (TT)+20 µg AGP formulated in an aqueous formulation (AF) in a volume of 20 µl. A secondary immunization (2°) was given 14 days later and a tertiary immunization (3°) identical in composition to the first and second was administered 14 days later. Mice were bled on day 21 (day 7 post 2°) and day 38 (day 10 post 3°) and day 48 (day 20 post 3°). Vaginal wash/fecal extract samples were taken on day 7 post 2° and day 7 post 3°. Serum and wash samples were assayed for anti-TT antibody by standard ELISA methods. Results of these assays are shown in Tables 21 and 22 below.

The aqueous formulation comprises the AGPs of the subject invention and one or more surfactants. Surfactants useful in an aqueous composition include glycodeoxycholate, deoxycholate, sphingomyelin, sphingosine, phosphatidylcholine, 1,2-Dimyristoyl-sn-glycero-3-phosphoethanolamine, L-α-phosphatidylethanolamine, and 1,2-Dipalmitoyl-sn-glycero-3-phosphocholine, or a mixture thereof. The aqueous formulation used in this example comprises the surfactant 1,2 dipalmitoyl-sn-glycero-3-phosphocholine (DPPC) and was prepared as follows: briefly; a 4 mg/ml solution of DPPC was prepared in ethanol. An aliquot of the ethanol solution is added to the dried AGPs and swirled gently to wet the AGP. The ethanol is removed by blowing a stream of filtered nitrogen gently over the vial. Water for Injection is added and the suspension is sonicated 10 min. at 60° C. until clear. The resulting aqueous formulation contains approximately 118 µg/ml DPPC, has particles of around 70 nm and was filter sterilized.

TABLE 21

Anti-tetanus toxoid antibody titers in treated mice.

Anti-Tetanus Toxoid Titer$^{-1}$

| | Vaginal Wash | | | | Fecal Extract | | | |
|---|---|---|---|---|---|---|---|---|
| | IgG | | IgA | | IgG | | IgA | |
| Material | 2° | 3° | 2° | 3° | 2° | 3° | 2° | 3° |
| B25 | 800 | 6400 | 6400 | 6400 | 50 | 200 | 3200 | 6400 |
| B15 | 400 | 800 | 6400 | 6400 | 50 | 100 | 6400 | 12,800 |
| B19 | 200 | 400 | 1600 | 3200 | 25 | 25 | 3200 | 6400 |
| B4 | 1600 | 400 | 1600 | 6400 | 25 | 50 | 3200 | 12,800 |
| B5 | 3200 | 800 | 3200 | 3200 | 50 | 100 | 3200 | 6400 |
| B3 | 1600 | 1600 | 6400 | 6400 | 50 | 100 | 3200 | 6400 |
| B22 | 400 | 800 | 800 | 3200 | 25 | 50 | 1600 | 6400 |
| PBS | <25 | <25 | <25 | <25 | <25 | <25 | <25 | <25 |
| Normal Sera | <25 | <25 | <25 | <25 | <25 | <25 | <25 | <25 |

TABLE 22

Serum anti-tetanus toxoid antibody titers in treated animals.

Anti-Tetanus Toxoid Titer$^{-1}$
Serum Pools

| | IgG$_1$ | | | IgG$_{2a}$ | | | IgA | | |
|---|---|---|---|---|---|---|---|---|---|
| | d21 | d38 | d48 | d21 | d38 | d48 | d21 | d38 | d48 |
| B25 | 1M* | 8M | 8M | 512K | 4M | 4M | 12.8K | 102.4K | 102.4K |
| B15 | 2M | 8M | 8M | 512K | 1M | 2M | 12.8K | 51.2K | 25.6K |
| B19 | 2M | 4M | 4M | 64K# | 256K | 128K | 6.4K | 25.6K | 12.8K |
| B4 | 1M | 8M | 8M | 1M | 2M | 2M | 25.6K | 102.4K | 102.4K |
| B5 | 2M | 8M | 8M | 512K | 2M | 2M | 25.6K | 102.4K | 102.4K |
| B3 | 512K | 4M | 8M | 512K | 2M | 2M | 12.8K | 51.2K | 51.2K |
| B22 | 1M | 2M | 4M | 64K | 256K | 256K | 6.4K | 25.6K | 25.6K |
| PBS | 1,000 | 16K | 16K | 1,000 | 1,000 | 1,000 | 200 | 200 | 200 |
| C | 200 | 200 | 200 | 100 | 100 | 100 | 200 | 200 | 200 |

*M = 10$^6$,
K = 10$^3$,
C = normal sera

Intranasal administration of TT formulated in AGP-AF induced both an antigen specific humoral immune response (Table 22) and a mucosal immune response (Table 21) to that antigen.

TEST EXAMPLE 9

STIMULATION OF AN IMMUNE RESPONSE TO HEPATITIS B SURFACE ANTIGEN BY INTRANASAL ADMINISTRATION

Mice administered hepatitis B surface antigen (HBsAg) intranasally with the compounds of the subject invention produced serum IgG and IgA titers to that antigen. Secretory IgA was detected in vaginal washes and the induction of a cytotoxic T-lymphocyte response was detected by a cytotoxicity assay.

Groups of BALB/c mice were given a primary immunization (1°) intranasally with 2.5 µg HBsAg+10 µg AGP-AF in a volume of 20 µl. AGP-AF was prepared as in TEST EXAMPLE 8. Twenty-one days later mice were given a secondary immunization (2°) of 7.5 µg HBSAG +10 µg AGP-AF intranasally in 20 µl volume. A tertiary immunization (3°) identical in composition to the secondary immunization was administered 28 days after the secondary immunization. Assays were conducted to detect cytotoxic T-lymphocyte activity at 16 days post secondary immunization (d16 post 2°) and 8 days post tertiary immunization (d8 post 3°). Serum and mucosal antibody titers were assessed at 22 days post secondary immunization (d22 post 2°) and 21 days post tertiary immunization (d21 post 3°). Antibody assays were conducted by standard ELISA methods. Cytotoxicity assays were conducted as described in TEST EXAMPLE 7. Results from this experiment are shown in Tables 23–26.

TABLE 23

Cytotoxic T-lymphocyte response of treated cells.

| | % Cytotoxicity (d16, post 2°) E/T | | | |
|---|---|---|---|---|
| Material | 50:1 | 25:1 | 12.5:1 | 6.25:1 |
| B25 | 36 | 20 | 13 | 9 |
| B15 | 13 | 5 | 4 | 4 |
| B19 | 26 | 20 | 11 | 9 |
| B4 | 28 | 17 | 9 | 7 |
| B3 | 43 | 26 | 17 | 11 |
| B5 | 43 | 30 | 20 | 11 |
| B22 | 33 | 21 | 15 | 8 |
| Vehicle | 3 | 2 | 0 | 0 |
| Normal Cells | 3 | 3 | 0 | 0 |

TABLE 24

Cytotoxic T-lymphocyte response of treated cells.

| | % Cytotoxicity (d8, post 3°) E/T | | | |
|---|---|---|---|---|
| Material | 50:1 | 25:1 | 12.5:1 | 6.25:1 |
| B25 | 30 | 19 | 13 | 8 |
| B15 | 56 | 42 | 25 | 16 |
| B19 | 71 | 54 | 33 | 24 |
| B4 | 23 | 15 | 9 | 5 |
| B3 | 54 | 45 | 32 | 20 |
| B5 | 44 | 30 | 19 | 12 |
| B22 | 22 | 13 | 7 | 5 |
| Vehicle | 5 | 2 | 1 | 1 |
| Normal Cells | 7 | 5 | 3 | 3 |

TABLE 25

Anti-hepatitis antibody titers in treated mice.

| | Anti HBsAg Titer$^{-1}$* | | |
|---|---|---|---|
| Material | IgG$_1$ | IgG$_{2a}$ | IgA |
| B25 | 256K# | 500K | 3,200 |
| B15 | 256K | 500K | 6,400 |
| B19 | 500K | 64K | 1,600 |
| B4 | 500K | 1000K | 6,400 |
| B3 | 1000K | 500K | 6,400 |
| B5 | 256K | 500K | 3,200 |
| B22 | 256K | 64K | 1,600 |
| Vehicle | <2K | <2K | <200 |

*day 22 post 2°, #K = $10^3$

TABLE 26

Anti-hepatitis antibody titers in treated mice.

| | Anti HBsAg Titer$^{-1}$* | | |
|---|---|---|---|
| Material | IgG$_1$ | IgG$_{2a}$ | IgA |
| B25 | 1000K# | 1000K | 25,600 |
| B15 | 2000K | 2000K | 25,600 |
| B19 | 2000K | 500K | 12,800 |
| B4 | 1000K | 2000K | 25,600 |
| B3 | 1000K | 1000K | 25,600 |
| B5 | 500K | 1000K | 12,800 |
| B22 | 500K | 500K | 12,800 |
| Vehicle | <2K | <2K | <200 |

*day 21 post 3°, #K = $10^3$

Groups of BALB/c mice were immunized with 2.5 µg HBsAg+10 µg AGP-AF intranasally and boosted intranasally with 7.5 µg HBsAg+10 µg AGP-AF 21 days later. Vaginal samples were collected 10 days after the booster immunization and 5 assayed for anti-HBsAg antibody. Results of this assay are shown in Table 27.

TABLE 27

| | Vaginal Wash Anti-HBsAg Titer$^{-1}$ | |
|---|---|---|
| Material | IgG | IgA |
| B25 | 100 | 800 |
| B15 | 50 | 3200 |
| B19 | <50 | 400 |

TABLE 27-continued

| | Vaginal Wash Anti-HBsAg Titer$^{-1}$ | |
|---|---|---|
| Material | IgG | IgA |
| B4 | 1600 | 6400 |
| B3 | 800 | 1600 |
| B5 | 1600 | 1600 |
| B22 | 100 | 800 |
| Vehicle | <50 | <50 |

The intranasal administration of HBsAg with the compounds of the subject invention stimulated both a humoral and cellular immune response to that antigen. Intranasal immunization with the antigen formulated in AGP-AF induced a cytotoxic T-lymphocyte response (Table 23–24) and antigen specific humoral (Table 25 and 26) and mucosal (Table 27) immune responses.

TEST EXAMPLE 10

GENERATION OF A PROTECTIVE IMMUNE RESPONSE TO INFLUENZA

Mice immunized intranasally with FLUSHIELD influenza vaccine containing hemagglutinin antigen and the AGPs of the subject invention produced both IgG and IgA, which were recovered in vaginal washes. Immunized mice were also protected from subsequent influenza challenge.

ICR mice were immunized three times at 21 day intervals intranasally with FLUSHIELD influenza vaccine (Wyeth-Lederle) containing 0.3 µg hemagglutinin antigen (HA)+10 µg AGP-AF or recombinant E. coli heat labile enterotoxin (LT). AGP-AF was prepared as in TEST EXAMPLE 8. LT was solubilized in saline at 1 µg/ml. Vaginal washes were collected 14 days after the second and third immunization. Serum samples were collected 14 days after the third immunization. Mice were challenged with 10 LD$_{50}$ (lethal dose 50) of infectious influenza A/HK/68 thirty-five days after the final immunization and monitored for mortality. Tables 28 and 29 show the results of assays conducted by standard ELISA methods to detect anti-influenza antibody titers in vaginal washes and sera.

TABLE 28

| | Vaginal Wash Samples | | | | Percent |
|---|---|---|---|---|---|
| | IgA | | IgG | | |
| Material | Secondary | Tertiary | Secondary | Tertiary | Protection |
| Nonimmune | <20 | <20 | <20 | <20 | 22 |
| Vehicle | 80 | 160 | 160 | 160 | 50 |
| B25 | 1280 | 1280 | 640 | 2560 | 100 |
| B19 | 320 | 5120 | 1280 | 1280 | 70 |
| B3 | 1280 | 2560 | 1280 | 1280 | 100 |
| B22 | 640 | 2560 | 320 | 640 | 75 |
| LT | 2560 | 2560 | 2560 | 640 | 100 |

TABLE 29

| | Serum Titers | | | | Percent |
|---|---|---|---|---|---|
| Material | Total IgG | IgG$_1$ | IgG$_{2a}$ | IgG$_{2b}$ | Protection |
| Nonimmune | <400 | <400 | <400 | <400 | 22 |
| Vehicle | 102,400 | 256,000 | 12,800 | 102,400 | 50 |

TABLE 29-continued

| Material | Serum Titers | | | | Percent Protection |
| --- | --- | --- | --- | --- | --- |
| | Total IgG | IgG$_1$ | IgG$_{2a}$ | IgG$_{2b}$ | |
| B25 | ≧819,200 | 102,400 | 819,200 | ≧819,200 | 100 |
| B19 | 819,200 | 51,200 | 102,400 | 819,200 | 70 |
| B3 | ≧819,200 | 51,200 | 819,200 | ≧819,200 | 100 |
| B22 | 819,200 | 51,200 | 102,400 | 819,200 | 75 |
| LT | ≧819,200 | ≧819,200 | ≧819,200 | ≧819,200 | 100 |

These data demonstrate that AGPs in AF when administered intranasally act as a mucosal adjuvants causing the production of IgA at mucosal sites. Increased protection is also induced against an upper respiratory pathogen that invades through the mucosa.

TEST EXAMPLE 11

GENERATION OF IMMUNE RESPONSES FROM STABLE EMULSION FORMULATIONS

The AGP compounds of the subject invention stimulated both humoral and cytotoxic T-lymphocyte responses when formulated in a stable emulsion (SE). AGPs were tested at 25 μg dose levels to adjuvantize Hepatitis B surface antigen (HBsAg) for the induction of CTL and antibody responses. BALB/c mice were immunized subcutaneously with 2.0 μg HBsAg plus 25 μg of AGP/SE on day 0 and day 21. The CTL assay was conducted as in TEST EXAMPLE 7. The AGPs were formulated in a stable emulsion (SE) and the compositions were designated AGP-SE. Methods for preparing the stable emulsion containing 10% v/v squalene, 0.091% w/v PLURONIC-F68 block copolymer, 1.909% w/v egg phosphatidyl choline, 1.8% v/v glycerol, 0.05% w/v α tocopherol, 10% ammonium phosphate buffer and 78.2% v/v Water for Injection should be readily apparent to one skilled in the art. The emulsion was homogenized to a particle size of ≧0.2 μm. Table 30 shows the AGPs of the subject invention induced a cytotoxic T-lymphocyte response to HBsAg.

TABLE 30

Cytotoxic T-lymphocyte response of treated cells.

| Material | Day | % Cytotoxicity E:T | | | |
| --- | --- | --- | --- | --- | --- |
| | | 50:1 | 25:1 | 12.5:1 | 6.25:1 |
| B25 | d17, post 1° | 27 | 12 | 9 | 5 |
| B19 | | 74 | 48 | 34 | 24 |
| B3 | | 28 | 15 | 9 | 5 |
| B22 | | 42 | 24 | 17 | 7 |
| Vehicle-SE | | 32 | 16 | 9 | 6 |
| B25 | d16, post 2° | 49 | 28 | 20 | 13 |
| B19 | | 73 | 62 | 42 | 31 |
| B3 | | 81 | 47 | 32 | 22 |
| B22 | | 78 | 69 | 58 | 39 |
| Vehicle-SE | | 38 | 23 | 14 | 8 |

The results of the antibody titer to HBsAg are shown on Table 31. Sera from bleeds taken on day 28 post 2° were titered on ELISA plates coated with either HBsAg or a 28 amino acid peptide (p72) which contains B-cell epitopes found in the S-antigen region, residues 110–137, of the HBsAg.

TABLE 31

Anti-HBsAg titer of treated mice.

| | Anti-HBsAg Titer[-1] | | | |
| --- | --- | --- | --- | --- |
| | HBsAg | | p72-Peptide | |
| Material | IgG$_1$ | IgG$_{2a}$ | IgG$_1$ | IgG$_{2a}$ |
| B25 | 2048K* | 2048K | 128K | 64K |
| B19 | 1024K | 1024K | 64K | 128K |
| B3 | 512K | 1024K | 16K | 128K |
| B22 | 1024K | 1024K | 128K | 128K |
| Vehicle SE | 1024K | 64K | 64K | 4K |

AGP-SE treated mice displayed both humoral (Table 31) and cytotoxic T-lymphocyte (Table 30) responses to the hepatitis B surface antigen. Of interest, AGP-SE treated mice in serum displayed a vigorous IgG$_{2a}$ specific antibody titer detected by both antigens, whereas the vehicle-SE induced only a modest IgG$_{2a}$ response.

TEXT EXAMPLE 12

STIMULATION OF SERUM ANTIBODY TITERS

The AGP compound B31 was evaluated for its ability to enhance serum antibody titers to an influenza virus vaccine as set forth in Text Example 3. In brief, ICR mice (10/group) were administered vaccines containing 1 HAU of formalin-inactivated influenza A/HK/68 plus or minus 25 μg RC-523 formulated in a 0.2% TEoA/water solution. The mice were, also, challenged with a lethal dose of infectious influenza virus in order to assess protection. The results of this experiment are presented in Table 32.

TABLE 32

| Material | Anti-influenza serum titers | | | | Protection |
| --- | --- | --- | --- | --- | --- |
| | IgG | IgG1 | IgG2a | IgG2b | |
| Nonimmune | 200 | 50 | 50 | 100 | 0 |
| Vehicle | 200 | 200 | 50 | 200 | 25 |
| B31 | 3200 | 1600 | 400 | 1600 | 70 |

TEXT EXAMPLE 13

INDUCIBLE NITRIC OXIDE SYNTHETIC ACTIVITY

Screening of respective AGP compounds of this invention included evaluation of inducible nitric oxide synthetase or iNOS activity (NOS ED$_{50}$), which correlates with macrophage activation, and can thus be viewed as a measure of immune stimulation. For this assay, mouse peritoneal exudates cells were harvested and the adherent cell population isolated. The adherent cells were exposed to varying concentrations of soluble AGP compounds and the resulting induction and secretion of nitrite measured. The NOS ED$_{50}$ value represents a concentration of AGP required to stimulate half the maximum amount of nitrite release and corresponds to the concentration required to stimulate macrophages.

The AGP compounds were also evaluated for their tendency to induce a fever response in rabbits. Each compound was formulated in 10% (v/v) ethanol/water solution at 100 mg/ml, then diluted with D$_5$W to the desired concentration.

The material was injected at 3 ml/kg body weight into 3 rabbits. The rise in core temperature of the rabbits was recorded. A compound inducing a cumulative rise of greater than or equal to 1.5 degree in the three rabbits is considered pyrogenic.

The results of these experiments are presented in Table 33.

TABLE 33

| # | NOS ED$_{50}$ (nanograms/ml) | | | PYROGENICITY Total Rise ° C., 3 rabbits | | MPD |
|---|---|---|---|---|---|---|
| | Exp. 1 | Exp 2 | Exp 3 | 2.5 ug/kg | 10 ug/kg | ug/kg |
| B1 | 150 | | | 0 | 0.1 | |
| B2 | 9 | | | 0.9 | 3.6 | 2.5–5 |
| B3 | 4 | | | 0 | 4.2 | |
| B4 | 5 | | | 0.1 | 3.4 | |
| B5 | 5 | | 3 | 0.1 | 4.1 | |
| B6 | | 1.8 | | 2.1 | — | |
| B7 | 21 | | | 0 | 4 | |
| B8 | ≧3000 | | | 3.6 | — | |
| B9 | 16 | | | 0 | 3.1 | |
| B10 | 4 | | | 0 | 5.8 | |
| B11 | 3 | | | 4.2 | — | 0.3–0.6 |
| B12 | | 0.9 | | 2.5 | — | |
| B13 | 0.1 | | | 3 | — | |
| B14 | 0.25 | | | 2.1 | — | |
| B15 | 0.06 | | | 4.2 | 3.1 | <0.06 |
| B16 | 0.46 | | | 1.8 | — | |
| B17 | | | 32.5 | 2.1 | 3.4 | |
| B18 | ≧3000 | | | 4.3 | — | |
| B19 | 100 | | | 0 | 0.3 | |
| B20 | 0.5 | | 1.5 | 0.3 | 4.6 | |
| B21 | 8 | | | 0.5 | 2 | |
| B22 | | | 51 | 1.7 | — | |
| B23 | | 159 | | 0.3 | 0.3 | |
| B24 | 20 | | 17 | 0.9 | 2.4 | 2.5–5 |
| B25 | 0.3 | | 0.5 | 0.6 | 4.2 | |
| B26 | 67 | | | 0.2 | 1.7 | 5 |
| B27 | | 1.65 | | 1.8 | 3.9 | |
| B28 | | | 0.3 | 4.2 | — | |
| B29 | ≧10,000 | | | 0.2 | 0.7 | |
| B30 | | | | 4.3 | — | |
| B31 | ≧10,000 | | | 0.5 | 1.6 | |
| B32 | | | | | | |
| B34 | ≧10,000 | | | 3.5 | 2.8 | |
| B35 | | 86 | | 3.2 | — | |
| B36 | | | | 1.8 | 3.4 | — |
| B37 | | | | 1.1 | 2.2 | — |
| B38 | | | ≧3000 | 3.6 | — | |
| B39 | | | ≧3000 | 3.2 | — | |
| B40 | | | ≧3000 | 3.8 | — | |
| B41 | | | | 6.3 | — | |
| B42 | | | | 5.2 | — | |
| B43 | | | 380 | 3.8 | — | |

TEXT EXAMPLE 14

CLINICAL EFFICACY DATA

This Example discloses primary efficacy results of a randomized, controlled study comparing the efficacy and safety of the AGP designated RC-210-04 (B19 in Table 1 and Example 20 herein above; chemical name 2-[(R)-3-Tetradecanoyloxytetradecanoylamino]ethyl 2-Deoxy-4-O-phosphono-3-O-[(R)-3-tetradecanoyloxytetradecanoyl]-2-[(R)-3-tetradecanoyloxytetradecanoylamino]-β-D-glucopyranoside Triethylammonium Salt)). Hepatitis B surface antigen (AgB) was administered to healthy adults, who are not immune to Hepatitis B virus (HBV), either alone or in conjunction with RC-210-04. After screening, subjects were randomized to one of two treatment arms and received three intramuscular (IM) injections of either AgB/RC-210-04 or AgB on Days 0, 30, and 180. Subjects were also seen by the study physician(s) on Days 60, 90, and 210 to evaluate safety and efficacy parameters. The primary efficacy objective of the study was to evaluate the number of subjects who became seroprotected (anti-HBsAg titer of ≧10 MIU/mL) at Day 90 with AgB/RC-210-04 compared to AgB.

Patient Demogaphics

Subject disposition data are summarized below for the intent-to-treat (ITT) population, defined as all subjects who were randomized. Summaries and statistical analyses of the demographic and efficacy data are presented for the efficacy evaluable (EE) population, defined as all subjects who were randomized and received both the Day 0 and Day 30 injections.

A total of 341 subjects were randomized at two sites (i.e., the ITT population). Table 34 summarizes the randomization of subjects at each center, the total number of subjects in the EE population, and the number of subjects in the EE population with data at the Day 0, Day 30, Day 60 and Day 90 visits.

TABLE 34

Subject Enrollment and Disposition by Investigator/Center

| Investigator Center No. | # Subjects in ITT Population | # Subjects in Efficacy Population | # Subjects in Efficacy Population with Data at Visit | | | |
|---|---|---|---|---|---|---|
| | | | Day 0 | Day 30 | Day 60 | Day 90 |
| Dupont 101 | 181 | 155 | 155 | 155 | 152 | 148 |
| Altclas 102 | 160 | 117 | 117 | 117 | 112 | 102 |
| Total: | 341 | 272 | 272 | 272 | 264 | 250 |

Table 35 summarizes the disposition of subjects and the reasons for discontinuation of treatment according to treatment group. A total of 272 of the 341 randomized subjects received both the Day 0 and Day 30 doses of study medication (EE Population). The treatment groups were comparable with respect to the number (%) of subjects in the EE population (p=0.332).

A total of 78/341 subjects (23%) discontinued participation in the study prior to the Day 90 visit (Table 35). The treatment groups were comparable with respect to the number (%) of subjects who discontinued participation in the study (p=0.187). The most reason for discontinuation was lost to follow-up (70/341 subjects [21%]). There was no apparent difference between the treatment groups in terms of withdrawal rates or reason for withdrawal.

TABLE 35

Subject Disposition and Reason for Discontinuation: ITT Population

|  | AgB | AgB/RC-210-04 |
| --- | --- | --- |
| Randomized | 171 | 170 |
| Number of vaccinations |  |  |
| 0 | 22 | 34 |
| 1 | 9 | 4 |
| 2 | 117 | 106 |
| 3 | 23 | 26 |
| Efficacy Evaluable Population[a] | 140 (81.9%) | 132 (77.6%) |
| Discontinued | 34 (19.9%) | 44 (25.9%) |
| Reason for discontinuation |  |  |
| Lost to follow-up | 30 (17.5%) | 42 (24.7%) |
| Withdrew consent | 2 (1.2%) |  |
| Investigator decision | 1 (0.6%) | 2 (1.2%) |
| Unknown | 1 (0.6%) |  |

[a]All subjects who are randomized and have received the Day 0 and Day 30 injections.

A toal of 263/341 subjects (77%) completed the Day 90 visit. The percentages of subjects who completed the Day 90 visit were similar for the two treatment groups. The percentages of subjects who completed each study visit are shown in Table 36.

TABLE 36

Number (%) of Subjects Who Completed Study Visits: ITT Population

| Visit Completed | AgB (N = 171) | AgB/RC-210-04 (N = 170) |
| --- | --- | --- |
| Day 0 | 148 (86.6%) | 136 (80.0%) |
| Day 30 | 141 (82.5%) | 132 (77.6%) |
| Day 60 | 137 (80.1%) | 128 (75.3%) |
| Day 90 | 130 (76.0%) | 121 (71.2%) |

Table 37 summarizes the demographic characteristics for the EE population. The study population was predominantly Caucasian, with a roughly equal division between male and female subjects. The mean age was about 27 years, but subjects in the AgB/RC-210-04 treatment group were significantly younger than those in the AgB treatment group (p=0.016). 50% of the subjects in the AgB/RC-210-04 treatment group were less than 25 years old, compared to 32% of subjects in the AgB treatment group (p=0.003). There were no other significant differences between the treatment groups with respect to the demographic variables summarized in Table 37 ($p \geq 0.222$).

TABLE 37

Demographic Characteristics: EE Population

| Characteristic | AgB (N = 140) | AgB/RC-210-04 (N = 132) | p-value |
| --- | --- | --- | --- |
| Age (yrs) |  |  |  |
| n | 140 | 132 |  |
| mean ± SD | 28.2 ± 6.0 | 26.4 ± 6.2 | 0.016[a] |
| median | 28 | 25 |  |
| range | 19–40 | 17–41 |  |
| <25 | 45 (32.1%) | 66 (50.0%) | 0.003[b] |
| ≧35 | 28 (20.0%) | 19 (14.4%) | 0.222[b] |
| Weight (kg) |  |  |  |
| n | 140 | 132 |  |
| mean ± SD | 70.0 ± 17.3 | 68.4 ± 13.6 | 0.398[a] |
| median | 68 | 67 |  |
| Gender |  |  |  |
| Male | 68 (48.6%) | 67 (50.8%) | 0.719[b] |
| Female | 72 (51.4%) | 65 (49.2%) |  |
| Race |  |  |  |
| Caucasian | 126 (90.0%) | 120 (90.9%) | 0.799[b] |
| Non-Caucasian | 14 (10.0%) | 12 (9.1%) |  |

[a]Analysis of variance.
[b]Chi-squared test.

Analysis of Efficacy

The primary efficacy endpoint was the number (%) of subjects achieving seroprotection at the Day 90 visit, defined as an anti-HBsAg titer of ≧10 MIU/mL. Secondary efficacy endpoints were: (1) the number (%) of subjects achieving seroprotection at the Day 30 and Day 60 visits; (2) the number (%) of subjects achieving seroconversion (defined as an anti-HBsAg titer of ≧1 MIU/mL) at the Day 30, Day 60 and Day 90 visits; and (3) the log-transformed anti-HBsAg titer levels at Days 30, Day 60, and Day 90.

Primary Efficacy Analysis: Seroprotection at Day 90

In the EE population, 126 of 132 (95.5%) of the subjects in the AgB/RC-210-04 treatment group achieved seroprotection by the Day 90 visit, compared to 115 of 140 (82.1%) of the subjects in the AgB treatment group. The difference in percentage of subjects achieving seroprotection was statistically significant (p=0.001). FIG. 1 summarizes the percentages of subjects in the EE population achieving seroprotection at the Day 90 visit for each of the two investigator sites, as well as for the two sites combined. These data showed that there were significantly more subjects seroprotected after two immunizations with AgB/RC-210-04 than with AgB alone.

Secondary Efficacy Analysis: Seroprotection at Day 30 and Day 60

Figure 2:
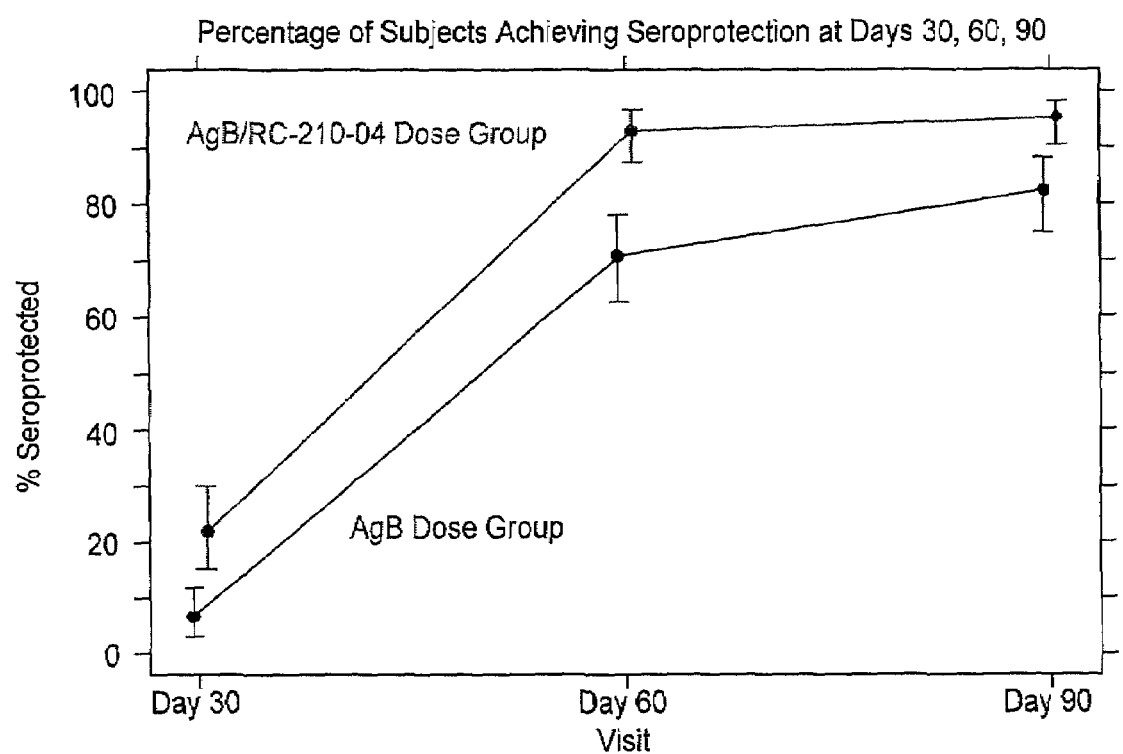
FIG. 2 is a graph depicting the percentage of human subjects achieving seroprotection (anti-HBsAg titer of ≦10 MIU/mL). Plot symbols show the percentages of EE population subjects who achieved seroprotection at each of the Day 30, 60, and 90 visits. The error bars show 95% confidence intervals for the percentages of subjects achieving seroprotection.

In the AgB/RC-210-04 treatment group, 29 of the 132 subjects (22.0%) had achieved seroprotection by the Day 30 visit, compared to 9 of the 140 subjects (6.4%) in the AgB treatment group. The difference between treatment groups in the rate of seroprotection by Day 30 was statistically significant (p<0.001). By the Day 60 visit, 123 of the 132 subjects (93.2%) in the AgB/RC-210-04 treatment group had achieved seroprotection, compared to 99 of the 140 subjects (70.7%) in the AgB treatment group. The between treatment group difference in the rate of seroprotection by the Day 60 visit was statistically significant (p<0.001). FIG. 2 summarizes the percentages of subjects in the two treatment groups who achieved seroprotection at each of the Day 30, 60, and 90 visits.

Secondary Efficacy Analysis: Seroconversion at Days 30, 60, and 90

Figure 3:
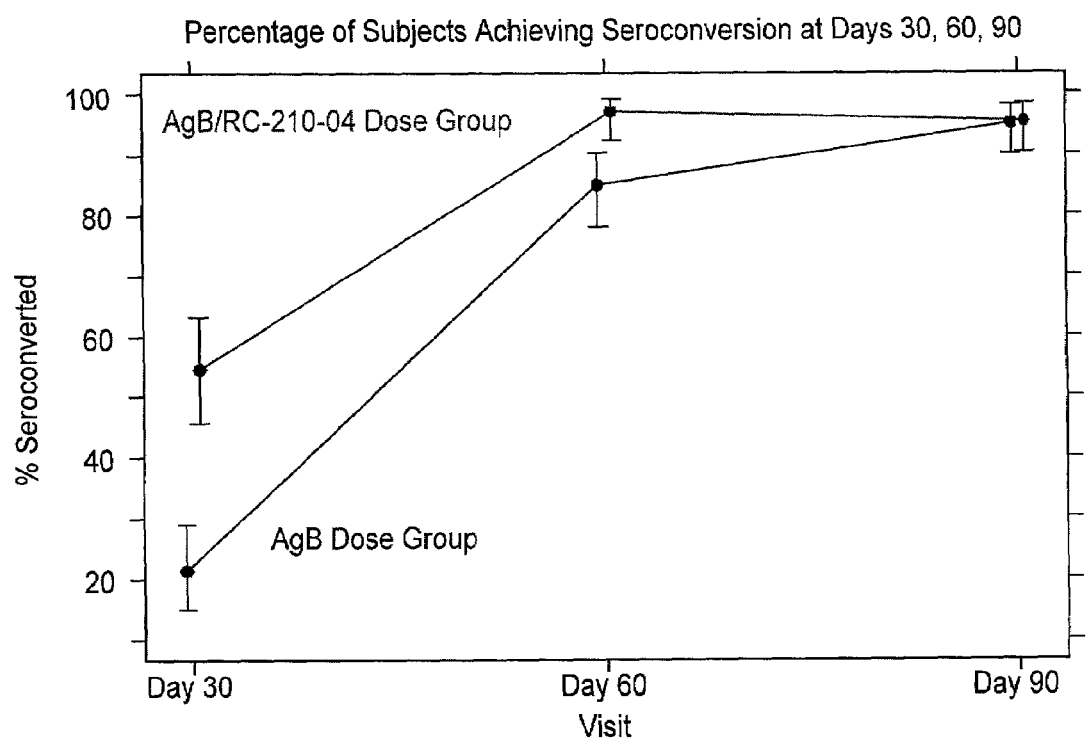
FIG. 3 is a graph depicting the percentage of human subjects achieving seroconversion (anti-HBsAg titer of ≦1 MIU/mL). Plot symbols show the percentages of EE population subjects who achieved seroconversion at each of the Day 30, 60, and 90 visits. The error bars show 95% confidence intervals for the percentages of subjects achieving seroconversion.

In the AgB/RC-210-04 treatment group, 72 of 132 subjects (54.6%) had achieved seroconversion at the Day 30 visit, compared to 30 of 140 subjects (21.4%) in the AgB treatment group. The difference between treatment groups in rate of seroconversion at the Day 30 visit was statistically significant (p<0.001). At the Day 60 visit, 128 of the 132 subjects (97.0%) in the AgB/RC-210-04 treatment group had achieved seroconversion, compared to 119 of 140 subjects (85.0%) in the AgB treatment group. The rate of seroconversion at the Day 60 visit differed significantly between the two treatment groups (p<0.001). At the Day 90 visit, 126 of the 132 subjects (95.5%) in the AgB/RC-210-04 treatment group had achieved seroconversion, while 133 of the 140 subjects (95.0%) in the AgB treatment group had achieved seroconversion. There was no statistically significant difference between the treatment groups in rate of seroconversion at the Day 90 visit (p=0.861). FIG. 3 summarizes the percentages of subjects in the two treatment groups who achieved seroconversion at each of the Day 30, 60, and 90 visits.

Secondary Efficacy Analysis: Log-Transformed Anti HBsAg Titer

Levels, EE Population at Days 30, Day 60, and Day 90

Table 38 summarizes the log-transformed anti-HBsAg titer levels in each treatment group, at each of the Day 30, Day 60, and Day 90 visits. Table 38 also shows the geometric mean of the anti-HBsAg titer levels in each dose at each visit (as the antilog of the mean of the log-transformed titer levels). Significant differences in mean log-transformed titer levels were found between the treatment groups at each of the Day 30, Day 60, and Day 90 visits (p<0.001, each visit).

TABLE 38

Log-Transformed Anti-HBsAg Titer Levels, Days 30, 60, 90: EE Population

| Visit | AgB (N = 140) | AgB/RC-210-04 (N = 132) | p-value |
|---|---|---|---|
| Day 30 | | | |
| n | 139 | 132 | |
| mean±SD | −0.66 ± 0.98 | 0.12 ± 1.21 | <0.001[a] |
| antilog(mean) | 0.22 | 1.33 | |
| Day 60 | | | |
| n | 137 | 128 | |
| mean±SD | 1.37 ± 1.16 | 2.23 ± 0.68 | <0.001[a] |
| antilog(mean) | 23.37 | 170.93 | |
| Day 90 | | | |
| n | 137 | 130 | |
| mean±SD | 1.86 ± 0.86 | 2.48 ± 0.61 | <0.001[a] |
| antilog(mean) | 71.66 | 302.62 | |

[a]Analysis of variance.

Figure 4:
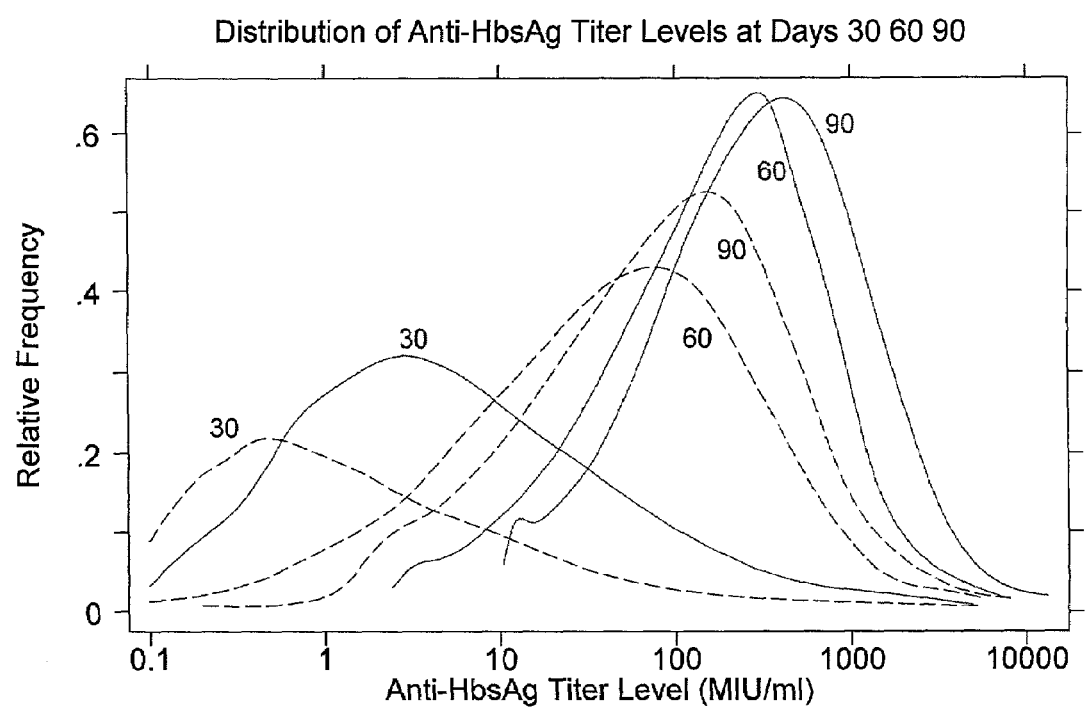
FIG. 4 is a graph depicting the distribution of Anti-HBsAg Titers in human subjects. Each curve shows a nonparametric estimate of the distribution of anti-HBsAg titers in a treatment group at a particular visit. Dashed curves correspond to the AgB group, solid curves correspond to the AgB/RC-210-04 treatment group. The numbers next to the curves show the nominal study day (visit) at which the data were collected. The area under each curve is proportional to the observed fraction of patients for whom a non-zero titer was measured.

FIG. 4 shows the estimated distributions of anti-HBsAg titer levels in both treatment groups at each of Days 30, 60, and 90. The estimated distributions were obtained by applying a nonparametric density estimator to the observed titer levels for all EE population patients for whom a positive titer level was obtained.

Results of all three secondary efficacy endpoints (seroprotection at Days 30 and 60, seroconversion rates, and geometric mean titers) supported the results of the primary endpoint. Significantly higher geometric mean titers in the AgB/RC-210-04 group suggest that post-vaccination titer level correlated with duration of seroprotection.

In total, the data presented in Test Example 14 demonstrate that addition of RC-210-04 to AgB resulted in an adjuvanted vaccine that illicited faster and greater antibody responses in healthy adults to Hepatitis B surface antigen.

AgB/RC-210-04 was efficacious for inducing early seroprotection to Hepatitis B virus after two immunizations.

It is understood that the foregoing examples are merely illustrative of the present invention. Certain modifications of the compositions and/or methods employed may be made and still achieve the objectives of the invention. Such modifications are contemplated as within the scope of the claimed invention.

REFERENCES

Bulusu, M. A. R. C., Waldstätten, P., Hildebrandt, J., Schüftze, E. and G. Schulz (1992) Cyclic Analogues of Lipid A: Synthesis and Biological Activities, *J. Med. Chem.* 35: 3463–3469.

Ikeda, K., Asahara, T. and K. Achiwa (1993) Synthesis of Biologically Active N-acylated L-serine-Containing Glucosaminide-4-Phosphate Derivatives of Lipid A, *Chem. Pharm. Bull.* 41(10): 1879–1881.

Miyajima, K., Ikeda, K. and K. Achiwa (1996) Lipid A and Related Compounds XXXI. Synthesis of Biologically Active N-Acylated L-Serine-Containing D-Glucosaminide 4-Phosphate Derivatives of Lipid A, *Chem. Pharm. Bull.* 44(12): 2268–2273.

Shimizu, T., Akiyama, S., Masuzawa, T., Yanagihara, Y., Nakamoto, S., Takahashi, T., Ikeda, K. and K. Achiwa (1985) Antitumor Activity and Biological Effects of Chemically Synthesized Monosaccharide Analogues of Lipid A in Mice. *Chem. Pharm. Bull.* 33(10): 4621–4624.

Shimizu, T., Sugiyama, K., Iwamoto, Y., Yanagihara, Y., Asahara, T., Ikeda, K. and K. Achiwa (1994) Biological Activities of Chemically Synthesized N-acylated Serine-linked Lipid A Analog in Mice, *Int. J. Immunopharmac.*, 16(8): 659–665.

Shimizu, T., Iida, K., Iwamoto, Y., Yanagihara, Y., Ryoyama, K., Asahara, T., Ikeda, K. and K. Achiwa (1995) Biological Activities and Antitumor Effects of Synthetic Lipid A Analogs Linked N-Acylated Serine, *Int. J. Immunopharmac.*, 17(5): 425–431.

What is claimed is:

1. A compound having the formula

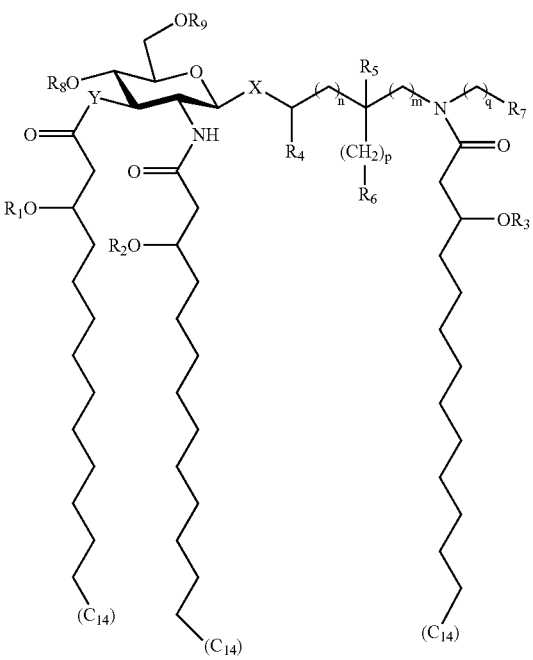

wherein X is O; Y is O; m, n, p and q are each 0; $R_4$, $R_5$, $R_7$ and $R_9$ are each H; $R_8$ is phosphono; $R_6$ is selected from OH, $CO_2H$ and $CONH_2$; and $R_1$, $R_2$ and $R_3$ are independently selected from $C_6$ acyl groups and $C_{10}$ acyl groups;
or a pharmaceutically acceptable salt thereof.

2. A compound according to claim 1, wherein at least one of $R_1$, $R_2$ and $R_3$ is a $C_6$ acyl group and at least one other of $R_1$, $R_2$ and $R_3$ is a $C_{10}$ acyl group.

3. A compound in accordance with claim 1, wherein two of $R_1$, $R_2$ and $R_3$ are $C_6$ acyl groups.

4. A compound in accordance with claim 1, wherein two of $R_1$, $R_2$, and $R_3$ are $C_{10}$ acyl groups.

5. A compound in accordance with claim 1, wherein $R_6$ is $CO_2H$.

6. A compound in accordance with claim 5, wherein $R_1$ is a $C_6$ acyl group and $R_2$ and $R_3$ are both $C_{10}$ acyl groups.

7. A compound in accordance with claim 5, wherein $R_3$ is a $C_{10}$ acyl group and $R_1$ and $R_2$ are both $C_6$ acyl groups.

8. A compound in accordance with claim 5, wherein $R_1$ is a $C_{10}$ acyl group and $R_2$ and $R_3$ are both $C_6$ acyl groups.

9. A compound in accordance with claim 5, wherein $R_1$, $R_2$ and $R_3$ are all $C_6$ acyl groups.

10. A pharmaceutically acceptable salt in accordance with claim 1.

11. A pharmaceutically acceptable salt in accordance with claim 2.

12. A pharmaceutical composition comprising a compound or a salt of claim 1 and a pharmaceutically acceptable carrier.

13. A method for enhancing the immune response of a mammal comprising administering to the mammal an effective amount of a compound or a salt of claim 1.

* * * * *